US010395207B2

(12) United States Patent
Jung et al.

(10) Patent No.: US 10,395,207 B2
(45) Date of Patent: Aug. 27, 2019

(54) FOOD SUPPLY CHAIN AUTOMATION GROCERY INFORMATION SYSTEM AND METHOD

(71) Applicant: ELWHA LLC, Bellevue, WA (US)

(72) Inventors: Edward K. Y. Jung, Bellevue, WA (US); Royce A. Levien, Lexington, MA (US); Mark A. Malamud, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 321 days.

(21) Appl. No.: 15/290,942

(22) Filed: Oct. 11, 2016

(65) Prior Publication Data

US 2017/0098187 A1  Apr. 6, 2017

Related U.S. Application Data

(63) Continuation of application No. 13/724,062, filed on Dec. 21, 2012, which is a continuation of application
(Continued)

(51) Int. Cl.
*G01N 25/72* (2006.01)
*G06Q 10/08* (2012.01)
(Continued)

(52) U.S. Cl.
CPC ........ *G06Q 10/0832* (2013.01); *G01N 25/72* (2013.01); *G01N 33/02* (2013.01);
(Continued)

(58) Field of Classification Search
None
See application file for complete search history.

(56) References Cited

U.S. PATENT DOCUMENTS 5,478,989 A   12/1995 Shepley
5,487,990 A    1/1996 Smith et al.
(Continued)

FOREIGN PATENT DOCUMENTS

WO    WO 01/27577 A2    4/2001
WO    WO 01/07555 A2   12/2001
(Continued)

OTHER PUBLICATIONS

U.S. Appl. No. 13/785,283, Jung et al.
(Continued)

*Primary Examiner* — Paul Danneman

(57) ABSTRACT

A computationally implemented system and method that is designed to, but is not limited to: electronically storing grocery operations information regarding at least in part one or more grocery implementation aspects pertaining to grocery related merchandizing of one or more commercial grocery products; and electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances. In addition to the foregoing, other method aspects are described in the claims, drawings, and text forming a part of the present disclosure.

20 Claims, 82 Drawing Sheets

Related U.S. Application Data

No. 13/721,558, filed on Dec. 20, 2012, now abandoned, application No. 15/290,942, which is a continuation-in-part of application No. 13/720,572, filed on Dec. 19, 2012, now abandoned, which is a continuation of application No. 13/709,831, filed on Dec. 10, 2012, application No. 15/290,942, which is a continuation-in-part of application No. 13/687,382, filed on Nov. 28, 2012, now abandoned, which is a continuation of application No. 13/682,939, filed on Nov. 21, 2012, now abandoned, application No. 15/290,942, which is a continuation-in-part of application No. 13/669,018, filed on Nov. 5, 2012, now abandoned, which is a continuation of application No. 13/668,977, filed on Nov. 5, 2012, now abandoned, application No. 15/290,942, which is a continuation-in-part of application No. 13/663,137, filed on Oct. 29, 2012, now Pat. No. 9,704,122, which is a continuation of application No. 13/663,095, filed on Oct. 29, 2012, now abandoned, application No. 15/290,942, which is a continuation-in-part of application No. 13/755,308, filed on Jan. 31, 2013, now abandoned, which is a continuation of application No. 13/755,095, filed on Jan. 31, 2013, now abandoned, application No. 15/290,942, which is a continuation-in-part of application No. 13/771,664, filed on Feb. 20, 2013, now abandoned, which is a continuation of application No. 13/771,506, filed on Feb. 20, 2013, now abandoned, application No. 15/290,942, which is a continuation-in-part of application No. 13/785,690, filed on Mar. 5, 2013, now abandoned, which is a continuation of application No. 13/785,283, filed on Mar. 5, 2013, now abandoned, application No. 15/290,942, which is a continuation-in-part of application No. 13/721,357, filed on Dec. 20, 2012, now abandoned, which is a continuation of application No. 13/715,309, filed on Dec. 14, 2012, now abandoned.

(60) Provisional application No. 61/698,334, filed on Sep. 7, 2012.

(51) Int. Cl.
*G06Q 10/06* (2012.01)
*G06Q 30/02* (2012.01)
*G01N 33/02* (2006.01)
*G06K 7/10* (2006.01)

(52) U.S. Cl.
CPC ..... *G06K 7/10009* (2013.01); *G06Q 10/0637* (2013.01); *G06Q 30/0201* (2013.01)

(56) References Cited

U.S. PATENT DOCUMENTS

| | | |
|---|---|---|
| 5,592,561 A | 1/1997 | Moore |
| 5,711,160 A | 1/1998 | Namisniak et al. |
| 5,768,384 A | 6/1998 | Berson |
| 5,913,170 A | 6/1999 | Wortham |
| 5,939,974 A | 8/1999 | Heagle et al. |
| 5,974,150 A | 10/1999 | Kaish et al. |
| 5,986,550 A | 11/1999 | Rapaport et al. |
| 6,005,960 A | 12/1999 | Moore |
| 6,069,955 A | 5/2000 | Coppersmith et al. |
| 6,226,619 B1 | 5/2001 | Halperin et al. |
| 6,375,077 B1 | 4/2002 | Hankins |
| 6,381,583 B1 | 4/2002 | Kennedy |
| 6,409,082 B1 | 6/2002 | Davis et al. |
| 6,442,276 B1 | 8/2002 | Doljack |
| 6,456,729 B1 | 9/2002 | Moore |
| 6,591,252 B1 | 7/2003 | Young |
| 6,671,698 B2 | 12/2003 | Pickett et al. |
| 6,788,800 B1 | 9/2004 | Carr et al. |
| 6,796,504 B2 | 9/2004 | Robinson |
| 6,806,478 B1 | 10/2004 | Hatfield |
| 6,859,672 B2 | 2/2005 | Roberts et al. |
| 6,874,000 B2 | 3/2005 | Sholl et al. |
| 6,973,437 B1 | 12/2005 | Olewicz et al. |
| 6,982,640 B2 | 1/2006 | Lindsay et al. |
| 6,995,675 B2 | 2/2006 | Curkendall et al. |
| 6,996,543 B1 | 2/2006 | Coppersmith et al. |
| 7,062,513 B2 | 6/2006 | Beck et al. |
| 7,085,777 B2 | 8/2006 | Beck et al. |
| 7,089,420 B1 | 8/2006 | Durst et al. |
| 7,170,391 B2 | 1/2007 | Lane et al. |
| 7,171,415 B2 | 1/2007 | Kan et al. |
| 7,182,257 B2 | 2/2007 | Ogihara et al. |
| 7,222,791 B2 | 5/2007 | Heilper et al. |
| 7,271,719 B2 | 9/2007 | Ku et al. |
| 7,283,630 B2 | 10/2007 | Doljack |
| 7,372,003 B2 | 5/2008 | Kates |
| 7,372,262 B2 | 5/2008 | Bertozzi et al. |
| 7,387,239 B2 | 6/2008 | Thomas et al. |
| 7,409,221 B2 | 8/2008 | Obradovich et al. |
| 7,472,274 B2 | 12/2008 | Moreaux et al. |
| 7,490,054 B2 | 2/2009 | Reade et al. |
| 7,497,379 B2 | 3/2009 | Chen et al. |
| 7,580,895 B2 | 8/2009 | Wilde et al. |
| 7,680,691 B2 | 3/2010 | Kimball et al. |
| 7,681,527 B2 | 3/2010 | Pratt |
| 7,705,735 B2 | 4/2010 | Pape et al. |
| 7,797,327 B2 | 9/2010 | Kataria et al. |
| 7,810,726 B2 | 10/2010 | De la Huerga |
| 7,861,542 B2 | 1/2011 | Rozendaal et al. |
| 7,874,489 B2 | 1/2011 | Mercolino |
| 7,878,396 B2 | 2/2011 | Wishnatzki et al. |
| 7,878,398 B2 | 2/2011 | Chen et al. |
| 7,909,239 B2 | 3/2011 | Grant et al. |
| 7,941,376 B2 | 5/2011 | Peckover |
| 7,949,154 B2 | 5/2011 | DeLuca |
| 7,954,711 B2 | 6/2011 | Adstedt et al. |
| 7,995,196 B1 | 8/2011 | Fraser |
| 7,996,319 B2 | 8/2011 | Dillon |
| 8,019,662 B2 | 9/2011 | Lucas |
| 8,028,891 B2 | 10/2011 | Harjani |
| 8,078,875 B2 | 12/2011 | Cowburn et al. |
| 8,087,585 B2 | 1/2012 | Greene |
| 8,101,892 B2 | 1/2012 | Kates |
| 8,103,046 B2 | 1/2012 | Cowburn |
| 8,108,309 B2 | 1/2012 | Tan |
| 8,152,063 B1 | 4/2012 | Grant et al. |
| 8,155,313 B2 | 4/2012 | Grant |
| 8,171,567 B1 | 5/2012 | Fraser et al. |
| 8,174,369 B2 | 5/2012 | Jones et al. |
| 8,196,827 B1 | 6/2012 | Grant |
| 8,210,430 B1 | 7/2012 | Grant et al. |
| 8,220,716 B2 | 7/2012 | Mercolino |
| 8,240,564 B2 | 8/2012 | Grant et al. |
| 8,243,930 B2 | 8/2012 | Harris |
| 8,244,747 B2 | 8/2012 | Agrawal et al. |
| 8,245,927 B2 | 8/2012 | Grant et al. |
| 8,249,350 B2 | 8/2012 | Voloshynovskyy et al. |
| 8,281,899 B2 | 10/2012 | Sutcliffe |
| 8,285,593 B2 | 10/2012 | Bhatt et al. |
| 8,553,886 B2 | 10/2013 | Sakai et al. |
| 8,560,403 B2 | 10/2013 | Adstedt et al. |
| 8,586,928 B2 | 11/2013 | Sinbar et al. |
| 8,635,179 B2 | 1/2014 | Cao et al. |
| 8,651,058 B1 | 2/2014 | Pierce |
| 8,712,851 B2 | 4/2014 | Koether et al. |
| 8,727,216 B2 | 5/2014 | Graves et al. |
| 9,053,616 B2 | 6/2015 | Grabiner et al. |
| 9,230,231 B1 | 1/2016 | Hodges |
| 9,696,326 B2 | 7/2017 | Parmee |
| 9,704,122 B2 | 7/2017 | Jung et al. |
| 9,830,604 B2 | 11/2017 | Aljawhari |
| 2001/0023410 A1 | 9/2001 | Hayes et al. |
| 2002/0007307 A1 | 1/2002 | Miller et al. |

(56) References Cited

U.S. PATENT DOCUMENTS

| | | |
|---|---|---|
| 2002/0026325 A1 | 2/2002 | Hirahara et al. |
| 2002/0059175 A1 | 5/2002 | Nakano |
| 2002/0095232 A1 | 7/2002 | Jorgenson et al. |
| 2002/0099771 A1 | 7/2002 | Ookushi |
| 2002/0158765 A1 | 10/2002 | Pape et al. |
| 2002/0191817 A1 | 12/2002 | Sato et al. |
| 2003/0034208 A1 | 2/2003 | Winfree et al. |
| 2003/0074239 A1 | 4/2003 | Hoffman et al. |
| 2003/0177025 A1 | 9/2003 | Curkendall et al. |
| 2003/0182260 A1 | 9/2003 | Pickett et al. |
| 2003/0226787 A1 | 12/2003 | Buisman et al. |
| 2003/0236768 A1 | 12/2003 | Sribhibhadh et al. |
| 2004/0049476 A1 | 3/2004 | Sai et al. |
| 2004/0080330 A1 | 4/2004 | Kunikiyo |
| 2004/0100380 A1 | 5/2004 | Lindsay et al. |
| 2004/0103043 A1 | 5/2004 | Reade et al. |
| 2004/0107141 A1 | 6/2004 | Conkel et al. |
| 2004/0185154 A1 | 9/2004 | Garwood |
| 2004/0195318 A1 | 10/2004 | Silverbrook et al. |
| 2004/0209312 A1 | 10/2004 | Harding et al. |
| 2004/0210621 A1 | 10/2004 | Antonellis |
| 2004/0230455 A1 | 11/2004 | McKinney et al. |
| 2005/0004682 A1 | 1/2005 | Gaddis et al. |
| 2005/0051199 A1 | 3/2005 | Drago et al. |
| 2005/0075900 A1 | 4/2005 | Arguimbau, III |
| 2005/0090233 A1 | 4/2005 | Chambers et al. |
| 2005/0156032 A1 | 7/2005 | Milstein |
| 2005/0216349 A1 | 9/2005 | Vaseloff et al. |
| 2005/0261991 A1 | 11/2005 | Kennamer |
| 2005/0273345 A1 | 12/2005 | Romero |
| 2006/0005018 A1 | 1/2006 | Alculumbre |
| 2006/0015416 A1 | 1/2006 | Hoffman et al. |
| 2006/0032427 A1* | 2/2006 | Ishii .............. B65D 79/02 116/217 |
| 2006/0069586 A1 | 3/2006 | Sutcliffe |
| 2006/0081653 A1 | 4/2006 | Boland et al. |
| 2006/0091220 A1 | 5/2006 | Fukui et al. |
| 2006/0185609 A1 | 8/2006 | Sato |
| 2006/0187048 A1 | 8/2006 | Curkendall et al. |
| 2006/0190494 A1 | 8/2006 | Beck et al. |
| 2006/0213904 A1* | 9/2006 | Kates .............. B65D 79/02 219/702 |
| 2006/0265290 A1 | 11/2006 | Perrier et al. |
| 2006/0266817 A1 | 11/2006 | Leger |
| 2006/0266827 A1 | 11/2006 | Hamilton |
| 2006/0271555 A1 | 11/2006 | Beck et al. |
| 2006/0282274 A1 | 12/2006 | Bennett |
| 2007/0022024 A1 | 1/2007 | Dowty et al. |
| 2007/0036470 A1 | 2/2007 | Piersol et al. |
| 2007/0058777 A1 | 3/2007 | Kondo |
| 2007/0059672 A1 | 3/2007 | Shaw |
| 2007/0148306 A1 | 6/2007 | Mattson et al. |
| 2007/0150371 A1 | 6/2007 | Gangji |
| 2007/0162325 A1 | 7/2007 | Singer-Harter |
| 2007/0185749 A1 | 8/2007 | Anderson et al. |
| 2007/0203818 A1 | 8/2007 | Farmer et al. |
| 2007/0208629 A1 | 9/2007 | Jung et al. |
| 2007/0208631 A1 | 9/2007 | Jung et al. |
| 2007/0222596 A1 | 9/2007 | Klejin et al. |
| 2007/0251521 A1 | 11/2007 | Schackmuth et al. |
| 2007/0260347 A1 | 11/2007 | Mirtsching et al. |
| 2007/0269557 A1 | 11/2007 | Culver et al. |
| 2007/0294129 A1 | 12/2007 | Froseth et al. |
| 2008/0010172 A1 | 1/2008 | Magill |
| 2008/0059330 A1 | 3/2008 | Stroman et al. |
| 2008/0217404 A1 | 9/2008 | Adstedt et al. |
| 2009/0012433 A1 | 1/2009 | Fernstrom et al. |
| 2009/0038552 A1 | 2/2009 | Baker et al. |
| 2009/0070163 A1 | 3/2009 | Angell et al. |
| 2009/0187583 A1 | 7/2009 | Pape et al. |
| 2009/0254460 A1 | 10/2009 | Farmer et al. |
| 2009/0275075 A1 | 11/2009 | Dodd et al. |
| 2009/0307599 A1 | 12/2009 | Davies et al. |
| 2009/0326687 A1 | 12/2009 | McCoy |
| 2009/0327104 A1 | 12/2009 | Sanders et al. |
| 2010/0010318 A1 | 1/2010 | Richter |
| 2010/0027849 A1 | 2/2010 | Mirtsching et al. |
| 2010/0030036 A1 | 2/2010 | Mottram et al. |
| 2010/0068345 A1 | 3/2010 | Tamminga et al. |
| 2010/0103241 A1 | 4/2010 | Linaker et al. |
| 2010/0106607 A1 | 4/2010 | Riddiford et al. |
| 2010/0140357 A1 | 6/2010 | Roslak et al. |
| 2010/0179857 A1 | 7/2010 | Kalaboukis et al. |
| 2010/0211477 A1 | 8/2010 | Jung et al. |
| 2010/0218407 A1 | 9/2010 | Kahng |
| 2010/0231358 A1 | 9/2010 | Mello |
| 2010/0253787 A1 | 10/2010 | Grant |
| 2010/0264205 A1 | 10/2010 | Iida |
| 2010/0268620 A1 | 10/2010 | Angert et al. |
| 2010/0280895 A1 | 11/2010 | Mottola |
| 2010/0332571 A1 | 12/2010 | Healey et al. |
| 2011/0029413 A1 | 2/2011 | Ben-Tzur et al. |
| 2011/0035326 A1 | 2/2011 | Sholl et al. |
| 2011/0151084 A1* | 6/2011 | Bell .............. A23B 4/16 426/418 |
| 2011/0156877 A1* | 6/2011 | Wong .............. F25D 29/003 340/10.1 |
| 2011/0211760 A1 | 9/2011 | Boncyk et al. |
| 2011/0218885 A1 | 9/2011 | Manksi et al. |
| 2011/0251868 A1 | 10/2011 | Mikurak |
| 2011/0291806 A1 | 12/2011 | Hoofman et al. |
| 2012/0005105 A1 | 1/2012 | Beier et al. |
| 2012/0073243 A1 | 3/2012 | Garrett et al. |
| 2012/0074027 A1 | 3/2012 | Nagpal et al. |
| 2012/0085828 A1 | 4/2012 | Ziegler |
| 2012/0085829 A1 | 4/2012 | Ziegler |
| 2012/0101972 A1 | 4/2012 | Cao et al. |
| 2012/0127314 A1 | 5/2012 | Clements |
| 2012/0135383 A1 | 5/2012 | Jang et al. |
| 2012/0136731 A1 | 5/2012 | Kidron et al. |
| 2012/0146792 A1 | 6/2012 | De Luca et al. |
| 2012/0150333 A1 | 6/2012 | De Luca et al. |
| 2012/0191817 A1 | 7/2012 | Sayan |
| 2012/0254058 A1 | 10/2012 | Walker et al. |
| 2012/0323809 A1 | 12/2012 | Fukui |
| 2012/0323948 A1 | 12/2012 | Li et al. |
| 2013/0041833 A1 | 2/2013 | Paikray et al. |
| 2013/0060813 A1 | 3/2013 | Eckberg et al. |
| 2013/0085599 A1 | 4/2013 | Nicol et al. |
| 2013/0103593 A1 | 4/2013 | Watts et al. |
| 2013/0105565 A1 | 5/2013 | Kamprath |
| 2013/0125835 A1 | 5/2013 | Sinn et al. |
| 2013/0140357 A1 | 6/2013 | Ure |
| 2013/0149677 A1 | 6/2013 | Slone et al. |
| 2013/0185104 A1 | 7/2013 | Klavins |
| 2013/0214938 A1 | 8/2013 | Kim et al. |
| 2013/0270341 A1 | 10/2013 | Janneh |
| 2013/0282625 A1 | 10/2013 | Chiu |
| 2013/0290852 A1 | 10/2013 | Silverman et al. |
| 2013/0337477 A1 | 12/2013 | Kuhr et al. |
| 2014/0012511 A1 | 1/2014 | Mensinger et al. |
| 2014/0026762 A1 | 1/2014 | Riefenstein |
| 2014/0074742 A1 | 3/2014 | Pratt |
| 2014/0088997 A1 | 3/2014 | Arefieg |
| 2014/0095192 A1 | 4/2014 | Rock et al. |
| 2014/0292490 A1 | 10/2014 | Butler et al. |
| 2014/0356858 A1 | 12/2014 | Harman |
| 2015/0083797 A1 | 3/2015 | Tran et al. |
| 2017/0243232 A1 | 8/2017 | Ross et al. |
| 2018/0039997 A1 | 2/2018 | Nilsson |
| 2018/0108024 A1 | 4/2018 | Greco et al. |

FOREIGN PATENT DOCUMENTS

| | | |
|---|---|---|
| WO | WO 03/090036 A2 | 10/2003 |
| WO | WO 2006/036978 A2 | 4/2006 |
| WO | WO 2007/103886 A2 | 9/2007 |
| WO | WO 2008/106720 A1 | 9/2008 |
| WO | WO 2009/047652 A1 | 4/2009 |
| WO | WO 2012/115297 A1 | 8/2012 |

(56) References Cited

FOREIGN PATENT DOCUMENTS

OTHER PUBLICATIONS

U.S. Appl. No. 13/771,664, Jung et al.
U.S. Appl. No. 13/771,506, Jung et al.
U.S. Appl. No. 13/755,308, Jung et al.
U.S. Appl. No. 13/755,095, Jung et al.
U.S. Appl. No. 13/724,062, Jung et al.
U.S. Appl. No. 13/721,558, Jung et al.
U.S. Appl. No. 13/721,357, Jung et al.
U.S. Appl. No. 13/720,572, Jung et al.
U.S. Appl. No. 13/715,309, Jung et al.
U.S. Appl. No. 13/709,831, Jung et al.
U.S. Appl. No. 13/687,382, Jung et al.
U.S. Appl. No. 13/682,939, Jung et al.
U.S. Appl. No. 13/669,018, Jung et al.
U.S. Appl. No. 13/668,977, Jung et al.
U.S. Appl. No. 13/663,137, Jung et al.
U.S. Appl. No. 13/633,095, Jung et al.
PCT International Search Report; International App. No. PCT/US2014/013664; dated Apr. 29, 2014; pp. 1-2.
PCT International Search Report; International App. No. PCT/US2014/013654; dated Apr. 22, 2014; pp. 1-2.
PCT International Search Report; International; App. No. PCT/US14/13649; dated May 22, 2014; pp. 1-3.
"A Review of the Beef Food Chain"; Safefood, Ireland Safe Food Board; bearing a date of Feb. 2008; pp. 1-119.
Akkaranggoon, Supalak; "Supply Chain Management Practices in the Hotel Industry: An Examination of Hotel Food Supply Chains in South West England"; University of Exeter, Exeter, South West England, United Kingdom; bearing a date of Oct. 2010; pp. 1-288.
Brown, Gregory B.; "A Quantitative Method for Evaluating Alternative Plant Layouts", published by Georgia Institute of Technology for Master's Thesis disclosure; bearing a date of Sep. 1970; pp. 1-126.
Chopra et al.; "Which e-Business Is Right for Your Supply Chain?"; Supply Chain Management Review; bearing a date of Jul./Aug. 2000; pp. 32-40; vol. 4 No. (3).
Exadaktylos et al.; "Real-time Recognition of sick pig cough sounds"; Computers and Electronics in Agriculture; bearing a date of Feb. 28, 2008; pp. 207-214; vol. 63; Science Direct; Elsvier.
James, Jennylynd; "Overview of Microbial Hazards in Fresh Fruit and Vegetables Operations"; from: Jennylynd James, Ed., "Microbial Hazard Identification in Fresh Fruit and Vegetables"; John Wiley & Sons; New York; bearing a date of 2006; pp. 1-36.
Raspor, P. et al,; "Novel Food Safety Concepts for Safe Food: Case Meat Processing Industry"; International 55$^{th}$ Meat Industry Conference; Tara, Serbia; tehnologija mesa 50; bearing a date of Jun. 17, 2009; pp. 1-10.
Schwagele et al.; "Tracking and Tracing in the Meat Area"; International 55$^{th}$ Meat Industry Conference (held from Jun. 15-17); tehnologija mesa 50, bearing a date of 2009; pp. 11-20.
Smith et al.; "Traceability from a US Perspective"; Meat Science; bearing a date of 2005; pp. 174-193; vol. 71.
Svensson et al.; "Designing and Evaluating Kalas: A Social Navigation System for Food Recipes", ACM Transactions on Computer-Human Interaction (TOCHI); bearing a date of Sep. 2005; pp. 374-400; vol. 12, No. 3.
Svensson et al.; "A Recipe Based On-Line Food Store"; Proceedings of the 5th International Conference on Intelligent User Interfaces; bearing a date of 2000; pp. 1-3.
Uchida et al.; "A New Traceability System for SMEs with Open Source Software"; WSEAS Transactions on Business and Economics; bearing a date of Jan. 2009; a pp. 1-10; Issue 1, vol. 6.
Wyler et al.; "CRS Report for Congress: International Illegal Trade in Wildlife: Threats and U.S. Policy"; Congressional Research Service; bearing a date of Mar. 3, 2008; CRS-1-CRS-45.
Beulens et al.; "Food safety and transparency in food chains and networks—Relationships and challenges"; Food Control; Oct. 13, 2003; pp. 481-486; vol. 16; Elsevier Ltd.
Pang et al.; "Global Fresh Food Tracking Service Enabled by Wide Area Wireless Sensor Network"; Royal Institute of Technology—Forum 120; 2009; 4 pp.; IEEE.
Puigjaner et al; "Tracking the Dynamics of the Supply Chain for Enhanced Production Sustainability"; Ind. Eng. Chem. Res.; Jul. 22, 2009; pp. 9556-9570; vol. 48, No. 21; American Chemical Society.
Ruiz-Garcia et al.; "A model and prototype implementation for tracking and tracing agricultural batch products along the food chain"; Food Control; 2010; pp. 112-121; vol. 21; Elsevier Ltd.
Stringer et al.; "A generic model of the integrated food supply chain to aid the investigation of food safety breakdowns"; Food Control; Jan. 11, 2006; pp. 755-765; vol. 18; Elsevier Ltd.
Wognum et al.; "Systems for sustainability and transparency of food supply chains—Current status and challenges"; Advanced Engineering Informatics; Jul. 2, 2010; pp. 65-76; vol. 25; Elsevier Ltd.
Yam et al; "Intelligent Packaging: Concepts and Applications"; Journal of Food Science; Dec. 22, 2004; pp. R1-R10; vol. 70, No. 1; Institute of Food Technologists.
Azaquar; "Food preservation by high pressure"; found at http://www.azaguar.com/en/doc/food-preservation-by-high-pressure with a date of Oct. 5, 2011; pp. 1-4; azaquar.com.
Buchanan et al.; "Traceability Within the British Columbia Halibut Industry—A Review of Traceability Practices, Readiness, and Opportunities"; Archipelago Marine Research Ltd.; Jul. 2012; pp. 1-44.
Dillon et al.; "A Guide to Traceability within the Fish Industry"; 2004; pp. 1-80; ISBN 1900134187.
Golan et al.; "Traceability in the U.S. Food Supply: Economic Theory and Industry Studies"; Agricultural Economic Report No. 830; Mar. 2004; pp. 1-48; USDA Economic Research Service.
Hsu et al.; "A RFID-Enabled Traceability System for the Supply Chain of Live Fish"; International Conference on Automation and Logistics; Sep. 2008; pp. 81-86; IEEE.
Randrup, Maria; "Case studies of quality, quality assurance, and traceable information in auction-based fish supply chains"; Mar. 2012; pp. 1-136; Technical University of Denmark, National Food Institute, Division of Industrial Food Research.

* cited by examiner

*Fig. 13* s100 control and information processing subsystem

| s102 microprocessor component | s104 central processing unit (CPU) component | s106 digital signal processor (DSP) component | s108 application specific integrated circuit (ASIC) component | s110 field programmable gate array (FPGA) component |
|---|---|---|---|---|
| s112 multiprocessor component | s114 optical processing component | s116 logic component | s118 remote processor component | s120 multi-core array component |
| s122 server processor component | s124 database engine component | s126 search engine component | s128 image recognition component | s130 audio recognition component |
| s132 spectrum analysis component | s134 lexigraphy engine component | s136 operating system component | s138 voice recognition component | s140 network processor component |

*Fig. 14* s200 information storage subsystem

| s202 random access memory (RAM) component | s204 dynamic random access memory (DRAM) component | s206 other volatile memory component | s208 persistent memory component | s210 read only memory (ROM) component |
| s212 electrically erasable programmable read only memory | s214 compact disk (CD) component | s216 digital versatile disk (DVD) component | s218 flash memory component | s220 other nonvolatile memory component |
| s222 hard drive component | s224 disk farm component | s226 disk cluster component | s228 remote backup component | s230 server component |
| s232 digital tape component | s234 optical storage component | s236 Blu Ray disk component | s238 computer readable signal bearing medium | s240 removable media component |

Fig. 16

| s400 sensing subsystem | | | |
|---|---|---|---|
| s402 electromagnetic sensing component | s404 antenna component | s406 photo detecting component | s408 micro-electro-mech sys (MEMS) detecting component | s410 weight sensing component |
| s412 temperature sensing component | s414 radio freq ID (RFID) sensing component | s416 chemical sensing component | s418 optical sensing component | s420 sound sensing component |
| s422 gas sensing component | s424 liquid sensing component | s426 solid sensing component | s428 climate sensing component | s430 vibration sensing component |
| s432 motion sensing component | s434 pressure sensing component | s436 pattern sensing component | s438 color sensing component | s440 encryption sensing component |

*Fig. 17* s500 electronic communication subsystem

| s502 network cable component | s504 optical network component | s506 waveguide network component | s508 internet network component | s510 wireless network component |
| s512 wired network component | s514 cellular network component | s516 wide area network component | s518 local area network component | s520 encrypted communication component |
| s522 transceiver component | s524 infrared network component | s526 transmitter component | s528 receiver component | s530 long-range communication component |
| s532 short-range communication component | s534 RFID communication component | s536 encrypted communication component | s538 SMS communication component | s540 tablet communication component |

*Fig. 18*

| s600 power subsystem | | | |
|---|---|---|---|
| s602 electrical component | s604 hydrocarbon fuel component | s606 hydrogen fuel component | s608 solid fuel component | s610 liquid fuel component |
| s612 gaseous fuel component | s614 battery component | s616 electrical generator component | s618 dry cell battery component | s620 hybrid fuel component |
| s622 rechargeable component | s624 thermoelectric component | s626 piezoelectric component | s628 capacitor component | s630 power cell component |
| s632 steam generation component | s634 solar cell component | s636 solar reflector component | s638 thermonuclear component | s640 co-generation component |

*Fig. 19* s700 material processing subsystem

| s702 heating component | s704 cooling component | s706 microwave component | s708 laser component | s710 light emitting diode (LED) component |
| s712 peltier cooling component | s714 blending component | s716 mixer component | s718 acoustic energy component | s720 stirring component |
| s722 shaker component | s724 energy emitting component | s726 pump component | s728 sorting component | s730 infrared component |
| s732 cutting component | s734 material storage component | s736 material receiving component | s738 material containing component | s740 material handling component |

Fig. 20 s800 merchandizing subsystem

| s802 stocking resources component | s804 receiving shipments component | s806 refrigeration operation component | s808 displaying operation component | s810 cleaning operation component |
| s812 shelving operation component | s814 deli operation component | s816 produce dept operation component | s818 dairy dept operation component | s820 meat dept operation component |
| s822 beverage dept operation component | s824 poultry dept operation component | s826 fish dept operation component | s828 infestation operation component | s830 health inspection component |
| s832 butcher operation component | s834 cereal dept operation component | s836 protein dept operation component | s838 fat dept operation component | s840 carbohydrate dept operation component |

Fig. 22

10 grocery information system

| | | | |
|---|---|---|---|
| e1120 storing worker handling elec circ arrange | e1121 storing aspect handling elec circ arrange | | |
| | | e1122 storing merchandizing substances elec circ arrange | e1123 storing events occurring elec circ arrange | e1124 storing test handling elec circ arrange |
| e1125 storing chemical test elec circ arrange | e1126 storing customer health elec circ arrange | e1127 storing test health elec circ arrange | e1128 storing worker guidelines elec circ arrange | e1129 storing forbidden human elec circ arrange |
| e1130 storing lack of behavior elec circ arrange | e1131 storing test observation elec circ arrange | e1132 storing audio test elec circ arrange | e1133 storing video test elec circ arrange | e1134 storing protein sales elec circ arrange |
| e1135 storing carbohydrate sales elec circ arrange | e1136 storing fat sales elec circ arrange | e1137 storing stock rotation elec circ arrange | e1138 storing equipment cleaning elec circ arrange | e1139 storing refrigeration factors elec circ arrange |

*Fig. 23*

10 grocery information system

- e1140 storing heat treating elec circ arrange
- e1141 storing stock storage elec circ arrange
- e1142 storing equipment use elec circ arrange
- e1143 storing deli support elec circ arrange
- e1144 storing deli hindrance elec circ arrange
- e1145 storing customer factors elec circ arrange
- e1146 storing store locations elec circ arrange
- e1147 storing clerk staff elec circ arrange
- e1148 storing compliance factors elec circ arrange
- e1149 storing butcher staff elec circ arrange
- e1150 storing health department elec circ arrange
- e1151 storing harvest location elec circ arrange
- e1152 storing genetically modified elec circ arrange
- e1153 storing advertisement items elec circ arrange
- e1154 storing food freshness elec circ arrange
- e1155 storing food contamination elec circ arrange
- e1156 storing organic labeling elec circ arrange
- e1157 storing toxin levels elec circ arrange
- e1158 storing food combining elec circ arrange
- e1159 storing food shipment elec circ arrange

*Fig. 24*

| 10 grocery information system | | | |
|---|---|---|---|
| e1160 storing displaying items elec circ arrange | e1161 storing dispensing prepackaged elec circ arrange | e1162 storing stocking shelves elec circ arrange | e1163 storing dispensing machines elec circ arrange | e1164 storing remote customers elec circ arrange |
| e1165 storing internet ordering elec circ arrange | e1166 storing whole produce elec circ arrange | e1167 storing mobile dispensaries elec circ arrange | e1168 storing packaged food elec circ arrange | e1169 storing canned items elec circ arrange |
| e1170 storing frozen dinners elec circ arrange | e1171 storing salad based elec circ arrange | e1172 storing beef items elec circ arrange | e1173 storing seafood items elec circ arrange | e1174 storing poultry items elec circ arrange |
| e1175 storing dairy items elec circ arrange | e1176 storing whole animal elec circ arrange | e1177 storing beverage items elec circ arrange | e1178 storing appetizer items elec circ arrange | e1179 storing sandwich items elec circ arrange |

*Fig. 26*

10 grocery information system

- e12 electronically associating elec circ arrange
- e1201 associating computer-based indices elec circ arrange
- e1202 associating computer-based pointers elec circ arrange
- e1203 associating relational databases elec circ arrange
- e1204 associating keyword associations elec circ arrange
- e1205 associating lookup tables elec circ arrange
- e1206 associating identification codes elec circ arrange
- e1207 associating encrypted identifications elec circ arrange
- e1208 associating naming information elec circ arrange
- e1209 associating alpha-numeric text elec circ arrange
- e1210 associating encoded data elec circ arrange
- e1211 associating frequency identification elec circ arrange
- e1212 associating electronic optical elec circ arrange
- e1213 associating quick response elec circ arrange
- e1214 associating computer servers elec circ arrange
- e1215 associating computer-based network elec circ arrange
- e1216 associating radio frequency elec circ arrange
- e1217 associating emitter beacons elec circ arrange
- e1218 associating barcode tags elec circ arrange
- e1219 associating genetic tags elec circ arrange

Fig. 27

10 grocery information system

- e1220 associating biochemical tags elec circ arrange
- e1221 associating chemical tags elec circ arrange
- e1222 associating isotopic tags elec circ arrange
- e1223 associating radioactive tags elec circ arrange
- e1224 associating signal emitting tags elec circ arrange
- e1225 associating identification tags elec circ arrange
- e1226 associating visual shapes elec circ arrange
- e1227 associating color patterns elec circ arrange
- e1228 associating audio emitters elec circ arrange
- e1229 associating electronic databases elec circ arrange
- e1230 associating electronic memories elec circ arrange
- e1231 associating identification information elec circ arrange
- e1232 associating factory to store elec circ arrange
- e1233 associating shelf life elec circ arrange
- e1234 associating affixed to items elec circ arrange
- e1235 associating pre-processed forms elec circ arrange
- e1236 associating physically connected elec circ arrange
- e1237 associating temporarily containing elec circ arrange

Fig. 29 s200 information storage subsystem

| i1120 storing worker handling instructions | i1121 storing aspect handling instructions | i1122 storing merchandizing substances instructions | i1123 storing events occurring instructions | i1124 storing test handling instructions |
| i1125 storing chemical test instructions | i1126 storing customer health instructions | i1127 storing test health instructions | i1128 storing worker guidelines instructions | i1129 storing forbidden human instructions |
| i1130 storing lack of behavior instructions | i1131 storing test observation instructions | i1132 storing audio test instructions | i1133 storing video test instructions | i1134 storing protein sales instructions |
| i1135 storing carbohydrate sales instructions | i1136 storing fat sales instructions | i1137 storing stock rotation instructions | i1138 storing equipment cleaning instructions | i1139 storing refrigeration factors instructions |

*Fig. 30* s200 information storage subsystem

| i1140 storing heat treating instructions | i1141 storing stock storage instructions | i1142 storing equipment use instructions | i1143 storing deli support instructions | i1144 storing deli hindrance instructions |
| --- | --- | --- | --- | --- |
| i1145 storing customer factors instructions | i1146 storing store locations instructions | i1147 storing clerk staff instructions | i1148 storing compliance factors instructions | i1149 storing butcher staff instructions |
| i1150 storing health department instructions | i1151 storing harvest location instructions | i1152 storing genetically modified instructions | i1153 storing advertisement items instructions | i1154 storing food freshness instructions |
| i1155 storing food contamination instructions | i1156 storing organic labeling instructions | i1157 storing toxin levels instructions | i1158 storing food combining instructions | i1159 storing food shipment instructions |

Fig. 31 s200 information storage subsystem

- i1160 storing displaying items instructions
- i1161 storing dispensing prepackaged instructions
- i1162 storing stocking shelves instructions
- i1163 storing dispensing machines instructions
- i1164 storing remote customers instructions
- i1165 storing internet ordering instructions
- i1166 storing whole produce instructions
- i1167 storing mobile dispensaries instructions
- i1168 storing packaged food instructions
- i1169 storing canned items instructions
- i1170 storing frozen dinners instructions
- i1171 storing salad based instructions
- i1172 storing beef items instructions
- i1173 storing seafood items instructions
- i1174 storing poultry items instructions
- i1175 storing dairy items instructions
- i1176 storing whole animal instructions
- i1177 storing beverage items instructions
- i1178 storing appetizer items instructions
- i1179 storing sandwich items instructions

Fig. 33 s200 information storage subsystem

| i12 electronically associating instructions | i1201 associating computer-based indices instructions | i1202 associating computer-based pointers instructions | i1203 associating relational databases instructions | i1204 associating keyword associations instructions |
| i1205 associating lookup tables instructions | i1206 associating identification codes instructions | i1207 associating encrypted identifications instructions | i1208 associating naming information instructions | i1209 associating alpha-numeric text instructions |
| i1210 associating encoded data instructions | i1211 associating frequency identification instructions | i1212 associating electronic optical instructions | i1213 associating quick response instructions | i1214 associating computer servers instructions |
| i1215 associating computer-based network instructions | i1216 associating radio frequency instructions | i1217 associating emitter beacons instructions | i1218 associating barcode tags instructions | i1219 associating genetic tags instructions |

Fig. 34 information storage subsystem

| i1220 associating biochemical tags instructions | i1221 associating chemical tags instructions | i1222 associating isotopic tags instructions | i1223 associating radioactive tags instructions | i1224 associating signal emitting tags instructions |
| --- | --- | --- | --- | --- |
| i1225 associating identification tags instructions | i1226 associating visual shapes instructions | i1227 associating color patterns instructions | i1228 associating audio emitters instructions | i1229 associating electronic databases instructions |
| i1230 associating electronic memories instructions | i1231 associating identification information instructions | i1232 associating factory to store instructions | i1233 associating shelf life instructions | i1234 associating affixed to items instructions |
| i1235 associating pre-processed forms instructions | i1236 associating physically connected instructions | i1237 associating temporarily containing instructions | | |

Fig. 40

| 10 grocery information system | | | |
|---|---|---|---|
| m12 electronically associating module | m1201 associating computer-based indices module | m1202 associating computer-based pointers module | m1203 associating relational databases module | m1204 associating keyword associations module |
| m1205 associating lookup tables module | m1206 associating identification codes module | m1207 associating encrypted identifications module | m1208 associating naming information module | m1209 associating alpha-numeric text module |
| m1210 associating encoded data module | m1211 associating frequency identification module | m1212 associating electronic optical module | m1213 associating quick response module | m1214 associating computer servers module |
| m1215 associating computer-based network module | m1216 associating radio frequency module | m1217 associating emitter beacons module | m1218 associating barcode tags module | m1219 associating genetic tags module |

Fig. 72 o12 electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances o1207 electronically associating at least a portion of grocery operations information concerning at least in part one or more grocery implementation aspects pertaining to grocery related merchandizing of one or more commercial grocery products the with identification information obtainable through one or more tags said one or more tags logged as being at least temporarily within at least a vicinity of one or more food based substances including at least in part one or more computer-based encrypted identifications o1208 electronically associating at least a portion of grocery operations information concerning at least in part one or more grocery implementation aspects pertaining to grocery related merchandizing of one or more commercial grocery products the with identification information obtainable through one or more tags said one or more tags logged as being at least temporarily within at least a vicinity of one or more food based substances including at least in part one or more computer-based naming information o1209 electronically associating at least a portion of grocery operations information concerning at least in part one or more grocery implementation aspects pertaining to grocery related merchandizing of one or more commercial grocery products the with identification information obtainable through one or more tags said one or more tags logged as being at least temporarily within at least a vicinity of one or more food based substances including at least in part one or more computer-based stored alpha-numeric text

Fig. 74 o12 electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances o1213 electronically associating at least a portion of grocery operations information concerning at least in part one or more grocery implementation aspects pertaining to grocery related merchandizing of one or more commercial grocery products the with identification information obtainable through one or more tags said one or more tags logged as being at least temporarily within at least a vicinity of one or more food based substances including at least in part one or more electronic quick response codes o1214 electronically associating at least a portion of grocery operations information concerning at least in part one or more grocery implementation aspects pertaining to grocery related merchandizing of one or more commercial grocery products with identification information the obtainable through one or more tags said one or more tags logged as being at least temporarily within at least a vicinity of one or more food based substances at least in part obtaining identification information from one or more electronic computer servers o1215 electronically associating at least a portion of grocery operations information concerning at least in part one or more grocery implementation aspects pertaining to grocery related merchandizing of one or more commercial grocery products with identification information the obtainable through one or more tags said one or more tags logged as being at least temporarily within at least a vicinity of one or more food based substances at least in part using information obtained from one or more tags to electronically access identification information via a computer-based network

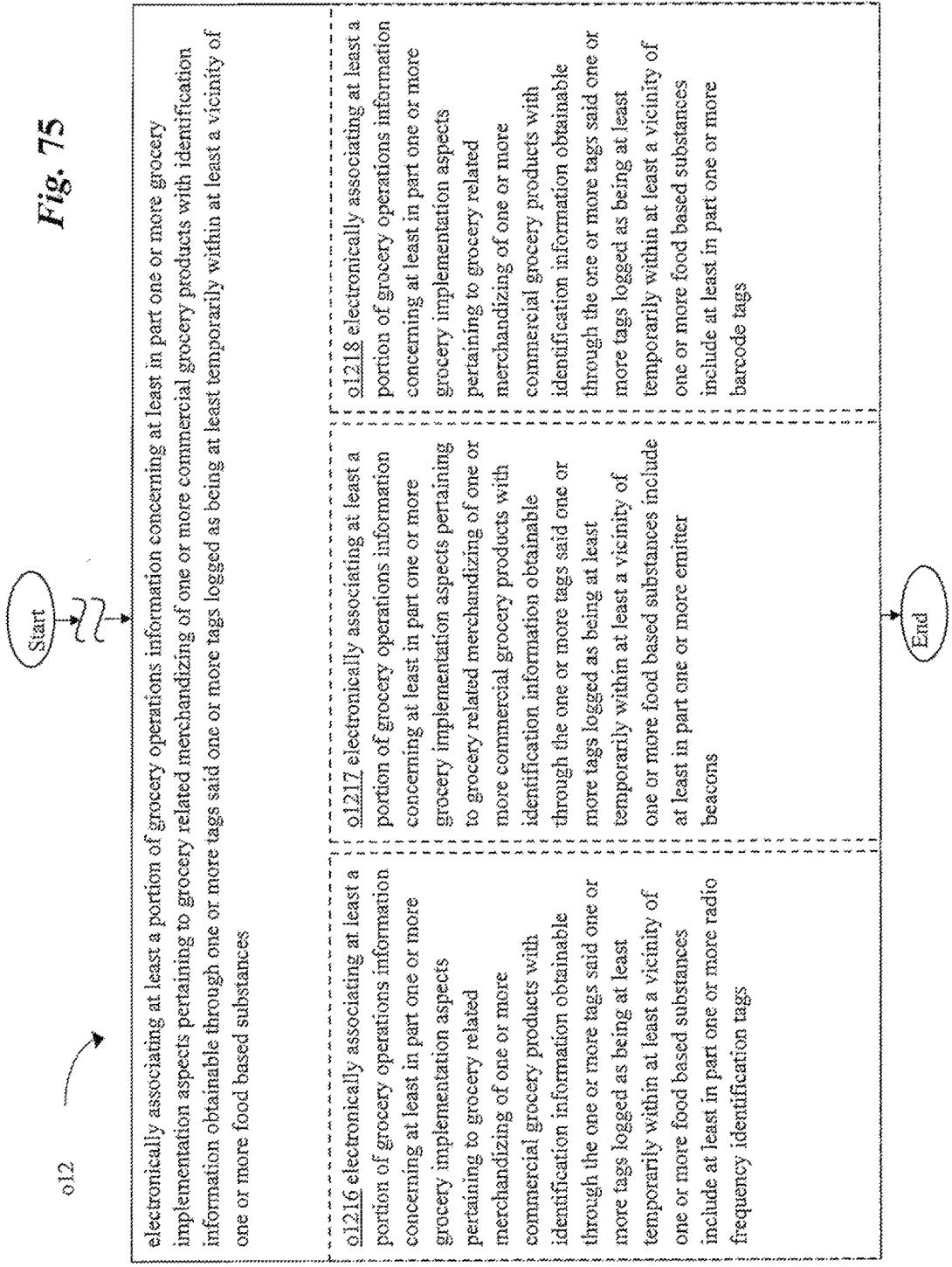

*Fig. 81*

o12

Start electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances o1234 electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily the within at least a vicinity of one or more food based substances including at least in part logged as affixed to one or more grocery items o1235 electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily the within at least a vicinity of one or more food based substances including at least in part logged as affixed to pre-processed forms of grocery items o1236 electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily the within at least a vicinity of one or more food based substances including at least in part affixed to another portion of a biological structure that is logged as being physically connected with one or more grocery items End

*Fig. 82*

o12 electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances o1237 electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily the within at least a vicinity of one or more food based substances including at least in part logged as affixed to one or more containers at least temporarily containing one or more grocery items

FOOD SUPPLY CHAIN AUTOMATION GROCERY INFORMATION SYSTEM AND METHOD

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 U.S.C. § 119(e) for provisional patent applications, for any and all parent, grandparent, great-grandparent, etc. applications of the Priority Application(s)). In addition, the present application is related to the "Related Application(s)," if any, listed below:

PRIORITY APPLICATIONS

For purposes of the USPTO extra-statutory requirements, the present application constitutes a continuation of U.S. patent application Ser. No. 13/724,062, entitled FOOD SUPPLY CHAIN AUTOMATION GROCERY INFORMATION SYSTEM AND METHOD, naming Edward K. Y. Jung, Royce A. Levien, and Mark A. Malamud as inventors, filed 21 Dec. 2012, which is currently co-pending or is an application of which a currently co-pending application is entitled to the benefit of the filing date, and which is a continuation of U.S. patent application Ser. No. 13/721,558, entitled FOOD SUPPLY CHAIN AUTOMATION GROCERY INFORMATION SYSTEM AND METHOD, naming Edward K. Y. Jung, Royce A. Levien, and Mark A. Malamud as inventors, filed 20 Dec. 2012, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/755,308, entitled FOOD SUPPLY CHAIN AUTOMATION GROCERY OPERATIONS INTERFACE INFORMATION SYSTEM AND METHOD, naming Edward K. Y. Jung, Royce A. Levien, and Mark A. Malamud as inventors, filed 31 Jan. 2013, which is currently co-pending or is an application of which a currently co-pending application is entitled to the benefit of the filing date, and which is a continuation of U.S. patent application Ser. No. 13/755,095, entitled FOOD SUPPLY CHAIN AUTOMATION GROCERY OPERATIONS INTERFACE INFORMATION SYSTEM AND METHOD, naming Edward K. Y. Jung, Royce A. Levien, and Mark A. Malamud as inventors, filed 31 Jan. 2013, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/771,664, entitled FOOD SUPPLY CHAIN AUTOMATION RESIDENTIAL INFORMATION SYSTEM AND METHOD, naming Edward K. Y. Jung, Royce A. Levien, and Mark A. Malamud as inventors, filed 20 Feb. 2013, which is currently co-pending or is an application of which a currently co-pending application is entitled to the benefit of the filing date, and which is a continuation of U.S. patent application Ser. No. 13/771,506, entitled FOOD SUPPLY CHAIN AUTOMATION RESIDENTIAL INFORMATION SYSTEM AND METHOD, naming Edward K. Y. Jung, Royce A. Levien, and Mark A. Malamud as inventors, filed 20 Feb. 2013, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/785,690, entitled FOOD SUPPLY CHAIN AUTOMATION RESIDENTIAL FOOD MANAGEMENT INTERFACE INFORMATION SYSTEM AND METHOD, naming Edward K. Y. Jung, Royce A. Levien, and Mark A. Malamud as inventors, filed 5 Mar. 2013, which is currently co-pending or is an application of which a currently co-pending application is entitled to the benefit of the filing date, and which is a continuation of U.S. patent application Ser. No. 13/785,283, entitled FOOD SUPPLY CHAIN AUTOMATION RESIDENTIAL FOOD MANAGEMENT INTERFACE INFORMATION SYSTEM AND METHOD, naming Edward K. Y. Jung, Royce A. Levien, and Mark A. Malamud as inventors, filed 5 Mar. 2013, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/721,357, entitled FOOD SUPPLY CHAIN AUTOMATION FOOD SERVICE INFORMATION INTERFACE SYSTEM AND METHOD, naming Edward K. Y Jung, Royce A. Levien, and Mark A. Malamud as inventors, filed 20 Dec. 2012, which is currently co-pending or is an application of which a currently co-pending application is entitled to the benefit of the filing date, and which is a continuation of U.S. patent application Ser. No. 13/715,309, entitled FOOD SUPPLY CHAIN AUTOMATION FOOD SERVICE INFORMATION INTERFACE SYSTEM AND METHOD, naming Edward K. Y Jung, Royce A. Levien, and Mark A. Malamud as inventors, filed 14 Dec. 2012, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/720,572, entitled FOOD SUPPLY CHAIN AUTOMATION FOOD SERVICE INFORMATION SYSTEM AND METHOD, naming Edward K. Y Jung, Royce A. Levien, and Mark A. Malamud as inventors, filed 19 Dec. 2012, which is currently co-pending or is an application of which a currently co-pending application is entitled to the benefit of the filing date, and which is a continuation of U.S. patent application Ser. No. 13/709,831, entitled FOOD SUPPLY CHAIN AUTOMATION FOOD SERVICE INFORMATION SYSTEM AND METHOD, naming Edward K. Y Jung, Royce A. Levien, and Mark A. Malamud as inventors, filed 10 Dec. 2012, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/687,382, entitled FOOD SUPPLY CHAIN AUTOMATION FARM INTERFACE SYSTEM AND METHOD, naming Edward K. Y. Jung, Royce A. Levien, and Mark A. Malamud as inventors, filed 28 Nov. 2012, which is currently co-pending or is an application of which a currently co-pending application is entitled to the benefit of the filing date, and which is a continuation of U.S. patent application Ser. No. 13/682,939, entitled FOOD SUPPLY CHAIN AUTOMATION FARM INTERFACE SYSTEM AND METHOD, naming Edward K. Y Jung, Royce A. Levien, and Mark A. Malamud as inventors, filed 21 Nov. 2012.

For purposes of the USPTO extra-statutory requirements, the present application constitutes a continuation-in-part of U.S. patent application Ser. No. 13/669,018, entitled FOOD SUPPLY CHAIN AUTOMATION FARM TESTING SYSTEM AND METHOD, naming Edward K. Y. Jung, Royce A. Levien, and Mark A. Malamud as inventors, filed 5 Nov. 2012, which is currently co-pending or is an application of which a currently co-pending application is entitled to the benefit of the filing date, and which is a continuation of U.S. patent application Ser. No. 13/668,977, entitled FOOD SUPPLY CHAIN AUTOMATION FARM TESTING SYSTEM AND METHOD, naming Edward K. Y Jung, Royce A. Levien, and Mark A. Malamud as inventors, filed 5 Nov. 2012.

For purposes of the USPTO extra-statutory requirements, the present application constitutes a continuation-in-part of U.S. patent application Ser. No. 13/663,137, entitled FOOD SUPPLY CHAIN AUTOMATION FARM TRACKING SYSTEM AND METHOD, naming Edward K. Y. Jung, Royce A. Levien, and Mark A. Malamud as inventors, filed 29 Oct. 2012, which is currently co-pending or is an application of which a currently co-pending application is entitled to the benefit of the filing date, and which is a continuation of U.S. patent application Ser. No. 13/663,095, entitled FOOD SUPPLY CHAIN AUTOMATION FARM TRACKING SYSTEM AND METHOD, naming Edward K. Y. Jung, Royce A. Levien, and Mark A. Malamud as inventors, filed 29 Oct. 2012, that application being a non-provisional application of U.S. provisional patent application Ser. No. 61/698,334, entitled INFORMATION FOOD SECURITY SYSTEM AND METHOD, naming Royce A. Levien, Richard T. Lord, Mark A. Malamud, and John D. Rinaldo, Jr. and inventors, filed 7 Sep. 2012.

RELATED APPLICATIONS

None.

The United States Patent and Trademark Office (USPTO) has published a notice to the effect that the USPTO's computer program require that patent applications both reference a serial number and indicate whether an application is a continuation, continuation-in-part, or divisional of a parent application. Stephen G. Kunin, *Benefit of Prior-Filed Application*, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listing of applications provided above is inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In one aspect, a computationally-implemented method includes, but is not limited to electronically storing grocery operations information regarding at least in part one or more grocery implementation aspects pertaining to grocery related merchandizing of one or more commercial grocery products; and electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances. In addition to the foregoing, other method aspects are described in the claims, drawings, and text forming a part of the disclosure set forth herein.

In one or more various aspects, related machines, compositions of matter, or manufactures of systems may include, but are not limited to, circuitry and/or programming for effecting the herein-referenced method aspects; the circuitry and/or programming can be virtually any combination of hardware, software, and/or firmware configured to effect the herein-referenced method aspects depending upon the design choices of the system designer (limited to patentable subject matter under 35 USC 101).

A computationally-implemented system includes, but is not limited to: means for electronically storing grocery operations information regarding at least in part one or more grocery implementation aspects pertaining to grocery related merchandizing of one or more commercial grocery products; and means for electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances. In addition to the foregoing, other system aspects are described in the claims, drawings, and text forming a part of the disclosure set forth herein.

A computationally-implemented system includes, but is not limited to a electronically storing electrical circuitry arrangement for electronically storing grocery operations information regarding at least in part one or more grocery implementation aspects pertaining to grocery related merchandizing of one or more commercial grocery products; and an electronically associating electrical circuitry arrangement for electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances. In addition to the foregoing, other system aspects are described in the claims, drawings, and text forming a part of the disclosure set forth herein.

A system includes, but is not limited to a electronically storing module configured to operate in accordance with electronically storing grocery operations information regarding at least in part one or more grocery implementation aspects pertaining to grocery related merchandizing of one or more commercial grocery products; and an electronically associating module configured to operate in accordance with electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances. In addition to the foregoing, other system aspects are described in the claims, drawings, and text forming a part of the disclosure set forth herein.

An article of manufacture including one or more non-transitory signal-bearing storage medium bearing one or more instructions for electronically storing grocery operations information regarding at least in part one or more grocery implementation aspects pertaining to grocery related merchandizing of one or more commercial grocery products; and one or more instructions for electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances. In addition to the foregoing, other computer program product aspects are described in the claims, drawings, and text forming a part of the disclosure set forth herein.

A system including one or more computing devices; and one or more instructions when executed on the one or more computing devices cause the one or more computing devices to perform electronically storing grocery operations information regarding at least in part one or more grocery implementation aspects pertaining to grocery related merchandizing of one or more commercial grocery products; and electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances. In addition to the foregoing, other computer program product aspects are described in the claims, drawings, and text forming a part of the disclosure set forth herein.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

For a more complete understanding of embodiments, reference now is made to the following descriptions taken in connection with the accompanying drawings. The use of the same symbols in different drawings typically indicates similar or identical items, unless context dictates otherwise.

With reference now to the figures, shown are one or more examples of is an example of grocery information system that may provide context, for instance, in introducing one or more processes and/or devices described herein

FIG. 13 is a block diagram depicting a control and information processing subsystem s100 of an exemplary implementation of the grocery information system 10 of FIG. 1.

FIG. 14 is a block diagram depicting an information storage subsystem s200 of an exemplary implementation of the grocery information system 10 of FIG. 1.

FIG. 16 is a block diagram depicting a sensing subsystem s400 of an exemplary implementation of the grocery information system 10 of FIG. 1.

FIG. 17 is a block diagram depicting an electronic communication subsystem s500 of an exemplary implementation of the grocery information system 10 of FIG. 1.

FIG. 18 is a block diagram depicting a power subsystem s600 of an exemplary implementation of the grocery information system 10 of FIG. 1.

FIG. 19 is a block diagram depicting a material processing subsystem s700 of an exemplary implementation of the grocery information system 10 of FIG. 1.

FIG. 20 is a block diagram depicting a preparation subsystem s800 of an exemplary implementation of the grocery information system 10 of FIG. 1.

FIG. 22 is a block diagram depicting one or more exemplary electrical circuitry arrangements of the grocery information system 10 of FIG. 1.

FIG. 23 is a block diagram depicting one or more exemplary electrical circuitry arrangements of the grocery information system 10 of FIG. 1.

FIG. 24 is a block diagram depicting one or more exemplary electrical circuitry arrangements of the grocery information system 10 of FIG. 1.

FIG. 26 is a block diagram depicting one or more exemplary electrical circuitry arrangements of the grocery information system 10 of FIG. 1.

FIG. 27 is a block diagram depicting one or more exemplary electrical circuitry arrangements of the grocery information system 10 of FIG. 1.

FIG. 29 is a block diagram depicting one or more exemplary instructions of the information storage subsystem s200 of the grocery information system 10 of FIG. 1.

FIG. 30 is a block diagram depicting one or more exemplary instructions of the information storage subsystem s200 of the grocery information system 10 of FIG. 1.

FIG. 31 is a block diagram depicting one or more exemplary instructions of the information storage subsystem s200 of the grocery information system 10 of FIG. 1.

FIG. 33 is a block diagram depicting one or more exemplary instructions of the information storage subsystem s200 of the grocery information system 10 of FIG. 1.

FIG. 34 is a block diagram depicting one or more exemplary instructions of the information storage subsystem s200 of the grocery information system 10 of FIG. 1.

FIG. 40 is a block diagram depicting one or more exemplary modules of the grocery information system 10 of FIG. 1.

FIG. 72 is a high-level flowchart including exemplary implementations of operation o12 of FIG. 42.

FIG. 74 is a high-level flowchart including exemplary implementations of operation o12 of FIG. 42.

FIG. 75 is a high-level flowchart including exemplary implementations of operation o12 of FIG. 42.

FIG. 81 is a high-level flowchart including exemplary implementations of operation o12 of FIG. 42.

FIG. 82 is a high-level flowchart including exemplary implementations of operation o12 of FIG. 42.

DETAILED DESCRIPTION

Figure 1:
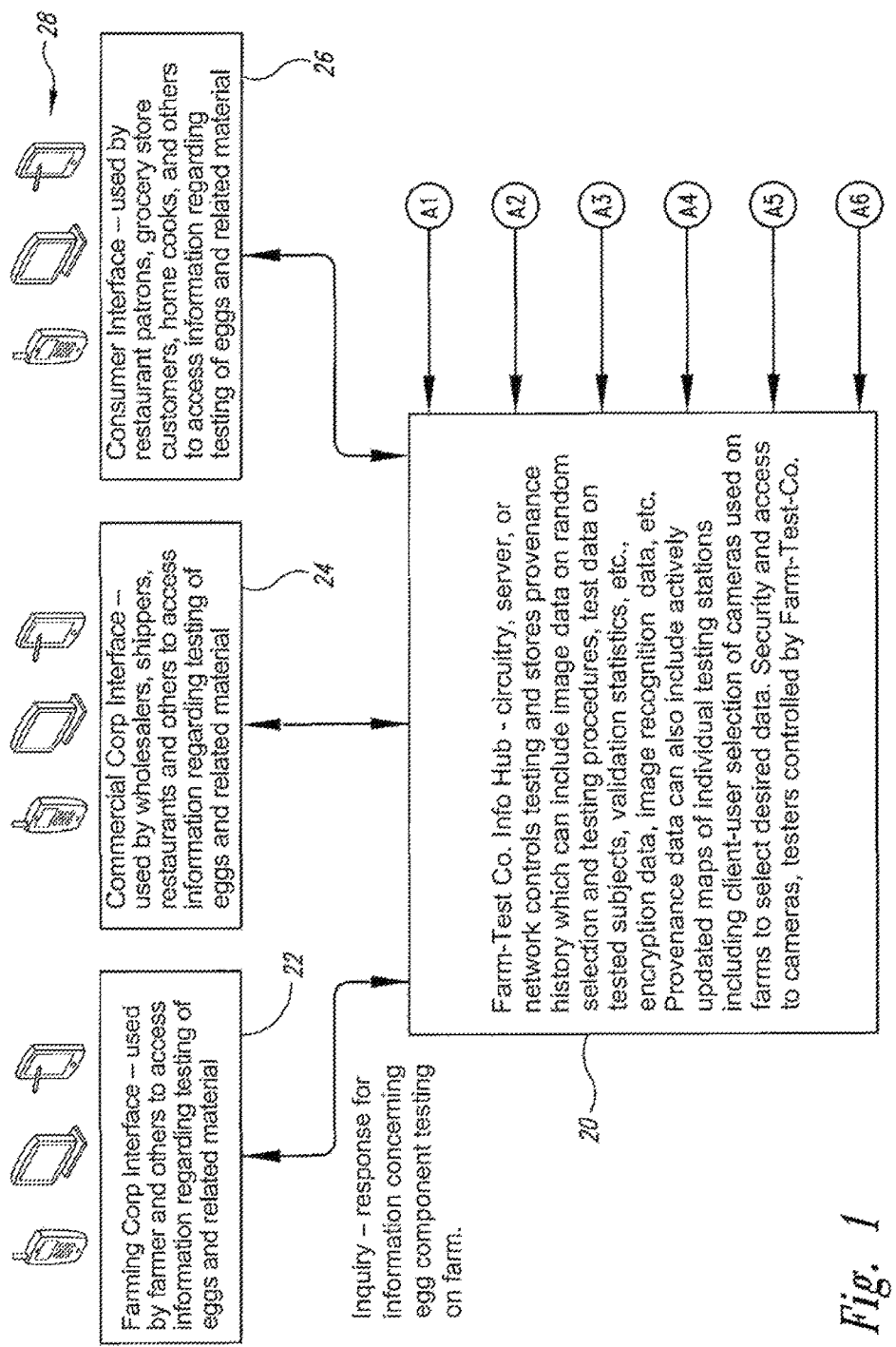
FIG. 1 is a schematic view depicting farm-test co. info hub aspects as related with a grocery information system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application may use formal outline headings for clarity of presentation. However, it is to be understood that the outline headings are for presentation purposes, and that different types of subject matter may be discussed throughout the application (e.g., device(s)/structure(s) may be described under process(es)/operations heading(s) and/or process(es)/operations may be discussed under structure(s)/process(es) headings; and/or descriptions of single topics may span two or more topic headings). Hence, the use of the formal outline headings is not intended to be in any way limiting.

Generally, both commercial and consumer interests are becoming more concerned regarding origins of their food and other ingestible materials. Thus, tracking and testing systems to provide in depth information concerning provenance and other data associated with food and other ingestible materials including farming related production and other handling and processing can also be of interest.

With reference now to the Figures, FIGS. 1-11 depict a schematic diagram of an environment(s) and/or an implementation(s) of technologies described herein. FIGS. 1-11 depict that including physical flows generally including indications as such by use of dashed arrows, the physical flows including that involving handling, testing, worker behavior, animal behavior, and other involvement of items, which can include feed, chicken, egg, carton, containers, transit, grocery store, receiving of containers, unpacking of cartons, shelving of cartons, shopping for cartons, in-store transit of cartons, purchase of carton, transit of carton to home, receiving carton at home, storage of carton at home, removal of egg and preparation of such, etc. Other physical flows are depicted to include transit of container to restaurant, receiving, unpacking, storage, etc. of container at restaurant, unpacking of egg and preparation of in dish, serving and purchasing of dish containing egg, etc. Physical flows are depicted to include testing of grain, chicken, egg, or other items.

FIGS. 1-11 depict that including information flows generally including indications as such by use of solid arrows, the information flows including image data sent from various imaging devices to information hubs, the image data including imaging of various stages of the physical flows. Information flows depicted also include inquiry-responses, initiating of devices, financial data, testing, etc. The information hubs are depicted to include those directed to information flows involving information obtained at farm, transit, restaurant, grocery, home or other locations. The information hubs are depicted to include interchange of information between each other. The information hubs are depicted to communicate with various interfaces to allow for communication therebetween by farming, commercial, restaurant, consumer and other interests. Information in information hubs can allow for research and other activities including determinations of compliance, noncompliance or errors made during one or more physical flows. The examples depicted in FIGS. 1-11 are for illustrative purposes but are not intended to limit aspects to only these examples. Rather they serve to exemplify how data on food provenance and other ingestible material and other sorts of source data can be acquired through various tracking and testing for retrieval and inquiry through such as interfaces shown.

Figure 2:
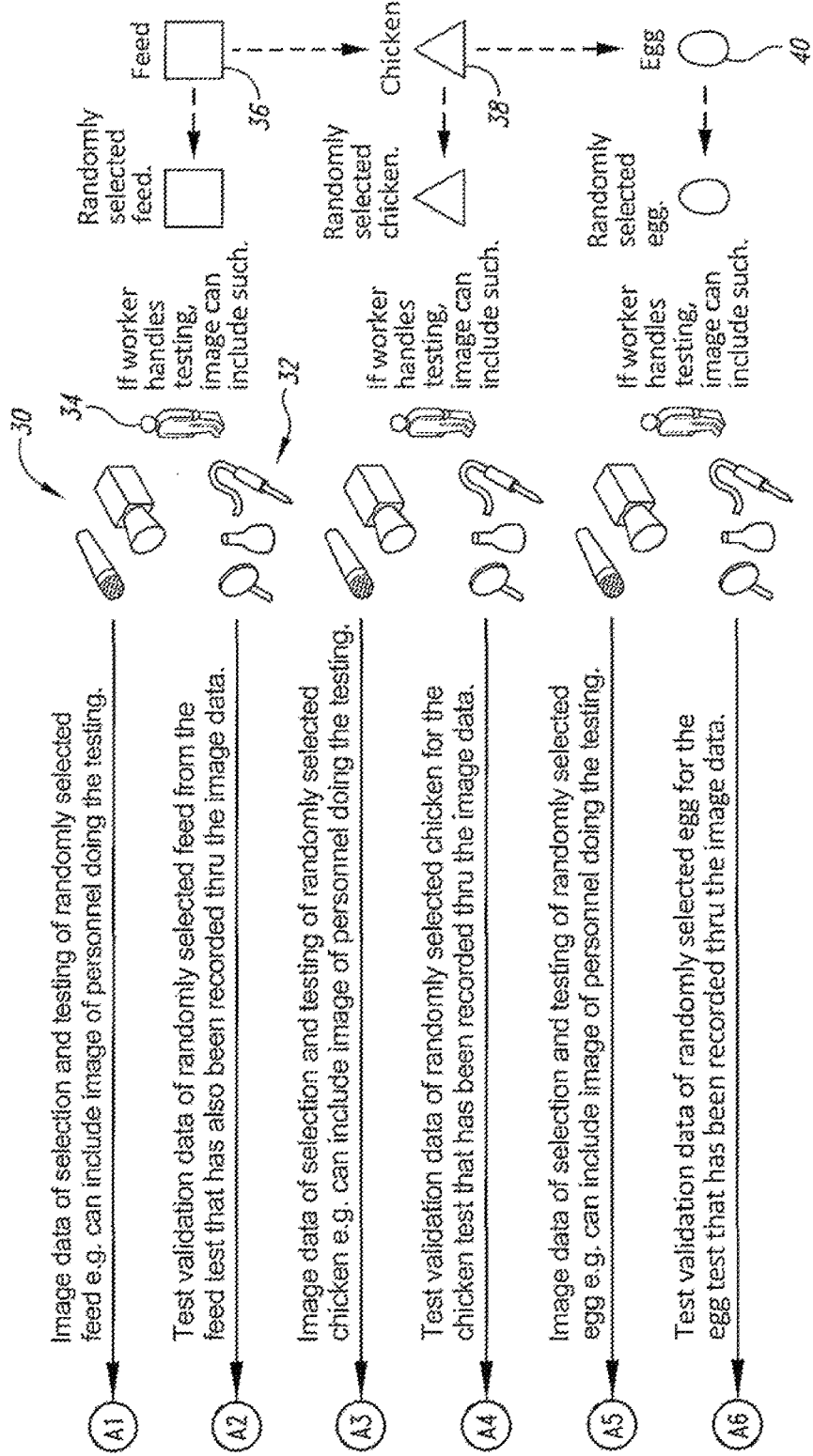
FIG. 2 is a schematic view depicting farm-tracking aspects as related with the grocery information system.

In particular, as shown in FIG. 1, interfaces 22, 24, and 26 are used to interact with Farm-Test Co. Info Hub 20 containing various information related to test of production factors and other items concerning one or more farming related production factors or other items. As shown in FIG. 2, production factors or ingestible material such as feed 36, chicken 38, and egg 40 can be monitored and tested through various sensors 30, 32 further described herein. Behavior of workers 34 can also be monitored.

Figure 3:
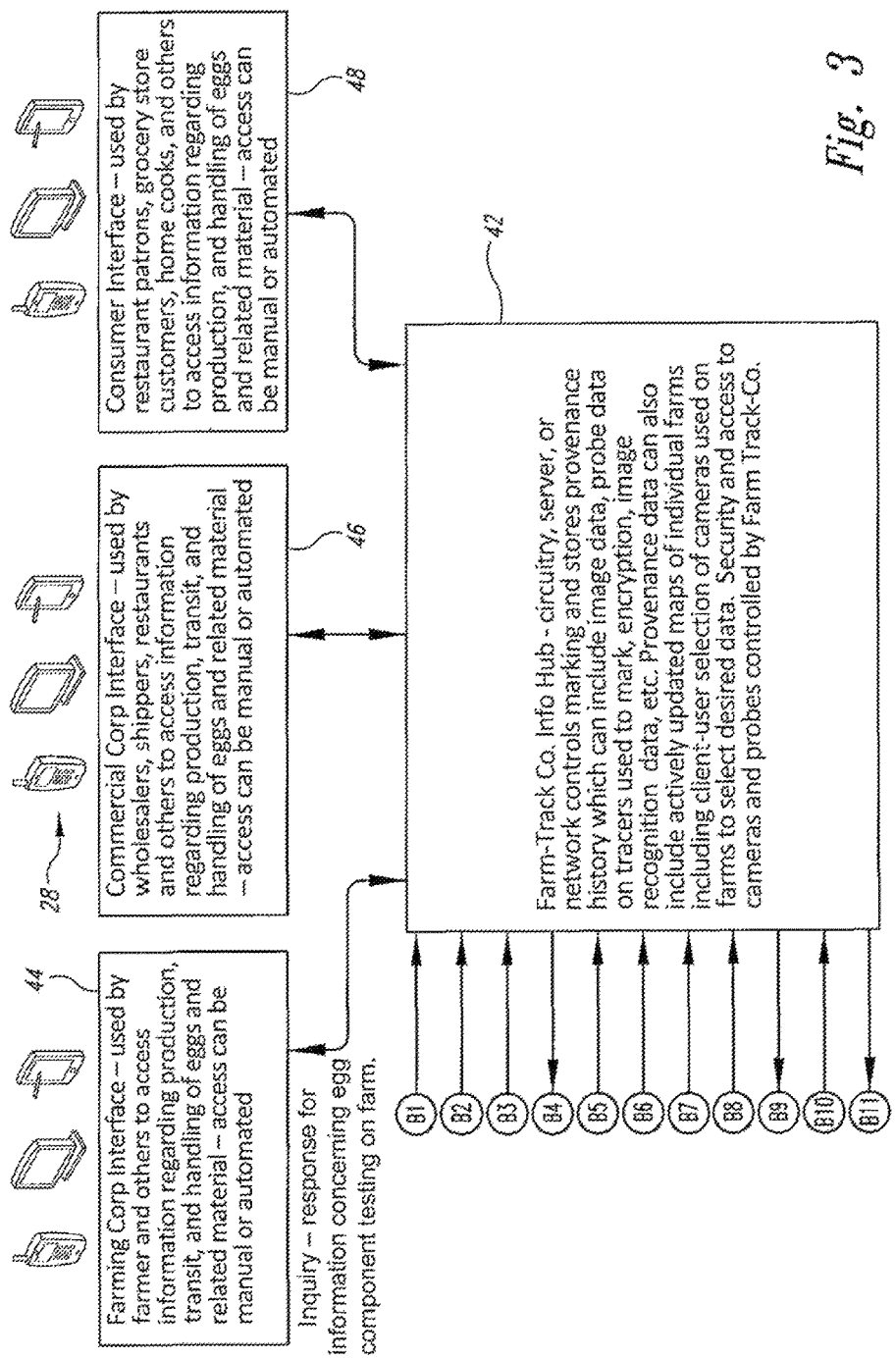
FIG. 3 is a schematic view depicting farm-track co. info hub aspects as related with the grocery information system.
Figure 4:
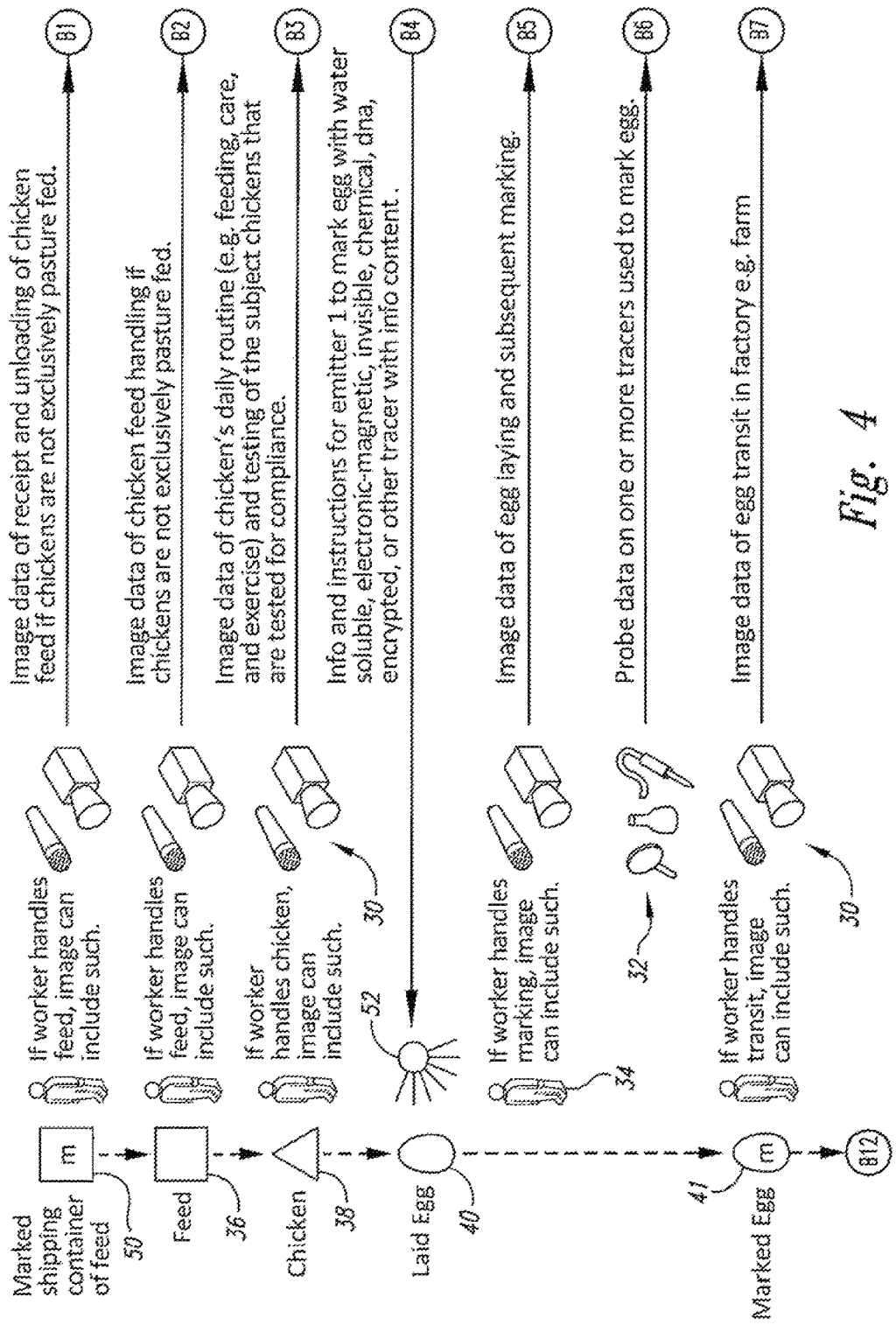
FIG. 4 is a schematic view depicting farm-tracking aspects as related with the grocery information system.
Figure 5:
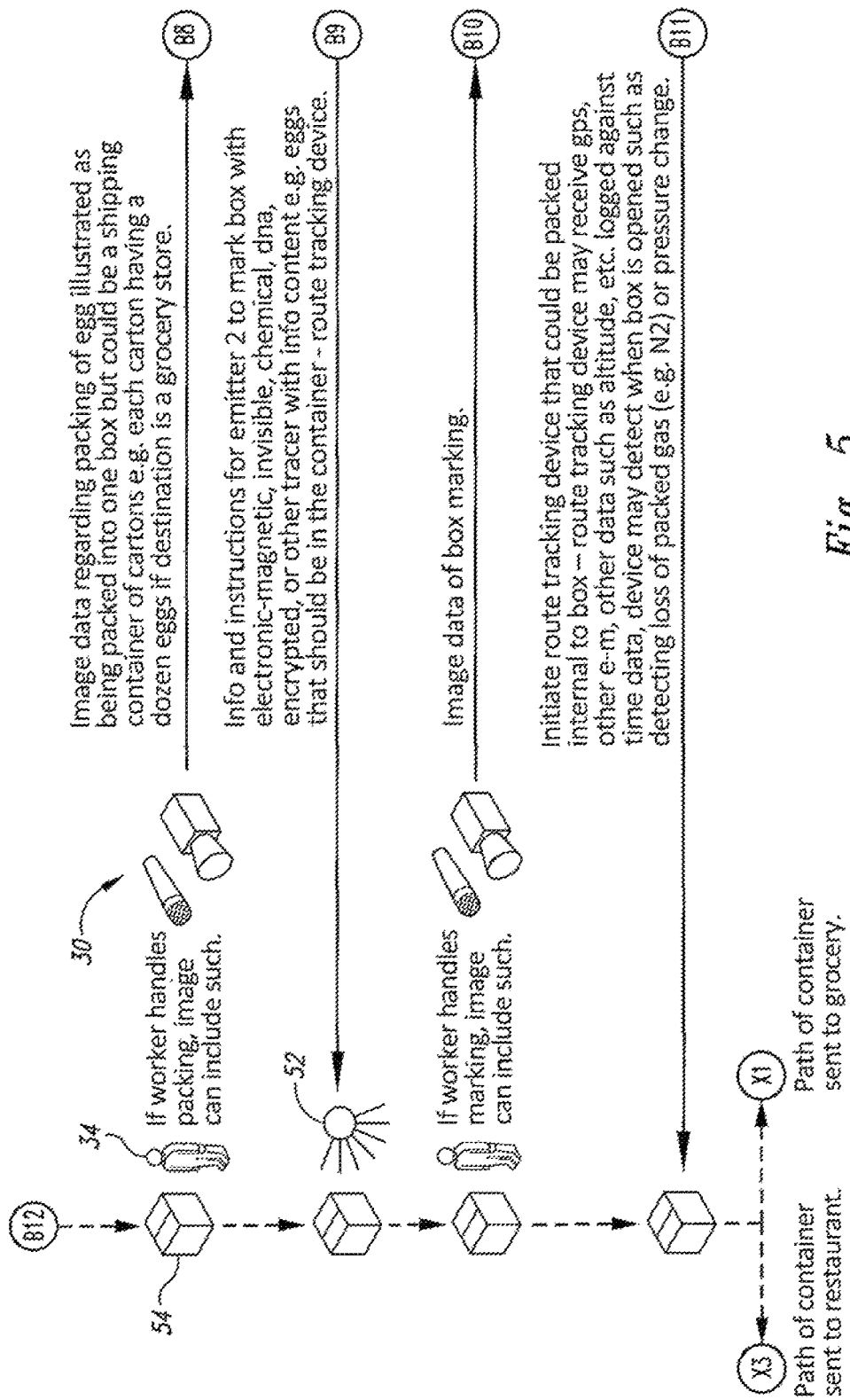
FIG. 5 is a schematic view depicting shipping aspects as related with the grocery information system.

As shown in FIG. 3, interfaces 44, 46, and 48 are used to interact with Farm-Track Co. Info Hub 42 containing various information related to monitoring of production factors and other items concerning one or more farming related production factors or other items. As ingestible material is produced such as egg 40 later becoming marked egg 41 is packed, all such activity involved with such can also be monitored as shown in FIG. 4. The monitoring can be associated with tracers or other labels or marks and also identifiers or other identification information. These associations can be used to access monitoring or testing information through use of tracers and associated identifiers. The tracers can be located at least momentarily in proximity to ingestible material or other production factors to assist in accessing monitoring or testing information. Packing of ingestible material into shipping containers 54 such as shown in FIG. 5 can also be subject to monitoring and labeling of containers through emitters 52.

Figure 6:
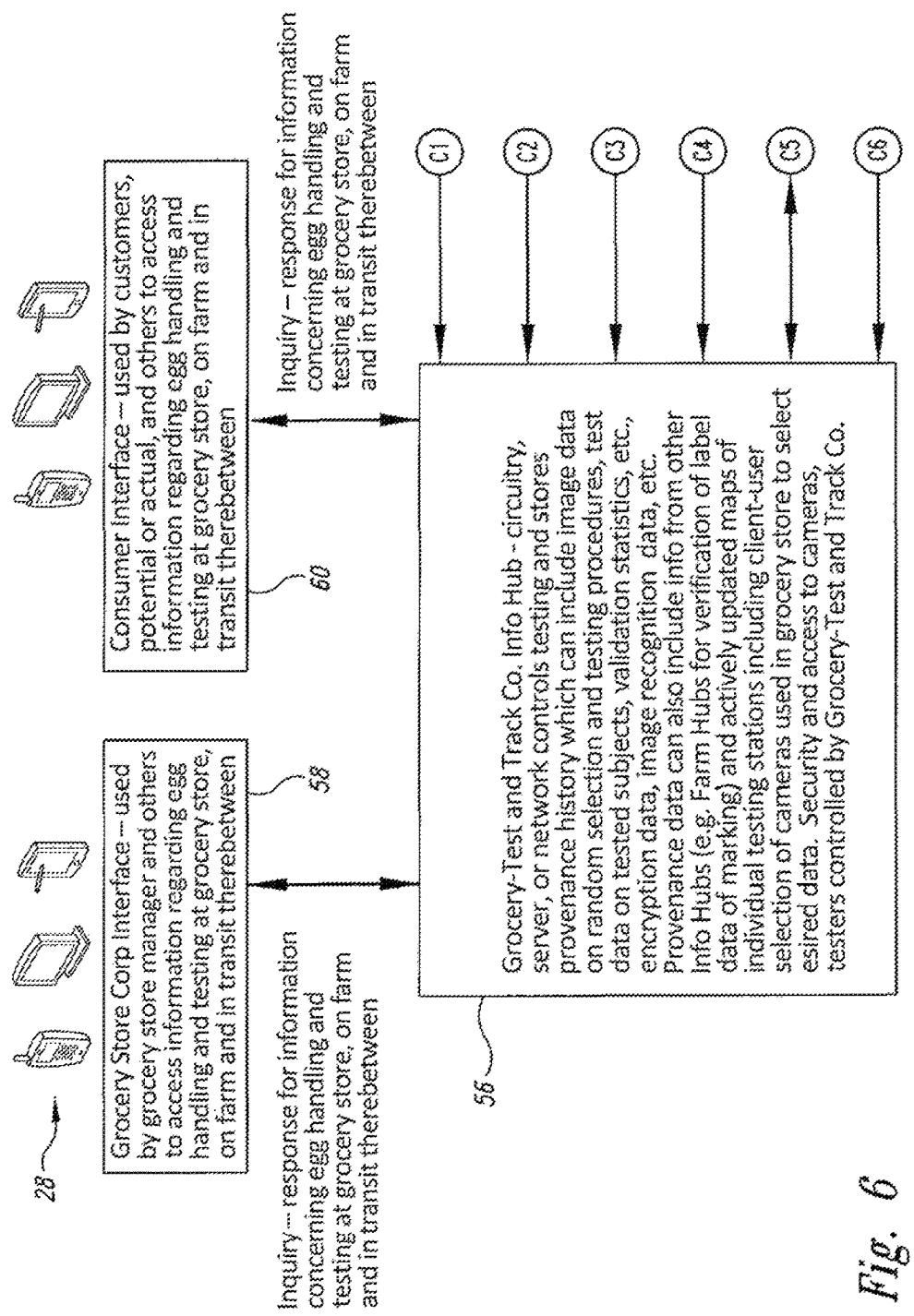
FIG. 6 is a schematic view depicting grocery test and track co. info hub aspects as related with the grocery information system.
Figure 7:
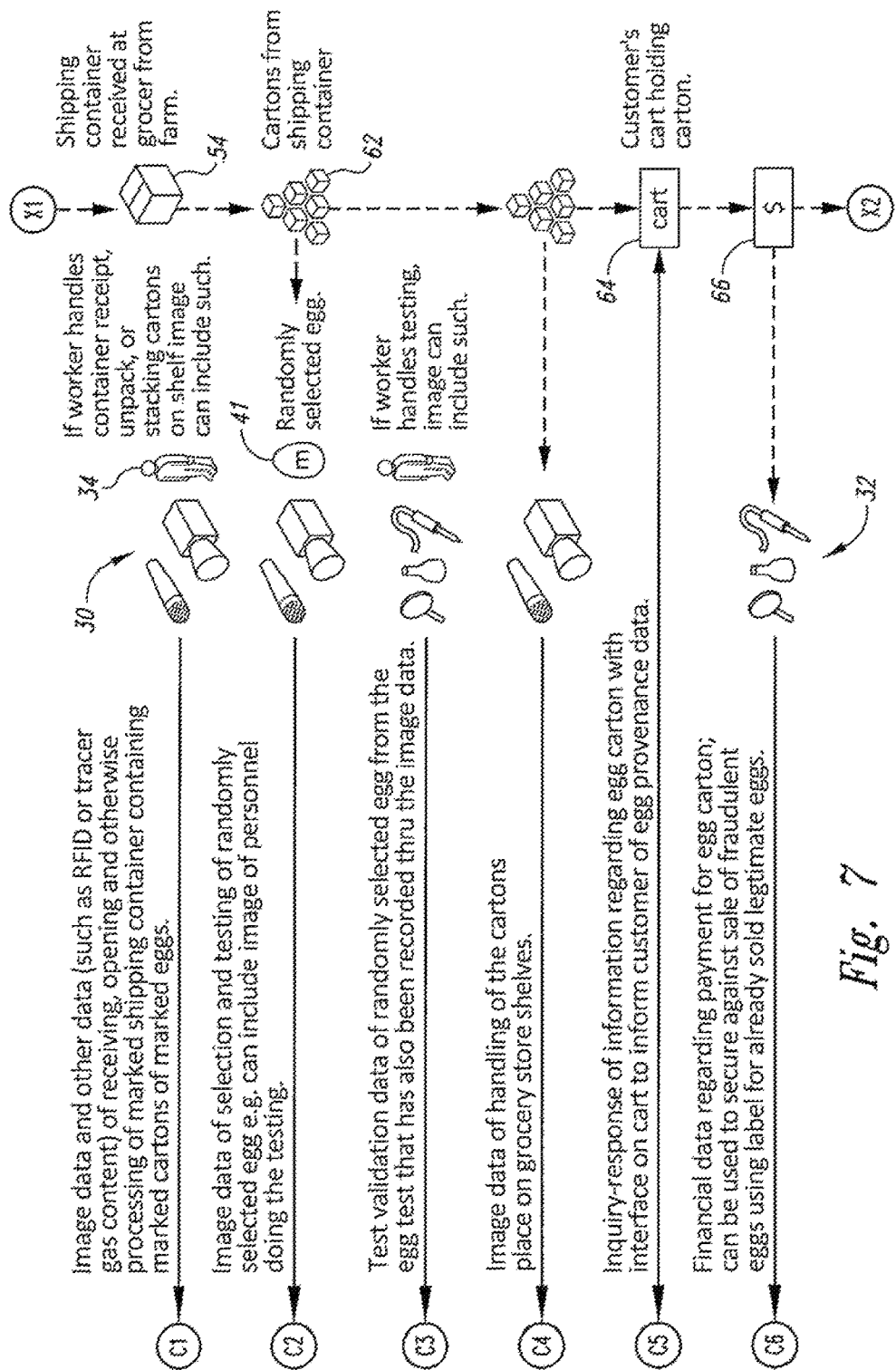
FIG. 7 is a schematic view depicting grocery tracking aspects as related with the grocery information system.

Further monitoring and testing can be performed at commercial locations with information stored on other information hubs such as grocery-test and track co info hub 56 as shown in FIG. 6. Monitoring of grocery activities, such as unpacking cartons 62, use of customer shopping carts 64, and purchase activity 66 shown in FIG. 7, can also be performed.

Figure 8:
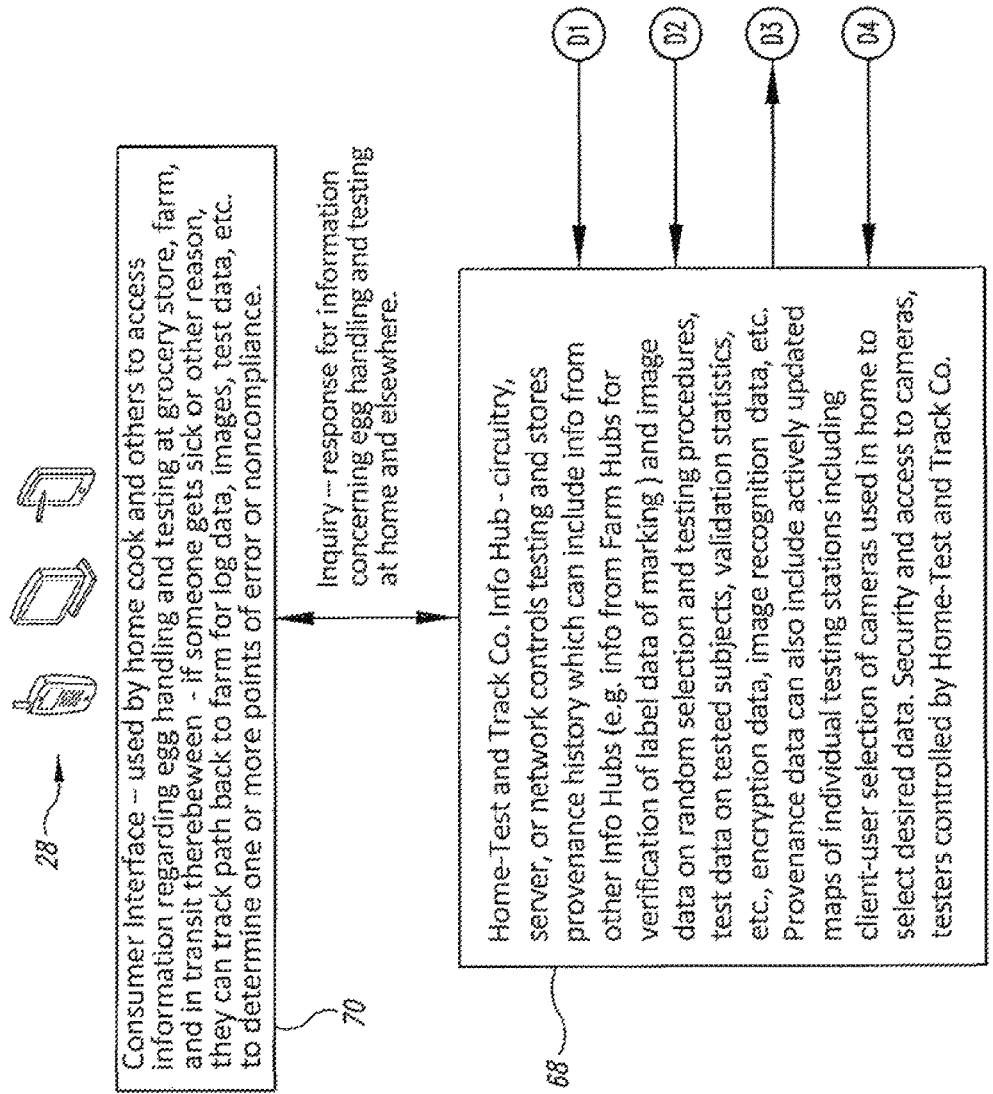
FIG. 8 is a schematic view depicting home-test and track co. info hub aspects as related with the grocery information system.
Figure 9:
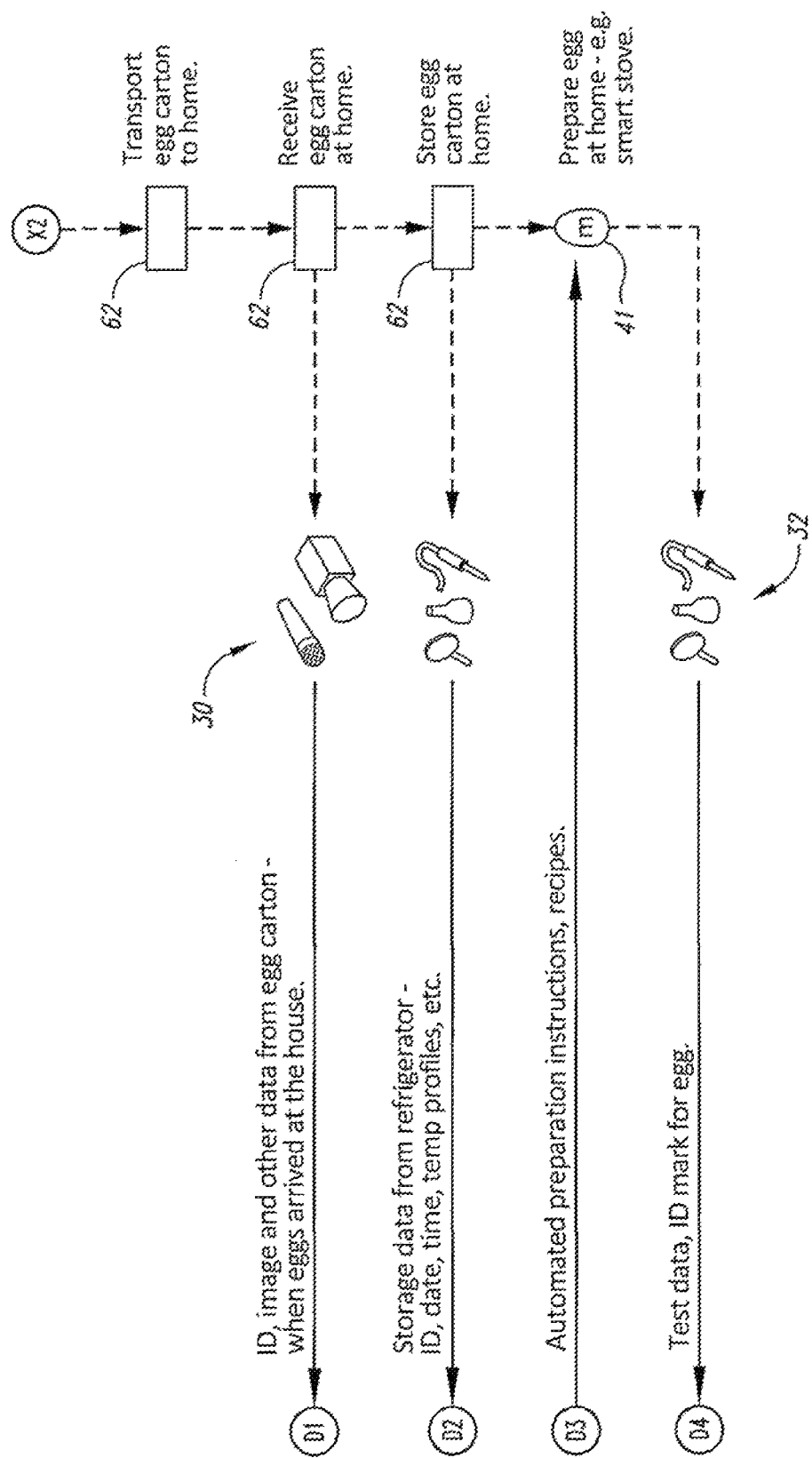
FIG. 9 is a schematic view depicting home tracking aspects as related with the grocery information system.

Monitoring, testing and accessing of data can be accomplished at home as well as depicted in FIG. 8 through use of a home-test track co. info hub 68 and consumer interfaces 28. Further illustrative home activities that can be monitored are shown in FIG. 9 to include transporting, receiving, storing and preparing ingestible material.

Figure 10:
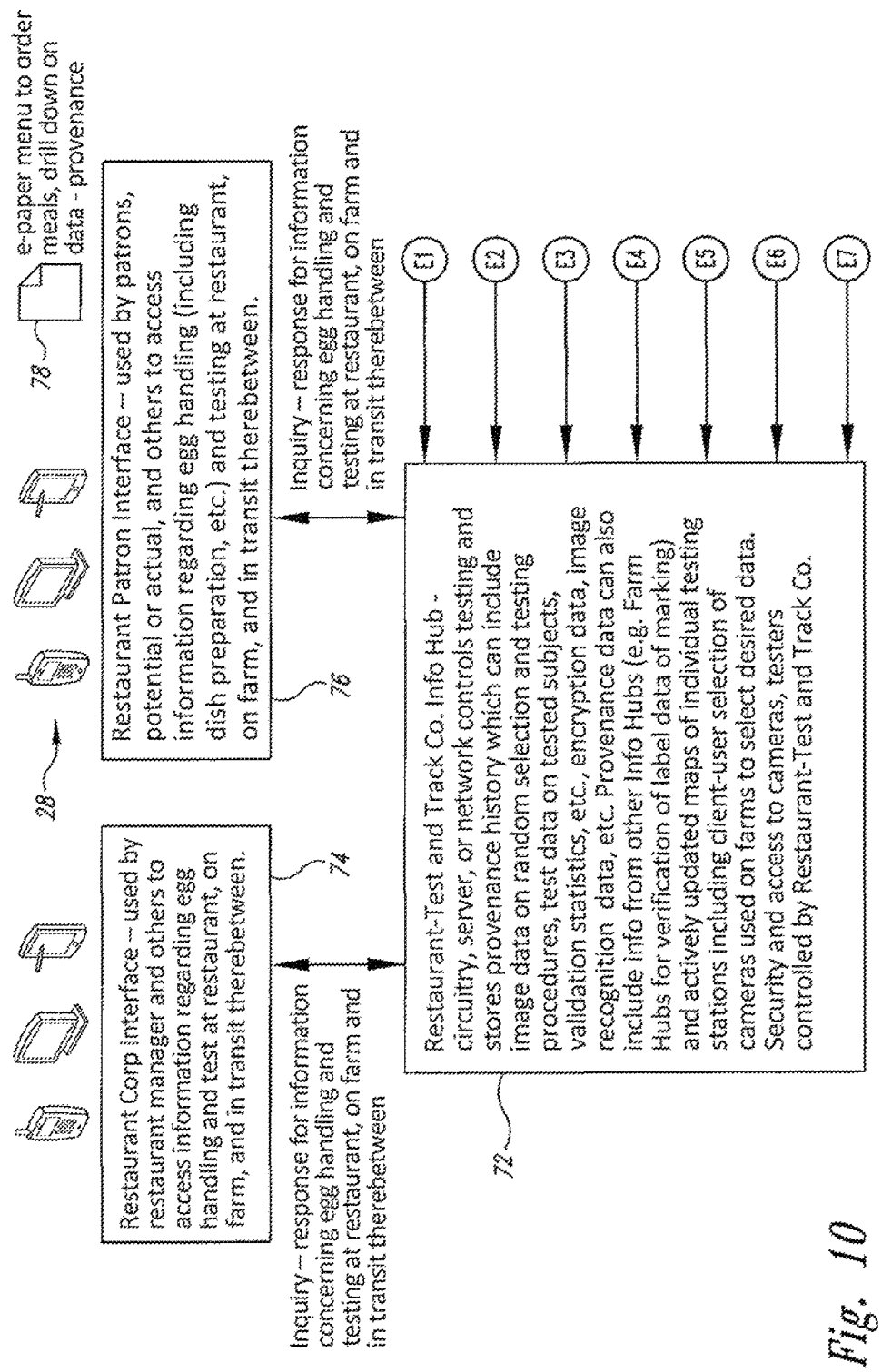
FIG. 10 is a schematic view depicting restaurant-test and track co. info hub aspects as related with the grocery information system.

Other commercial venues for monitoring and testing can include restaurants as illustrated in FIG. 10 to include restaurant-test and track co. info hub 72 that can be used for storage and access of provenance data and also monitoring data of activities conducted at a restaurant. This data can be access by both restaurant personnel and restaurant patrons such as through interfaces 74, 76, and 78 to include menuing systems for the patrons.

Figure 11:
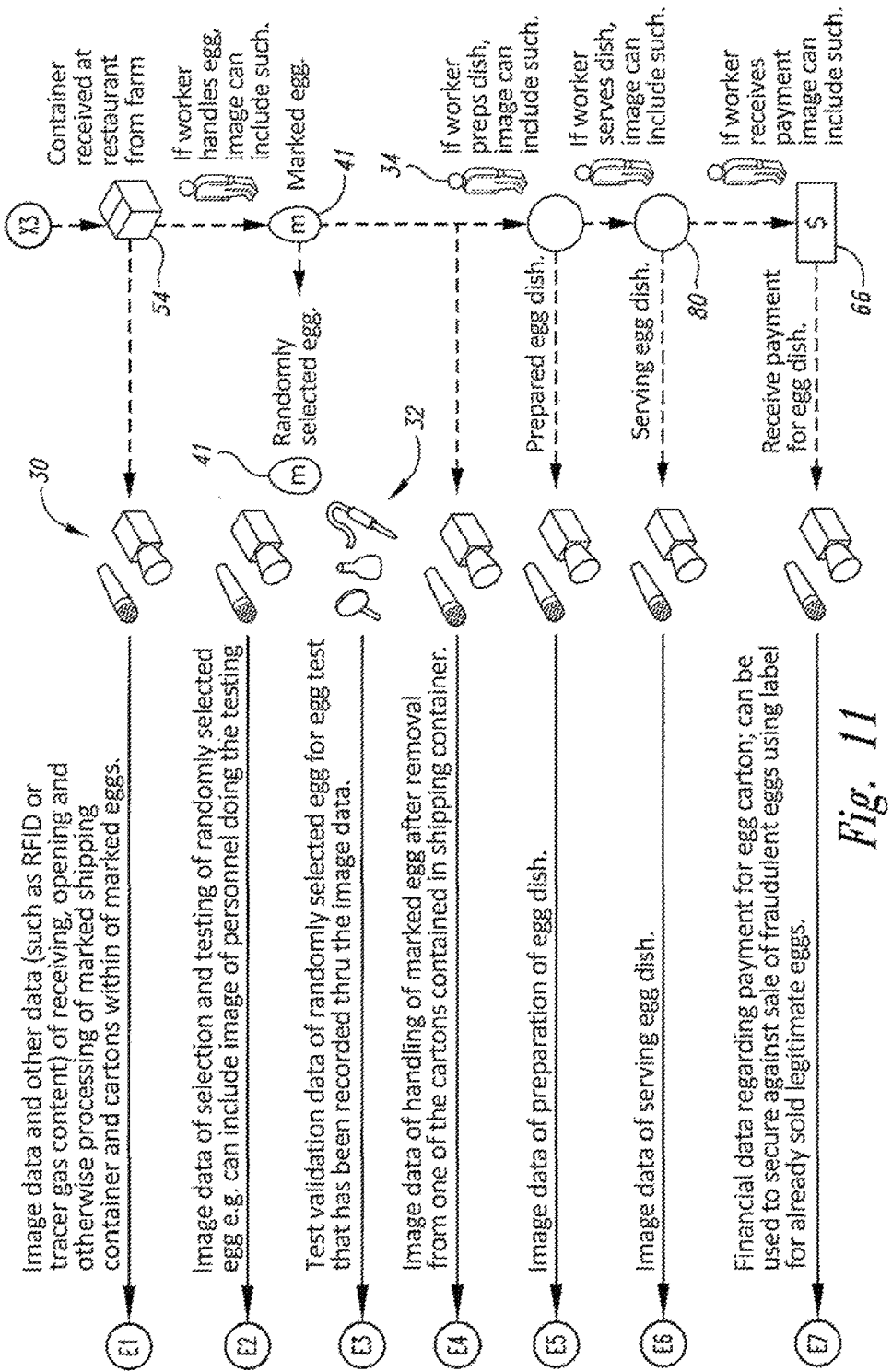
FIG. 11 is a schematic view depicting restaurant tracking aspects as related with the grocery information system.

Activities conducted in a restaurant including those depicted in FIG. 11 such as receiving, handling, preparing, serving 80, and transacting payment can be included in monitoring and testing aspects to be stored on the restaurant-test and track co info hub 72 or elsewhere.

Various aspects embodied and illustrated through FIGS. 1-11 can be enumerated below and are provided to provide examples but are not intended to be limiting.

Food Supply Chain Automation

Figure 12:
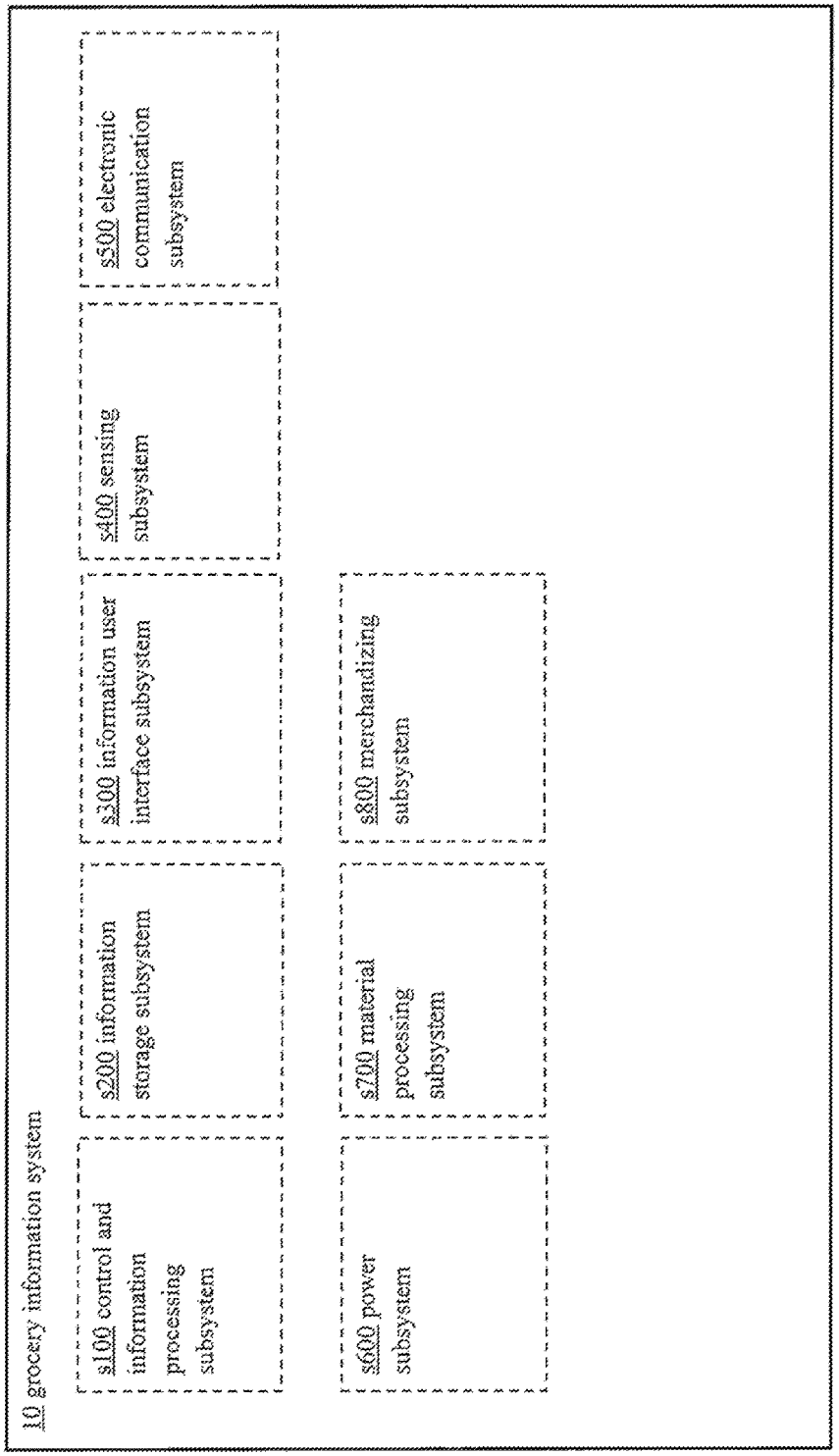
FIG. 12 is a block diagram depicting an exemplary implementation of the grocery information system 10 of FIG. 1 including exemplary subsystems.

1. Feed (e.g. grain) Farm Track Information Hub
   a. receive fertilizer track and test hub information
   b. receive fertilizer container tracer information or fertilizer tracer information
   c. verify fertilizer container tracer information or fertilizer tracer information with fertilizer track hub information
   d. receive internal fertilizer container tracker information
   e. verify internal fertilizer container tracker information with fertilizer track hub information
   f. receive local fertilizer container handling audio-video and sensor information
   g. scan local fertilizer container handling audio-video and sensor information for error or noncompliance
   h. receive accounting information of production factor use for local fertilizer container handling
   i. correlate local fertilizer container handling audio-video and sensor information with accounting information of production factor use for local fertilizer container handling
   j. associate local fertilizer container handling audio-video and sensor information with fertilizer tracer information
   k. receive local fertilizer handling audio-video and sensor information
   l. scan local fertilizer handling audio-video and sensor information for error or noncompliance
   m. receive accounting information of production factor use for local fertilizer handling
   n. correlate local fertilizer behavior and handling audio-video and sensor information with accounting information of production factor use for local fertilizer handling
   o. associate local fertilizer handling audio-video and sensor information with animal tracer information
   p. receive local feed (grain) handling audio-video and sensor information
   q. associate local feed handling audio-video and sensor information with feed container tracer information or feed tracer information
   r. receive local grain field handling audio-video and sensor information
   s. scan local grain field handling audio-video and sensor information for error or noncompliance
   t. receive accounting information of production factor use for local grain field handling
   u. correlate local grain field handling audio-video and sensor information with accounting information of production factor use for local fertilizer handling
   v. associate local grain field handling audio-video and sensor information with animal tracer information 2. Animal (e.g. chicken) Farm Track and Test Information Hub
   a. receive feed track hub information
   b. receive feed container tracer information or feed tracer information
   c. verify feed container tracer information or feed tracer information with feed track hub information
   d. receive internal feed container tracker information
   e. verify internal feed container tracker information with feed track hub information
   f. receive local feed handling audio-video and sensor information
   g. associate local feed handling audio-video and sensor information with chicken tracer information
   h. scan local feed handling audio-video and sensor information for error or noncompliance
   i. receive accounting information of production factor use for local feed handling
   j. correlate local feed handling audio-video and sensor information with accounting information of production factor use for local feed handling
   k. send alert to initiate feed sample test event
   l. receive feed test sample tracer information
   m. verify feed test sample tracer information with egg track hub information
   n. receive feed test sample handling audio-video and sensor information
   o. associate feed test sample handling audio-video and sensor information with chicken tracer information
   p. scan feed test sample handling audio-video and sensor information for error or noncompliance
   q. receive accounting information of production factor use for feed test sample handling
   r. correlate feed test sample handling audio-video and sensor information with accounting information of production factor use for feed test sample handling
   s. receive test results for feed test sample
   t. associate test results for feed test sample with feed test sample tracer information
   u. update feed (grain) farm track information hub re butchered chicken portion test sample testing
   v. receive local chicken behavior and handling audio-video and sensor information
   w. associate local chicken behavior and handling audio-video and sensor information with chicken tracer information x. scan local chicken behavior and handling audio-video and sensor information for error or noncompliance y. receive accounting information of production factor use for local chicken behavior and handling z. correlate local chicken behavior and handling audio-video and sensor information with accounting information of production factor use for local chicken behavior and handling aa. send alert to initiate chicken sample test event bb. receive chicken test sample tracer information cc. verify chicken test sample tracer information with egg track hub information dd. receive chicken test sample handling audio-video and sensor information ee. associate chicken test sample handing audio-video and sensor information with chicken tracer information ff. scan chicken test sample handling audio-video and sensor information for error or noncompliance gg. receive accounting information of production factor use for chicken test sample handling hh. correlate chicken test sample handling audio-video and sensor information with accounting information of production factor use for chicken test sample handling ii. receive test results for chicken test sample jj. associate test results for chicken test sample with chicken test sample tracer information kk. update feed (grain) farm track information hub re chicken test sample testing ll. scan chicken behavior and handling audio-video and sensor information to determine egg was laid mm. instruct emitter to mark laid egg with egg tracer(s) upon determining egg was laid nn. receive local egg marking audio-video and sensor information oo. scan local egg marking audio-video and sensor information for error or noncompliance pp. receive accounting information of production factor use for local egg marking qq. correlate local egg marking audio-video and sensor information with accounting information of production factor use for local egg marking rr. associate audio-video and sensor information of egg marking with egg tracer information ss. associate egg tracer information with tracer information of chicken that laid egg tt. receive local egg handling audio-video and sensor information uu. scan local egg handling audio-video and sensor information for error or noncompliance vv. receive accounting information of production factor use for local egg handling ww. correlate local egg handling audio-video and sensor information with accounting information of production factor use for local egg handling xx. associate local egg handling audio-video and sensor information with egg tracer information yy. send alert to initiate egg sample test event zz. receive egg test sample tracer information aaa. verify egg test sample tracer information with egg track hub information bbb. receive egg test sample handling audio-video and sensor information ccc. associate egg test sample handing audio-video and sensor information with chicken tracer information ddd. scan egg test sample handling audio-video and sensor information for error or noncompliance eee. receive accounting information of production factor use for egg test sample handling fff. correlate egg test sample handling audio-video and sensor information with accounting information of production factor use for egg test sample handling ggg. receive test results for egg test sample hhh. associate test results for egg test sample with egg test sample tracer information iii. update feed (grain) farm track information hub re egg test sample testing jjj. receive local egg hatching into hatched chicken audio-video and sensor information kkk. scan local egg hatching into hatched audio-video and sensor information for error or noncompliance lll. receive accounting information of production factor use for local egg hatching into hatched chicken mmm. correlate local egg hatching audio-video and sensor information with accounting information of production factor use for local egg hatching into hatched chicken nnn. associate local egg hatching into hatched chicken audio-video and sensor information with egg tracer information ooo. send alert to initiate hatched chicken sample test event ppp. receive hatched chicken test sample tracer information qqq. verify hatched chicken test sample tracer information with egg track hub information rrr. receive hatched chicken test sample handling audio-video and sensor information sss. associate hatched chicken test sample handing audio-video and sensor information with chicken tracer information ttt. scan hatched chicken test sample handling audio-video and sensor information for error or noncompliance uuu. receive accounting information of production factor use for hatched chicken test sample handling vvv. correlate hatched chicken test sample handling audio-video and sensor information with accounting information of production factor use for hatched chicken test sample handling www. receive test results for hatched chicken test sample xxx. associate test results for hatched chicken test sample with hatched chicken test sample tracer information yyy. update feed (grain) farm track information hub re hatched chicken test sample testing zzz. instruct emitter to mark local hatched chicken with hatched chicken tracer(s)

aaaa. receive local hatched chicken marking audio-video and sensor information bbbb. scan local hatched chicken marking audio-video and sensor information for error or noncompliance cccc. receive accounting information of production factor use for local hatched chicken marking dddd. correlate local hatched chicken marking audio-video and sensor information with accounting information of production factor use for local hatched chicken marking eeee. associate local hatched chicken audio-video and sensor information with local hatched chicken tracer information ffff. receive local hatched chicken behavior audio-video and sensor information gggg. scan local hatched chicken behavior audio-video and sensor information for error or noncompliance hhhh. receive accounting information of production factor use for local hatched chicken behavior iiii. correlate local hatched chicken behavior audio-video and sensor information with accounting information of production factor use for local hatched chicken behavior jjjj. associate local hatched chicken behavior audio-video and sensor information with local hatched chicken tracer information kkkk. send alert to initiate hatched chicken sample test event llll. receive hatched chicken test sample tracer information mmmm. verify hatched chicken test sample tracer information with egg track hub information nnnn. receive hatched chicken test sample handling audio-video and sensor information oooo. associate hatched chicken test sample handing audio-video and sensor information with chicken tracer information pppp. scan hatched chicken test sample handling audio-video and sensor information for error or noncompliance qqqq. receive accounting information of production factor use for hatched chicken test sample handling rrrr. correlate hatched chicken test sample handling audio-video and sensor information with accounting information of production factor use for hatched chicken test sample handling ssss. receive test results for hatched chicken test sample tttt. associate test results for hatched chicken test sample with hatched chicken test sample tracer information uuuu. update feed (grain) farm track information hub re hatched chicken test sample testing vvvv. scan handling and behavior of local hatched chicken to determine when slaughter of local hatched chicken occurs wwww. scan handling of slaughter of local hatched chicken for error or noncompliance xxxx. receive accounting information of production factor use for slaughter of local hatched chicken yyyy. correlate slaughter of local hatched chicken behavior audio-video and sensor information with accounting information of production factor use for slaughter of local hatched chicken zzzz. associate slaughter of local hatched chicken audio-video and sensor information with local hatched chicken tracer information aaaaa. scan handling and behavior of local hatched chicken to determine when butcher of local hatched chicken occurs bbbbb. scan handling of butcher of local hatched chicken for error or noncompliance ccccc. receive accounting information of production factor use for butcher of local hatched chicken ddddd. correlate butcher of local hatched chicken audio-video and sensor information with accounting information of production factor use for butcher of local hatched chicken eeeee. associate butcher of local hatched chicken audio-video and sensor information with local hatched chicken tracer fffff. instruct emitter to mark each portion of butchered chicken with chicken portion tracer(s)

ggggg. receive butchered chicken portion marking audio-video and sensor information hhhhh. scan butchered chicken portion marking audio-video and sensor information for error or noncompliance iiiii. receive accounting information of production factor use for butchered chicken portion marking jjjjj. correlate butchered chicken portion marking audio-video and sensor information with accounting information of production factor use for butchered chicken portion marking kkkkk. associate butchered chicken portion marking audio-video and sensor information with butchered chicken portion tracer information lllll. send alert to initiate butchered chicken portion sample test event mmmmm. receive butchered chicken portion test sample tracer information nnnnn. verify butchered chicken portion test sample tracer information with egg track hub information ooooo. receive butchered chicken portion test sample handling audio-video and sensor information ppppp. associate butchered chicken portion test sample handing audio-video and sensor information with chicken tracer information qqqqq. scan butchered chicken portion test sample handling audio-video and sensor information for error or noncompliance rrrrr. receive accounting information of production factor use for butchered chicken portion test sample handling sssss. correlate butchered chicken portion test sample handling audio-video and sensor information with accounting information of production factor use for butchered chicken portion test sample handling ttttt. receive test results for butchered chicken portion test sample uuuuu. associate test results for butchered chicken portion test sample with butchered chicken portion test sample tracer information vvvvv. update feed (grain) farm track information hub re butchered chicken portion test sample testing wwwww. receive local packing butchered chicken portion into butchered chicken portion carton audio-video and sensor information xxxxx. scan local packing butchered chicken portion into butchered chicken portion carton handling audio-video and sensor information for error or noncompliance yyyyy. receive accounting information of production factor use for local packing butchered chicken portion into butchered chicken portion carton zzzzz. correlate local packing butchered chicken portion into butchered chicken portion carton handling audio-video and sensor information with accounting information of production factor use for local packing butchered chicken portion into butchered chicken portion carton aaaaaa. associate local packing butchered chicken portion into butchered chicken portion carton audio-video and sensor information with butchered chicken portion tracer information bbbbbb. instruct emitter to mark butchered chicken portion carton with butchered chicken portion carton tracer(s)

cccccc. receive local butchered chicken portion carton marking audio-video and sensor information dddddd. scan local butchered chicken portion carton marking audio-video and sensor information for error or noncompliance eeeeee. receive accounting information of production factor use for local butchered chicken portion carton marking ffffff. correlate local butchered chicken portion carton marking audio-video and sensor information with accounting information of production factor use for local butchered chicken portion carton marking ggggggg. associate butchered chicken portion carton marking audio-video and sensor information with butchered chicken portion carton tracer information hhhhhh. receive local packing butchered chicken portion carton into carton container audio-video and sensor information iiiiii. scan local packing butchered chicken portion carton into carton container audio-video and sensor information for error or noncompliance jjjjjj. receive accounting information of production factor use for local packing butchered chicken portion carton into carton container kkkkkk. correlate local packing butchered chicken portion carton into carton container audio-video and sensor information with accounting information of production factor use for local packing butchered chicken portion carton into carton container llllll. associate local packing butchered chicken portion carton into carton container audio-video and sensor information with carton container tracer information mmmmmm. instruct emitter to mark carton container with carton container tracer(s)

nnnnnn. receive local carton container marking audio-video and sensor information oooooo. scan local carton container marking audio-video and sensor information for error or noncompliance pppppp. receive accounting information of production factor use for local carton container marking qqqqqq. correlate local carton container marking audio-video and sensor information with accounting information of production factor use for local carton container marking rrrrrr. associate local carton container marking audio-video and sensor information with carton container tracer information 3. Egg Farm Track Information Hub a. receive feed track hub information b. receive feed container tracer information or feed tracer information c. verify feed container tracer information or feed tracer information with feed track hub information d. receive internal feed container tracker information e. verify internal feed container tracker information with feed track hub information f. receive local feed handling audio-video and sensor information g. associate local feed handling audio-video and sensor information with chicken tracer information h. scan local feed handling audio-video and sensor information for error or noncompliance i. receive accounting information of production factor use for local feed handling j. correlate local feed handling audio-video and sensor information with accounting information of production factor use for local feed handling k. receive chicken track hub information l. receive chicken container tracer information or chicken tracer information m. verify chicken container tracer information or chicken tracer information with chicken track hub information n. receive internal chicken container tracker information o. verify internal chicken container tracker information with chicken track hub information p. receive local chicken behavior and handling audio-video and sensor information q. associate local chicken behavior and handling audio-video and sensor information with chicken tracer information r. scan local chicken behavior and handling audio-video and sensor information for error or noncompliance s. receive accounting information of production factor use for local chicken behavior and handling t. correlate local chicken behavior and handling audio-video and sensor information with accounting information of production factor use for local chicken behavior and handling u. scan chicken behavior and handling audio-video and sensor information to determine egg was laid v. instruct emitter to mark laid egg with egg tracer(s) upon determining egg was laid w. receive local egg marking audio-video and sensor information x. scan local egg marking audio-video and sensor information for error or noncompliance y. receive accounting information of production factor use for local egg marking z. correlate local egg marking audio-video and sensor information with accounting information of production factor use for local egg marking aa. associate audio-video and sensor information of egg marking with egg tracer information bb. associate egg tracer information with tracer information of chicken that laid egg cc. receive local egg handling (includes marking) audio-video and sensor information dd. scan local egg handling audio-video and sensor information for error or noncompliance ee. receive accounting information of production factor use for local egg handling ff. correlate local egg handling audio-video and sensor information with accounting information of production factor use for local egg handling gg. associate local egg handling audio-video and sensor information with egg tracer information hh. receive local packing egg into egg carton audio-video and sensor information ii. scan local packing egg into egg carton handling audio-video and sensor information for error or noncompliance jj. receive accounting information of production factor use for local packing egg into egg carton kk. correlate local packing egg into egg carton handling audio-video and sensor information with accounting information of production factor use for local packing egg into egg carton ll. associate local packing egg into egg carton audio-video and sensor information with egg tracer information mm. instruct emitter to mark egg carton with egg carton tracer(s)

nn. receive local egg carton marking audio-video and sensor information oo. scan local egg carton marking audio-video and sensor information for error or noncompliance pp. receive accounting information of production factor use for local egg carton marking qq. correlate local egg carton marking audio-video and sensor information with accounting information of production factor use for local egg carton marking rr. associate egg carton marking audio-video and sensor information with egg carton tracer information ss. receive local egg carton handling audio-video and sensor handling information tt. scan local egg carton handling audio-video and sensor information for error or noncompliance uu. receive accounting information of production factor use for local egg carton handling vv. correlate local egg carton handling audio-video and sensor information with accounting information of production factor use for local egg carton handling ww. associate local egg carton handling audio-video and sensor information with egg carton tracer information xx. associate carton tracer information with egg tracer information yy. receive local packing egg carton into carton container audio-video and sensor information zz. scan local packing egg carton into carton container audio-video and sensor information for error or noncompliance aaa. receive accounting information of production factor use for local packing egg carton into carton container bbb. correlate local packing egg carton into carton container audio-video and sensor information with accounting information of production factor use for local packing egg carton into carton container ccc. associate local packing egg carton into carton container audio-video and sensor information with carton container tracer information ddd. instruct emitter to mark carton container with carton container tracer(s)

eee. receive local carton container marking audio-video and sensor information fff. scan local carton container marking audio-video and sensor information for error or noncompliance ggg. receive accounting information of production factor use for local carton container marking hhh. correlate local carton container marking audio-video and sensor information with accounting information of production factor use for local carton container marking iii. associate local carton container marking audio-video and sensor information with carton container tracer information jjj. receive local carton container handling audio-video and sensor information kkk. scan local carton container handling audio-video and sensor information for error or noncompliance lll. receive accounting information of production factor use for local carton container handling mmm. correlate local carton container handling audio-video and sensor information with accounting information of production factor use for local carton container handling nnn. associate carton container handling audio-video and sensor information with carton container tracer information ooo. associate carton container tracer information with egg carton tracer information ppp. initiate tracker placed internally in carton container during packing thereof qqq. receive egg test hub information 4. Egg Farm Test Information Hub a. receive egg track hub information b. send alert to initiate local feed sample test event c. receive local feed test sample tracer information d. verify local feed test sample tracer information with egg track hub information e. receive local feed test sample handling audio-video and sensor information f. associate local feed test sample handing audio-video and sensor information with local feed test sample tracer information g. scan local feed test sample handling audio-video and sensor information for error or noncompliance h. receive accounting information of production factor use for local feed test sample handling i. correlate local feed test sample handling audio-video and sensor information with accounting information of production factor use for local feed test sample handling j. receive test results for local feed test sample k. associate test results for local feed test sample with local feed test sample tracer information l. update egg farm track information hub re local feed test sample testing m. update chicken farm track information hub re local feed test sample testing n. update feed (grain) farm track information hub re local feed test sample testing o. send alert to initiate local chicken sample test event p. receive local chicken test sample tracer information q. verify local chicken test sample tracer information with egg track hub information r. receive local chicken test sample handling audio-video and sensor information s. associate local chicken test sample handing audio-video and sensor information with chicken tracer information t. scan local chicken test sample handling audio-video and sensor information for error or noncompliance u. receive accounting information of production factor use for local chicken test sample handling v. correlate local chicken test sample handling audio-video and sensor information with accounting information of production factor use for local chicken test sample handling w. receive test results for local chicken test sample x. associate test results for local chicken test sample with local chicken test sample tracer information y. update egg farm track information hub re local chicken test sample testing z. update chicken farm track information hub re local chicken test sample testing aa. update feed (grain) farm track information hub re local chicken test sample testing bb. receive local egg test sample tracer information cc. verify local egg test sample tracer information with egg track hub information dd. receive local egg test sample handling audio-video and sensor information ee. associate local egg test sample handing audio-video and sensor information with egg tracer information ff. scan local egg test sample handling audio-video and sensor information for error or noncompliance gg. receive accounting information of production factor use for local egg test sample handling hh. correlate local egg test sample handling audio-video and sensor information with accounting information of production factor use for local egg test sample handling ii. receive test results for local egg test sample jj. associate test results for local egg test sample with local egg test sample tracer information kk. update egg farm track information hub re local egg test sample testing ll. update chicken farm track information hub re local egg test sample testing mm. update feed (grain) farm track information hub re local egg test sample testing 5. Restaurant Test and Track Information Hub a. receive egg farm track hub information b. receive egg farm test hub information c. receive carton container tracer information d. verify carton container tracer information with egg track hub information e. receive internal carton container tracker information f. verify internal carton container tracker information with egg track hub information g. receive local carton container handling audio-video and sensor information h. scan local carton container handling audio-video and sensor information for error or noncompliance i. receive accounting information of production factor use for local carton container handling j. correlate local carton container handling audio-video and sensor information with accounting information of production factor use for local carton container handling k. associate local handling of carton container audio-video and sensor information with carton container tracer information l. receive local egg carton handling audio-video and sensor information m. scan local egg carton handling audio-video and sensor information for error or noncompliance n. receive accounting information of production factor use for local egg carton handling o. correlate local egg carton handling audio-video and sensor information with accounting information of production factor use for local egg carton handling p. associate local egg carton handling audio-video and sensor information with egg carton tracer information q. receive local egg handling audio-video and sensor information r. scan local egg handling audio-video and sensor information for error or noncompliance s. receive accounting information of production factor use for local egg handling t. correlate local egg handling audio-video and sensor information with accounting information of production factor use for local egg handling u. associate local egg handling audio-video and sensor information with egg tracer information v. send alert to initiate local egg sample test event w. receive local egg test sample tracer information x. verify local egg test sample tracer information with egg track hub information y. receive local egg test sample handling audio-video and sensor information z. associate local egg test sample handing audio-video and sensor information with egg tracer information aa. scan local egg test sample handling audio-video and sensor information for error or noncompliance bb. receive accounting information of production factor use for local egg test sample handling cc. correlate local egg test sample handling audio-video and sensor information with accounting information of production factor use for local egg test sample handling dd. receive test results for local egg test sample ee. associate test results for local egg test sample with local egg test sample tracer information ff. update egg farm track information hub re local egg test sample testing gg. update chicken farm track information hub re local egg test sample testing hh. update feed (grain) farm track information hub re local egg test sample testing ii. receive local egg dish preparation audio-video and sensor information jj. scan local egg dish preparation audio-video and sensor information for error or noncompliance kk. receive accounting information of production factor use for local egg dish preparation ll. correlate local egg dish preparation audio-video and sensor information with accounting information of production factor use for local egg dish preparation mm. associate local egg dish preparation audio-video and sensor information with egg tracer information nn. receive local egg dish serving audio-video and sensor information oo. scan local egg dish serving audio-video and sensor information for error or noncompliance pp. receive accounting information of production factor use for local egg dish serving qq. correlate local egg dish serving audio-video and sensor information with accounting information of production factor use for local egg dish serving rr. associate local egg dish serving audio-video and sensor information with egg tracer information ss. receive local egg dish payment audio-video and sensor information tt. scan local egg dish payment audio-video and sensor information for error or noncompliance uu. receive accounting information of production factor use for local egg dish payment vv. correlate local egg dish payment audio-video and sensor information with accounting information of production factor use for local egg dish payment ww. associate local egg dish payment audio-video and sensor information with egg tracer information 6. Grocery Test and Track Information Hub a. receive egg farm track hub information b. receive egg farm test hub information c. receive carton container tracer information d. verify carton container tracer information with egg track hub information e. receive internal carton container tracker information f. verify internal carton container tracker information with egg track hub information g. receive local carton container handling audio-video and sensor information h. scan local carton container handling audio-video and sensor information for error or noncompliance i. receive accounting information of production factor use for local carton container handling j. correlate local carton container handling audio-video and sensor information with accounting information of production factor use for local carton container handling k. associate local handling of carton container audio-video and sensor information with carton container tracer information l. receive local egg carton handling audio-video and sensor information m. scan local egg carton handling audio-video and sensor information for error or noncompliance n. receive accounting information of production factor use for local egg carton handling o. correlate local egg carton handling audio-video and sensor information with accounting information of production factor use for local egg carton handling p. associate local egg carton handling audio-video and sensor information with egg carton tracer information q. send alert to initiate local egg sample test event r. receive local egg test sample tracer information s. verify local egg test sample tracer information with egg track hub information t. receive local egg test sample handling audio-video and sensor information u. associate local egg test sample handing audio-video and sensor information with egg tracer information v. scan local egg test sample handling audio-video and sensor information for error or noncompliance w. receive accounting information of production factor use for local egg test sample handling x. correlate local egg test sample handling audio-video and sensor information with accounting information of production factor use for local egg test sample handling y. receive test results for local egg test sample z. associate test results for local egg test sample with local egg test sample tracer information aa. update egg farm track information hub re local egg test sample testing bb. update chicken farm track information hub re local egg test sample testing cc. update feed (grain) farm track information hub re local egg test sample testing dd. receive local egg carton payment audio-video and sensor information ee. scan local egg carton payment audio-video and sensor information for error or noncompliance ff. receive accounting information of production factor use for local egg carton payment gg. correlate local egg carton payment audio-video and sensor information with accounting information of production factor use for local egg carton payment hh. associate local egg carton payment audio-video and sensor information with egg carton tracer information 7. Home Test and Track Information Hub a. receive grocery test and track hub information b. receive egg carton tracer information c. verify egg carton tracer information with egg track hub information d. receive internal carton container tracker information e. verify internal carton container tracker information with egg track hub information f. receive local egg carton handling audio-video and sensor information g. scan local egg carton handling audio-video and sensor information for error or noncompliance h. receive accounting information of production factor use for local egg carton handling i. correlate local egg carton handling audio-video and sensor information with accounting information of production factor use for local egg carton handling j. associate local egg carton handling audio-video and sensor information with egg carton tracer information k. receive local egg handling audio-video and sensor information l. scan local egg handling audio-video and sensor information for error or noncompliance m. receive accounting information of production factor use for local egg handling n. correlate local egg handling audio-video and sensor information with accounting information of production factor use for local egg handling o. associate local egg handling audio-video and sensor information with egg tracer information p. send alert to initiate local egg sample test event q. receive local egg test sample tracer information r. verify local egg test sample tracer information with egg track hub information s. receive local egg test sample handling audio-video and sensor information t. associate local egg test sample handing audio-video and sensor information with egg tracer information u. scan local egg test sample handling audio-video and sensor information for error or noncompliance v. receive accounting information of production factor use for local egg test sample handling w. correlate local egg test sample handling audio-video and sensor information with accounting information of production factor use for local egg test sample handling x. receive test results for local egg test sample y. associate test results for local egg test sample with local egg test sample tracer information z. update grocery track information hub re local egg test sample testing aa. update egg farm track information hub re local egg test sample testing bb. update chicken farm track information hub re local egg test sample testing cc. update feed (grain) farm track information hub re local egg test sample testing dd. receive local egg dish preparation audio-video and sensor information ee. scan local egg dish preparation audio-video and sensor information for error or noncompliance ff. receive accounting information of production factor use for local egg dish preparation gg. correlate local egg dish preparation audio-video and sensor information with accounting information of production factor use for local egg dish preparation hh. associate local egg dish preparation audio-video and sensor information with egg tracer information ii. receive local egg dish serving audio-video and sensor information jj. scan local egg dish serving audio-video and sensor information for error or noncompliance kk. receive accounting information of production factor use for local egg dish serving ll. correlate local egg dish serving audio-video and sensor information with accounting information of production factor use for local egg dish serving mm. associate local egg dish serving audio-video and sensor information with egg tracer information An exemplary version of the grocery information system 10 is shown in FIG. 12 to optionally include various subsystems such as control and information processing subsystem s100, information storage subsystem s200, information user interface subsystem s300, sensing subsystem s400, electronic communication subsystem s500, power subsystem s600, material processing subsystem s700, and preparation subsystem s800.

An exemplary implementation of the control and information processing subsystem s100 is shown in FIG. 13 to optionally include various components such as microprocessor component s102, central processing unit (CPU) component s104, digital signal processor (DSP) component s106, application specific integrated circuit (ASIC) component s108, field programmable gate array (FPGA) component s110, multiprocessor component s112, optical processing component s114, logic component s116, remote processor component s118, multi-core array component s120, server processor component s122, database engine component s124, search engine component s126, image recognition component s128, audio recognition component s130, spectrum analysis component s132, lexigraphy engine component s134, operating system component s136, voice recognition component s138, and network processor component s140.

An exemplary implementation of the information storage subsystem s200 is shown in FIG. 14 to optionally include various components such as random access memory (RAM) component s202, dynamic random access memory (DRAM)

component s204, other volatile memory component s206, persistent memory component s208, read only memory (ROM) component s210, electrically erasable programmable read only memory (EEPROM) component s212, compact disk (CD) component s214, digital versatile disk (DVD) component s216, flash memory component s218, other nonvolatile memory component s220, hard drive component s222, disk farm component s224, disk cluster component s226, remote backup component s228, server component s230, digital tape component s232, optical storage component s234, Blu Ray disk component s236, computer readable signal bearing medium s238, and removable media component s240.

Figure 15:
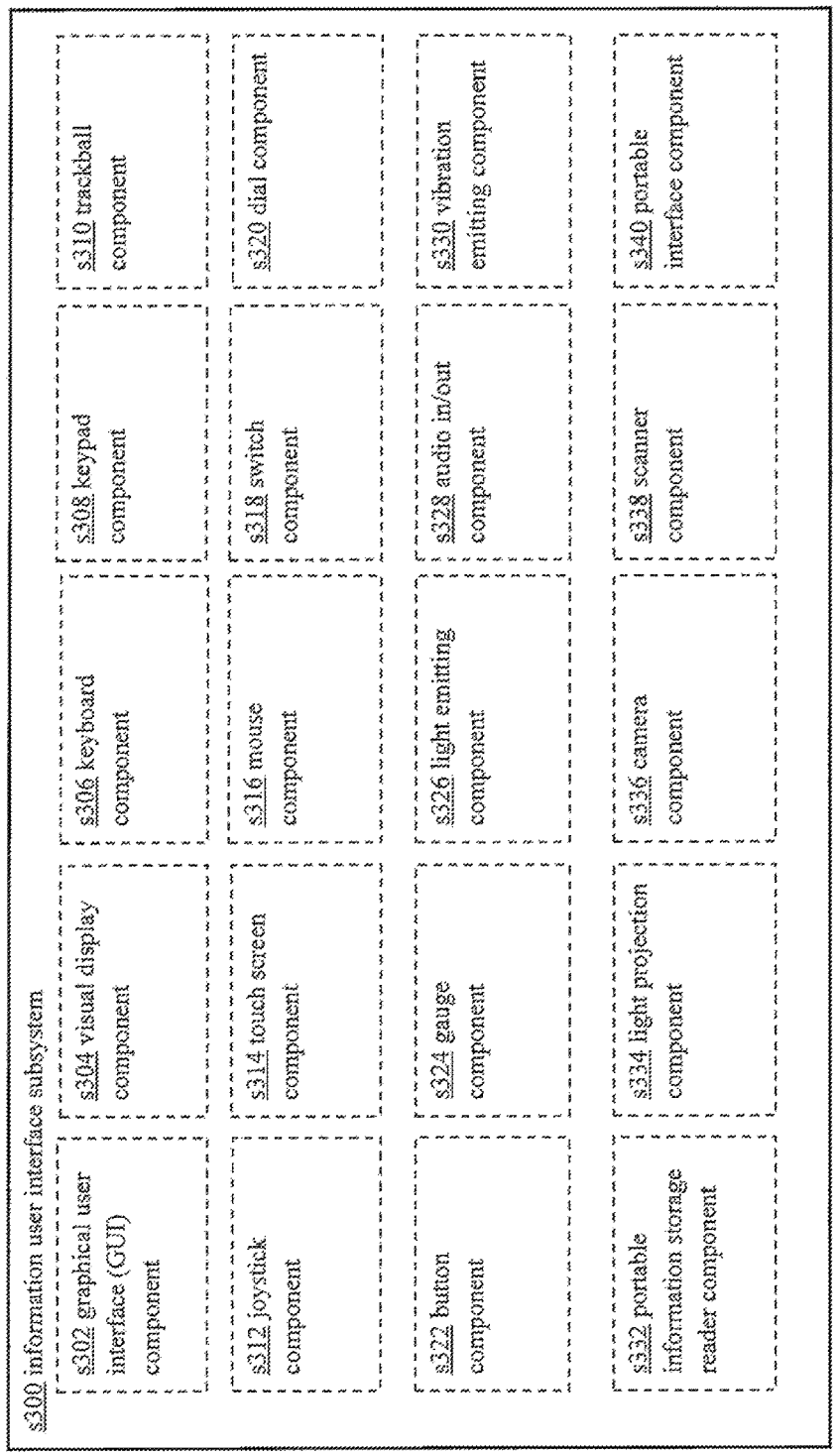
FIG. 15 is a block diagram depicting an information user interface subsystem s300 of an exemplary implementation of the grocery information system 10 of FIG. 1.

An exemplary implementation of the information user interface subsystem s300 is shown in FIG. 15 to optionally include various components such as graphical user interface (GUI) component s302, visual display component s304, keyboard component s306, keypad component s308, trackball component s310, joystick component s312, touch screen component s314, mouse component s316, switch component s318, dial component s320, button component s322, gauge component s324, light emitting component s326, audio in/out component s328, vibration emitting component s330, portable information storage reader component s332, light projection component s334, camera component s336, scanner component s338, and portable interface component s340.

An exemplary implementation of the sensing subsystem s400 is shown in FIG. 16 to optionally include various components such as electromagnetic sensing component s402, antenna component s404, photo detecting component s406, micro-electro-mech sys (MEMS) detecting component s408, weight sensing component s410, temperature sensing component s412, radio freq ID (RFID) sensing component s414, chemical sensing component s416, optical sensing component s418, sound sensing component s420, solid sensing component s422, liquid sensing component s424, solid sensing component s426, climate sensing component s428, vibration sensing component s430, motion sensing component s432, pressure sensing component s434, pattern sensing component s436, color sensing component s438, and encryption sensing component s440.

An exemplary implementation of the electronic communication subsystem s500 is shown in FIG. 17 to optionally include various components such as network cable component s502, optical network component s504, waveguide network component s506, internet network component s508, wireless network component s510, wired network component s512, cellular network component s514, wide area network component s516, local area network component s518, encrypted communication component s520, transceiver component s522, infrared network component s524, transmitter component s526, receiver component s528, receiver component s528, long-range communication component s530, short-range communication component s532, RFID communication component s534, encrypted communication component s536, SMS communication component s538, and tablet communication component s540.

An exemplary implementation of the power subsystem s600 is shown in FIG. 18 to optionally include various components such as electrical component s602, hydrocarbon fuel component s604, hydrogen fuel component s606, solid fuel component s608, liquid fuel component s610, gaseous fuel component s612, battery component s614, battery component s622, battery component s624, battery component s626, battery component s628, power cell component s630, steam generation component s632, solar cell component s634, solar reflector component s636, thermonuclear component s638, and co-generation component s640.

An exemplary implementation of the material processing subsystem s700 is shown in FIG. 19 to optionally include various components such as heating component s702, cooling component s704, microwave component s706, laser component s708, light emitting diode (LED) component s710, peltier cooling component s712, blending component s714, mixer component s716, acoustic energy component s718, stirring component s720, shaker component s722, energy emitting component s724, pump component s726, sorting component s728, infrared component s730, cutting component s732, material storage component s734, material receiving component s736, material containing component s738, and material handling component s740.

An exemplary implementation of the preparation subsystem s800 is shown in FIG. 20 to optionally include various components such as stocking resources component s802, receiving shipments component s804, refrigeration operation component s806, displaying operation component s808, cleaning operation component s810, shelving operation component s812, deli operation component s814, produce dept operation component s816, dairy dept. operation component s818, meat dept operation component s820, beverage dept operation component s822, poultry dept operation component s824, fish dept operation component s826, infestation operation component s828, health inspection component s830, butcher operation component s832, cereal dept operation component s834, protein dept operation component s836, fat dept operation component s838, and carbohydrate dept operation component s840.

Figure 21:
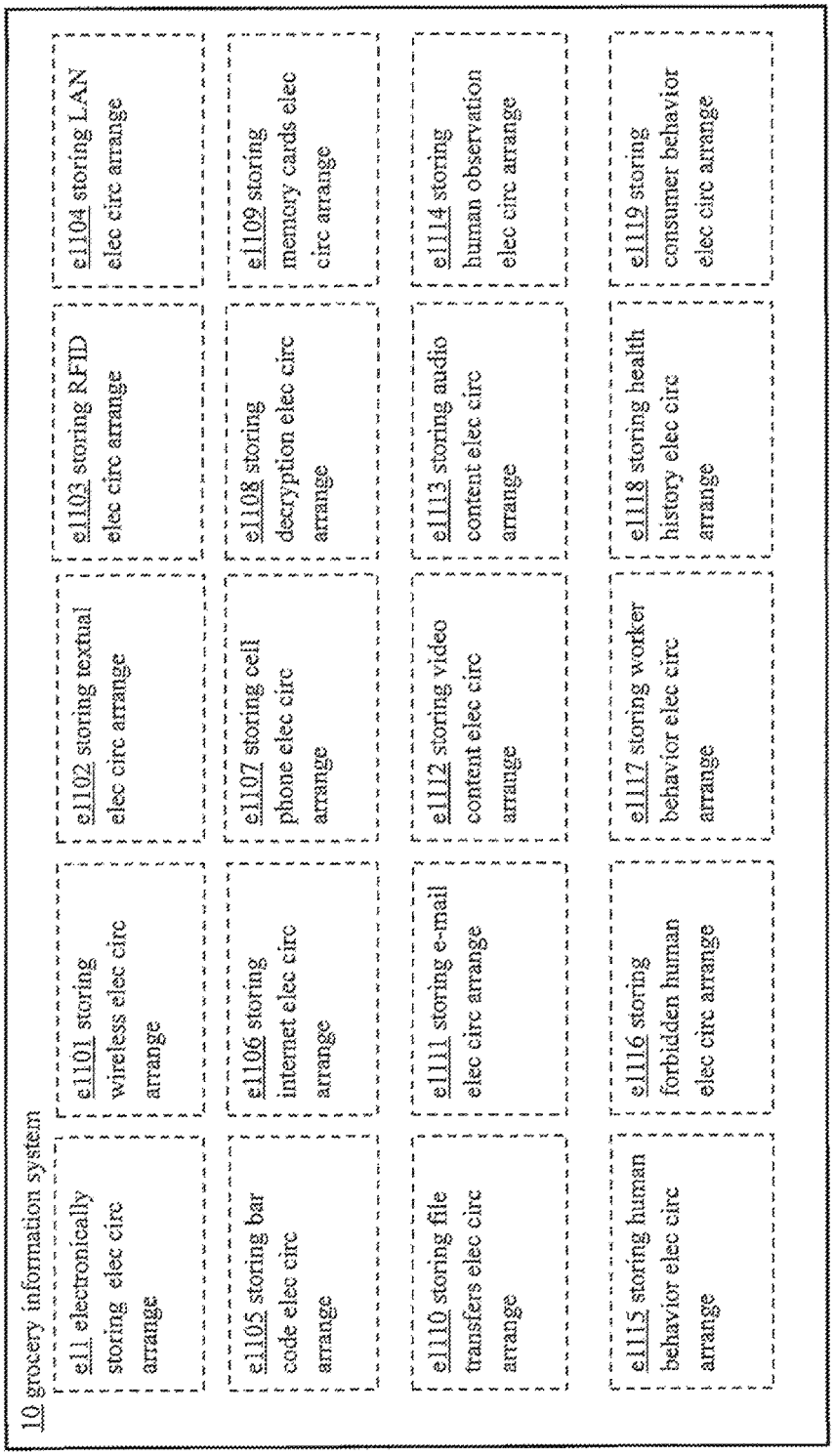
FIG. 21 is a block diagram depicting one or more exemplary electrical circuitry arrangements of the grocery information system 10 of FIG. 1.

Implementations involve different combinations (otherwise known as "electrical circuitry arrangements") of components from the subsystems of the grocery information system 10. Exemplary depictions of some of these electrical circuitry arrangements are shown in FIG. 21 to include electronically storing electrical circuitry arrangement e11, storing wireless electrical circuitry arrangement e1101, storing textual electrical circuitry arrangement e1102, storing RFID electrical circuitry arrangement e1103, storing LAN electrical circuitry arrangement e1104, storing bar code electrical circuitry arrangement e1105, storing internet electrical circuitry arrangement e1106, storing cell phone electrical circuitry arrangement e1107, storing decryption electrical circuitry arrangement e1108, storing memory cards electrical circuitry arrangement e1109, storing file transfers electrical circuitry arrangement e1110, storing e-mail electrical circuitry arrangement e1111, storing video content electrical circuitry arrangement e1112, storing audio content electrical circuitry arrangement e1113, storing human observation electrical circuitry arrangement e1114, storing human behavior electrical circuitry arrangement e1115, storing forbidden human electrical circuitry arrangement e1116, storing worker behavior electrical circuitry arrangement e1117, storing health history electrical circuitry arrangement e1118, and storing consumer behavior electrical circuitry arrangement e1119.

Some of these electrical circuitry arrangements are depicted in FIG. 22 to include storing worker handling electrical circuitry arrangement e1120, storing aspect handling electrical circuitry arrangement e1121, storing merchandizing substances electrical circuitry arrangement e1122, storing events occurring electrical circuitry arrangement e1123, storing test handling electrical circuitry arrangement e1124, storing chemical test electrical circuitry arrangement e1125, storing customer health electrical circuitry arrangement e1126, storing test health electrical circuitry arrangement e1127, storing worker guidelines electrical circuitry arrangement e1128, storing forbidden human electrical circuitry arrangement e1129, storing lack of behavior electrical circuitry arrangement e1130, storing test observation electrical circuitry arrangement e113, storing audio test electrical circuitry arrangement e1132, storing videotest electrical circuitry arrangement e1133, storing protein sales electrical circuitry arrangement e1134, storing carbohydrate sales electrical circuitry arrangement e1135, storing fat sales electrical circuitry arrangement e1136, storing stock rotation electrical circuitry arrangement e1137, storing equipment cleaning electrical circuitry arrangement e1138, and storing refrigeration factors electrical circuitry arrangement e1139.

Some of these electrical circuitry arrangements are depicted in FIG. 23 to include storing heat treating electrical circuitry arrangement e1140, storing stock storage electrical circuitry arrangement e1141, storing equipment use electrical circuitry arrangement e1142, storing deli support electrical circuitry arrangement e1143, storing deli hindrance electrical circuitry arrangement e1144, storing customer factors electrical circuitry arrangement e1145, storing store locations electrical circuitry arrangement e1146, storing clerk staff electrical circuitry arrangement e1147, storing compliance factors electrical circuitry arrangement e1148, storing butcher staff electrical circuitry arrangement e1149, storing health department electrical circuitry arrangement e1150, storing harvest location electrical circuitry arrangement e1151, storing genetically modified electrical circuitry arrangement e1152, storing advertisement items electrical circuitry arrangement e1153, storing food freshness electrical circuitry arrangement e1154, storing food contamination electrical circuitry arrangement e1155, storing organic labeling electrical circuitry arrangement e1156, storing toxin levels electrical circuitry arrangement e1157, storing food combining electrical circuitry arrangement e1158, and storing food shipment electrical circuitry arrangement e1159.

Some of these electrical circuitry arrangements are depicted in FIG. 24 to include storing displaying items electrical circuitry arrangement e1160, storing dispensing prepackaged electrical circuitry arrangement e1161, storing stocking shelves electrical circuitry arrangement e1162, storing dispensing machines electrical circuitry arrangement e1163, storing remote customers electrical circuitry arrangement e1164, storing internet ordering electrical circuitry arrangement e1165, and storing whole produce electrical circuitry arrangement e1166, storing mobile dispensaries electrical circuitry arrangement e1167, storing packaged food electrical circuitry arrangement e1168, storing canned items electrical circuitry arrangement e1169, storing frozen dinners electrical circuitry arrangement e1170, storing salad based electrical circuitry arrangement e1171, storing beef items electrical circuitry arrangement e1172, storing seafood items electrical circuitry arrangement e1173, storing poultry items electrical circuitry arrangement e1174, storing dairy items electrical circuitry arrangement e1175, storing whole animal electrical circuitry arrangement e1176, storing beverage items electrical circuitry arrangement e1177, storing appetizer items electrical circuitry arrangement e1178, and storing sandwich items electrical circuitry arrangement e1179.

Figure 25:
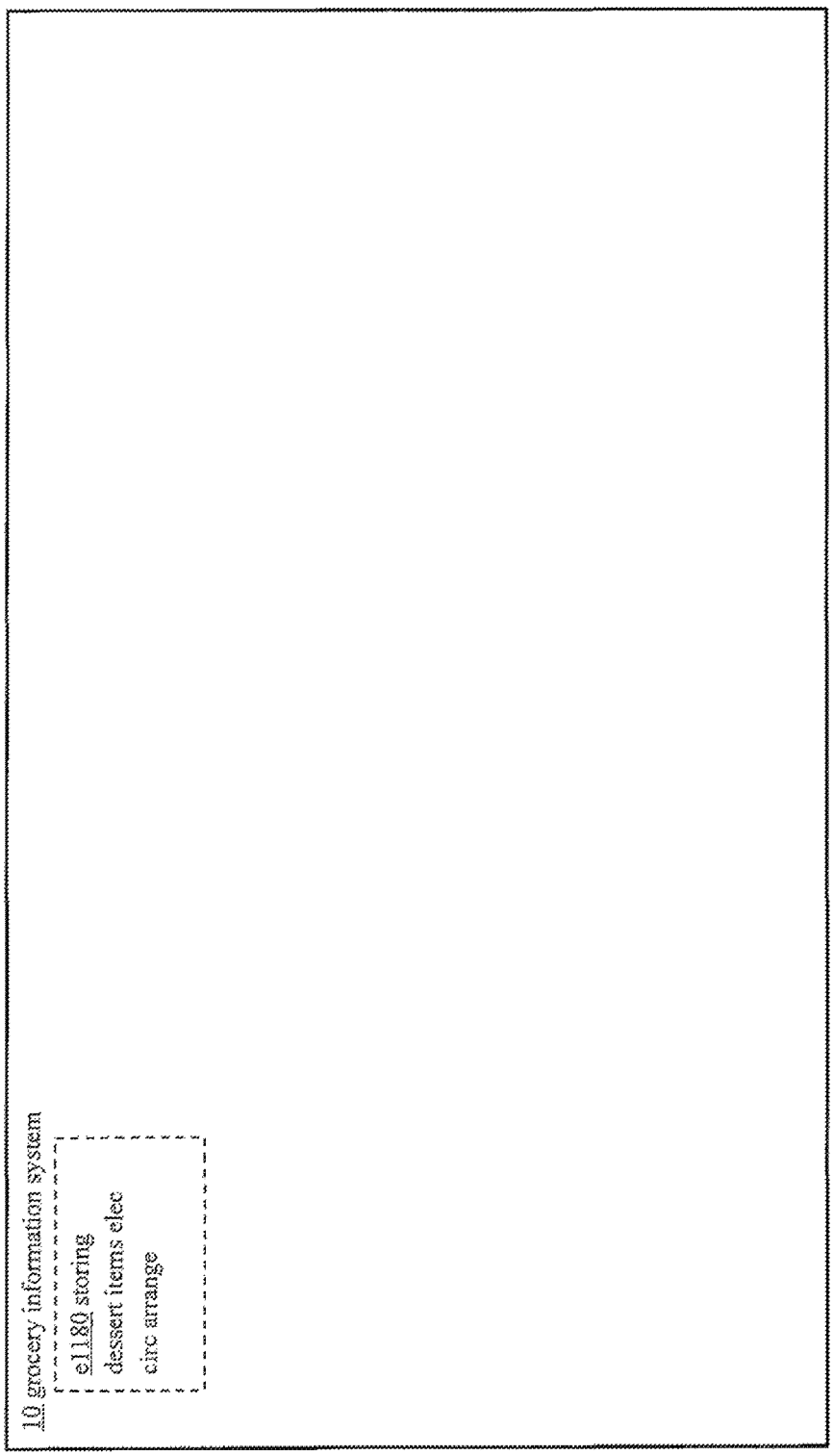
FIG. 25 is a block diagram depicting one or more exemplary electrical circuitry arrangements of the grocery information system 10 of FIG. 1.

Some of these electrical circuitry arrangements are depicted in FIG. 25 to include storing dessert items electrical circuitry arrangement e1180.

Some of these electrical circuitry arrangements are depicted in FIG. 26 to include electronically associating electrical circuitry arrangement e12, associating computer-based indices electrical circuitry arrangement e1201, associating computer-based pointers electrical circuitry arrangement e1202, associating relational databases electrical circuitry arrangement e1203, associating keyword associations electrical circuitry arrangement e1204, associating lookup tables electrical circuitry arrangement e1205, associating identification codes electrical circuitry arrangement e1206, associating encrypted identifications electrical circuitry arrangement e1207, associating naming information electrical circuitry arrangement e1208, associating alphanumeric text electrical circuitry arrangement e1209, associating encoded data electrical circuitry arrangement e1210, associating frequency identification electrical circuitry arrangement e1211, and associating electronic optical electrical circuitry arrangement e1212, associating quick response electrical circuitry arrangement e1213, associating computer servers electrical circuitry arrangement e1214, associating computer-based network electrical circuitry arrangement e1215, associating radio frequency electrical circuitry arrangement e1216, associating emitter beacons electrical circuitry arrangement e1217, associating barcode tags electrical circuitry arrangement e1218, and associating genetic tags electrical circuitry arrangement e1219.

Some of these electrical circuitry arrangements are depicted in FIG. 27 to include associating biochemical tags electrical circuitry arrangement e1220, associating chemical tags electrical circuitry arrangement e1221, associating isotopic tags electrical circuitry arrangement e1222, associating radioactive tags electrical circuitry arrangement e1223, associating signal emitting tags electrical circuitry arrangement e1224, associating identification tags electrical circuitry arrangement e1225, associating visual shapes electrical circuitry arrangement e1226, associating color patterns electrical circuitry arrangement e1227, associating audio emitters electrical circuitry arrangement e1228, associating electronic databases electrical circuitry arrangement e1229, associating affixed to items electrical circuitry arrangement e1234, associating identification information electrical circuitry arrangement e1231, associating factory to store electrical circuitry arrangement e1232, associating shelf life electrical circuitry arrangement e1233, associating affixed to items electrical circuitry arrangement e1234, associating pre-processed forms electrical circuitry arrangement e1235, associating physically connected electrical circuitry arrangement e1236, and associating temporarily containing electrical circuitry arrangement e1237.

In implementations one or more instructions are stored and/or otherwise borne in various subsystems, components, and/or accessories of the grocery information system 10 such as being borne in a non-transitory signal bearing medium of information storage subsystem s200. One or more exemplary instructions depicted in FIG. 28 as being borne in an exemplary version of a non-transitory signal bearing medium of information storage subsystem s200 include one or more electronically storing instructions i11, one or more storing wireless instructions i1101, one or more storing textual instructions i1102, one or more storing RFID instructions i1103, one or more storing LAN instructions i1104, one or more storing bar code instructions i1105, one or more storing internet instructions i1106, one or more storing cell phone instructions i1107, one or more storing decryption instructions i1108, one or more storing memory cards instructions i1109, one or more storing file transfers instructions i1110, one or more storing e-mail instructions i1111, one or more storing video content instructions i1112, one or more storing audio content instructions i1113, one or more storing human observation instructions i1114, one or more storing human behavior instructions i1115, one or more storing forbidden human instructions i1116, one or more storing worker behavior instructions i1117, one or more storing health history instructions i1118, and one or more storing consumer behavior instructions i1119.

One or more exemplary instructions depicted in FIG. 29 as being borne in an exemplary version of a non-transitory signal bearing medium of information storage subsystem s200 include one or more storing worker handling instructions i1120, one or more storing aspect handling instructions i1121, one or more storing merchandizing substances instructions i1122, one or more storing events occurring instructions i1123, one or more storing test handling instructions i1124, one or more storing chemical test instructions i1125, one or more storing customer health instructions i1126, one or more storing test health instructions i1127, one or more storing worker guidelines instructions i1128, one or more storing forbidden human instructions i1129, one or more storing lack of behavior instructions i1130, one or more storing test observation instructions i1131, one or more storing audio test instructions i1132, one or more storing videotest instructions i1133, one or more storing protein sales instructions i1134, one or more storing carbohydrate sales instructions i1135, one or more storing fat sales instructions i1136, one or more storing stock rotation instructions i1137, one or more storing equipment cleaning instructions i1138, and one or more storing refrigeration factors instructions i1139.

One or more exemplary instructions depicted in FIG. 30 as being borne in an exemplary version of a non-transitory signal bearing medium of information storage subsystem s200 include one or more storing heat treating instructions i1140, one or more storing stock storage instructions i1141, one or more storing equipment use instructions i1142, one or more storing deli support instructions i1143, one or more storing deli hindrance instructions i1144, one or more storing customer factors instructions i1145, one or more storing store locations instructions i1146, one or more storing clerk staff instructions i1147, one or more storing compliance factors instructions i1148, one or more storing butcher staff instructions i1149, one or more storing health department instructions i1150, one or more storing harvest location instructions i1151, one or more storing genetically modified instructions i1152, one or more storing advertisement items instructions i1153, one or more storing food freshness instructions i1154, one or more storing food contamination instructions i1155, one or more storing organic labeling instructions i1156, one or more storing toxin levels instructions i1157, one or more storing food combining instructions i1158, and one or more storing food shipment instructions i1159.

One or more exemplary instructions depicted in FIG. 31 as being borne in an exemplary version of a non-transitory signal bearing medium of information storage subsystem s200 include one or more storing displaying items instructions i1160, one or more storing dispensing prepackaged instructions i1161, one or more storing stocking shelves instructions i1162, one or more storing dispensing machines instructions i1163, one or more storing remote customers instructions i1164, one or more storing internet ordering instructions i1165, and one or more storing whole produce instructions i1166, one or more storing mobile dispensaries instructions i1167, one or more storing packaged food instructions i1168, one or more storing canned items instructions i1169, one or more storing frozen dinners instructions i1170, one or more storing salad based instructions i1171, one or more storing beef items instructions i1172, one or more storing seafood items instructions i1173, one or more storing poultry items instructions i1174, one or more storing dairy items instructions i1175, one or more storing whole animal instructions i1176, one or more storing beverage items instructions i1177, one or more storing appetizer items instructions i1178, and one or more storing sandwich items instructions i1179.

Figure 32:
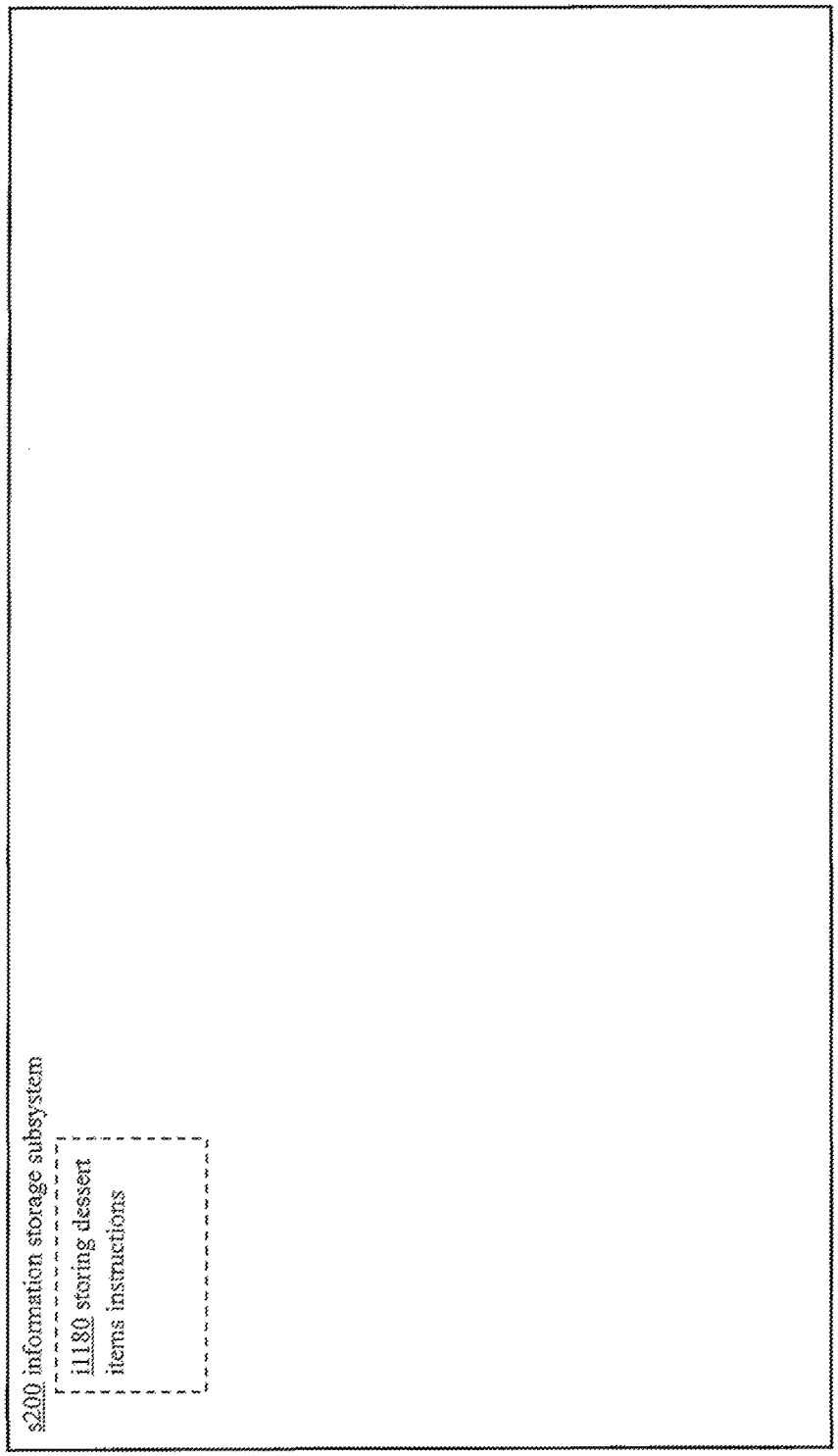
FIG. 32 is a block diagram depicting one or more exemplary instructions of the information storage subsystem s200 of the grocery information system 10 of FIG. 1.

One or more exemplary instructions depicted in FIG. 32 as being borne in an exemplary version of a non-transitory signal bearing medium of information storage subsystem s200 include one or more storing dessert items instructions i1180.

One or more exemplary instructions depicted in FIG. 33 as being borne in an exemplary version of a non-transitory signal bearing medium of information storage subsystem s200 include one or more electronically associating instructions i12, one or more associating computer-based indices instructions i1201, one or more associating computer-based pointers instructions i1202, one or more associating relational databases instructions i1203, one or more associating keyword associations instructions i1204, one or more associating lookup tables instructions i1205, one or more associating identification codes instructions i1206, one or more associating encrypted identifications instructions i1207, one or more associating naming information instructions i1208, one or more associating alpha-numeric text instructions i1209, one or more associating encoded data instructions i1210, one or more associating frequency identification instructions i1211, one or more associating electronic optical instructions i1212, one or more associating quick response instructions i1213, one or more associating computer servers instructions i1214, one or more associating computer-based network instructions i1215, one or more associating radio frequency instructions i1216, one or more associating emitter beacons instructions i1217, one or more associating barcode tags instructions i1218, and one or more associating genetic tags instructions i1219.

One or more exemplary instructions depicted in FIG. 34 as being borne in an exemplary version of a non-transitory signal bearing medium of information storage subsystem s200 include one or more associating biochemical tags instructions i1220, one or more associating chemical tags instructions i1221, one or more associating isotopic tags instructions i1222, one or more associating radioactive tags instructions i1223, one or more associating signal emitting tags instructions i1224, one or more associating identification tags instructions i1225, one or more associating visual shapes instructions i1226, one or more associating color patterns instructions i1227, one or more associating audio emitters instructions i1228, one or more associating electronic databases instructions i1229, one or more associating affixed to items instructions i1234, one or more associating identification information instructions i1231, one or more associating factory to store instructions i1232, one or more associating shelf life instructions i1233, one or more associating affixed to items instructions i1234, one or more associating pre-processed forms instructions i1235, one or more associating physically connected instructions i1236, and one or more associating temporarily containing instructions i1237.

Figure 35:
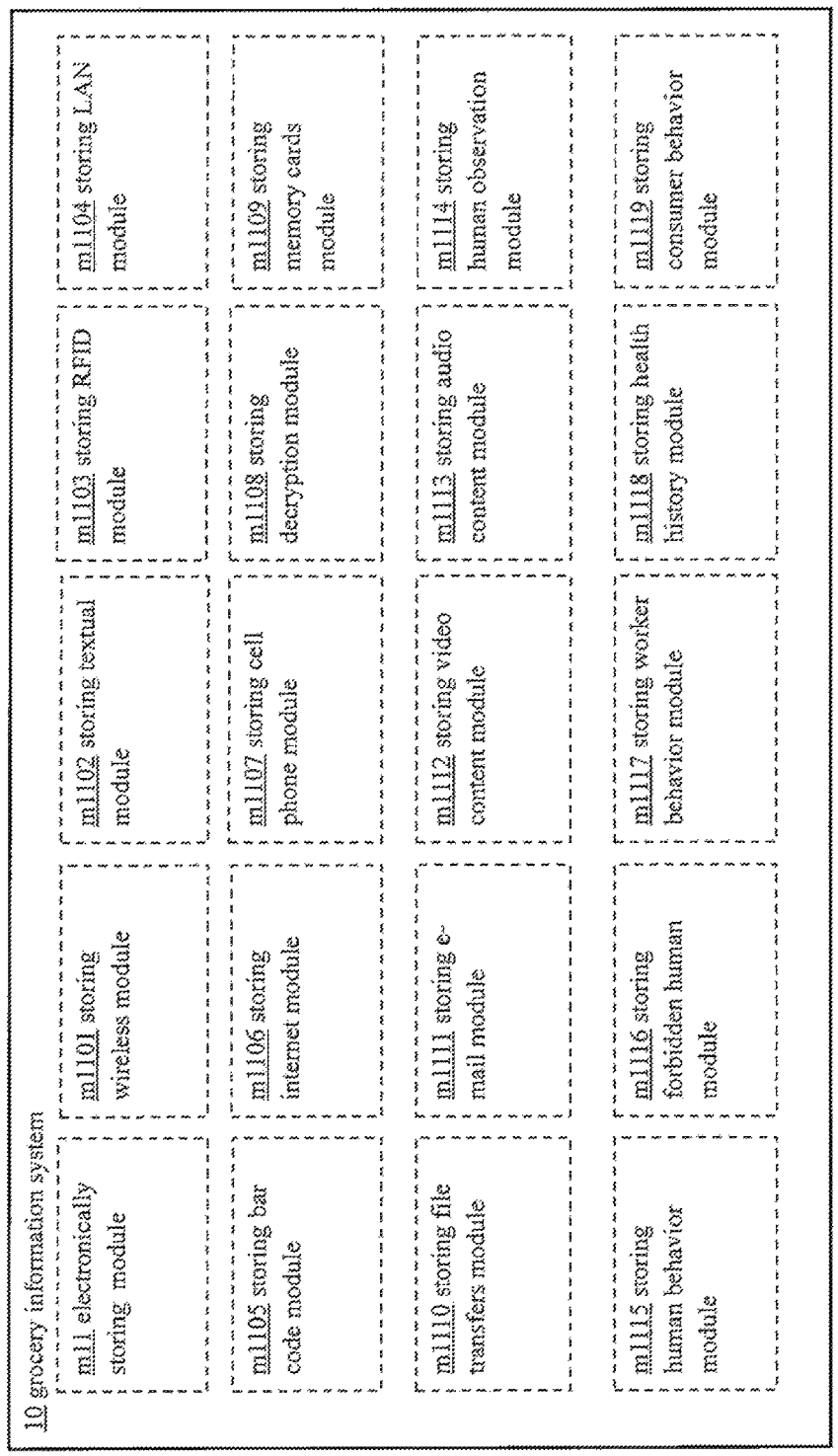
FIG. 35 is a block diagram depicting one or more exemplary modules of the grocery information system 10 of FIG. 1.

Implementations of modules involve different combinations (limited to patentable subject matter under 35 U.S.C. 101) of one or more aspects from one or more of the electrical circuitry arrangements and/or one or more aspects from one or more of the instructions of the grocery information system 10. Exemplary depictions of some of these modules are shown in FIG. 35 to include electronically storing module m11, storing wireless module m1101, storing textual module m1102, storing RFID module m1103, storing LAN module m1104, storing bar code module m1105, storing internet module m1106, storing cell phone module m1107, storing decryption module m1108, storing memory cards module m1109, storing file transfers module m1110, storing e-mail module m1111, storing video content module m1112, storing audio content module m1113, storing human observation module m1114, storing human behavior module m1115, storing forbidden human module m1116, storing worker behavior module m1117, storing health history module m1118, and storing consumer behavior module m1119.

Figure 36:
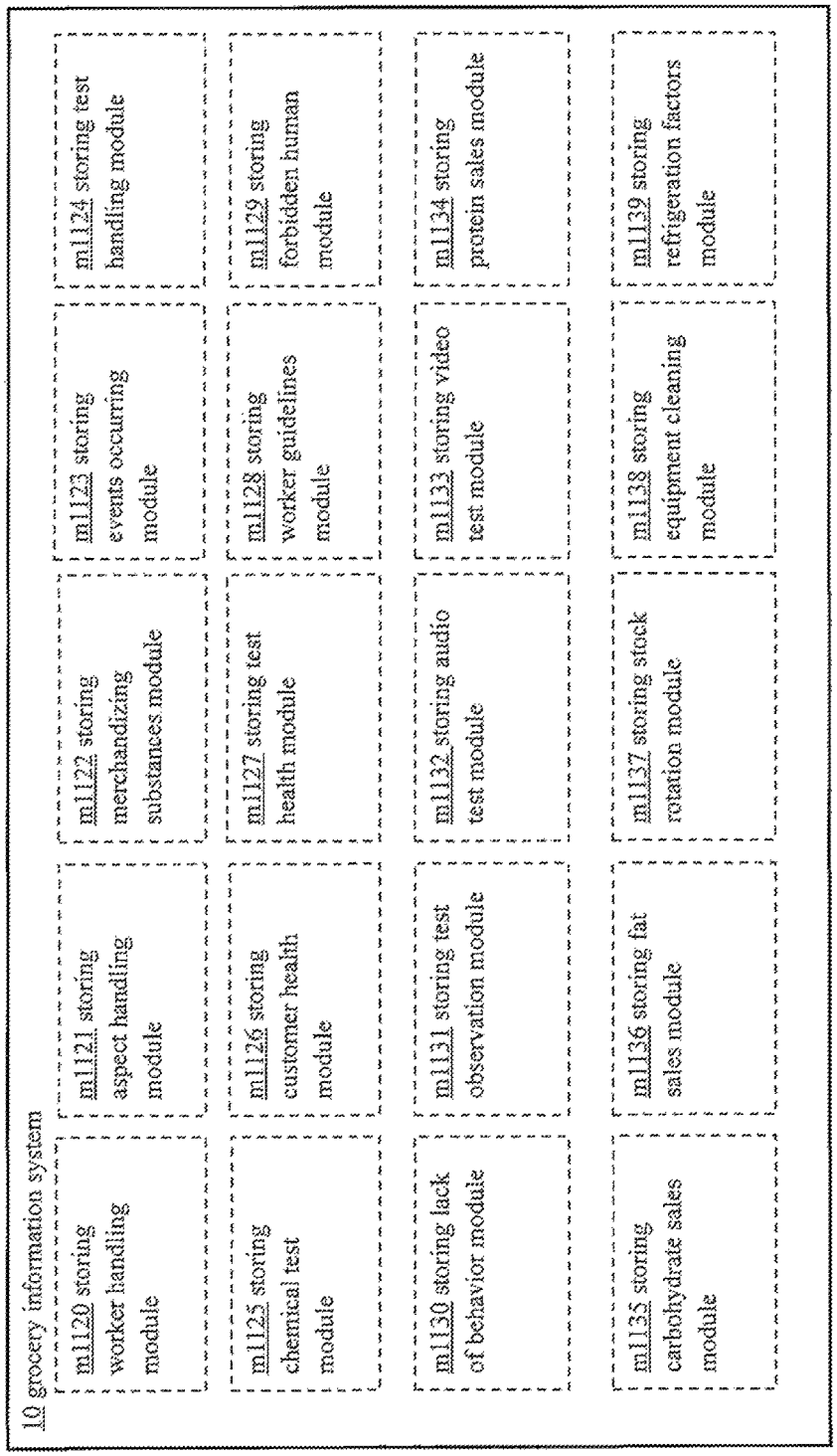
FIG. 36 is a block diagram depicting one or more exemplary modules of the grocery information system 10 of FIG. 1.

Some of these modules are depicted in FIG. 36 to include storing worker handling module m1120, storing aspect handling module m1121, storing merchandizing substances module m1122, storing events occurring module m1123, storing test handling module m1124, storing chemical test module m1125, storing customer health module m1126, storing test health module m1127, storing worker guidelines module m1128, storing forbidden human module m1129, storing lack of behavior module m1130, storing test observation module m113, storing audio test module m1132, storing videotest module m1133, storing protein sales module m1134, storing carbohydrate sales module m1135, storing fat sales module m1136, storing stock rotation module m1137, storing equipment cleaning module m1138, and storing refrigeration factors module m1139.

Figure 37:
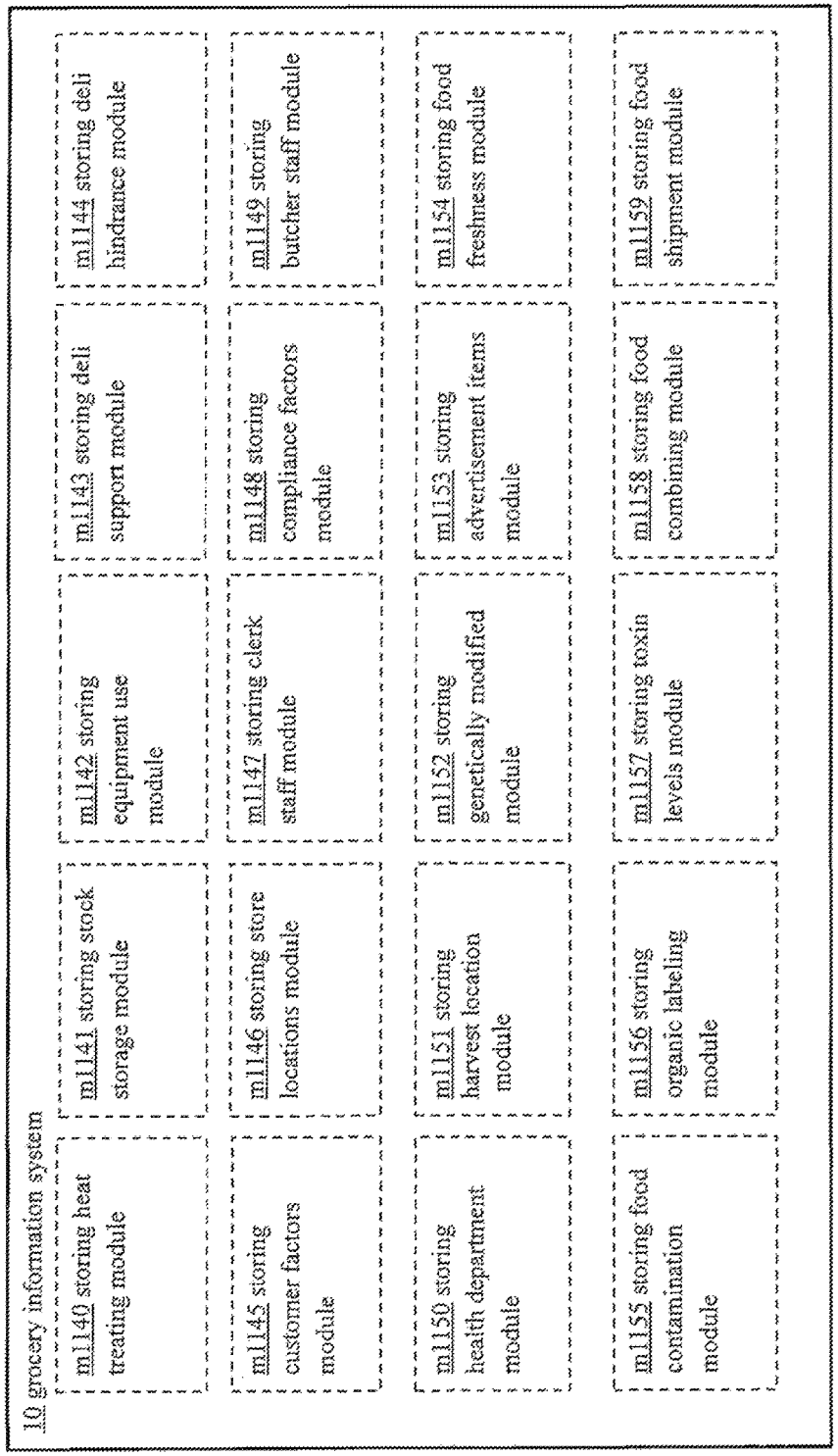
FIG. 37 is a block diagram depicting one or more exemplary modules of the grocery information system 10 of FIG. 1.

Some of these modules are depicted in FIG. 37 to include storing heat treating module m1140, storing stock storage module m1141, storing equipment use module m1142, storing deli support module m1143, storing deli hindrance module m1144, storing customer factors module m1145, storing store locations module m1146, storing clerk staff module m1147, storing compliance factors module m1148, storing butcher staff module m1149, storing health department module m1150, storing harvest location module m1151, storing genetically modified module m1152, storing advertisement items module m1153, storing food freshness module m1154, storing food contamination module m1155, storing organic labeling module m1156, storing toxin levels module m1157, storing food combining module m1158, and storing food shipment module m1159.

Figure 38:
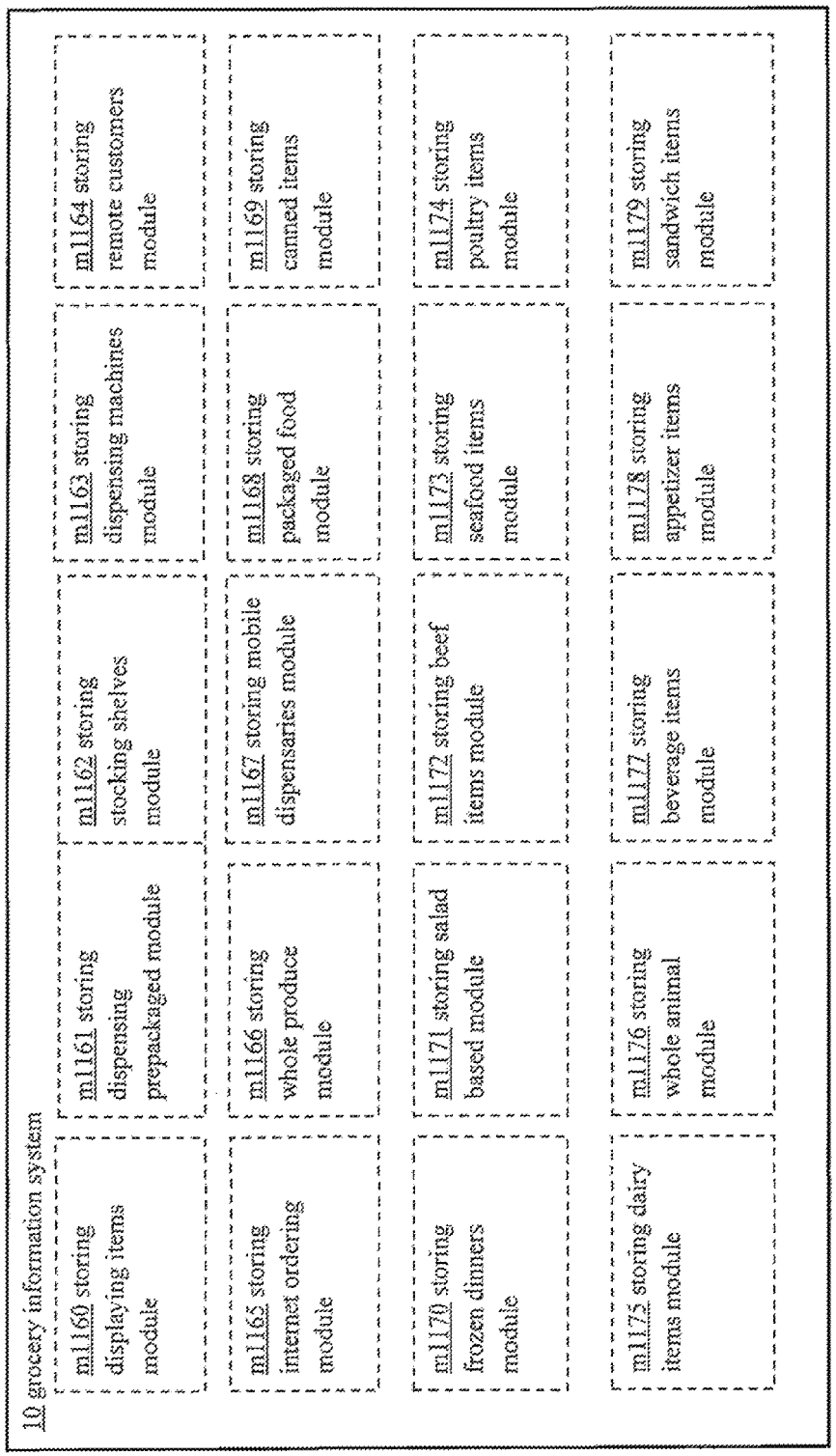
FIG. 38 is a block diagram depicting one or more exemplary modules of the grocery information system 10 of FIG. 1.

Some of these modules are depicted in FIG. 38 to include storing displaying items module m1160, storing dispensing prepackaged module m1161, storing stocking shelves module m1162, storing dispensing machines module m1163, storing remote customers module m1164, storing internet ordering module m1165, and storing whole produce module m1166, storing mobile dispensaries module m1167, storing packaged food module m1168, storing canned items module m1169, storing frozen dinners module m1170, storing salad based module m1171, storing beef items module m1172, storing seafood items module m1173, storing poultry items module m1174, storing dairy items module m1175, storing whole animal module m1176, storing beverage items module m1177, storing appetizer items module m1178, and storing sandwich items module m1179.

Figure 39:
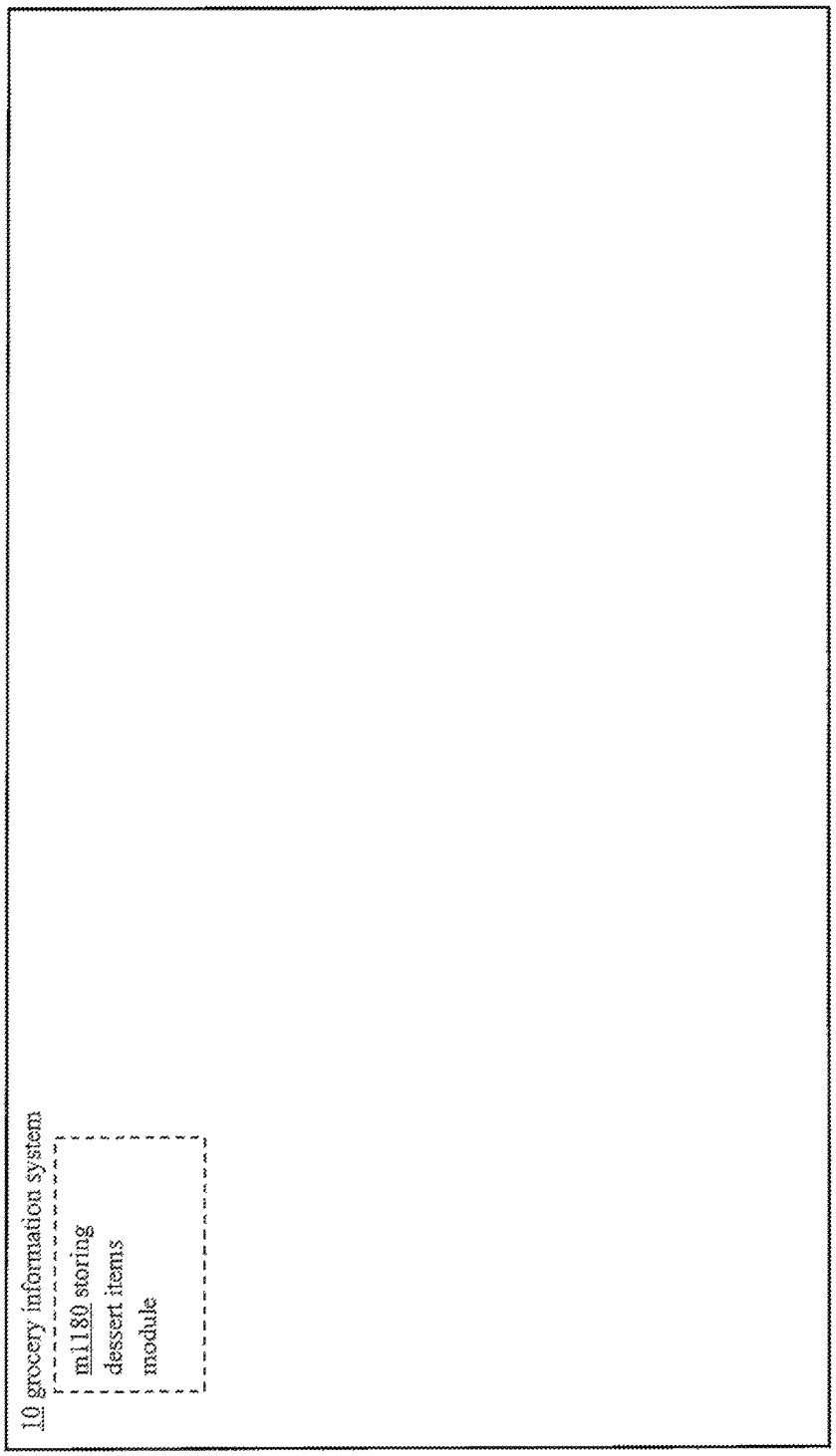
FIG. 39 is a block diagram depicting one or more exemplary modules of the grocery information system 10 of FIG. 1.

Some of these modules are depicted in FIG. 39 to include storing dessert items module m1180.

Some of these modules are depicted in FIG. 40 to include electronically associating module m12, associating computer-based indices module m1201, associating computer-based pointers module m1202, associating relational databases module m1203, associating keyword associations module m1204, associating lookup tables module m1205, associating identification codes module m1206, associating encrypted identifications module m1207, associating naming information module m1208, associating alpha-numeric text module m1209, associating encoded data module m1210, associating frequency identification module m1211, and associating electronic optical module m1212, associating quick response module m1213, associating computer servers module m1214, associating computer-based network module m1215, associating radio frequency module m1216, associating emitter beacons module m1217, associating barcode tags module m1218, and associating genetic tags module m1219.

Figure 41:
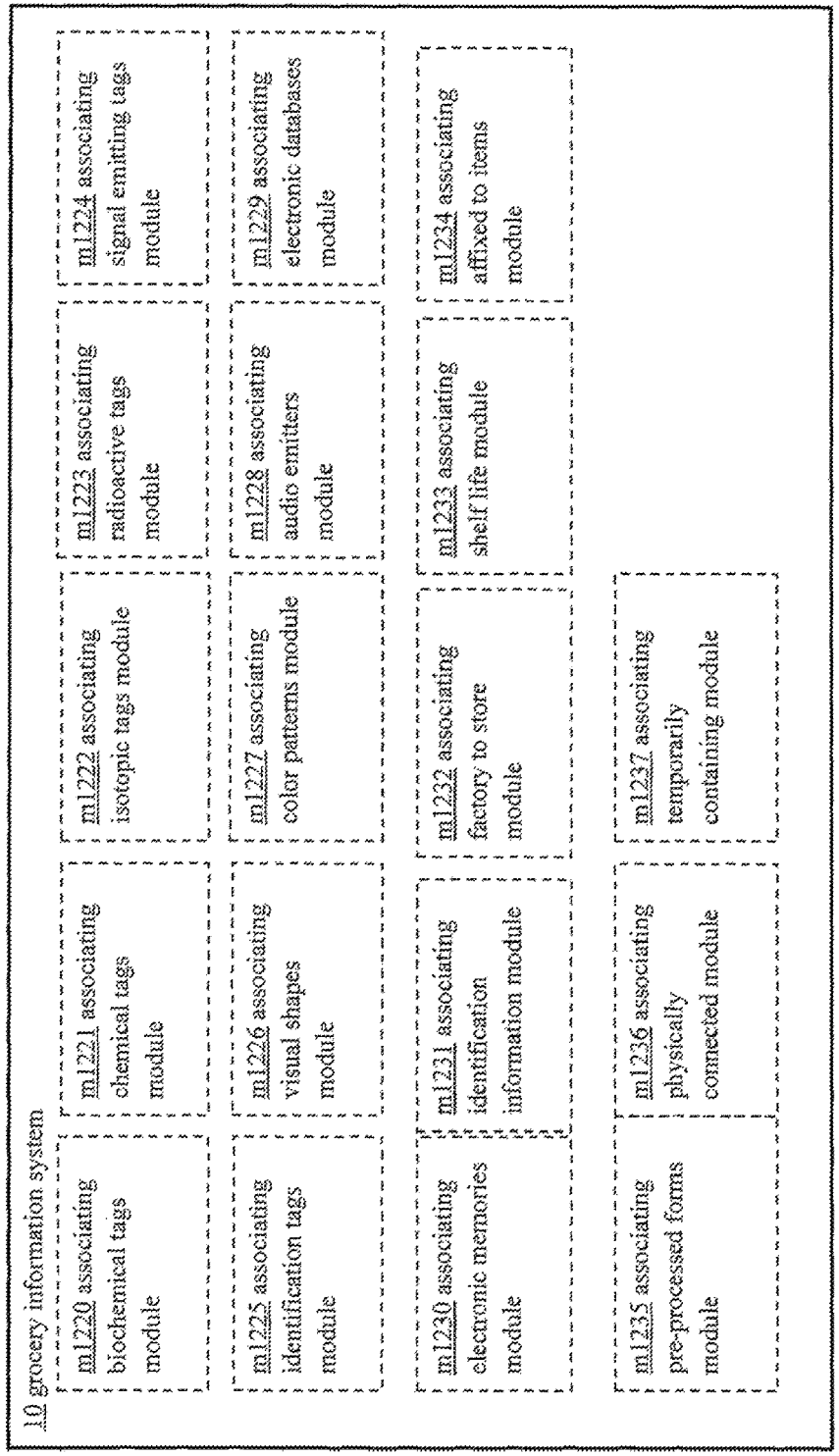
FIG. 41 is a block diagram depicting one or more exemplary modules of the grocery information system 10 of FIG. 1.

Some of these modules are depicted in FIG. 41 to include associating biochemical tags module m12, associating chemical tags module m1221, associating isotopic tags module m1222, associating radioactive tags module m1223, associating signal emitting tags module m1224, associating identification tags module m1225, associating visual shapes module m1226, associating color patterns module m1227, associating audio emitters module m1228, associating electronic databases module m1229, associating affixed to items module m1234, associating identification information module m1231, associating factory to store module m1232, associating shelf life module m1233, associating affixed to items module m1234, associating pre-processed forms module m1235, associating physically connected module m1236, and associating temporarily containing module m1237.

In some implementations, non-transitory signal-bearing medium of information storage subsystem s200 as articles of manufacture may store the one or more exemplary instructions. In some implementations, the non-transitory signal bearing medium may include a computer-readable medium. In some implementations, the non-transitory signal-bearing medium may include a recordable medium. In some implementations, the signal-bearing medium may include a communication medium.

The various subsystems and components of the grocery information system s10 such as the control and information processing subsystem s100, the information storage subsystem s200, the information user interface subsystems 300, the sensing subsystem s400 and the electronic communication subsystem s500 and their sub-components and the other exemplary entities depicted may be embodied by hardware, software and/or firmware (limited to patentable subject matter under 35 USC 101). For example, in some implementations of the grocery information system s10, aspects may be implemented with a processor (e.g., microprocessor, controller, and so forth) executing computer readable instructions (e.g., computer program product) stored in a storage medium (e.g., volatile or non-volatile memory) such as a signal-bearing medium. Alternatively, hardware such as application specific integrated circuit (ASIC) may be employed in order to implement such modules in some alternative implementations.

Figure 42:
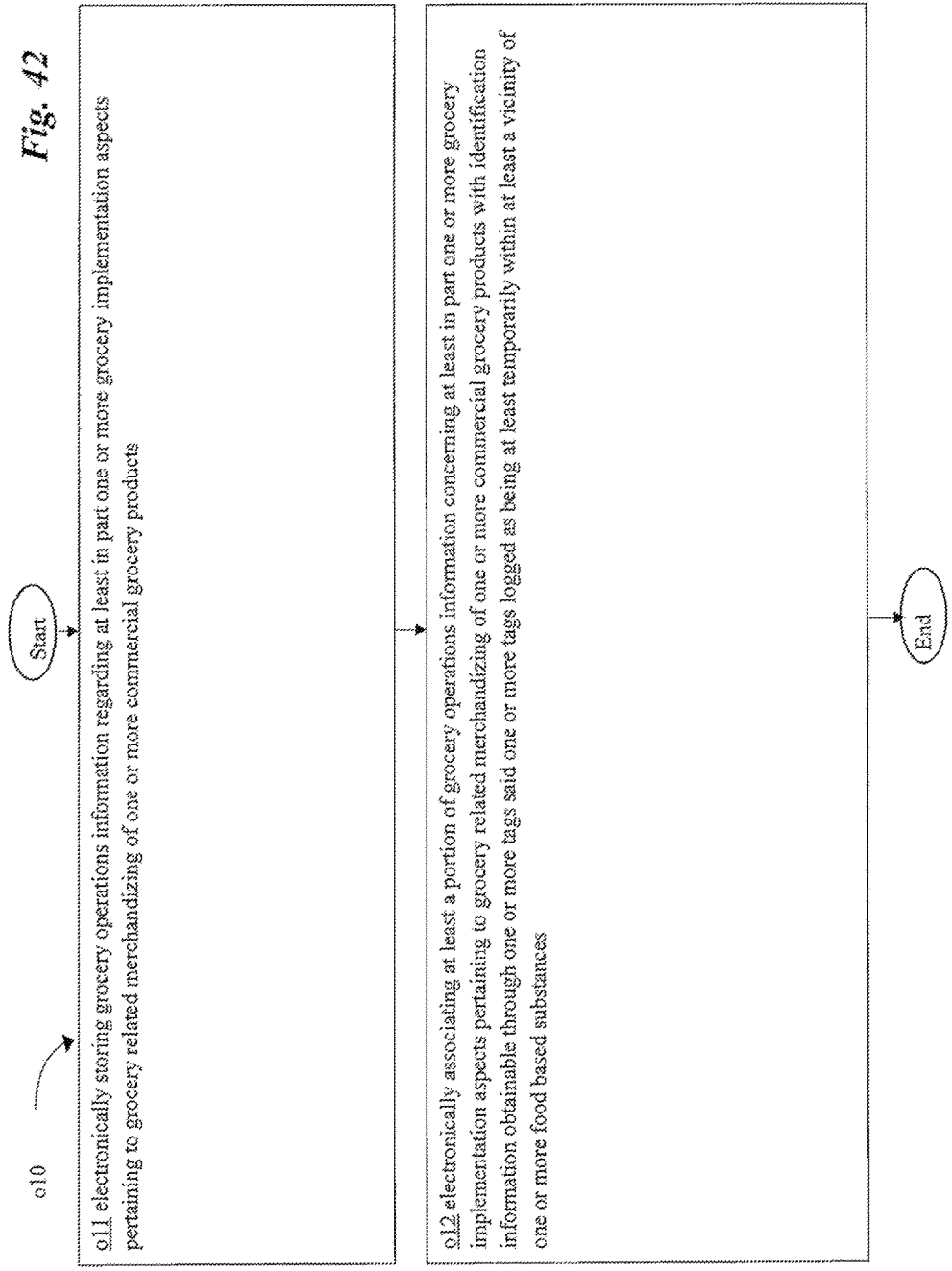
FIG. 42 is a high-level flowchart illustrating an operational flow o10 representing exemplary operations related to electronically storing grocery operations information regarding at least in part one or more grocery implementation aspects pertaining to grocery related merchandizing of one or more commercial grocery products, and electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances at least associated with the depicted exemplary implementations of the system.

An operational flow o10 as shown in FIG. 42 represents example operations related to electronically storing grocery operations information regarding at least in part one or more grocery implementation aspects pertaining to grocery related merchandizing of one or more commercial grocery products and electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances.

FIG. 42 and those figures that follow may have various examples of operational flows, and explanation may be provided with respect to the above-described examples of FIGS. 1-11 and/or with respect to other examples and contexts. Nonetheless, it should be understood that the operational flows may be executed in a number of other environments and contexts, and/or in modified versions of FIGS. 1-11. Furthermore, although the various operational flows are presented in the sequence(s) illustrated, it should be understood that the various operations may be performed in other orders than those which are illustrated, or may be performed concurrently.

In FIG. 42 and those figures that follow, various operations may be depicted in a box-within-a-box manner. Such depictions may indicate that an operation in an internal box may comprise an optional exemplary implementation of the operational step illustrated in one or more external boxes. However, it should be understood that internal box operations may be viewed as independent operations separate from any associated external boxes and may be performed in any sequence with respect to all other illustrated operations, or may be performed concurrently.

For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

As shown in FIG. 42, the operational flow o10 proceeds to operation o11 for electronically storing grocery operations information regarding at least in part one or more grocery implementation aspects pertaining to grocery related merchandizing of one or more commercial grocery products. An exemplary version of a non-transitory signal bearing medium of information storage subsystem s200 is depicted as bearing one or more electronically storing instructions i11 that when executed will direct performance of the operation o11. In an implementation, the one or more electronically storing instructions i11 when executed direct electronically storing (e.g. from wifi, from laptop entry, from RFID scan, etc.) grocery operations information (e.g. AVI file format, MP3 file format, audio listening, etc.) regarding at least in part (e.g. associated, affected, affecting, etc.) one or more grocery implementation aspects (e.g. organic produce delivery schedule, cost of labor, record keeping methods, etc.) pertaining to (e.g. associated, affected, affecting, etc.) grocery related merchandizing of (e.g. fine dining grocery item preparation, fast food grocery item preparation, family buffet grocery item preparation, etc.) one or more commercial grocery products (e.g. beef main course grocery item, pork main course grocery item, fish main course grocery item, etc.). Furthermore, the electronically storing electrical circuitry arrangement ("elec circ arrange") e11 when activated will perform the operation o1101. Also, the storing wireless module m1101, when executed and/or activated, will direct performance of and/or performs the operation o11. In an implementation, the electronically storing electrical circuitry arrangement e11, when activated performs electronically storing (e.g. from wifi, from laptop entry, from RFID scan, etc.) grocery operations information (e.g. AVI file format, MP3 file format, audio listening, etc.) regarding at least in part (e.g. associated, affected, affecting, etc.) one or more grocery implementation aspects (e.g. organic produce delivery schedule, cost of labor, record keeping methods, etc.) pertaining to (e.g. associated, affected, affecting, etc.) grocery related merchandizing of (e.g. fine dining grocery item preparation, fast food grocery item preparation, family buffet grocery item preparation, etc.) one or more commercial grocery products (e.g. beef main course grocery item, pork main course grocery item, fish main course grocery item, etc.). Also, the electronically storing module m11, when executed and/or activated, will direct performance of and/or perform the operation o11. In an implementation, the electronically storing grocery operations information regarding at least in part one or more grocery implementation aspects pertaining to grocery related merchandizing of one or more commercial grocery products is carried out by electronically storing (e.g. from wifi, from laptop entry, from RFID scan, etc.) grocery operations information (e.g. AVI file format, MP3 file format, audio listening, etc.) regarding at least in part (e.g. associated, affected, affecting, etc.) one or more grocery implementation aspects (e.g. organic produce delivery schedule, cost of labor, record keeping methods, etc.) pertaining to (e.g. associated, affected, affecting, etc.) grocery related merchandizing of (e.g. fine dining grocery item preparation, fast food grocery item preparation, family buffet grocery item preparation, etc.) one or more commercial grocery products (e.g. beef main course grocery item, pork main course grocery item, fish main course grocery item, etc.). For example, in one embodiment information associated with shipment route, transit time, delivery location, delivery time, inventory storage location, shelf location, shelf time, and/or persons involved thereof, with respect to a produce item, can be obtained and stored in an electronic location. Furthering the example, a potential consumer of the produce item can scan a tag associated with the produce item while at a grocery store to obtain at least some of the aforementioned information using a smart phone, which information can support a decision as to whether or not to purchase the produce item. As another example, upon checkout location at a grocery store, any of the above referenced information may be evaluated to determine whether or not a minimum or maximum value defined by the consumer has been violated (e.g., max storage shelf time or max time in temperatures exceeding 70 degrees Fahrenheit). If a violation has been found, the consumer can be alerted and such offending item can be removed from any purchase. As a further example, if a deli worker at a grocery store has been diagnosed with a contagious condition, as provided by a health authority, all products handled by the deli worker, as provided by a grocery store, for a predetermined period of time prior to the diagnosis may be identified. Information can then be recorded against those products to alert potential consumers as to any potential risks associated with handling and/or consumption.

Figure 28:
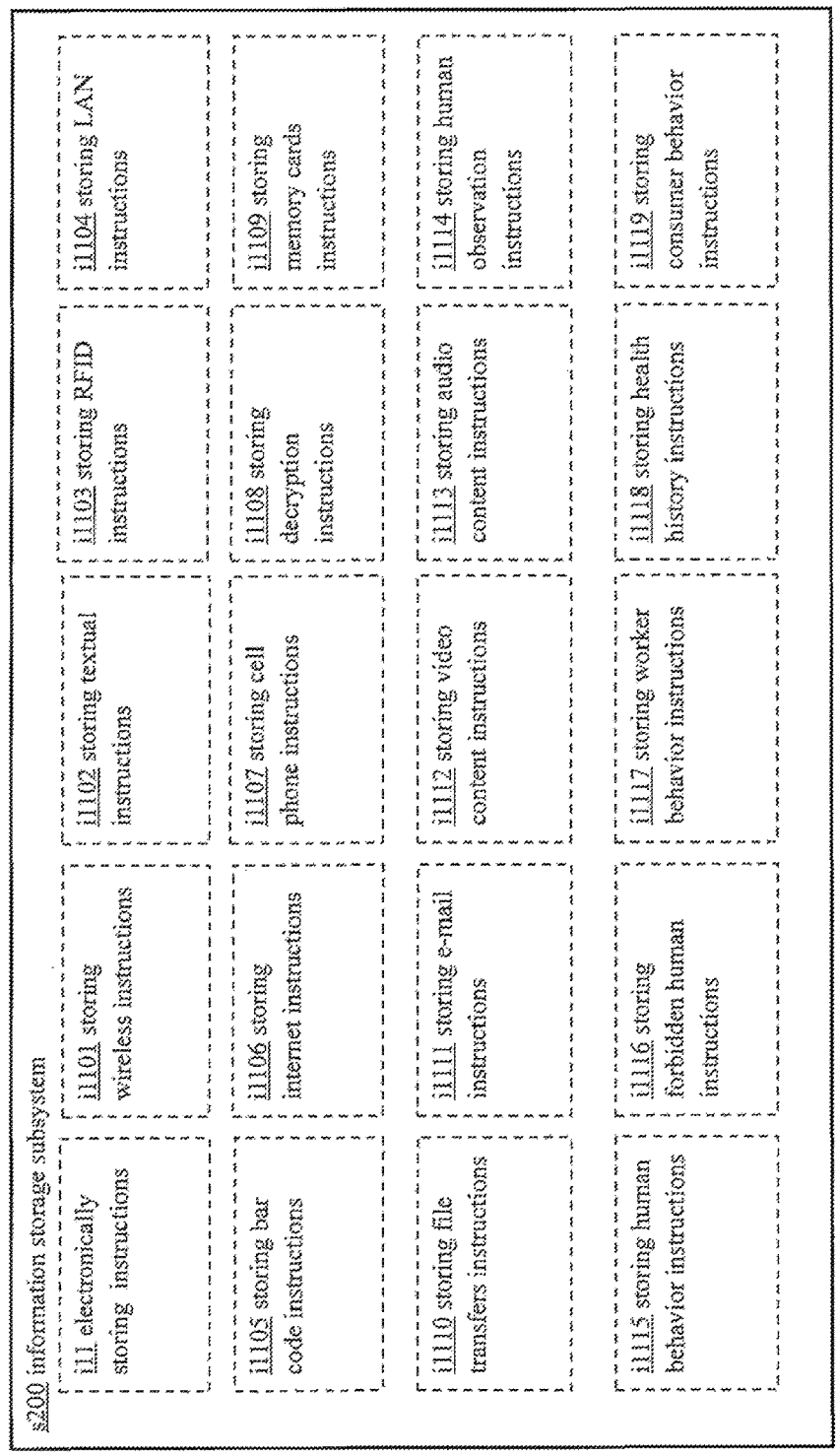
FIG. 28 is a block diagram depicting one or more exemplary instructions of the information storage subsystem s200 of the grocery information system 10 of FIG. 1.
Figure 43:
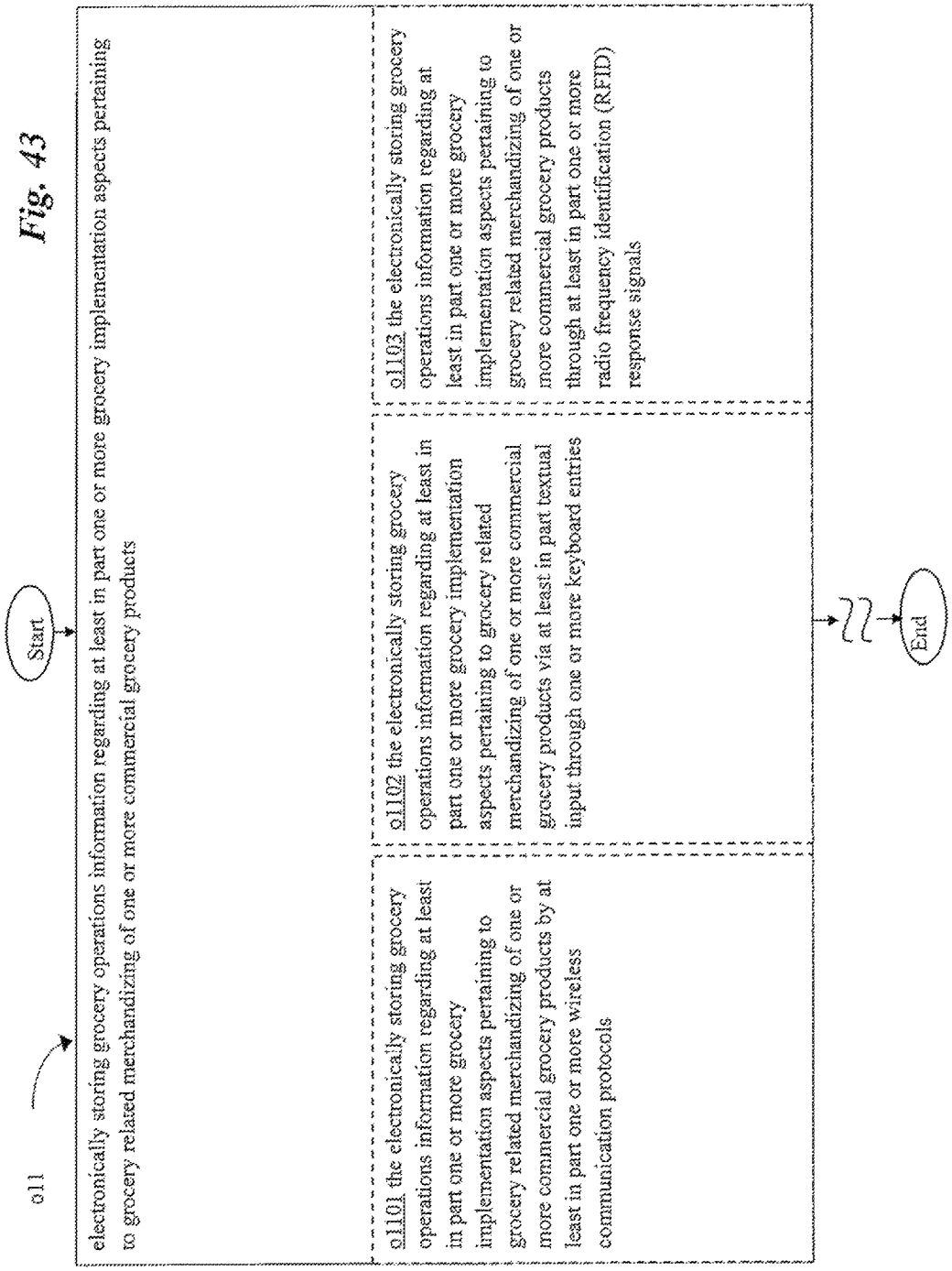
FIG. 43 is a high-level flowchart including exemplary implementations of operation o11 of FIG. 42.

In one or more implementations, as shown in FIG. 43, operation o11 includes an operation o1101 for the electronically storing grocery operations information regarding at least in part one or more grocery implementation aspects pertaining to grocery related merchandizing of one or more commercial grocery products by at least in part one or more wireless communication protocols. Origination of an illustratively derived storing wireless component group can be accomplished through skilled in the art design choice selection of one or more of the above depicted components from one or more of the above depicted subsystems shown in FIG. 12. Components from the storing wireless component group can be used in implementing execution of the one or more storing wireless instructions i1101 of FIG. 28, can be used in performance of the storing wireless electrical circuitry arrangement e1101 of FIG. 21, and/or can be used in otherwise fulfillment of the operation o1101. An exemplary non-transitory signal bearing medium version of the information storage subsystem s200 is depicted in FIG. 28 as bearing the one or more storing wireless instructions i1101 that when executed will direct performance of the operation o1101. Furthermore, the storing wireless electrical circuitry arrangement ("elec circ arrange") e1101, when activated, will perform the operation o1101. Also, the storing wireless module m1101, when executed and/or activated, will direct performance of and/or perform the operation o1101. For instance, in one or more exemplary implementations, the one or more storing wireless instructions i1101, when executed, direct performance of the operation o1101 in the illustrative depiction as follows, and/or the storing wireless electrical circuitry arrangement e1101, when activated, performs the operation o1101 in the illustrative depiction as follows, and/or the storing wireless module m1101, when executed and/or activated, directs performance of and/or performs the operation o1101 in the illustrative depiction as follows, and/or the operation o1101 is otherwise carried out in the illustrative depiction as follows: the electronically storing (e.g. from wifi, etc.) grocery operations information (e.g. AVI file format, etc.) regarding at least in part (e.g. associated, etc.) one or more grocery implementation aspects (e.g. organic produce delivery schedule, etc.) pertaining to (e.g. associated, etc.) grocery related merchandizing of (e.g. fine dining grocery item preparation, etc.) one or more commercial grocery products (e.g. beef main course grocery item, etc.) by at least in part one or more wireless communication protocols (e.g. wifi, etc.).

In one or more implementations, as shown in FIG. 43, operation o11 includes an operation o1102 for the electronically storing grocery operations information regarding at least in part one or more grocery implementation aspects pertaining to grocery related merchandizing of one or more commercial grocery products via at least in part textual input through one or more keyboard entries. Origination of an illustratively derived storing textual component group can be accomplished through skilled in the art design choice selection of one or more of the above depicted components from one or more of the above depicted subsystems shown in FIG. 12. Components from the storing textual component group can be used in implementing execution of the one or more storing textual instructions i1102 of FIG. 28, can be used in performance of the storing textual electrical circuitry arrangement e1102 of FIG. 21, and/or can be used in otherwise fulfillment of the operation o1102. An exemplary non-transitory signal bearing medium version of the information storage subsystem s200 is depicted in FIG. 28 as bearing the one or more storing textual instructions i1102 that when executed will direct performance of the operation o1102. Furthermore, the storing textual electrical circuitry arrangement ("elec circ arrange") e1102, when activated, will perform the operation o1102. Also, the storing textual module m1102, when executed and/or activated, will direct performance of and/or perform the operation o1102. For instance, in one or more exemplary implementations, the one or more storing textual instructions i1102, when executed, direct performance of the operation o1102 in the illustrative depiction as follows, and/or the storing textual electrical circuitry arrangement e1102, when activated, performs the operation o1102 in the illustrative depiction as follows, and/or the storing textual module m1102, when executed and/or activated, directs performance of and/or performs the operation o1102 in the illustrative depiction as follows, and/or the operation o1102 is otherwise carried out in the illustrative depiction as follows: the electronically storing (e.g. from laptop entry, etc.) grocery operations information (e.g. MP3 file format, etc.) regarding at least in part (e.g. affected, etc.) one or more grocery implementation aspects (e.g. cost of labor, etc.) pertaining to (e.g. affected, etc.) grocery related merchandizing of (e.g. fast food grocery item preparation, etc.) one or more commercial grocery products (e.g. pork main course grocery item, etc.) via at least in part textual input through one or more keyboard entries (e.g. laptop entry, etc.).

In one or more implementations, as shown in FIG. 43, operation o11 includes an operation o1103 for the electronically storing grocery operations information regarding at least in part one or more grocery implementation aspects pertaining to grocery related merchandizing of one or more commercial grocery products through at least in part one or more radio frequency identification (RFID) response signals. Origination of an illustratively derived storing RFID component group can be accomplished through skilled in the art design choice selection of one or more of the above depicted components from one or more of the above depicted subsystems shown in FIG. 12. Components from the storing RFID component group can be used in implementing execution of the one or more storing RFID instructions i1103 of FIG. 28, can be used in performance of the storing RFID electrical circuitry arrangement e1103 of FIG. 21, and/or can be used in otherwise fulfillment of the operation o1103. An exemplary non-transitory signal bearing medium version of the information storage subsystem s200 is depicted in FIG. 28 as bearing the one or more storing RFID instructions i1103 that when executed will direct performance of the operation o1103. Furthermore, the storing RFID electrical circuitry arrangement ("elec circ arrange") e1103, when activated, will perform the operation o1103. Also, the storing RFID module m1103, when executed and/or activated, will direct performance of and/or perform the operation o1103. For instance, in one or more exemplary implementations, the one or more storing RFID instructions i1103, when executed, direct performance of the operation o1103 in the illustrative depiction as follows, and/or the storing RFID electrical circuitry arrangement e1103, when activated, performs the operation o1103 in the illustrative depiction as follows, and/or the storing RFID module m1103, when executed and/or activated, directs performance of and/or performs the operation o1103 in the illustrative depiction as follows, and/or the operation o1103 is otherwise carried out in the illustrative depiction as follows: the electronically storing (e.g. from RFID scan, etc.) grocery operations information (e.g. audio listening, etc.) regarding at least in part (e.g. affecting, etc.) one or more grocery implementation aspects (e.g. record keeping methods, etc.) pertaining to (e.g. affecting, etc.) grocery related merchandizing of (e.g. family buffet grocery item preparation, etc.) one or more commercial grocery products (e.g. fish main course grocery item, etc.) through at least in part one or more radio frequency identification (RFID) response signals (e.g. RFID scan, etc.).

Figure 44:
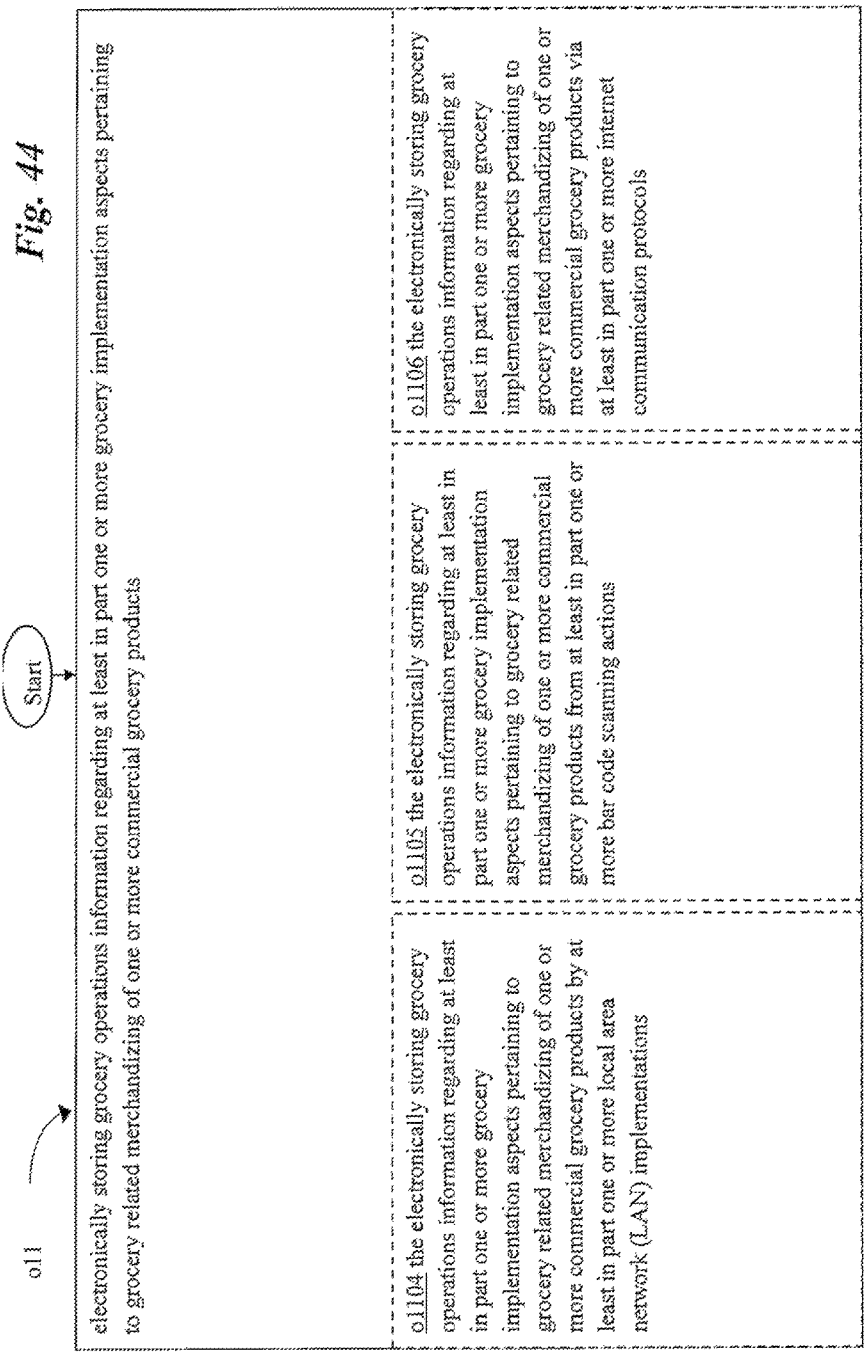
FIG. 44 is a high-level flowchart including exemplary implementations of operation o11 of FIG. 42.

In one or more implementations, as shown in FIG. 44, operation o11 includes an operation o1104 for the electronically storing grocery operations information regarding at least in part one or more grocery implementation aspects pertaining to grocery related merchandizing of one or more commercial grocery products by at least in part one or more local area network (LAN) implementations. Origination of an illustratively derived storing LAN component group can be accomplished through skilled in the art design choice selection of one or more of the above depicted components from one or more of the above depicted subsystems shown in FIG. 12. Components from the storing LAN component group can be used in implementing execution of the one or more storing LAN instructions i1104 of FIG. 28, can be used in performance of the storing LAN electrical circuitry arrangement e1104 of FIG. 21, and/or can be used in otherwise fulfillment of the operation o1104. An exemplary non-transitory signal bearing medium version of the information storage subsystem s200 is depicted in FIG. 28 as bearing the one or more storing LAN instructions i1104 that when executed will direct performance of the operation o1104. Furthermore, the storing LAN electrical circuitry arrangement ("elec circ arrange") e1104, when activated, will perform the operation o1104. Also, the storing LAN module m1104, when executed and/or activated, will direct performance of and/or perform the operation o1104. For instance, in one or more exemplary implementations, the one or more storing LAN instructions i1104, when executed, direct performance of the operation o1104 in the illustrative depiction as follows, and/or the storing LAN electrical circuitry arrangement e1104, when activated, performs the operation o1104 in the illustrative depiction as follows, and/or the storing LAN module m1104, when executed and/or activated, directs performance of and/or performs the operation o1104 in the illustrative depiction as follows, and/or the operation o1104 is otherwise carried out in the illustrative depiction as follows: the electronically storing (e.g. from ethernet, etc.) grocery operations information (e.g. disobeying safety protocols, etc.) regarding at least in part (e.g. argue, etc.) one or more grocery implementation aspects (e.g. certification deadlines, etc.) pertaining to (e.g. argue, etc.) grocery related merchandizing of (e.g. mobile catering grocery item preparation, etc.) one or more commercial grocery products (e.g. tofu main course grocery item, etc.) by at least in part one or more local area network (LAN) implementations (e.g. ethernet, etc.).

In one or more implementations, as shown in FIG. 44, operation o11 includes an operation o1105 for the electronically storing grocery operations information regarding at least in part one or more grocery implementation aspects pertaining to grocery related merchandizing of one or more commercial grocery products from at least in part one or more bar code scanning actions. Origination of an illustratively derived storing bar code component group can be accomplished through skilled in the art design choice selection of one or more of the above depicted components from one or more of the above depicted subsystems shown in FIG. 12. Components from the storing bar code component group can be used in implementing execution of the one or more storing bar code instructions i1105 of FIG. 28, can be used in performance of the storing bar code electrical circuitry arrangement e1105 of FIG. 21, and/or can be used in otherwise fulfillment of the operation o1105. An exemplary non-transitory signal bearing medium version of the information storage subsystem s200 is depicted in FIG. 28 as bearing the one or more storing bar code instructions i1105 that when executed will direct performance of the operation o1105. Furthermore, the storing bar code electrical circuitry arrangement ("elec circ arrange") e1105, when activated, will perform the operation o1105. Also, the storing bar code module m1105, when executed and/or activated, will direct performance of and/or perform the operation o1105. For instance, in one or more exemplary implementations, the one or more storing bar code instructions i1105, when executed, direct performance of the operation o1105 in the illustrative depiction as follows, and/or the storing bar code electrical circuitry arrangement e1105, when activated, performs the operation o1105 in the illustrative depiction as follows, and/or the storing bar code module m1105, when executed and/or activated, directs performance of and/or performs the operation o1105 in the illustrative depiction as follows, and/or the operation o1105 is otherwise carried out in the illustrative depiction as follows: the electronically storing (e.g. from UPC scan, etc.) grocery operations information (e.g. preparation rates of grocery items, etc.) regarding at least in part (e.g. connected, etc.) one or more grocery implementation aspects (e.g. types of grocery items on order, etc.) pertaining to (e.g. connected, etc.) grocery related merchandizing of (e.g. institutional grocery item preparation, etc.) one or more commercial grocery products (e.g. chicken main course grocery item, etc.) from at least in part one or more bar code scanning actions (e.g. UPC scan, etc.).

In one or more implementations, as shown in FIG. 44, operation o11 includes an operation o1106 for the electronically storing grocery operations information regarding at least in part one or more grocery implementation aspects pertaining to grocery related merchandizing of one or more commercial grocery products via at least in part one or more internet communication protocols. Origination of an illustratively derived storing internet component group can be accomplished through skilled in the art design choice selection of one or more of the above depicted components from one or more of the above depicted subsystems shown in FIG. 12. Components from the storing internet component group can be used in implementing execution of the one or more storing internet instructions i1106 of FIG. 28, can be used in performance of the storing internet electrical circuitry arrangement e1106 of FIG. 21, and/or can be used in otherwise fulfillment of the operation o1106. An exemplary non-transitory signal bearing medium version of the information storage subsystem s200 is depicted in FIG. 28 as bearing the one or more storing internet instructions i1106 that when executed will direct performance of the operation o1106. Furthermore, the storing internet electrical circuitry arrangement ("elec circ arrange") e1106, when activated, will perform the operation o1106. Also, the storing internet module m1106, when executed and/or activated, will direct performance of and/or perform the operation o1106. For instance, in one or more exemplary implementations, the one or more storing internet instructions i1106, when executed, direct performance of the operation o1106 in the illustrative depiction as follows, and/or the storing internet electrical circuitry arrangement e1106, when activated, performs the operation o1106 in the illustrative depiction as follows, and/or the storing internet module m1106, when executed and/or activated, directs performance of and/or performs the operation o1106 in the illustrative depiction as follows, and/or the operation o1106 is otherwise carried out in the illustrative depiction as follows: the electronically storing (e.g. from HTML code, etc.) grocery operations information (e.g. food poisoning reports, etc.) regarding at least in part (e.g. commit to, etc.) one or more grocery implementation aspects (e.g. banned grocery handling practices, etc.) pertaining to (e.g. commit to, etc.) grocery related merchandizing of (e.g. school cafeteria grocery item preparation, etc.) one or more commercial grocery products (e.g.

seafood main course grocery item, etc.) via at least in part one or more internet communication protocols (e.g. HTML code, etc.).

Figure 45:
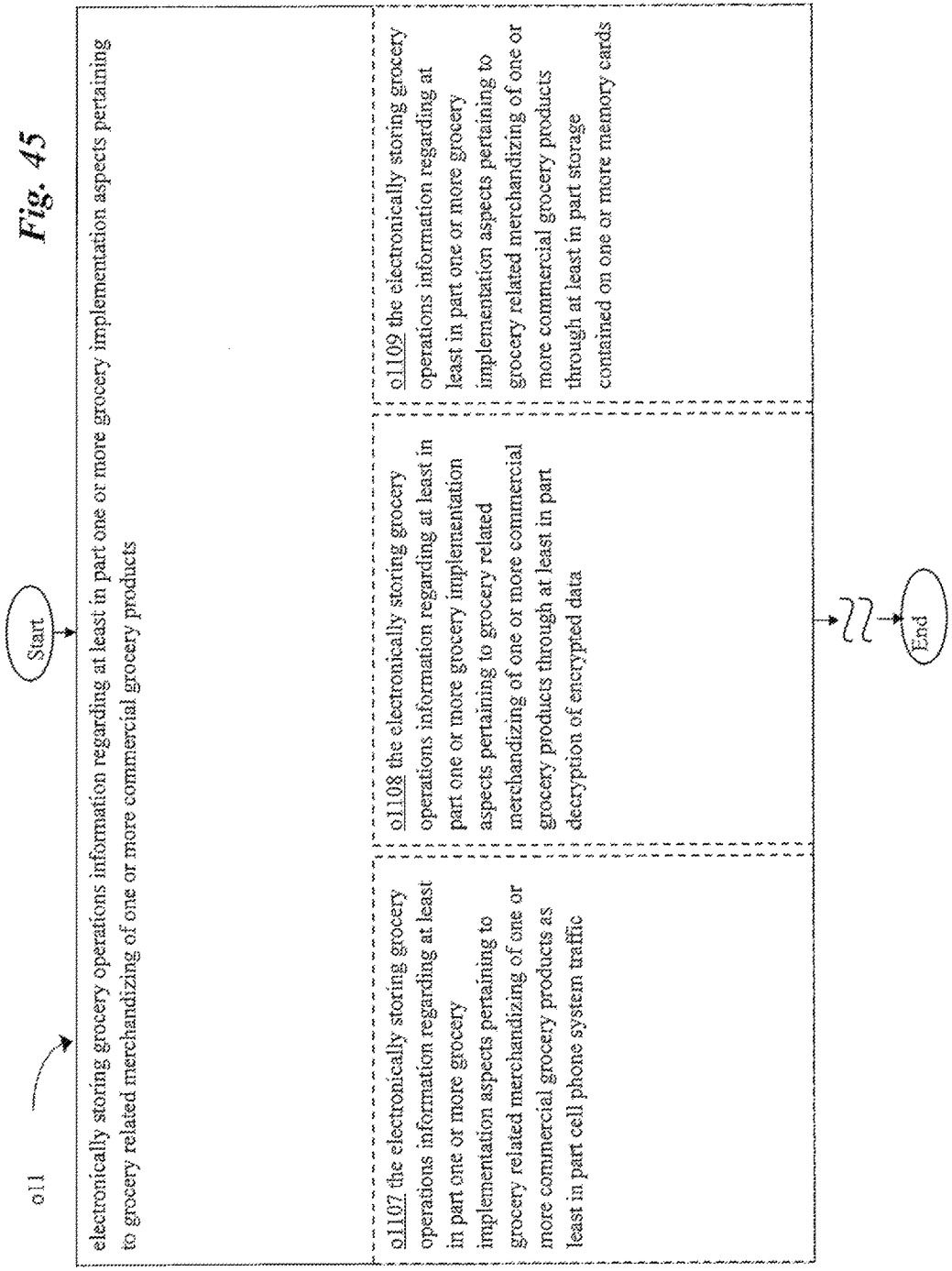
FIG. 45 is a high-level flowchart including exemplary implementations of operation o11 of FIG. 42.

In one or more implementations, as shown in FIG. 45, operation o11 includes an operation o1107 for the electronically storing grocery operations information regarding at least in part one or more grocery implementation aspects pertaining to grocery related merchandizing of one or more commercial grocery products as least in part cell phone system traffic. Origination of an illustratively derived storing cell phone component group can be accomplished through skilled in the art design choice selection of one or more of the above depicted components from one or more of the above depicted subsystems shown in FIG. 12. Components from the storing cell phone component group can be used in implementing execution of the one or more storing cell phone instructions i1107 of FIG. 28, can be used in performance of the storing cell phone electrical circuitry arrangement e1107 of FIG. 21, and/or can be used in otherwise fulfillment of the operation o1107. An exemplary non-transitory signal bearing medium version of the information storage subsystem s200 is depicted in FIG. 28 as bearing the one or more storing cell phone instructions i1107 that when executed will direct performance of the operation o1107. Furthermore, the storing cell phone electrical circuitry arrangement ("elec circ arrange") e1107, when activated, will perform the operation o1107. Also, the storing cell phone module m1107, when executed and/or activated, will direct performance of and/or perform the operation o1107. For instance, in one or more exemplary implementations, the one or more storing cell phone instructions i1107, when executed, direct performance of the operation o1107 in the illustrative depiction as follows, and/or the storing cell phone electrical circuitry arrangement e1107, when activated, performs the operation o1107 in the illustrative depiction as follows, and/or the storing cell phone module m1107, when executed and/or activated, directs performance of and/or performs the operation o1107 in the illustrative depiction as follows, and/or the operation o1107 is otherwise carried out in the illustrative depiction as follows: the electronically storing (e.g. from MMS, etc.) grocery operations information (e.g. worker illness reports, etc.) regarding at least in part (e.g. absorbed by, etc.) one or more grocery implementation aspects (e.g. amount of seasonal grocery customer traffic, etc.) pertaining to (e.g. absorbed by, etc.) grocery related merchandizing of (e.g. nursing home grocery item preparation, etc.) one or more commercial grocery products (e.g. poultry main course grocery item, etc.) as least in part cell phone system traffic (e.g. MMS, etc.).

In one or more implementations, as shown in FIG. 45, operation o11 includes an operation o1108 for the electronically storing grocery operations information regarding at least in part one or more grocery implementation aspects pertaining to grocery related merchandizing of one or more commercial grocery products through at least in part decryption of encrypted data. Origination of an illustratively derived storing decryption component group can be accomplished through skilled in the art design choice selection of one or more of the above depicted components from one or more of the above depicted subsystems shown in FIG. 12. Components from the storing decryption component group can be used in implementing execution of the one or more storing decryption instructions i1108 of FIG. 28, can be used in performance of the storing decryption electrical circuitry arrangement e1108 of FIG. 21, and/or can be used in otherwise fulfillment of the operation o1108. An exemplary non-transitory signal bearing medium version of the information storage subsystem s200 is depicted in FIG. 28 as bearing the one or more storing decryption instructions i1108 that when executed will direct performance of the operation o1108. Furthermore, the storing decryption electrical circuitry arrangement ("elec circ arrange") e1108, when activated, will perform the operation o1108. Also, the storing decryption module m1108, when executed and/or activated, will direct performance of and/or perform the operation o1108. For instance, in one or more exemplary implementations, the one or more storing decryption instructions i1108, when executed, direct performance of the operation o1108 in the illustrative depiction as follows, and/or the storing decryption electrical circuitry arrangement e1108, when activated, performs the operation o1108 in the illustrative depiction as follows, and/or the storing decryption module m1108, when executed and/or activated, directs performance of and/or performs the operation o1108 in the illustrative depiction as follows, and/or the operation o1108 is otherwise carried out in the illustrative depiction as follows: the electronically storing (e.g. as 256-bit AES, etc.) grocery operations information (e.g. customer occupancy rates, etc.) regarding at least in part (e.g. embraced by, etc.) one or more grocery implementation aspects (e.g. predicted amounts of revenue from particular grocery items, etc.) pertaining to (e.g. embraced by, etc.) grocery related merchandizing of (e.g. street vendor grocery item preparation, etc.) one or more commercial grocery products (e.g. diary main course grocery item, etc.) through at least in part decryption of encrypted data (e.g. 256-bit AES, etc.).

In one or more implementations, as shown in FIG. 45, operation o11 includes an operation o1109 for the electronically storing grocery operations information regarding at least in part one or more grocery implementation aspects pertaining to grocery related merchandizing of one or more commercial grocery products through at least in part storage contained on one or more memory cards. Origination of an illustratively derived storing memory cards component group can be accomplished through skilled in the art design choice selection of one or more of the above depicted components from one or more of the above depicted subsystems shown in FIG. 12. Components from the storing memory cards component group can be used in implementing execution of the one or more storing memory cards instructions i1109 of FIG. 28, can be used in performance of the storing memory cards electrical circuitry arrangement e1109 of FIG. 21, and/or can be used in otherwise fulfillment of the operation o1109. An exemplary non-transitory signal bearing medium version of the information storage subsystem s200 is depicted in FIG. 28 as bearing the one or more storing memory cards instructions i1109 that when executed will direct performance of the operation o1109. Furthermore, the storing memory cards electrical circuitry arrangement ("elec circ arrange") e1109, when activated, will perform the operation o1109. Also, the storing memory cards module m1109, when executed and/or activated, will direct performance of and/or perform the operation o1109. For instance, in one or more exemplary implementations, the one or more storing memory cards instructions i1109, when executed, direct performance of the operation o1109 in the illustrative depiction as follows, and/or the storing memory cards electrical circuitry arrangement e1109, when activated, performs the operation o1109 in the illustrative depiction as follows, and/or the storing memory cards module m1109, when executed and/or activated, directs performance of and/or performs the operation o1109 in the illustrative depiction as follows, and/or the operation o1109 is otherwise carried out in the illustrative depiction as follows:

the electronically storing (e.g. onto compact flash, etc.) grocery operations information (e.g. total customer expenditures, etc.) regarding at least in part (e.g. containing, etc.) one or more grocery implementation aspects (e.g. fluctuations in workforce at, etc.) pertaining to (e.g. containing, etc.) grocery related merchandizing of (e.g. mobile kitchen grocery item preparation, etc.) one or more commercial grocery products (e.g. vegetarian main course grocery item, etc.) through at least in part storage contained on one or more memory cards (e.g. compact flash, etc.).

Figure 46:
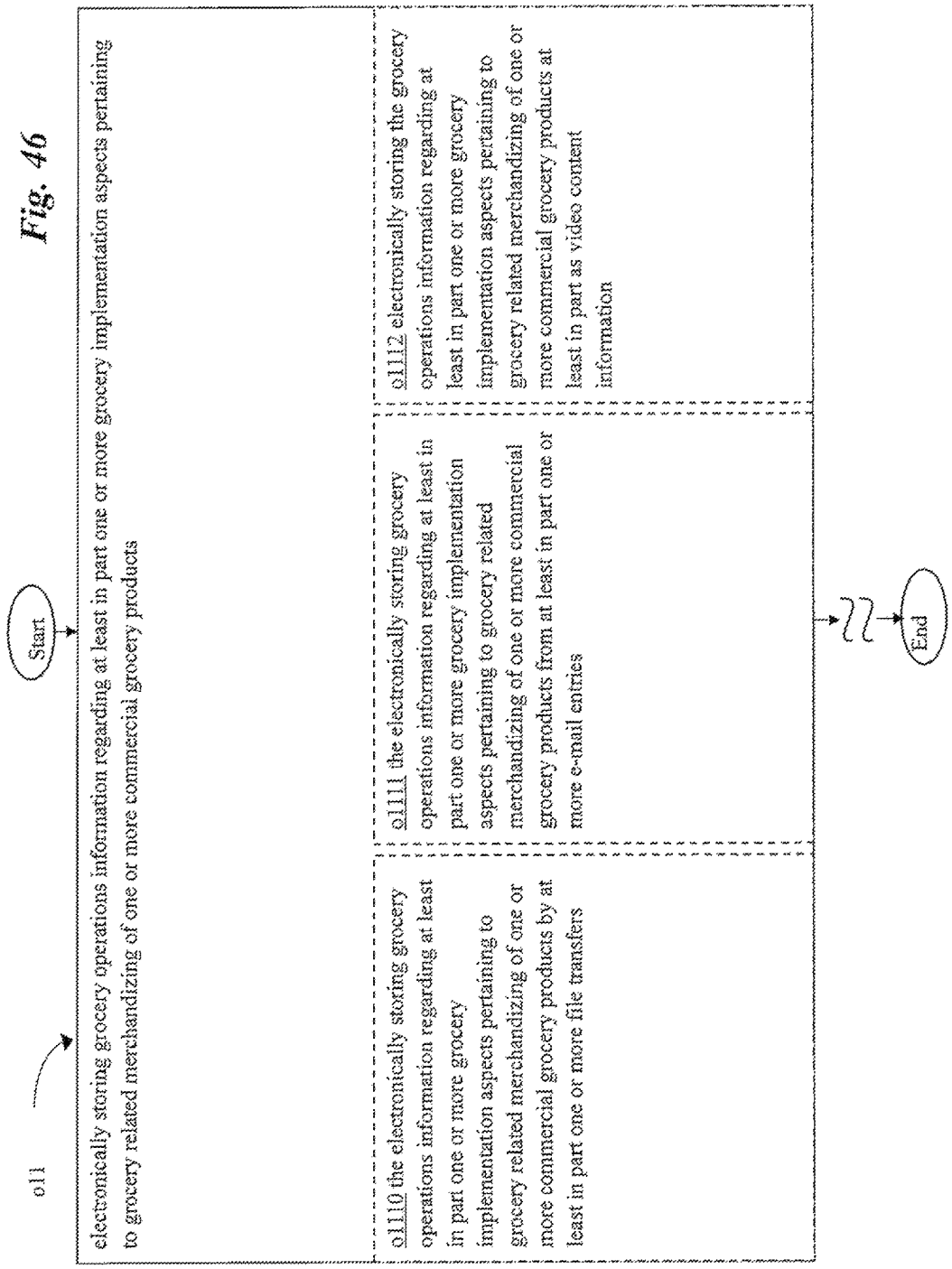
FIG. 46 is a high-level flowchart including exemplary implementations of operation o11 of FIG. 42.

In one or more implementations, as shown in FIG. 46, operation o11 includes an operation o1110 for the electronically storing grocery operations information regarding at least in part one or more grocery implementation aspects pertaining to grocery related merchandizing of one or more commercial grocery products by at least in part one or more file transfers. Origination of an illustratively derived storing file transfers component group can be accomplished through skilled in the art design choice selection of one or more of the above depicted components from one or more of the above depicted subsystems shown in FIG. 12. Components from the storing file transfers component group can be used in implementing execution of the one or more storing file transfers instructions i1110 of FIG. 28, can be used in performance of the storing file transfers electrical circuitry arrangement e1110 of FIG. 21, and/or can be used in otherwise fulfillment of the operation o1110. An exemplary non-transitory signal bearing medium version of the information storage subsystem s200 is depicted in FIG. 28 as bearing the one or more storing file transfers instructions i1110 that when executed will direct performance of the operation o1110. Furthermore, the storing file transfers electrical circuitry arrangement ("elec circ arrange") e1110, when activated, will perform the operation o1110. Also, the storing file transfers module m1110, when executed and/or activated, will direct performance of and/or perform the operation o1110. For instance, in one or more exemplary implementations, the one or more storing file transfers instructions i1110, when executed, direct performance of the operation o1110 in the illustrative depiction as follows, and/or the storing file transfers electrical circuitry arrangement e1110, when activated, performs the operation o1110 in the illustrative depiction as follows, and/or the storing file transfers module m1110, when executed and/or activated, directs performance of and/or performs the operation o1110 in the illustrative depiction as follows, and/or the operation o1110 is otherwise carried out in the illustrative depiction as follows: the electronically storing (e.g. via push-based, etc.) grocery operations information (e.g. average shelf life of produce used, etc.) regarding at least in part (e.g. engaging, etc.) one or more grocery implementation aspects (e.g. cost factors for labor, etc.) pertaining to (e.g. engaging, etc.) grocery related merchandizing of (e.g. hospital grocery item preparation, etc.) one or more commercial grocery products (e.g. salad main course grocery item, etc.) by at least in part one or more file transfers (e.g. push-based, etc.).

In one or more implementations, as shown in FIG. 46, operation o11 includes an operation o1111 for the electronically storing grocery operations information regarding at least in part one or more grocery implementation aspects pertaining to grocery related merchandizing of one or more commercial grocery products from at least in part one or more e-mail entries. Origination of an illustratively derived storing e-mail component group can be accomplished through skilled in the art design choice selection of one or more of the above depicted components from one or more of the above depicted subsystems shown in FIG. 12. Components from the storing e-mail component group can be used in implementing execution of the one or more storing e-mail instructions i1111 of FIG. 28, can be used in performance of the storing e-mail electrical circuitry arrangement e1111 of FIG. 21, and/or can be used in otherwise fulfillment of the operation o1111. An exemplary non-transitory signal bearing medium version of the information storage subsystem s200 is depicted in FIG. 28 as bearing the one or more storing e-mail instructions i1111 that when executed will direct performance of the operation o1111. Furthermore, the storing e-mail electrical circuitry arrangement ("elec circ arrange") e1111, when activated, will perform the operation o1111. Also, the storing e-mail module m1111, when executed and/or activated, will direct performance of and/or perform the operation o1111. For instance, in one or more exemplary implementations, the one or more storing e-mail instructions i1111, when executed, direct performance of the operation o1111 in the illustrative depiction as follows, and/or the storing e-mail electrical circuitry arrangement e1111, when activated, performs the operation o1111 in the illustrative depiction as follows, and/or the storing e-mail module m1111, when executed and/or activated, directs performance of and/or performs the operation o1111 in the illustrative depiction as follows, and/or the operation o1111 is otherwise carried out in the illustrative depiction as follows: the electronically storing (e.g. onto SMTP server, etc.) grocery operations information (e.g. worker accident reports, etc.) regarding at least in part (e.g. engaged by, etc.) one or more grocery implementation aspects (e.g. shipping costs incurred, etc.) pertaining to (e.g. engaged by, etc.) grocery related merchandizing of (e.g. deli department grocery item preparation, etc.) one or more commercial grocery products (e.g. grain main course grocery item, etc.) from at least in part one or more e-mail entries (e.g. SMTP server, etc.).

In one or more implementations, as shown in FIG. 46, operation o11 includes an operation o1112 for electronically storing the grocery operations information regarding at least in part one or more grocery implementation aspects pertaining to grocery related merchandizing of one or more commercial grocery products at least in part as video content information. Origination of an illustratively derived storing video content component group can be accomplished through skilled in the art design choice selection of one or more of the above depicted components from one or more of the above depicted subsystems shown in FIG. 12. Components from the storing video content component group can be used in implementing execution of the one or more storing video content instructions i1112 of FIG. 28, can be used in performance of the storing video content electrical circuitry arrangement e1112 of FIG. 21, and/or can be used in otherwise fulfillment of the operation o1112. An exemplary non-transitory signal bearing medium version of the information storage subsystem s200 is depicted in FIG. 28 as bearing the one or more storing video content instructions i1112 that when executed will direct performance of the operation o1112. Furthermore, the storing video content electrical circuitry arrangement ("elec circ arrange") e1112, when activated, will perform the operation o1112. Also, the storing video content module m1112, when executed and/or activated, will direct performance of and/or perform the operation o1112. For instance, in one or more exemplary implementations, the one or more storing video content instructions i1112, when executed, direct performance of the operation o1112 in the illustrative depiction as follows, and/or the storing video content electrical circuitry arrangement e1112, when activated, performs the operation o1112 in the illustrative depiction as follows, and/or the storing video content module m1112, when executed and/or activated, directs performance of and/or performs the operation o1112 in the illustrative depiction as follows, and/or the operation o1112 is otherwise carried out in the illustrative depiction as follows: electronically storing (e.g. from radio wave, etc.) the grocery operations information (e.g. duration of time required to store received stock in refrigeration, etc.) regarding at least in part (e.g. incorporating, etc.) one or more grocery implementation aspects (e.g. shipping schedules involved with grocery items received by various wholesalers or farms, etc.) pertaining to (e.g. incorporating, etc.) grocery related merchandizing of (e.g. fine dining grocery item sales, etc.) one or more commercial grocery products (e.g. bean main course grocery item, etc.) at least in part as video content information (e.g. video content of workers receiving shipments, etc.).

Figure 47:
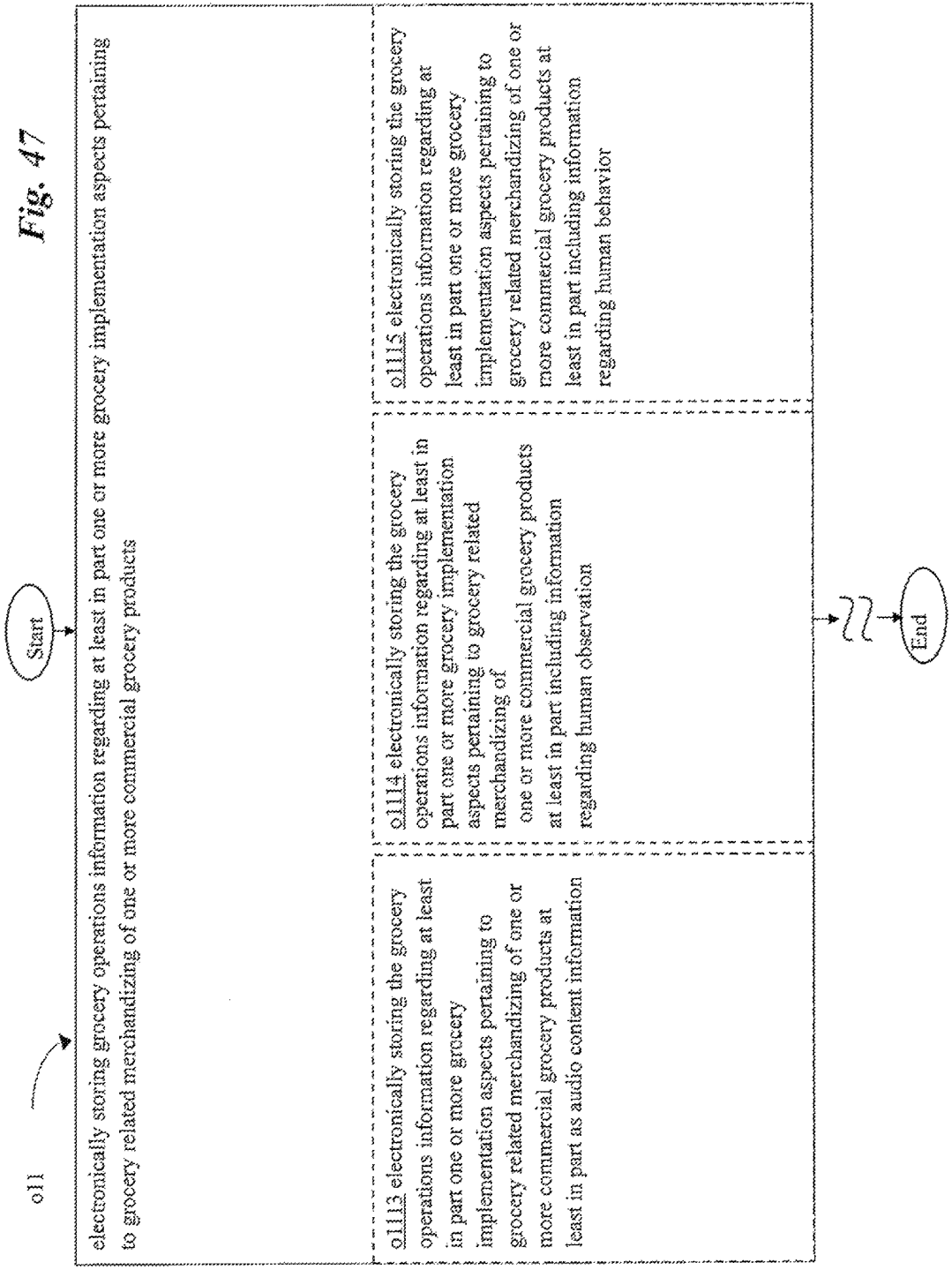
FIG. 47 is a high-level flowchart including exemplary implementations of operation o11 of FIG. 42.

In one or more implementations, as shown in FIG. 47, operation o11 includes an operation o1113 for electronically storing the grocery operations information regarding at least in part one or more grocery implementation aspects pertaining to grocery related merchandizing of one or more commercial grocery products at least in part as audio content information. Origination of an illustratively derived storing audio content component group can be accomplished through skilled in the art design choice selection of one or more of the above depicted components from one or more of the above depicted subsystems shown in FIG. 12. Components from the storing audio content component group can be used in implementing execution of the one or more storing audio content instructions i1113 of FIG. 28, can be used in performance of the storing audio content electrical circuitry arrangement e1113 of FIG. 21, and/or can be used in otherwise fulfillment of the operation o1113. An exemplary non-transitory signal bearing medium version of the information storage subsystem s200 is depicted in FIG. 28 as bearing the one or more storing audio content instructions i1113 that when executed will direct performance of the operation o1113. Furthermore, the storing audio content electrical circuitry arrangement ("elec circ arrange") e1113, when activated, will perform the operation o1113. Also, the storing audio content module m1113, when executed and/or activated, will direct performance of and/or perform the operation o1113. For instance, in one or more exemplary implementations, the one or more storing audio content instructions i1113, when executed, direct performance of the operation o1113 in the illustrative depiction as follows, and/or the storing audio content electrical circuitry arrangement e1113, when activated, performs the operation o1113 in the illustrative depiction as follows, and/or the storing audio content module m1113, when executed and/or activated, directs performance of and/or performs the operation o1113 in the illustrative depiction as follows, and/or the operation o1113 is otherwise carried out in the illustrative depiction as follows: electronically storing (e.g. from infra-red, etc.) the grocery operations information (e.g. WAV file format, etc.) regarding at least in part (e.g. engrossing, etc.) one or more grocery implementation aspects (e.g. known pandemic status, etc.) pertaining to (e.g. engrossing, etc.) grocery related merchandizing of (e.g. fast grocery item sales, etc.) one or more commercial grocery products (e.g. cooked main course grocery item, etc.) at least in part as audio content information (e.g. WAV file format, etc.).

In one or more implementations, as shown in FIG. 47, operation o11 includes an operation o1114 for electronically storing the grocery operations information regarding at least in part one or more grocery implementation aspects pertaining to grocery related merchandizing of one or more commercial grocery products at least in part including information regarding human observation. Origination of an illustratively derived storing human observation component group can be accomplished through skilled in the art design choice selection of one or more of the above depicted components from one or more of the above depicted subsystems shown in FIG. 12. Components from the storing human observation component group can be used in implementing execution of the one or more storing human observation instructions i1114 of FIG. 28, can be used in performance of the storing human observation electrical circuitry arrangement e1114 of FIG. 21, and/or can be used in otherwise fulfillment of the operation o1114. An exemplary non-transitory signal bearing medium version of the information storage subsystem s200 is depicted in FIG. 28 as bearing the one or more storing human observation instructions i1114 that when executed will direct performance of the operation o1114. Furthermore, the storing human observation electrical circuitry arrangement ("elec circ arrange") e1114, when activated, will perform the operation o1114. Also, the storing human observation module m1114, when executed and/or activated, will direct performance of and/or perform the operation o1114. For instance, in one or more exemplary implementations, the one or more storing human observation instructions i1114, when executed, direct performance of the operation o1114 in the illustrative depiction as follows, and/or the storing human observation electrical circuitry arrangement e1114, when activated, performs the operation o1114 in the illustrative depiction as follows, and/or the storing human observation module m1114, when executed and/or activated, directs performance of and/or performs the operation o1114 in the illustrative depiction as follows, and/or the operation o1114 is otherwise carried out in the illustrative depiction as follows: electronically storing (e.g. from bluetooth, etc.) the grocery operations information (e.g. visual observation, etc.) regarding at least in part (e.g. implicate, etc.) one or more grocery implementation aspects (e.g. market demands, etc.) pertaining to (e.g. implicate, etc.) grocery related merchandizing of (e.g. family buffet grocery item sales, etc.) one or more commercial grocery products (e.g. raw main course grocery item, etc.) at least in part including information regarding human observation (e.g. visual observation of grocery food quality, etc.).

In one or more implementations, as shown in FIG. 47, operation o11 includes an operation o1115 for electronically storing the grocery operations information regarding at least in part one or more grocery implementation aspects pertaining to grocery related merchandizing of one or more commercial grocery products at least in part including information regarding human behavior. Origination of an illustratively derived storing human behavior component group can be accomplished through skilled in the art design choice selection of one or more of the above depicted components from one or more of the above depicted subsystems shown in FIG. 12. Components from the storing human behavior component group can be used in implementing execution of the one or more storing human behavior instructions i1115 of FIG. 28, can be used in performance of the storing human behavior electrical circuitry arrangement e1115 of FIG. 21, and/or can be used in otherwise fulfillment of the operation o1115. An exemplary non-transitory signal bearing medium version of the information storage subsystem s200 is depicted in FIG. 28 as bearing the one or more storing human behavior instructions i1115 that when executed will direct performance of the operation o1115. Furthermore, the storing human behavior electrical circuitry arrangement ("elec circ arrange") e1115, when activated, will perform the operation o1115. Also, the storing human behavior module m1115, when executed and/or activated, will direct performance of and/or perform the operation o1115. For instance, in one or more exemplary implementations, the one or more storing human behavior instructions i1115, when executed, direct performance of the operation o1115 in the illustrative depiction as follows, and/or the storing human behavior electrical circuitry arrangement e1115, when activated, performs the operation o1115 in the illustrative depiction as follows, and/or the storing human behavior module m1115, when executed and/or activated, directs performance of and/or performs the operation o1115 in the illustrative depiction as follows, and/or the operation o1115 is otherwise carried out in the illustrative depiction as follows: electronically storing (e.g. from webpage, etc.) the grocery operations information (e.g. following safety protocols, etc.) regarding at least in part (e.g. necessitate, etc.) one or more grocery implementation aspects (e.g. crop disease status, etc.) pertaining to (e.g. necessitate, etc.) grocery related merchandizing of (e.g. mobile catering grocery item sales, etc.) one or more commercial grocery products (e.g. buffet main course grocery item, etc.) at least in part including information regarding human behavior (e.g. following health safety protocols, etc.).

Figure 48:
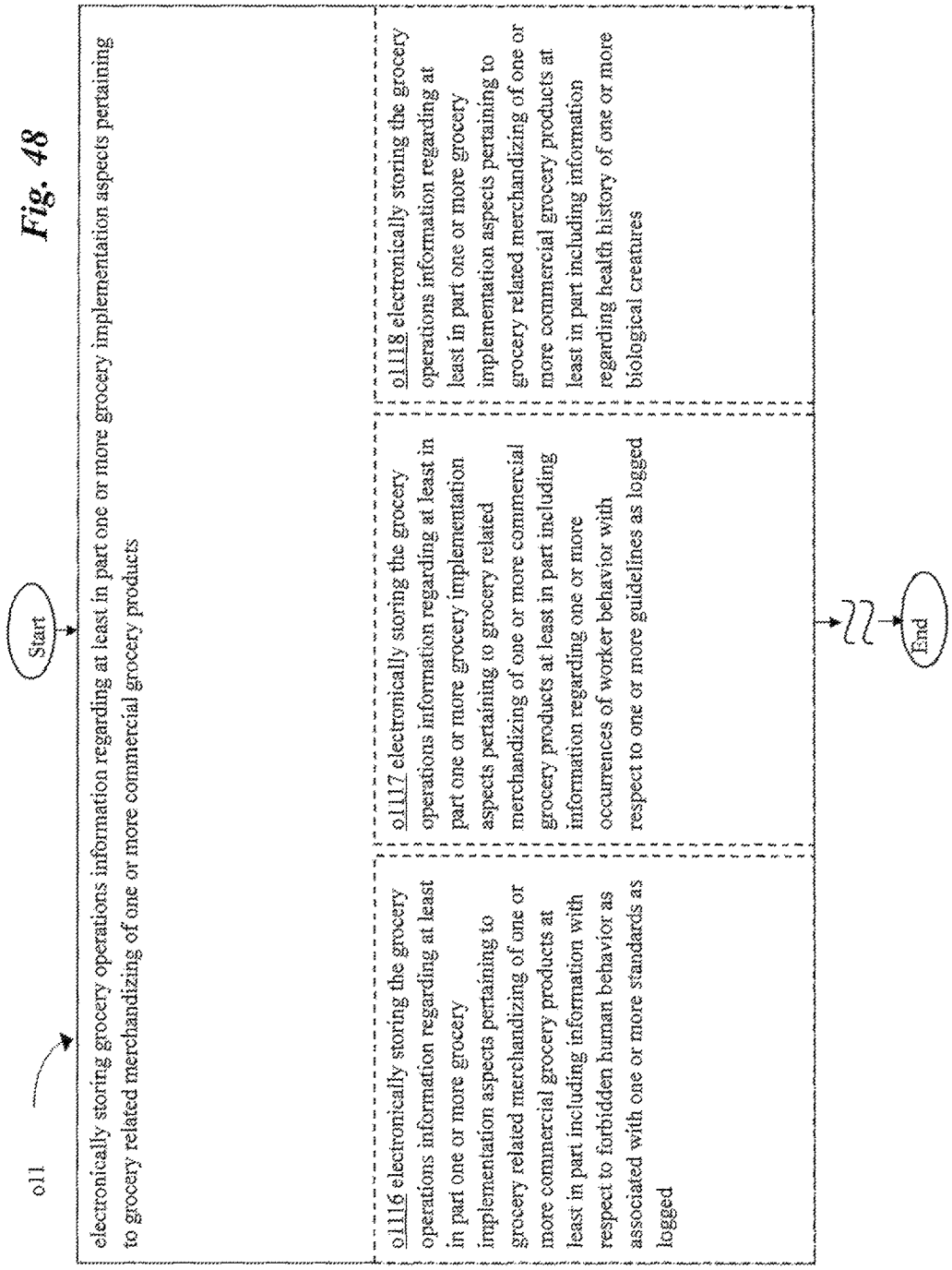
FIG. 48 is a high-level flowchart including exemplary implementations of operation o11 of FIG. 42.

In one or more implementations, as shown in FIG. 48, operation o11 includes an operation o1116 for electronically storing the grocery operations information regarding at least in part one or more grocery implementation aspects pertaining to grocery related merchandizing of one or more commercial grocery products at least in part including information with respect to forbidden human behavior as associated with one or more standards as logged. Origination of an illustratively derived storing forbidden human component group can be accomplished through skilled in the art design choice selection of one or more of the above depicted components from one or more of the above depicted subsystems shown in FIG. 12. Components from the storing forbidden human component group can be used in implementing execution of the one or more storing forbidden human instructions i1116 of FIG. 28, can be used in performance of the storing forbidden human electrical circuitry arrangement e1116 of FIG. 21, and/or can be used in otherwise fulfillment of the operation o1116. An exemplary non-transitory signal bearing medium version of the information storage subsystem s200 is depicted in FIG. 28 as bearing the one or more storing forbidden human instructions i1116 that when executed will direct performance of the operation o1116. Furthermore, the storing forbidden human electrical circuitry arrangement ("elec circ arrange") e1116, when activated, will perform the operation o1116. Also, the storing forbidden human module m1116, when executed and/or activated, will direct performance of and/or perform the operation o1116. For instance, in one or more exemplary implementations, the one or more storing forbidden human instructions i1116, when executed, direct performance of the operation o1116 in the illustrative depiction as follows, and/or the storing forbidden human electrical circuitry arrangement e1116, when activated, performs the operation o1116 in the illustrative depiction as follows, and/or the storing forbidden human module m1116, when executed and/or activated, directs performance of and/or performs the operation o1116 in the illustrative depiction as follows, and/or the operation o1116 is otherwise carried out in the illustrative depiction as follows: electronically storing (e.g. from website, etc.) the grocery operations information (e.g. certification forgery, etc.) regarding at least in part (e.g. presuppose, etc.) one or more grocery implementation aspects (e.g. climate conditions near the grocery facilities, etc.) pertaining to (e.g. presuppose, etc.) grocery related merchandizing of (e.g. institutional grocery item sales, etc.) one or more commercial grocery products (e.g. soup main course grocery item, etc.) at least in part including information with respect to forbidden human behavior as associated with one or more standards as logged (e.g. certification document forgery, etc.). For example, sensors may be attached to soap dispenseries in employee bathrooms of a grocery store. If soap has not been dispensed following usage of the bathroom, then an indication of such may be provided to an electronic record, which can be accessed by one or more potential consumers of items from the grocery store.

In one or more implementations, as shown in FIG. 48, operation o11 includes an operation o1117 for electronically storing the grocery operations information regarding at least in part one or more grocery implementation aspects pertaining to grocery related merchandizing of one or more commercial grocery products at least in part including information regarding one or more occurrences of worker behavior with respect to one or more guidelines as logged. Origination of an illustratively derived storing worker behavior component group can be accomplished through skilled in the art design choice selection of one or more of the above depicted components from one or more of the above depicted subsystems shown in FIG. 12. Components from the storing worker behavior component group can be used in implementing execution of the one or more storing worker behavior instructions i1117 of FIG. 28, can be used in performance of the storing worker behavior electrical circuitry arrangement e1117 of FIG. 21, and/or can be used in otherwise fulfillment of the operation o1117. An exemplary non-transitory signal bearing medium version of the information storage subsystem s200 is depicted in FIG. 28 as bearing the one or more storing worker behavior instructions i1117 that when executed will direct performance of the operation o1117. Furthermore, the storing worker behavior electrical circuitry arrangement ("elec circ arrange") e1117, when activated, will perform the operation o1117. Also, the storing worker behavior module m1117, when executed and/or activated, will direct performance of and/or perform the operation o1117. For instance, in one or more exemplary implementations, the one or more storing worker behavior instructions i1117, when executed, direct performance of the operation o1117 in the illustrative depiction as follows, and/or the storing worker behavior electrical circuitry arrangement e1117, when activated, performs the operation o1117 in the illustrative depiction as follows, and/or the storing worker behavior module m1117, when executed and/or activated, directs performance of and/or performs the operation o1117 in the illustrative depiction as follows, and/or the operation o1117 is otherwise carried out in the illustrative depiction as follows: electronically storing (e.g. from cellphone entry, etc.) the grocery operations information (e.g. grocery customer demographics, etc.) regarding at least in part (e.g. related to, etc.) one or more grocery implementation aspects (e.g. hygiene practices of the grocery workers, etc.) pertaining to (e.g. related to, etc.) grocery related merchandizing of (e.g. school cafeteria grocery item sales, etc.) one or more commercial grocery products (e.g. stew main course grocery item, etc.) at least in part including information regarding one or more occurrences of worker behavior with respect to one or more guidelines as logged (e.g. manufacture recalls regarding equipment used to process grocery shipments, etc.).

In one or more implementations, as shown in FIG. 48, operation o11 includes an operation o1118 for electronically storing the grocery operations information regarding at least in part one or more grocery implementation aspects pertaining to grocery related merchandizing of one or more commercial grocery products at least in part including information regarding health history of one or more biological creatures. Origination of an illustratively derived storing health history component group can be accomplished through skilled in the art design choice selection of one or more of the above depicted components from one or more of the above depicted subsystems shown in FIG. 12. Components from the storing health history component group can be used in implementing execution of the one or more storing health history instructions i1118 of FIG. 28, can be used in performance of the storing health history electrical circuitry arrangement e1118 of FIG. 21, and/or can be used in otherwise fulfillment of the operation o1118. An exemplary non-transitory signal bearing medium version of the information storage subsystem s200 is depicted in FIG. 28 as bearing the one or more storing health history instructions i1118 that when executed will direct performance of the operation o1118. Furthermore, the storing health history electrical circuitry arrangement ("elec circ arrange") e1118, when activated, will perform the operation o1118. Also, the storing health history module m1118, when executed and/or activated, will direct performance of and/or perform the operation o1118. For instance, in one or more exemplary implementations, the one or more storing health history instructions i1118, when executed, direct performance of the operation o1118 in the illustrative depiction as follows, and/or the storing health history electrical circuitry arrangement e1118, when activated, performs the operation o1118 in the illustrative depiction as follows, and/or the storing health history module m1118, when executed and/or activated, directs performance of and/or performs the operation o1118 in the illustrative depiction as follows, and/or the operation o1118 is otherwise carried out in the illustrative depiction as follows: electronically storing (e.g. from satellite transmission, etc.) the grocery operations information (e.g. facility temperature, etc.) regarding at least in part (e.g. relationship, etc.) one or more grocery implementation aspects (e.g. turnover rate of produce supply, etc.) pertaining to (e.g. relationship, etc.) grocery related merchandizing of (e.g. nursing home grocery item sales, etc.) one or more commercial grocery products (e.g. hot dish main course grocery item, etc.) at least in part including information regarding health history of one or more biological creatures (e.g. identification and description of farm animals used at least in part to produce one or more grocery items, etc.). For example, coughing sounds in an inventory area of a grocery store may be detected and stored in one or more records associated with one or more items present in that inventory area. Such information can be accessed by one or more individuals interested in considering one or more purchases of the one or more items.

Figure 49:
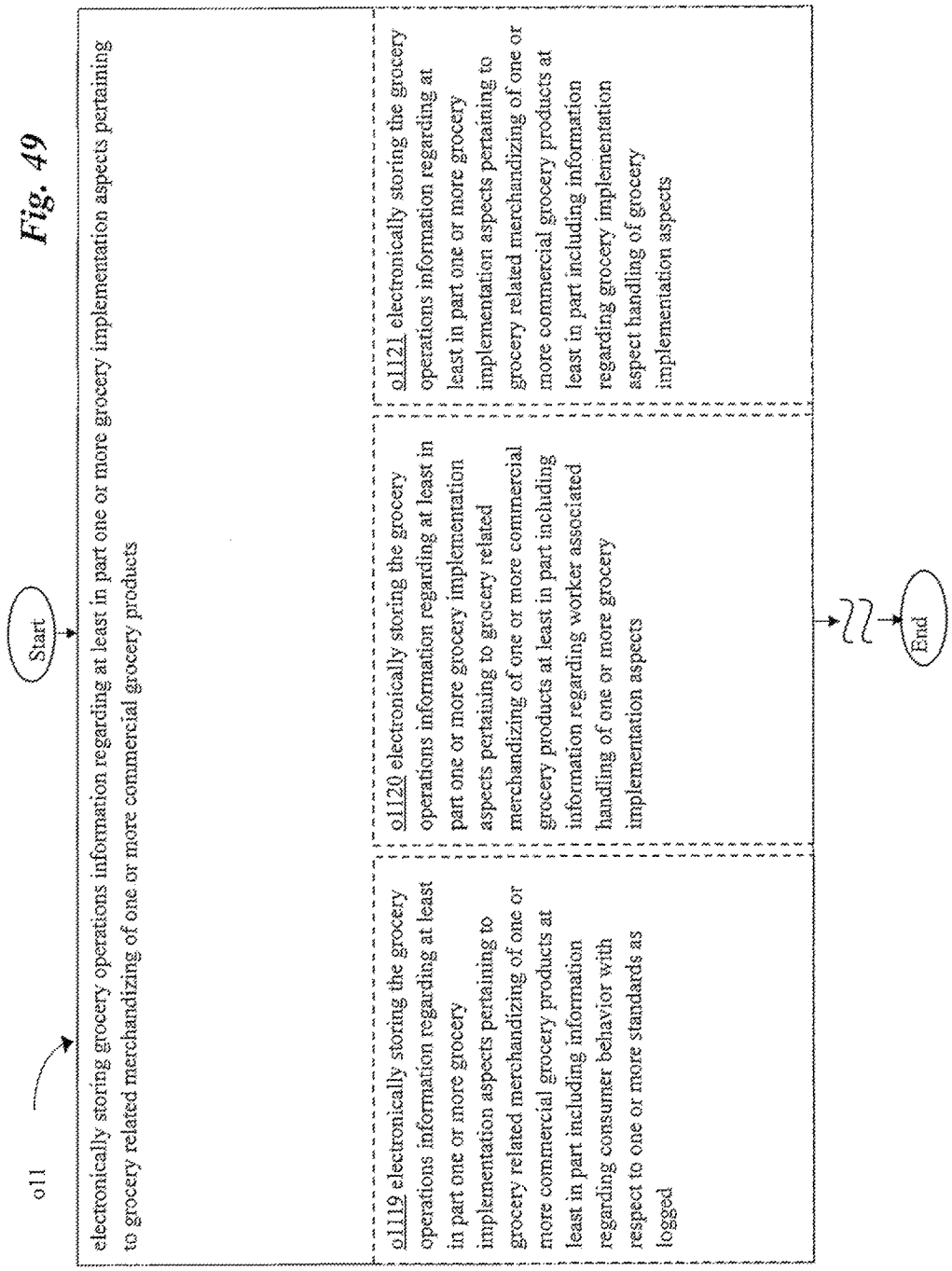
FIG. 49 is a high-level flowchart including exemplary implementations of operation o11 of FIG. 42.

In one or more implementations, as shown in FIG. 49, operation o11 includes an operation o1119 for electronically storing the grocery operations information regarding at least in part one or more grocery implementation aspects pertaining to grocery related merchandizing of one or more commercial grocery products at least in part including information regarding consumer behavior with respect to one or more standards as logged. Origination of an illustratively derived storing consumer behavior component group can be accomplished through skilled in the art design choice selection of one or more of the above depicted components from one or more of the above depicted subsystems shown in FIG. 12. Components from the storing consumer behavior component group can be used in implementing execution of the one or more storing consumer behavior instructions i1119 of FIG. 28, can be used in performance of the storing consumer behavior electrical circuitry arrangement e1119 of FIG. 21, and/or can be used in otherwise fulfillment of the operation o1119. An exemplary non-transitory signal bearing medium version of the information storage subsystem s200 is depicted in FIG. 28 as bearing the one or more storing consumer behavior instructions i1119 that when executed will direct performance of the operation o1119. Furthermore, the storing consumer behavior electrical circuitry arrangement ("elec circ arrange") e1119, when activated, will perform the operation o1119. Also, the storing consumer behavior module m1119, when executed and/or activated, will direct performance of and/or perform the operation o1119. For instance, in one or more exemplary implementations, the one or more storing consumer behavior instructions i1119, when executed, direct performance of the operation o1119 in the illustrative depiction as follows, and/or the storing consumer behavior electrical circuitry arrangement e1119, when activated, performs the operation o1119 in the illustrative depiction as follows, and/or the storing consumer behavior module m1119, when executed and/or activated, directs performance of and/or performs the operation o1119 in the illustrative depiction as follows, and/or the operation o1119 is otherwise carried out in the illustrative depiction as follows: electronically storing (e.g. via pull-based, etc.) the grocery operations information (e.g. cold packing, etc.) regarding at least in part (e.g. suggest, etc.) one or more grocery implementation aspects (e.g. shipment time required from farm through wholesaler to grocery facility, etc.) pertaining to (e.g. suggest, etc.) grocery related merchandizing of (e.g. street vendor grocery item sales, etc.) one or more commercial grocery products (e.g. cold dish main course grocery item, etc.) at least in part including information regarding consumer behavior with respect to one or more standards as logged (e.g. which grocery items are most popular as correlated with what farms and wholesalers were used to supply ingestible materials to constitute at least in part the grocery items, etc.).

In one or more implementations, as shown in FIG. 49, operation o11 includes an operation o1120 for electronically storing the grocery operations information regarding at least in part one or more grocery implementation aspects pertaining to grocery related merchandizing of one or more commercial grocery products at least in part including information regarding worker associated handling of one or more grocery implementation aspects. Origination of an illustratively derived storing worker handling component group can be accomplished through skilled in the art design choice selection of one or more of the above depicted components from one or more of the above depicted subsystems shown in FIG. 12. Components from the storing worker handling component group can be used in implementing execution of the one or more storing worker handling instructions i1120 of FIG. 29, can be used in performance of the storing worker handling electrical circuitry arrangement e1120 of FIG. 22, and/or can be used in otherwise fulfillment of the operation o1120. An exemplary non-transitory signal bearing medium version of the information storage subsystem s200 is depicted in FIG. 29 as bearing the one or more storing worker handling instructions i1120 that when executed will direct performance of the operation o1120. Furthermore, the storing worker handling electrical circuitry arrangement ("elec circ arrange") e1120, when activated, will perform the operation o1120. Also, the storing worker handling module m1120, when executed and/or activated, will direct performance of and/or perform the operation o1120. For instance, in one or more exemplary implementations, the one or more storing worker handling instructions i1120, when executed, direct performance of the operation o1120 in the illustrative depiction as follows, and/or the storing worker handling electrical circuitry arrangement e1120, when activated, performs the operation o1120 in the illustrative depiction as follows, and/or the storing worker handling module m1120, when executed and/or activated, directs performance of and/or performs the operation o1120 in the illustrative depiction as follows, and/or the operation o1120 is otherwise carried out in the illustrative depiction as follows: electronically storing (e.g. onto POP3 server, etc.) the grocery operations information (e.g. oven operation, etc.) regarding at least in part (e.g. tangle, etc.) one or more grocery implementation aspects (e.g. maintenance procedure on grocery equipment, etc.) pertaining to (e.g. tangle, etc.) grocery related merchandizing of (e.g. mobile kitchen grocery item sales, etc.) one or more commercial grocery products (e.g. weight loss, etc.) at least in part including information regarding worker associated handling of one or more grocery implementation aspects (e.g. compliance with maintenance and cleaning procedures for the grocery item preparation equipment, etc.).

In one or more implementations, as shown in FIG. 49, operation o11 includes an operation o1121 for electronically storing the grocery operations information regarding at least in part one or more grocery implementation aspects pertaining to grocery related merchandizing of one or more commercial grocery products at least in part including information regarding grocery implementation aspect handling of grocery implementation aspects. Origination of an illustratively derived storing aspect handling component group can be accomplished through skilled in the art design choice selection of one or more of the above depicted components from one or more of the above depicted subsystems shown in FIG. 12. Components from the storing aspect handling component group can be used in implementing execution of the one or more storing aspect handling instructions i1121 of FIG. 29, can be used in performance of the storing aspect handling electrical circuitry arrangement e1121 of FIG. 22, and/or can be used in otherwise fulfillment of the operation o1121. An exemplary non-transitory signal bearing medium version of the information storage subsystem s200 is depicted in FIG. 29 as bearing the one or more storing aspect handling instructions i1121 that when executed will direct performance of the operation o1121. Furthermore, the storing aspect handling electrical circuitry arrangement ("elec circ arrange") e1121, when activated, will perform the operation o1121. Also, the storing aspect handling module m1121, when executed and/or activated, will direct performance of and/or perform the operation o1121. For instance, in one or more exemplary implementations, the one or more storing aspect handling instructions i1121, when executed, direct performance of the operation o1121 in the illustrative depiction as follows, and/or the storing aspect handling electrical circuitry arrangement e1121, when activated, performs the operation o1121 in the illustrative depiction as follows, and/or the storing aspect handling module m1121, when executed and/or activated, directs performance of and/or performs the operation o1121 in the illustrative depiction as follows, and/or the operation o1121 is otherwise carried out in the illustrative depiction as follows: electronically storing (e.g. as hardware based encryption, etc.) the grocery operations information (e.g. electricity usage, etc.) regarding at least in part (e.g. exclude, etc.) one or more grocery implementation aspects (e.g. cost of extra equipment rental, etc.) pertaining to (e.g. exclude, etc.) grocery related merchandizing of (e.g. hospital grocery item sales, etc.) one or more commercial grocery products (e.g. sports nutrition main course grocery item, etc.) at least in part including information regarding grocery implementation aspect handling of grocery implementation aspects (e.g. handling of machines to prepare produce to be used in canning of such for grocery items, etc.).

Figure 50:
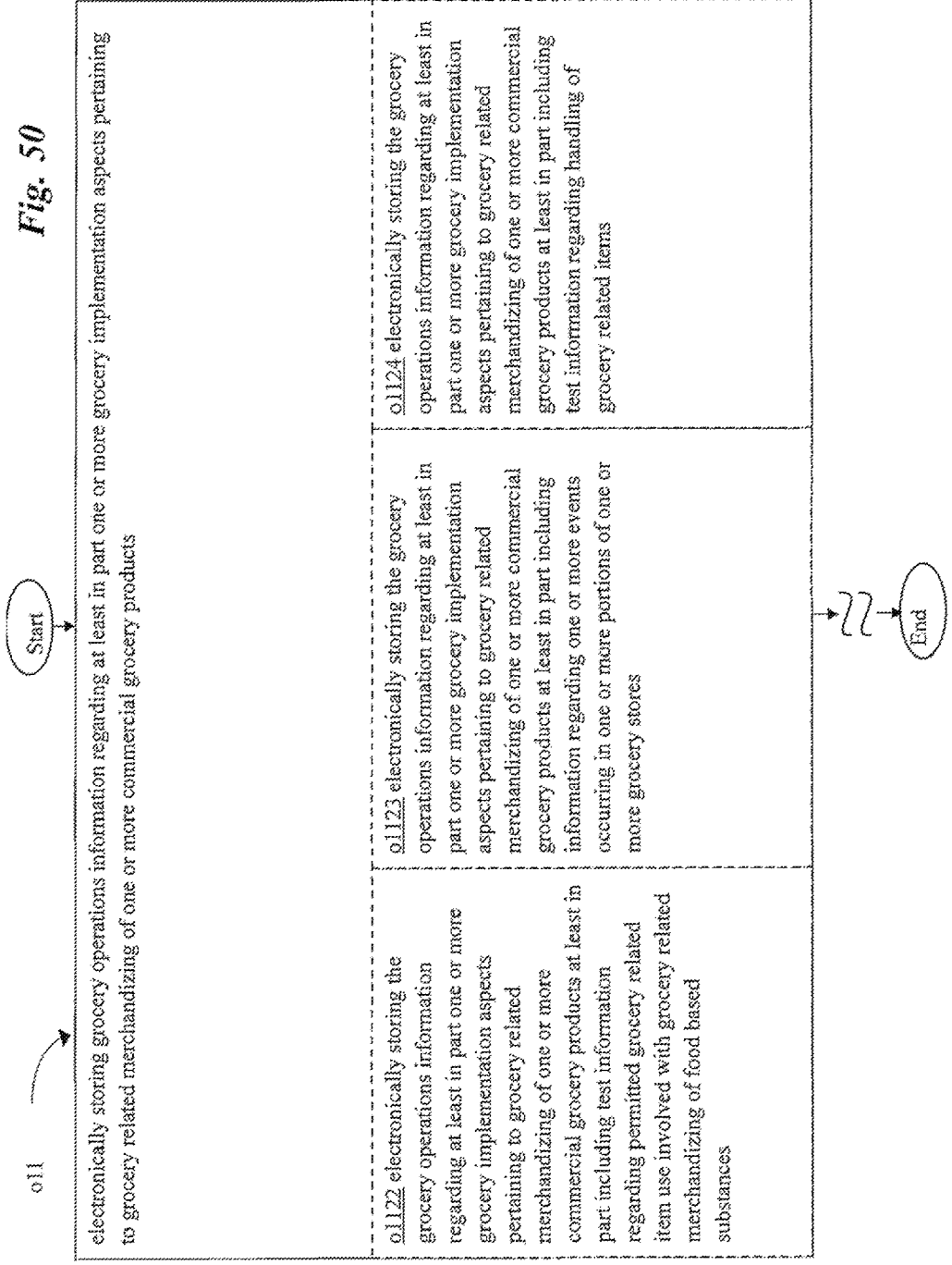
FIG. 50 is a high-level flowchart including exemplary implementations of operation o11 of FIG. 42.

In one or more implementations, as shown in FIG. 50, operation o11 includes an operation o1122 for electronically storing the grocery operations information regarding at least in part one or more grocery implementation aspects pertaining to grocery related merchandizing of one or more commercial grocery products at least in part including test information regarding permitted grocery related item use involved with grocery related merchandizing of food based substances. Origination of an illustratively derived storing merchandizing substances component group can be accomplished through skilled in the art design choice selection of one or more of the above depicted components from one or more of the above depicted subsystems shown in FIG. 12. Components from the storing merchandizing substances component group can be used in implementing execution of the one or more storing merchandizing substances instructions i1122 of FIG. 29, can be used in performance of the storing merchandizing substances electrical circuitry arrangement e1122 of FIG. 22, and/or can be used in otherwise fulfillment of the operation o1122. An exemplary non-transitory signal bearing medium version of the information storage subsystem s200 is depicted in FIG. 29 as bearing the one or more storing merchandizing substances instructions i1122 that when executed will direct performance of the operation o1122. Furthermore, the storing merchandizing substances electrical circuitry arrangement ("elec circ arrange") e1122, when activated, will perform the operation o1122. Also, the storing merchandizing substances module m1122, when executed and/or activated, will direct performance of and/or perform the operation o1122. For instance, in one or more exemplary implementations, the one or more storing merchandizing substances instructions i1122, when executed, direct performance of the operation o1122 in the illustrative depiction as follows, and/or the storing merchandizing substances electrical circuitry arrangement e1122, when activated, performs the operation o1122 in the illustrative depiction as follows, and/or the storing merchandizing substances module m1122, when executed and/or activated, directs performance of and/or performs the operation o1122 in the illustrative depiction as follows, and/or the operation o1122 is otherwise carried out in the illustrative depiction as follows: electronically storing (e.g. as software based encryption, etc.) the grocery operations information (e.g. refrigeration temperatures, etc.) regarding at least in part (e.g. bound, etc.) one or more grocery implementation aspects (e.g. equipment maintenance schedule, etc.) pertaining to (e.g. bound, etc.) grocery related merchandizing of (e.g. deli department grocery item sales, etc.) one or more commercial grocery products (e.g. baked main course grocery item, etc.) at least in part including test information regarding permitted grocery related item use involved with grocery related merchandizing of food based substances (e.g. testing for toxin levels with organic produce to confirm quality claims for the produce, etc.).

In one or more implementations, as shown in FIG. 50, operation o11 includes an operation o1123 for electronically storing the grocery operations information regarding at least in part one or more grocery implementation aspects pertaining to grocery related merchandizing of one or more commercial grocery products at least in part including information regarding one or more events occurring in one or more portions of one or more grocery stores. Origination of an illustratively derived storing events occurring component group can be accomplished through skilled in the art design choice selection of one or more of the above depicted components from one or more of the above depicted subsystems shown in FIG. 12. Components from the storing events occurring component group can be used in implementing execution of the one or more storing events occurring instructions i1123 of FIG. 29, can be used in performance of the storing events occurring electrical circuitry arrangement e1123 of FIG. 22, and/or can be used in otherwise fulfillment of the operation o1123. An exemplary non-transitory signal bearing medium version of the information storage subsystem s200 is depicted in FIG. 29 as bearing the one or more storing events occurring instructions i1123 that when executed will direct performance of the operation o1123. Furthermore, the storing events occurring electrical circuitry arrangement ("elec circ arrange") e1123, when activated, will perform the operation o1123. Also, the storing events occurring module m1123, when executed and/or activated, will direct performance of and/or perform the operation o1123. For instance, in one or more exemplary implementations, the one or more storing events occurring instructions i1123, when executed, direct performance of the operation o1123 in the illustrative depiction as follows, and/or the storing events occurring electrical circuitry arrangement e1123, when activated, performs the operation o1123 in the illustrative depiction as follows, and/or the storing events occurring module m1123, when executed and/or activated, directs performance of and/or performs the operation o1123 in the illustrative depiction as follows, and/or the operation o1123 is otherwise carried out in the illustrative depiction as follows: electronically storing (e.g. onto SD card, etc.) the grocery operations information (e.g. sanitization protocol observance, etc.) regarding at least in part (e.g. requiring, etc.) one or more grocery implementation aspects (e.g. tool requirements for repair of grocery equipment, etc.) pertaining to (e.g. requiring, etc.) grocery related merchandizing of (e.g. fine dining grocery item serving, etc.) one or more commercial grocery products (e.g. fried main course grocery item, etc.) at least in part including information regarding one or more events occurring in one or more portions of one or more grocery stores (e.g. health inspection of a warehouse and grocery receiving areas, etc.).

In one or more implementations, as shown in FIG. 50, operation o11 includes an operation o1124 for electronically storing the grocery operations information regarding at least in part one or more grocery implementation aspects pertaining to grocery related merchandizing of one or more commercial grocery products at least in part including test information regarding handling of grocery related items. Origination of an illustratively derived storing test handling component group can be accomplished through skilled in the art design choice selection of one or more of the above depicted components from one or more of the above depicted subsystems shown in FIG. 12. Components from the storing test handling component group can be used in implementing execution of the one or more storing test handling instructions i1124 of FIG. 29, can be used in performance of the storing test handling electrical circuitry arrangement e1124 of FIG. 22, and/or can be used in otherwise fulfillment of the operation o1124. An exemplary non-transitory signal bearing medium version of the information storage subsystem s200 is depicted in FIG. 29 as bearing the one or more storing test handling instructions i1124 that when executed will direct performance of the operation o1124. Furthermore, the storing test handling electrical circuitry arrangement ("elec circ arrange") e1124, when activated, will perform the operation o1124. Also, the storing test handling module m1124, when executed and/or activated, will direct performance of and/or perform the operation o1124. For instance, in one or more exemplary implementations, the one or more storing test handling instructions i1124, when executed, direct performance of the operation o1124 in the illustrative depiction as follows, and/or the storing test handling electrical circuitry arrangement e1124, when activated, performs the operation o1124 in the illustrative depiction as follows, and/or the storing test handling module m1124, when executed and/or activated, directs performance of and/or performs the operation o1124 in the illustrative depiction as follows, and/or the operation o1124 is otherwise carried out in the illustrative depiction as follows: electronically storing (e.g. onto SIM card, etc.) the grocery operations information (e.g. presence of insecticides in food, etc.) regarding at least in part (e.g. enveloped, etc.) one or more grocery implementation aspects (e.g. local regulations, etc.) pertaining to (e.g. enveloped, etc.) grocery related merchandizing of (e.g. fast grocery item serving, etc.) one or more commercial grocery products (e.g. grilled main course grocery item, etc.) at least in part including test information regarding handling of grocery related items (e.g. bacteria testing of surfaces used in preparing grocery items, etc.).

Figure 51:
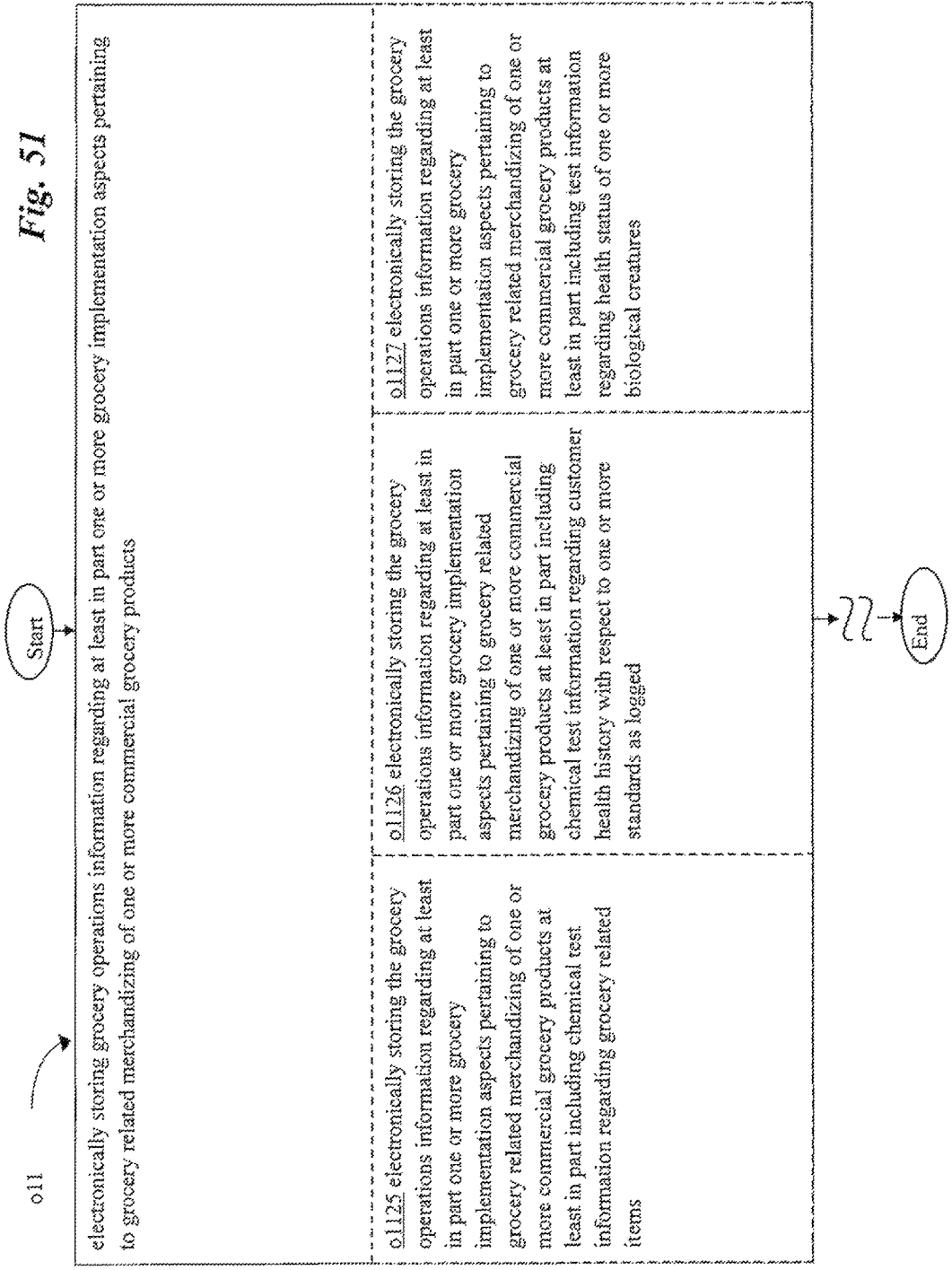
FIG. 51 is a high-level flowchart including exemplary implementations of operation o11 of FIG. 42.

In one or more implementations, as shown in FIG. 51, operation o11 includes an operation o1125 for electronically storing the grocery operations information regarding at least in part one or more grocery implementation aspects pertaining to grocery related merchandizing of one or more commercial grocery products at least in part including chemical test information regarding grocery related items. Origination of an illustratively derived storing chemical test component group can be accomplished through skilled in the art design choice selection of one or more of the above depicted components from one or more of the above depicted subsystems shown in FIG. 12. Components from the storing chemical test component group can be used in implementing execution of the one or more storing chemical test instructions i1125 of FIG. 29, can be used in performance of the storing chemical test electrical circuitry arrangement e1125 of FIG. 22, and/or can be used in otherwise fulfillment of the operation o1125. An exemplary non-transitory signal bearing medium version of the information storage subsystem s200 is depicted in FIG. 29 as bearing the one or more storing chemical test instructions i1125 that when executed will direct performance of the operation o1125. Furthermore, the storing chemical test electrical circuitry arrangement ("elec circ arrange") e1125, when activated, will perform the operation o1125. Also, the storing chemical test module m1125, when executed and/or activated, will direct performance of and/or perform the operation o1125. For instance, in one or more exemplary implementations, the one or more storing chemical test instructions i1125, when executed, direct performance of the operation o1125 in the illustrative depiction as follows, and/or the storing chemical test electrical circuitry arrangement e1125, when activated, performs the operation o1125 in the illustrative depiction as follows, and/or the storing chemical test module m1125, when executed and/or activated, directs performance of and/or performs the operation o1125 in the illustrative depiction as follows, and/or the operation o1125 is otherwise carried out in the illustrative depiction as follows: electronically storing (e.g. from email, etc.) the grocery operations information (e.g. stocking speed of grocery clerks, etc.) regarding at least in part (e.g. envelope, etc.) one or more grocery implementation aspects (e.g. type of grocery items sold by grocery facility, etc.) pertaining to (e.g. envelope, etc.) grocery related merchandizing of (e.g. family buffet grocery item serving, etc.) one or more commercial grocery products (e.g. steamed main course grocery item, etc.) at least in part including chemical test information regarding grocery related items (e.g. residue testing to determine levels of toxins on surfaces food materials used to prepare grocery items, etc.).

In one or more implementations, as shown in FIG. 51, operation o11 includes an operation o1126 for electronically storing the grocery operations information regarding at least in part one or more grocery implementation aspects pertaining to grocery related merchandizing of one or more commercial grocery products at least in part including chemical test information regarding customer health history with respect to one or more standards as logged. Origination of an illustratively derived storing customer health component group can be accomplished through skilled in the art design choice selection of one or more of the above depicted components from one or more of the above depicted subsystems shown in FIG. 12. Components from the storing customer health component group can be used in implementing execution of the one or more storing customer health instructions i1126 of FIG. 29, can be used in performance of the storing customer health electrical circuitry arrangement e1126 of FIG. 22, and/or can be used in otherwise fulfillment of the operation o1126. An exemplary non-transitory signal bearing medium version of the information storage subsystem s200 is depicted in FIG. 29 as bearing the one or more storing customer health instructions i1126 that when executed will direct performance of the operation o1126. Furthermore, the storing customer health electrical circuitry arrangement ("elec circ arrange") e1126, when activated, will perform the operation o1126. Also, the storing customer health module m1126, when executed and/or activated, will direct performance of and/or perform the operation o1126. For instance, in one or more exemplary implementations, the one or more storing customer health instructions i1126, when executed, direct performance of the operation o1126 in the illustrative depiction as follows, and/or the storing customer health electrical circuitry arrangement e1126, when activated, performs the operation o1126 in the illustrative depiction as follows, and/or the storing customer health module m1126, when executed and/or activated, directs performance of and/or performs the operation o1126 in the illustrative depiction as follows, and/or the operation o1126 is otherwise carried out in the illustrative depiction as follows: electronically storing (e.g. via peer to peer, etc.) the grocery operations information (e.g. labor force scheduling, etc.) regarding at least in part (e.g. associate with, etc.) one or more grocery implementation aspects (e.g. demographic location of grocery facility, etc.) pertaining to (e.g. associate with, etc.) grocery related merchandizing of (e.g. mobile catering grocery item serving, etc.) one or more commercial grocery products (e.g. chilled main course grocery item, etc.) at least in part including chemical test information regarding customer health history with respect to one or more standards as logged (e.g. public testing results for outbreaks of illness generally found in the public, etc.).

In one or more implementations, as shown in FIG. 51, operation o11 includes an operation o1127 for electronically storing the grocery operations information regarding at least in part one or more grocery implementation aspects pertaining to grocery related merchandizing of one or more commercial grocery products at least in part including test information regarding health status of one or more biological creatures. Origination of an illustratively derived storing test health component group can be accomplished through skilled in the art design choice selection of one or more of the above depicted components from one or more of the above depicted subsystems shown in FIG. 12. Components from the storing test health component group can be used in implementing execution of the one or more storing test health instructions i1127 of FIG. 29, can be used in performance of the storing test health electrical circuitry arrangement e1127 of FIG. 22, and/or can be used in otherwise fulfillment of the operation o1127. An exemplary non-transitory signal bearing medium version of the information storage subsystem s200 is depicted in FIG. 29 as bearing the one or more storing test health instructions i1127 that when executed will direct performance of the operation o1127. Furthermore, the storing test health electrical circuitry arrangement ("elec circ arrange") e1127, when activated, will perform the operation o1127. Also, the storing test health module m1127, when executed and/or activated, will direct performance of and/or perform the operation o1127. For instance, in one or more exemplary implementations, the one or more storing test health instructions i1127, when executed, direct performance of the operation o1127 in the illustrative depiction as follows, and/or the storing test health electrical circuitry arrangement e1127, when activated, performs the operation o1127 in the illustrative depiction as follows, and/or the storing test health module m1127, when executed and/or activated, directs performance of and/or performs the operation o1127 in the illustrative depiction as follows, and/or the operation o1127 is otherwise carried out in the illustrative depiction as follows: electronically storing (e.g. from 10-key, etc.) the grocery operations information (e.g. future market demands, etc.) regarding at least in part (e.g. embroil, etc.) one or more grocery implementation aspects (e.g. age of equipment used in the grocery facility, etc.) pertaining to (e.g. embroil, etc.) grocery related merchandizing of (e.g. institutional grocery item serving, etc.) one or more commercial grocery products (e.g. microwaved main course grocery item, etc.) at least in part including test information regarding health status of one or more biological creatures (e.g. infectious disease testing of farm animals used in grocery items, etc.).

Figure 52:
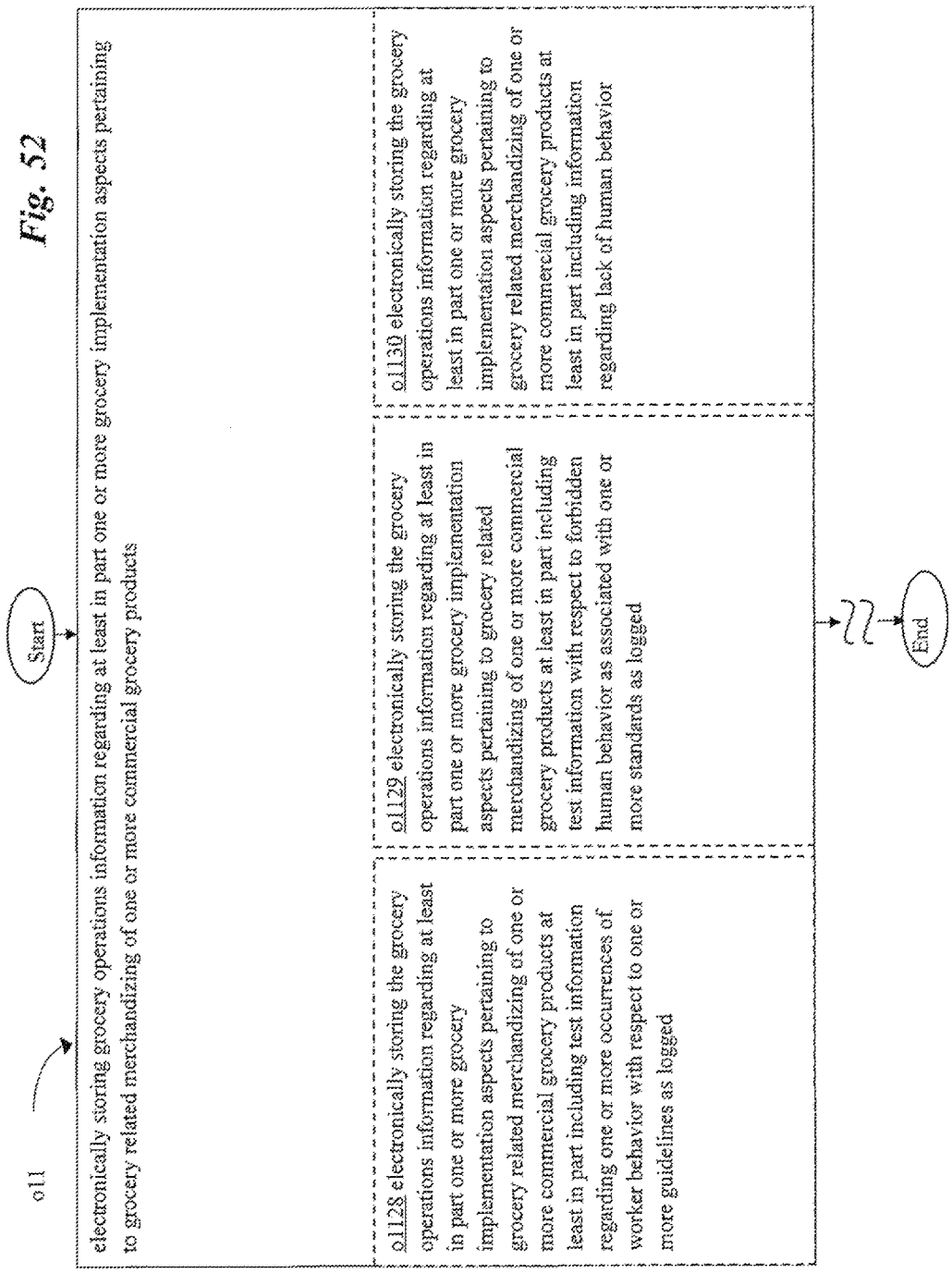
FIG. 52 is a high-level flowchart including exemplary implementations of operation o11 of FIG. 42.

In one or more implementations, as shown in FIG. 52, operation o11 includes an operation o1128 for electronically storing the grocery operations information regarding at least in part one or more grocery implementation aspects pertaining to grocery related merchandizing of one or more commercial grocery products at least in part including test information regarding one or more occurrences of worker behavior with respect to one or more guidelines as logged. Origination of an illustratively derived storing worker guidelines component group can be accomplished through skilled in the art design choice selection of one or more of the above depicted components from one or more of the above depicted subsystems shown in FIG. 12. Components from the storing worker guidelines component group can be used in implementing execution of the one or more storing worker guidelines instructions i1128 of FIG. 29, can be used in performance of the storing worker guidelines electrical circuitry arrangement e1128 of FIG. 22, and/or can be used in otherwise fulfillment of the operation o1128. An exemplary non-transitory signal bearing medium version of the information storage subsystem s200 is depicted in FIG. 29 as bearing the one or more storing worker guidelines instructions i1128 that when executed will direct performance of the operation o1128. Furthermore, the storing worker guidelines electrical circuitry arrangement ("elec circ arrange") e1128, when activated, will perform the operation o1128. Also, the storing worker guidelines module m1128, when executed and/or activated, will direct performance of and/or perform the operation o1128. For instance, in one or more exemplary implementations, the one or more storing worker guidelines instructions i1128, when executed, direct performance of the operation o1128 in the illustrative depiction as follows, and/or the storing worker guidelines electrical circuitry arrangement e1128, when activated, performs the operation o1128 in the illustrative depiction as follows, and/or the storing worker guidelines module m1128, when executed and/or activated, directs performance of and/or performs the operation o1128 in the illustrative depiction as follows, and/or the operation o1128 is otherwise carried out in the illustrative depiction as follows: electronically storing (e.g. from USB port, etc.) the grocery operations information (e.g. improper data calculation, etc.) regarding at least in part (e.g. take in, etc.) one or more grocery implementation aspects (e.g. distribution of various type of grocery items sold, etc.) pertaining to (e.g. take in, etc.) grocery related merchandizing of (e.g. school cafeteria grocery item serving, etc.) one or more commercial grocery products (e.g. convection oven prepared main course grocery item, etc.) at least in part including test information regarding one or more occurrences of worker behavior with respect to one or more guidelines as logged (e.g. grocery worker hygiene habits, etc.).

In one or more implementations, as shown in FIG. 52, operation o11 includes an operation o1129 for electronically storing the grocery operations information regarding at least in part one or more grocery implementation aspects pertaining to grocery related merchandizing of one or more commercial grocery products at least in part including test information with respect to forbidden human behavior as associated with one or more standards as logged. Origination of an illustratively derived storing forbidden human component group can be accomplished through skilled in the art design choice selection of one or more of the above depicted components from one or more of the above depicted subsystems shown in FIG. 12. Components from the storing forbidden human component group can be used in implementing execution of the one or more storing forbidden human instructions i1129 of FIG. 29, can be used in performance of the storing forbidden human electrical circuitry arrangement e1129 of FIG. 22, and/or can be used in otherwise fulfillment of the operation o1129. An exemplary non-transitory signal bearing medium version of the information storage subsystem s200 is depicted in FIG. 29 as bearing the one or more storing forbidden human instructions i1129 that when executed will direct performance of the operation o1129. Furthermore, the storing forbidden human electrical circuitry arrangement ("elec circ arrange") e1129, when activated, will perform the operation o1129. Also, the storing forbidden human module m1129, when executed and/or activated, will direct performance of and/or perform the operation o1129. For instance, in one or more exemplary implementations, the one or more storing forbidden human instructions i1129, when executed, direct performance of the operation o1129 in the illustrative depiction as follows, and/or the storing forbidden human electrical circuitry arrangement e1129, when activated, performs the operation o1129 in the illustrative depiction as follows, and/or the storing forbidden human module m1129, when executed and/or activated, directs performance of and/or performs the operation o1129 in the illustrative depiction as follows, and/or the operation o1129 is otherwise carried out in the illustrative depiction as follows: electronically storing (e.g. as FTP, etc.) the grocery operations information (e.g. infestation of grocery, etc.) regarding at least in part (e.g. comprised of, etc.) one or more grocery implementation aspects (e.g. labor laws, etc.) pertaining to (e.g. comprised of, etc.) grocery related merchandizing of (e.g. nursing home grocery item serving, etc.) one or more commercial grocery products (e.g. smoked main course grocery item, etc.) at least in part including test information with respect to forbidden human behavior as associated with one or more standards as logged (e.g. lack of sanitary measures performed by grocery workers, etc.).

In one or more implementations, as shown in FIG. 52, operation o11 includes an operation o1130 for electronically storing the grocery operations information regarding at least in part one or more grocery implementation aspects pertaining to grocery related merchandizing of one or more commercial grocery products at least in part including information regarding lack of human behavior. Origination of an illustratively derived storing lack of behavior component group can be accomplished through skilled in the art design choice selection of one or more of the above depicted components from one or more of the above depicted subsystems shown in FIG. 12. Components from the storing lack of behavior component group can be used in implementing execution of the one or more storing lack of behavior instructions i1130 of FIG. 29, can be used in performance of the storing lack of behavior electrical circuitry arrangement e1130 of FIG. 22, and/or can be used in otherwise fulfillment of the operation o1130. An exemplary non-transitory signal bearing medium version of the information storage subsystem s200 is depicted in FIG. 29 as bearing the one or more storing lack of behavior instructions i1130 that when executed will direct performance of the operation o1130. Furthermore, the storing lack of behavior electrical circuitry arrangement ("elec circ arrange") e1130, when activated, will perform the operation o1130. Also, the storing lack of behavior module m1130, when executed and/or activated, will direct performance of and/or perform the operation o1130. For instance, in one or more exemplary implementations, the one or more storing lack of behavior instructions i1130, when executed, direct performance of the operation o1130 in the illustrative depiction as follows, and/or the storing lack of behavior electrical circuitry arrangement e1130, when activated, performs the operation o1130 in the illustrative depiction as follows, and/or the storing lack of behavior module m1130, when executed and/or activated, directs performance of and/or performs the operation o1130 in the illustrative depiction as follows, and/or the operation o1130 is otherwise carried out in the illustrative depiction as follows: electronically storing (e.g. as HTTP, etc.) the grocery operations information (e.g. sanitizer usage, etc.) regarding at least in part (e.g. comprehend, etc.) one or more grocery implementation aspects (e.g. safety regulations, etc.) pertaining to (e.g. comprehend, etc.) grocery related merchandizing of (e.g. street vendor grocery item serving, etc.) one or more commercial grocery products (e.g. boiled main course grocery item, etc.) at least in part including information regarding lack of human behavior (e.g. degree of absence of human supervisors during testing procedures, etc.).

Figure 53:
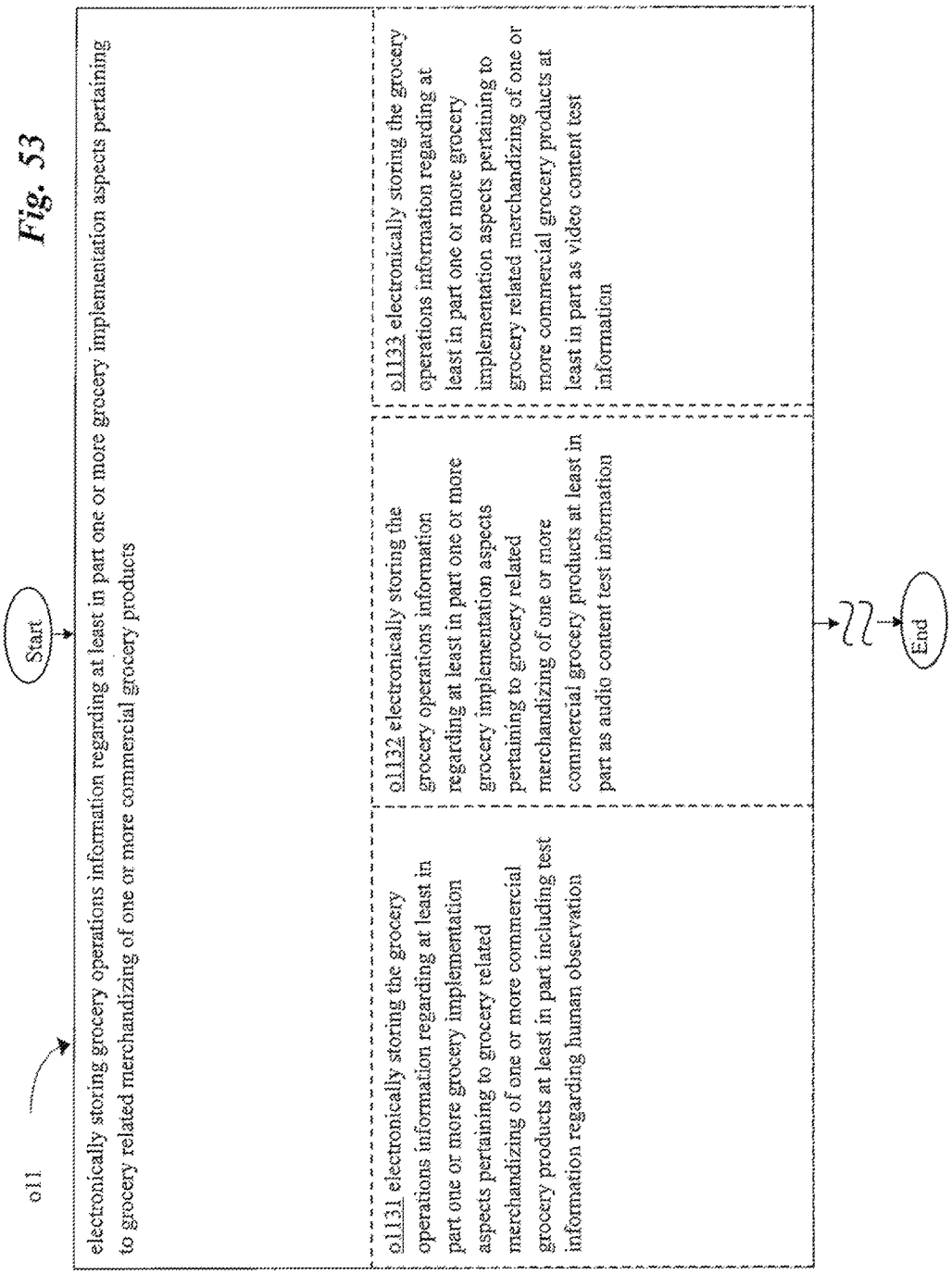
FIG. 53 is a high-level flowchart including exemplary implementations of operation o11 of FIG. 42.

In one or more implementations, as shown in FIG. 53, operation o11 includes an operation o1131 for electronically storing the grocery operations information regarding at least in part one or more grocery implementation aspects pertaining to grocery related merchandizing of one or more commercial grocery products at least in part including test information regarding human observation. Origination of an illustratively derived storing test observation component group can be accomplished through skilled in the art design choice selection of one or more of the above depicted components from one or more of the above depicted subsystems shown in FIG. 12. Components from the storing test observation component group can be used in implementing execution of the one or more storing test observation instructions i1131 of FIG. 29, can be used in performance of the storing test observation electrical circuitry arrangement e1131 of FIG. 22, and/or can be used in otherwise fulfillment of the operation o1131. An exemplary non-transitory signal bearing medium version of the information storage subsystem s200 is depicted in FIG. 29 as bearing the one or more storing test observation instructions i1131 that when executed will direct performance of the operation o1131. Furthermore, the storing test observation electrical circuitry arrangement ("elec circ arrange") e1131, when activated, will perform the operation o1131. Also, the storing test observation module m1131, when executed and/or activated, will direct performance of and/or perform the operation o1131. For instance, in one or more exemplary implementations, the one or more storing test observation instructions i1131, when executed, direct performance of the operation o1131 in the illustrative depiction as follows, and/or the storing test observation electrical circuitry arrangement e1131, when activated, performs the operation o1131 in the illustrative depiction as follows, and/or the storing test observation module m1131, when executed and/or activated, directs performance of and/or performs the operation o1131 in the illustrative depiction as follows, and/or the operation o1131 is otherwise carried out in the illustrative depiction as follows: electronically storing (e.g. from bittorent, etc.) the grocery operations information (e.g. cleaning protocols implemented, etc.) regarding at least in part (e.g. associated, etc.) one or more grocery implementation aspects (e.g. neighboring grocery facilities, etc.) pertaining to (e.g. associated, etc.) grocery related merchandizing of (e.g. mobile kitchen grocery item serving, etc.) one or more commercial grocery products (e.g. sandwich main course grocery item, etc.) at least in part including test information regarding human observation (e.g. human perception of grocery food stuffs regarding their level of quality, etc.).

In one or more implementations, as shown in FIG. 53, operation o11 includes an operation o1132 for electronically storing the grocery operations information regarding at least in part one or more grocery implementation aspects pertaining to grocery related merchandizing of one or more commercial grocery products at least in part as audio content test information. Origination of an illustratively derived storing audio test component group can be accomplished through skilled in the art design choice selection of one or more of the above depicted components from one or more of the above depicted subsystems shown in FIG. 12. Components from the storing audio test component group can be used in implementing execution of the one or more storing audio test instructions i1132 of FIG. 29, can be used in performance of the storing audio test electrical circuitry arrangement e1132 of FIG. 22, and/or can be used in otherwise fulfillment of the operation o1132. An exemplary non-transitory signal bearing medium version of the information storage subsystem s200 is depicted in FIG. 29 as bearing the one or more storing audio test instructions i1132 that when executed will direct performance of the operation o1132. Furthermore, the storing audio test electrical circuitry arrangement ("elec circ arrange") e1132, when activated, will perform the operation o1132. Also, the storing audio test module m1132, when executed and/or activated, will direct performance of and/or perform the operation o1132. For instance, in one or more exemplary implementations, the one or more storing audio test instructions i1132, when executed, direct performance of the operation o1132 in the illustrative depiction as follows, and/or the storing audio test electrical circuitry arrangement e1132, when activated, performs the operation o1132 in the illustrative depiction as follows, and/or the storing audio test module m1132, when executed and/or activated, directs performance of and/or performs the operation o1132 in the illustrative depiction as follows, and/or the operation o1132 is otherwise carried out in the illustrative depiction as follows: electronically storing (e.g. from gnutella, etc.) the grocery operations information (e.g. humidity of storage units, etc.) regarding at least in part (e.g. affected, etc.) one or more grocery implementation aspects (e.g. any quarantines imposed in surrounding area, etc.) pertaining to (e.g. affected, etc.) grocery related merchandizing of (e.g. hospital grocery item serving, etc.) one or more commercial grocery products (e.g. rotisserie main course grocery item, etc.) at least in part as audio content test information (e.g. grocery tester verbal comments regarding grocery item quality, etc.).

In one or more implementations, as shown in FIG. 53, operation o11 includes an operation o1133 for electronically storing the grocery operations information regarding at least in part one or more grocery implementation aspects pertaining to grocery related merchandizing of one or more commercial grocery products at least in part as video content test information. Origination of an illustratively derived storing videotest component group can be accomplished through skilled in the art design choice selection of one or more of the above depicted components from one or more of the above depicted subsystems shown in FIG. 12. Components from the storing videotest component group can be used in implementing execution of the one or more storing videotest instructions i1133 of FIG. 29, can be used in performance of the storing videotest electrical circuitry arrangement e1133 of FIG. 22, and/or can be used in otherwise fulfillment of the operation o1133. An exemplary non-transitory signal bearing medium version of the information storage subsystem s200 is depicted in FIG. 29 as bearing the one or more storing videotest instructions i1133 that when executed will direct performance of the operation o1133. Furthermore, the storing videotest electrical circuitry arrangement ("elec circ arrange") e1133, when activated, will perform the operation o1133. Also, the storing videotest module m1133, when executed and/or activated, will direct performance of and/or perform the operation o1133. For instance, in one or more exemplary implementations, the one or more storing videotest instructions i1133, when executed, direct performance of the operation o1133 in the illustrative depiction as follows, and/or the storing videotest electrical circuitry arrangement e1133, when activated, performs the operation o1133 in the illustrative depiction as follows, and/or the storing videotest module m1133, when executed and/or activated, directs performance of and/or performs the operation o1133 in the illustrative depiction as follows, and/or the operation o1133 is otherwise carried out in the illustrative depiction as follows: electronically storing (e.g. via TCP/IP, etc.) the grocery operations information (e.g. oxygen sensor of storage equipment, etc.) regarding at least in part (e.g. affecting, etc.) one or more grocery implementation aspects (e.g. pesticide levels of food materials for grocery items, etc.) pertaining to (e.g. affecting, etc.) grocery related merchandizing of (e.g. deli department grocery item serving, etc.) one or more commercial grocery products (e.g. braised main course grocery item, etc.) at least in part as video content test information (e.g. video recording of grocery item testing procedures, etc.).

Figure 54:
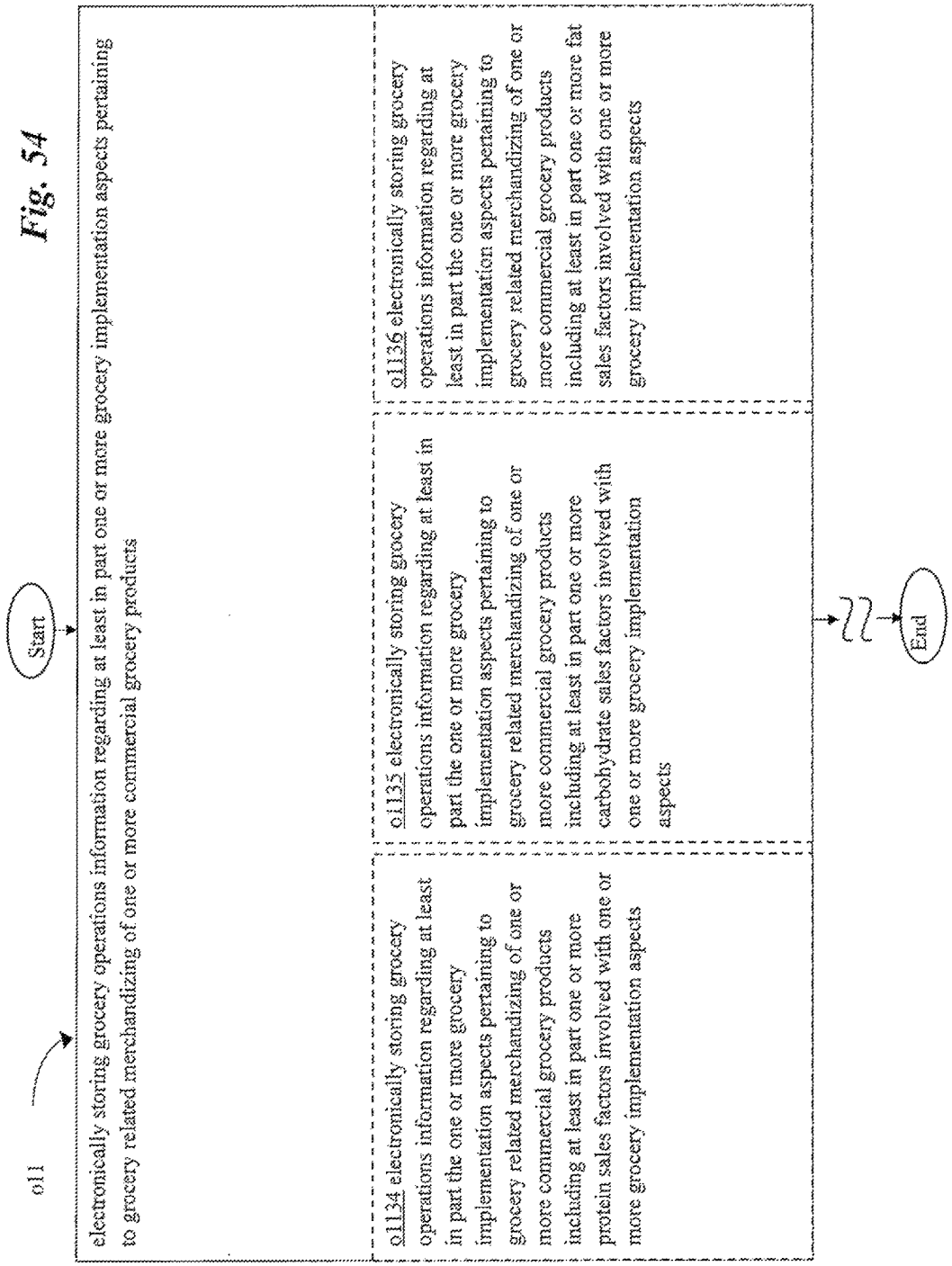
FIG. 54 is a high-level flowchart including exemplary implementations of operation o11 of FIG. 42.

In one or more implementations, as shown in FIG. 54, operation o11 includes an operation o1134 for electronically storing grocery operations information regarding at least in part the one or more grocery implementation aspects pertaining to grocery related merchandizing of one or more commercial grocery products including at least in part one or more protein sales factors involved with one or more grocery implementation aspects. Origination of an illustratively derived storing protein sales component group can be accomplished through skilled in the art design choice selection of one or more of the above depicted components from one or more of the above depicted subsystems shown in FIG. 12. Components from the storing protein sales component group can be used in implementing execution of the one or more storing protein sales instructions i1134 of FIG. 29, can be used in performance of the storing protein sales electrical circuitry arrangement e1134 of FIG. 22, and/or can be used in otherwise fulfillment of the operation o1134. An exemplary non-transitory signal bearing medium version of the information storage subsystem s200 is depicted in FIG. 29 as bearing the one or more storing protein sales instructions i1134 that when executed will direct performance of the operation o1134. Furthermore, the storing protein sales electrical circuitry arrangement ("elec circ arrange") e1134, when activated, will perform the operation o1134. Also, the storing protein sales module m1134, when executed and/or activated, will direct performance of and/or perform the operation o1134. For instance, in one or more exemplary implementations, the one or more storing protein sales instructions i1134, when executed, direct performance of the operation o1134 in the illustrative depiction as follows, and/or the storing protein sales electrical circuitry arrangement e1134, when activated, performs the operation o1134 in the illustrative depiction as follows, and/or the storing protein sales module m1134, when executed and/or activated, directs performance of and/or performs the operation o1134 in the illustrative depiction as follows, and/or the operation o1134 is otherwise carried out in the illustrative depiction as follows: electronically storing (e.g. from RS-232, etc.) grocery operations information (e.g. carton psi, etc.) regarding at least in part (e.g. argue, etc.) the one or more grocery implementation aspects (e.g. type of sanitizers used, etc.) pertaining to (e.g. argue, etc.) grocery related merchandizing of (e.g. fine dining grocery item receiving, etc.) one or more commercial grocery products (e.g. sous-vide main course grocery item, etc.) including at least in part one or more protein sales factors involved with one or more grocery implementation aspects (e.g. highest demand sources of beef used in grocery items, etc.).

In one or more implementations, as shown in FIG. 54, operation o11 includes an operation o1135 for electronically storing grocery operations information regarding at least in part the one or more grocery implementation aspects pertaining to grocery related merchandizing of one or more commercial grocery products including at least in part one or more carbohydrate sales factors involved with one or more grocery implementation aspects. Origination of an illustratively derived storing carbohydrate sales component group can be accomplished through skilled in the art design choice selection of one or more of the above depicted components from one or more of the above depicted subsystems shown in FIG. 12. Components from the storing carbohydrate sales component group can be used in implementing execution of the one or more storing carbohydrate sales instructions i1135 of FIG. 29, can be used in performance of the storing carbohydrate sales electrical circuitry arrangement e1135 of FIG. 22, and/or can be used in otherwise fulfillment of the operation o1135. An exemplary non-transitory signal bearing medium version of the information storage subsystem s200 is depicted in FIG. 29 as bearing the one or more storing carbohydrate sales instructions i1135 that when executed will direct performance of the operation o1135. Furthermore, the storing carbohydrate sales electrical circuitry arrangement ("elec circ arrange") e1135, when activated, will perform the operation o1135. Also, the storing carbohydrate sales module m1135, when executed and/or activated, will direct performance of and/or perform the operation o1135. For instance, in one or more exemplary implementations, the one or more storing carbohydrate sales instructions i1135, when executed, direct performance of the operation o1135 in the illustrative depiction as follows, and/or the storing carbohydrate sales electrical circuitry arrangement e1135, when activated, performs the operation o1135 in the illustrative depiction as follows, and/or the storing carbohydrate sales module m1135, when executed and/or activated, directs performance of and/or performs the operation o1135 in the illustrative depiction as follows, and/or the operation o1135 is otherwise carried out in the illustrative depiction as follows: electronically storing (e.g. from tablet entry, etc.) grocery operations information (e.g. carton in Hg, etc.) regarding at least in part (e.g. connected, etc.) the one or more grocery implementation aspects (e.g. whether any GMO foods are sold, etc.) pertaining to (e.g. connected, etc.) grocery related merchandizing of (e.g. fast grocery item receiving, etc.) one or more commercial grocery products (e.g. blended main course grocery item, etc.) including at least in part one or more carbohydrate sales factors involved with one or more grocery implementation aspects (e.g. sales records of GMO carbohydrate based grocery items, etc.).

In one or more implementations, as shown in FIG. 54, operation o11 includes an operation o1136 for electronically storing grocery operations information regarding at least in part the one or more grocery implementation aspects pertaining to grocery related merchandizing of one or more commercial grocery products including at least in part one or more fat sales factors involved with one or more grocery implementation aspects. Origination of an illustratively derived storing fat sales component group can be accomplished through skilled in the art design choice selection of one or more of the above depicted components from one or more of the above depicted subsystems shown in FIG. 12. Components from the storing fat sales component group can be used in implementing execution of the one or more storing fat sales instructions i1136 of FIG. 29, can be used in performance of the storing fat sales electrical circuitry arrangement e1136 of FIG. 22, and/or can be used in otherwise fulfillment of the operation o1136. An exemplary non-transitory signal bearing medium version of the information storage subsystem s200 is depicted in FIG. 29 as bearing the one or more storing fat sales instructions i1136 that when executed will direct performance of the operation o1136. Furthermore, the storing fat sales electrical circuitry arrangement ("elec circ arrange") e1136, when activated, will perform the operation o1136. Also, the storing fat sales module m1136, when executed and/or activated, will direct performance of and/or perform the operation o1136. For instance, in one or more exemplary implementations, the one or more storing fat sales instructions i1136, when executed, direct performance of the operation o1136 in the illustrative depiction as follows, and/or the storing fat sales electrical circuitry arrangement e1136, when activated, performs the operation o1136 in the illustrative depiction as follows, and/or the storing fat sales module m1136, when executed and/or activated, directs performance of and/or performs the operation o1136 in the illustrative depiction as follows, and/or the operation o1136 is otherwise carried out in the illustrative depiction as follows: electronically storing (e.g. from PDA entry, etc.) grocery operations information (e.g. equipment maintenance, etc.) regarding at least in part (e.g. commit to, etc.) the one or more grocery implementation aspects (e.g. instances of health violations in grocery facilities, etc.) pertaining to (e.g. commit to, etc.) grocery related merchandizing of (e.g. family buffet grocery item receiving, etc.) one or more commercial grocery products (e.g. beverage main course grocery item, etc.) including at least in part one or more fat sales factors involved with one or more grocery implementation aspects (e.g. instances of health violations in handling of oils to be sold as grocery items, etc.).

Figure 55:
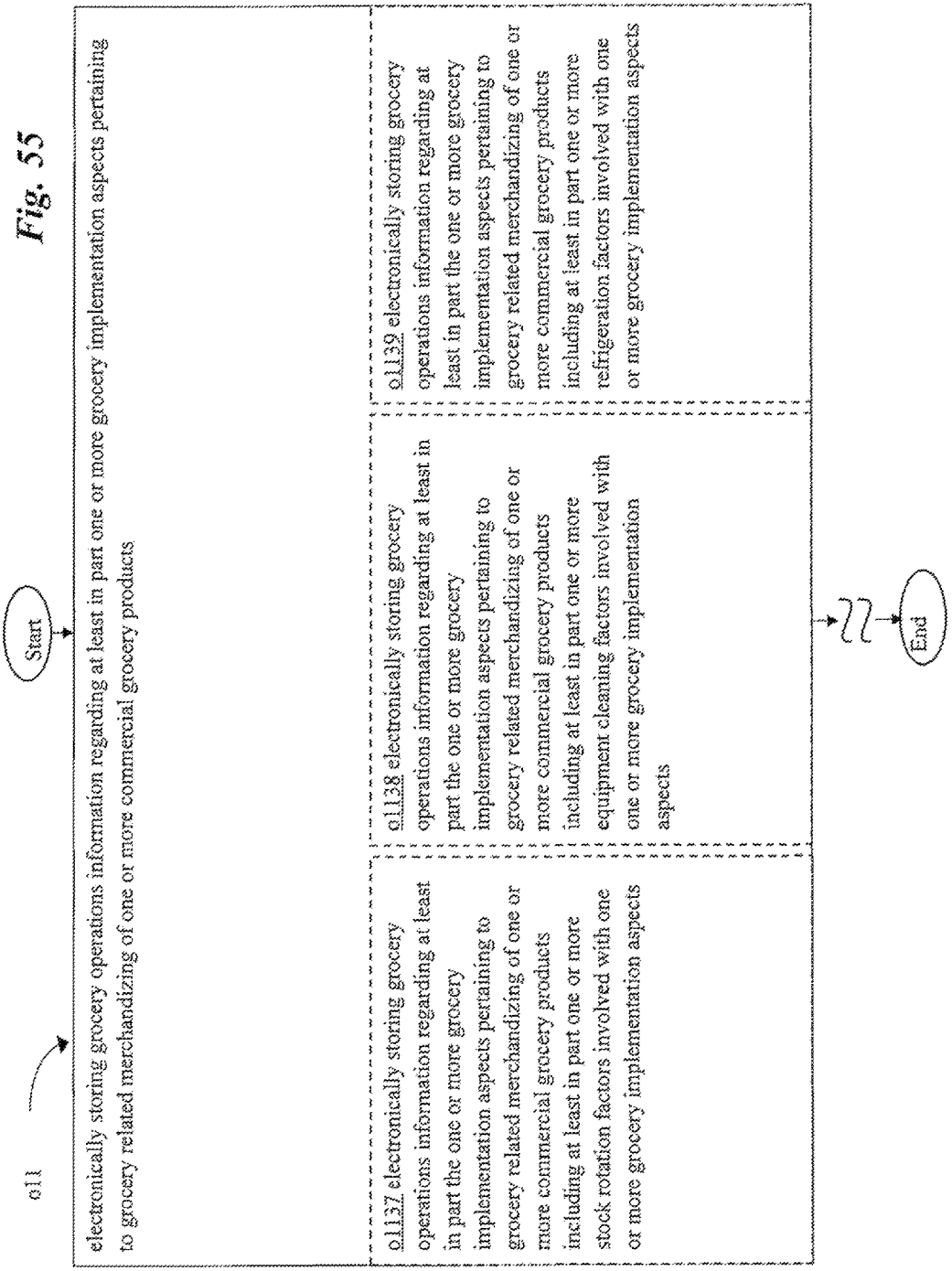
FIG. 55 is a high-level flowchart including exemplary implementations of operation o11 of FIG. 42.

In one or more implementations, as shown in FIG. 55, operation o11 includes an operation o1137 for electronically storing grocery operations information regarding at least in part the one or more grocery implementation aspects pertaining to grocery related merchandizing of one or more commercial grocery products including at least in part one or more stock rotation factors involved with one or more grocery implementation aspects. Origination of an illustratively derived storing stock rotation component group can be accomplished through skilled in the art design choice selection of one or more of the above depicted components from one or more of the above depicted subsystems shown in FIG. 12. Components from the storing stock rotation component group can be used in implementing execution of the one or more storing stock rotation instructions i1137 of FIG. 29, can be used in performance of the storing stock rotation electrical circuitry arrangement e1137 of FIG. 22, and/or can be used in otherwise fulfillment of the operation o1137. An exemplary non-transitory signal bearing medium version of the information storage subsystem s200 is depicted in FIG. 29 as bearing the one or more storing stock rotation instructions i1137 that when executed will direct performance of the operation o1137. Furthermore, the storing stock rotation electrical circuitry arrangement ("elec circ arrange") e1137, when activated, will perform the operation o1137. Also, the storing stock rotation module m1137, when executed and/or activated, will direct performance of and/or perform the operation o1137. For instance, in one or more exemplary implementations, the one or more storing stock rotation instructions i1137, when executed, direct performance of the operation o1137 in the illustrative depiction as follows, and/or the storing stock rotation electrical circuitry arrangement e1137, when activated, performs the operation o1137 in the illustrative depiction as follows, and/or the storing stock rotation module m1137, when executed and/or activated, directs performance of and/or performs the operation o1137 in the illustrative depiction as follows, and/or the operation o1137 is otherwise carried out in the illustrative depiction as follows: electronically storing (e.g. from desktop entry, etc.) grocery operations information (e.g. nitrogen gas levels of storage units, etc.) regarding at least in part (e.g. absorbed by, etc.) the one or more grocery implementation aspects (e.g. purchasing patterns from wholesalers, etc.) pertaining to (e.g. absorbed by, etc.) grocery related merchandizing of (e.g. mobile catering grocery item receiving, etc.) one or more commercial grocery products (e.g. protein main course grocery item, etc.) including at least in part one or more stock rotation factors involved with one or more grocery implementation aspects (e.g. availability patterns from wholesalers as it impacts stock rotations, etc.).

In one or more implementations, as shown in FIG. 55, operation o11 includes an operation o1138 for electronically storing grocery operations information regarding at least in part the one or more grocery implementation aspects pertaining to grocery related merchandizing of one or more commercial grocery products including at least in part one or more equipment cleaning factors involved with one or more grocery implementation aspects. Origination of an illustratively derived storing equipment cleaning component group can be accomplished through skilled in the art design choice selection of one or more of the above depicted components from one or more of the above depicted subsystems shown in FIG. 12. Components from the storing equipment cleaning component group can be used in implementing execution of the one or more storing equipment cleaning instructions i1138 of FIG. 29, can be used in performance of the storing equipment cleaning electrical circuitry arrangement e1138 of FIG. 22, and/or can be used in otherwise fulfillment of the operation o1138. An exemplary non-transitory signal bearing medium version of the information storage subsystem s200 is depicted in FIG. 29 as bearing the one or more storing equipment cleaning instructions i1138 that when executed will direct performance of the operation o1138. Furthermore, the storing equipment cleaning electrical circuitry arrangement ("elec circ arrange") e1138, when activated, will perform the operation o1138. Also, the storing equipment cleaning module m1138, when executed and/or activated, will direct performance of and/or perform the operation o1138. For instance, in one or more exemplary implementations, the one or more storing equipment cleaning instructions i1138, when executed, direct performance of the operation o1138 in the illustrative depiction as follows, and/or the storing equipment cleaning electrical circuitry arrangement e1138, when activated, performs the operation o1138 in the illustrative depiction as follows, and/or the storing equipment cleaning module m1138, when executed and/or activated, directs performance of and/or performs the operation o1138 in the illustrative depiction as follows, and/or the operation o1138 is otherwise carried out in the illustrative depiction as follows: electronically storing (e.g. as acoustic energy, etc.) grocery operations information (e.g. amount of waste to disposed of, etc.) regarding at least in part (e.g. embraced by, etc.) the one or more grocery implementation aspects (e.g. rodent infestation history, etc.) pertaining to (e.g. embraced by, etc.) grocery related merchandizing of (e.g. institutional grocery item receiving, etc.) one or more commercial grocery products (e.g. carbohydrate main course grocery item, etc.) including at least in part one or more equipment cleaning factors involved with one or more grocery implementation aspects (e.g. rodent infestation history, etc.).

In one or more implementations, as shown in FIG. 55, operation o11 includes an operation o1139 for electronically storing grocery operations information regarding at least in part the one or more grocery implementation aspects pertaining to grocery related merchandizing of one or more commercial grocery products including at least in part one or more refrigeration factors involved with one or more grocery implementation aspects. Origination of an illustratively derived storing refrigeration factors component group can be accomplished through skilled in the art design choice selection of one or more of the above depicted components from one or more of the above depicted subsystems shown in FIG. 12. Components from the storing refrigeration factors component group can be used in implementing execution of the one or more storing refrigeration factors instructions i1139 of FIG. 29, can be used in performance of the storing refrigeration factors electrical circuitry arrangement e1139 of FIG. 22, and/or can be used in otherwise fulfillment of the operation o1139. An exemplary non-transitory signal bearing medium version of the information storage subsystem s200 is depicted in FIG. 29 as bearing the one or more storing refrigeration factors instructions i1139 that when executed will direct performance of the operation o1139. Furthermore, the storing refrigeration factors electrical circuitry arrangement ("elec circ arrange") e1139, when activated, will perform the operation o1139. Also, the storing refrigeration factors module m1139, when executed and/or activated, will direct performance of and/or perform the operation o1139. For instance, in one or more exemplary implementations, the one or more storing refrigeration factors instructions i1139, when executed, direct performance of the operation o1139 in the illustrative depiction as follows, and/or the storing refrigeration factors electrical circuitry arrangement e1139, when activated, performs the operation o1139 in the illustrative depiction as follows, and/or the storing refrigeration factors module m1139, when executed and/or activated, directs performance of and/or performs the operation o1139 in the illustrative depiction as follows, and/or the operation o1139 is otherwise carried out in the illustrative depiction as follows: electronically storing (e.g. from VHF, etc.) grocery operations information (e.g. carrier information for grocery shipments, etc.) regarding at least in part (e.g. containing, etc.) the one or more grocery implementation aspects (e.g. recycling practices implemented, etc.) pertaining to (e.g. containing, etc.) grocery related merchandizing of (e.g. school cafeteria grocery item receiving, etc.) one or more commercial grocery products (e.g. fat dominant main course grocery item, etc.) including at least in part one or more refrigeration factors involved with one or more grocery implementation aspects (e.g. operational temperature profiles for refrigeration systems, etc.).

Figure 56:
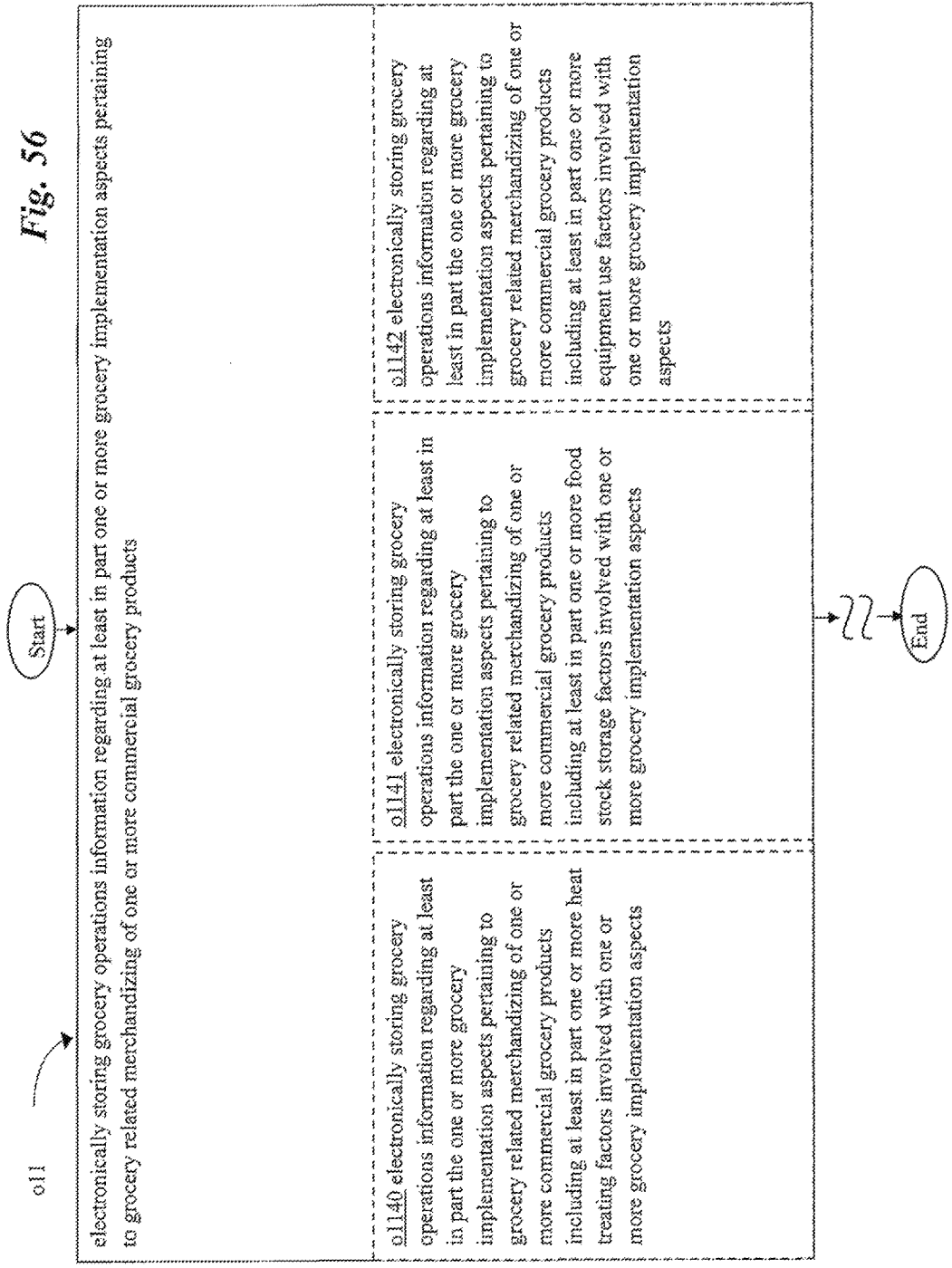
FIG. 56 is a high-level flowchart including exemplary implementations of operation o11 of FIG. 42.

In one or more implementations, as shown in FIG. 56, operation o11 includes an operation o1140 for electronically storing grocery operations information regarding at least in part the one or more grocery implementation aspects pertaining to grocery related merchandizing of one or more commercial grocery products including at least in part one or more heat treating factors involved with one or more grocery implementation aspects. Origination of an illustratively derived storing heat treating component group can be accomplished through skilled in the art design choice selection of one or more of the above depicted components from one or more of the above depicted subsystems shown in FIG. 12. Components from the storing heat treating component group can be used in implementing execution of the one or more storing heat treating instructions i1140 of FIG. 30, can be used in performance of the storing heat treating electrical circuitry arrangement e1140 of FIG. 23, and/or can be used in otherwise fulfillment of the operation o1140. An exemplary non-transitory signal bearing medium version of the information storage subsystem s200 is depicted in FIG. 30 as bearing the one or more storing heat treating instructions i1140 that when executed will direct performance of the operation o1140. Furthermore, the storing heat treating electrical circuitry arrangement ("elec circ arrange") e1140, when activated, will perform the operation o1140. Also, the storing heat treating module m1140, when executed and/or activated, will direct performance of and/or perform the operation o1140. For instance, in one or more exemplary implementations, the one or more storing heat treating instructions i1140, when executed, direct performance of the operation o1140 in the illustrative depiction as follows, and/or the storing heat treating electrical circuitry arrangement e1140, when activated, performs the operation o1140 in the illustrative depiction as follows, and/or the storing heat treating module m1140, when executed and/or activated, directs performance of and/or performs the operation o1140 in the illustrative depiction as follows, and/or the operation o1140 is otherwise carried out in the illustrative depiction as follows: electronically storing (e.g. from UFH, etc.) grocery operations information (e.g. water usage, etc.) regarding at least in part (e.g. engaging, etc.) the one or more grocery implementation aspects (e.g. demographics of grocery customers, etc.) pertaining to (e.g. engaging, etc.) grocery related merchandizing of (e.g. nursing home grocery item receiving, etc.) one or more commercial grocery products (e.g. pasta main course grocery item, etc.) including at least in part one or more heat treating factors involved with one or more grocery implementation aspects (e.g. temperature settings of ovens used to prepare grocery items, etc.).

In one or more implementations, as shown in FIG. 56, operation o11 includes an operation o1141 for electronically storing grocery operations information regarding at least in part the one or more grocery implementation aspects pertaining to grocery related merchandizing of one or more commercial grocery products including at least in part one or more food stock storage factors involved with one or more grocery implementation aspects. Origination of an illustratively derived storing stock storage component group can be accomplished through skilled in the art design choice selection of one or more of the above depicted components from one or more of the above depicted subsystems shown in FIG. 12. Components from the storing stock storage component group can be used in implementing execution of the one or more storing stock storage instructions i1141 of FIG. 30, can be used in performance of the storing stock storage electrical circuitry arrangement e1141 of FIG. 23, and/or can be used in otherwise fulfillment of the operation o1141. An exemplary non-transitory signal bearing medium version of the information storage subsystem s200 is depicted in FIG. 30 as bearing the one or more storing stock storage instructions i1141 that when executed will direct performance of the operation o1141. Furthermore, the storing stock storage electrical circuitry arrangement ("elec circ arrange") e1141, when activated, will perform the operation o1141. Also, the storing stock storage module m1141, when executed and/or activated, will direct performance of and/or perform the operation o1141. For instance, in one or more exemplary implementations, the one or more storing stock storage instructions i1141, when executed, direct performance of the operation o1141 in the illustrative depiction as follows, and/or the storing stock storage electrical circuitry arrangement e1141, when activated, performs the operation o1141 in the illustrative depiction as follows, and/or the storing stock storage module m1141, when executed and/or activated, directs performance of and/or performs the operation o1141 in the illustrative depiction as follows, and/or the operation o1141 is otherwise carried out in the illustrative depiction as follows: electronically storing (e.g. from FRS, etc.) grocery operations information (e.g. produce quality observed as received from various warehouses, etc.) regarding at least in part (e.g. engaged by, etc.) the one or more grocery implementation aspects (e.g. stocking rates for various grocery items, etc.) pertaining to (e.g. engaged by, etc.) grocery related merchandizing of (e.g. street vendor grocery item receiving, etc.) one or more commercial grocery products (e.g. beef side dish grocery item, etc.) including at least in part one or more food stock storage factors involved with one or more grocery implementation aspects (e.g. statistical distribution of stock rotation periods, etc.).

In one or more implementations, as shown in FIG. 56, operation o11 includes an operation o1142 for electronically storing grocery operations information regarding at least in part the one or more grocery implementation aspects pertaining to grocery related merchandizing of one or more commercial grocery products including at least in part one or more equipment use factors involved with one or more grocery implementation aspects. Origination of an illustratively derived storing equipment use component group can be accomplished through skilled in the art design choice selection of one or more of the above depicted components from one or more of the above depicted subsystems shown in FIG. 12. Components from the storing equipment use component group can be used in implementing execution of the one or more storing equipment use instructions i1142 of FIG. 30, can be used in performance of the storing equipment use electrical circuitry arrangement e1142 of FIG. 23, and/or can be used in otherwise fulfillment of the operation o1142. An exemplary non-transitory signal bearing medium version of the information storage subsystem s200 is depicted in FIG. 30 as bearing the one or more storing equipment use instructions i1142 that when executed will direct performance of the operation o1142. Furthermore, the storing equipment use electrical circuitry arrangement ("elec circ arrange") e1142, when activated, will perform the operation o1142. Also, the storing equipment use module m1142, when executed and/or activated, will direct performance of and/or perform the operation o1142. For instance, in one or more exemplary implementations, the one or more storing equipment use instructions i1142, when executed, direct performance of the operation o1142 in the illustrative depiction as follows, and/or the storing equipment use electrical circuitry arrangement e1142, when activated, performs the operation o1142 in the illustrative depiction as follows, and/or the storing equipment use module m1142, when executed and/or activated, directs performance of and/or performs the operation o1142 in the illustrative depiction as follows, and/or the operation o1142 is otherwise carried out in the illustrative depiction as follows: electronically storing (e.g. from GMRS, etc.) grocery operations information (e.g. meat quality observed as received from various slaughter houses, etc.) regarding at least in part (e.g. incorporating, etc.) the one or more grocery implementation aspects (e.g. profit margin on various grocery items, etc.) pertaining to (e.g. incorporating, etc.) grocery related merchandizing of (e.g. mobile kitchen grocery item receiving, etc.) one or more commercial grocery products (e.g. pork side dish grocery item, etc.) including at least in part one or more equipment use factors involved with one or more grocery implementation aspects (e.g. equipment repair and maintenance histories, etc.).

Figure 57:
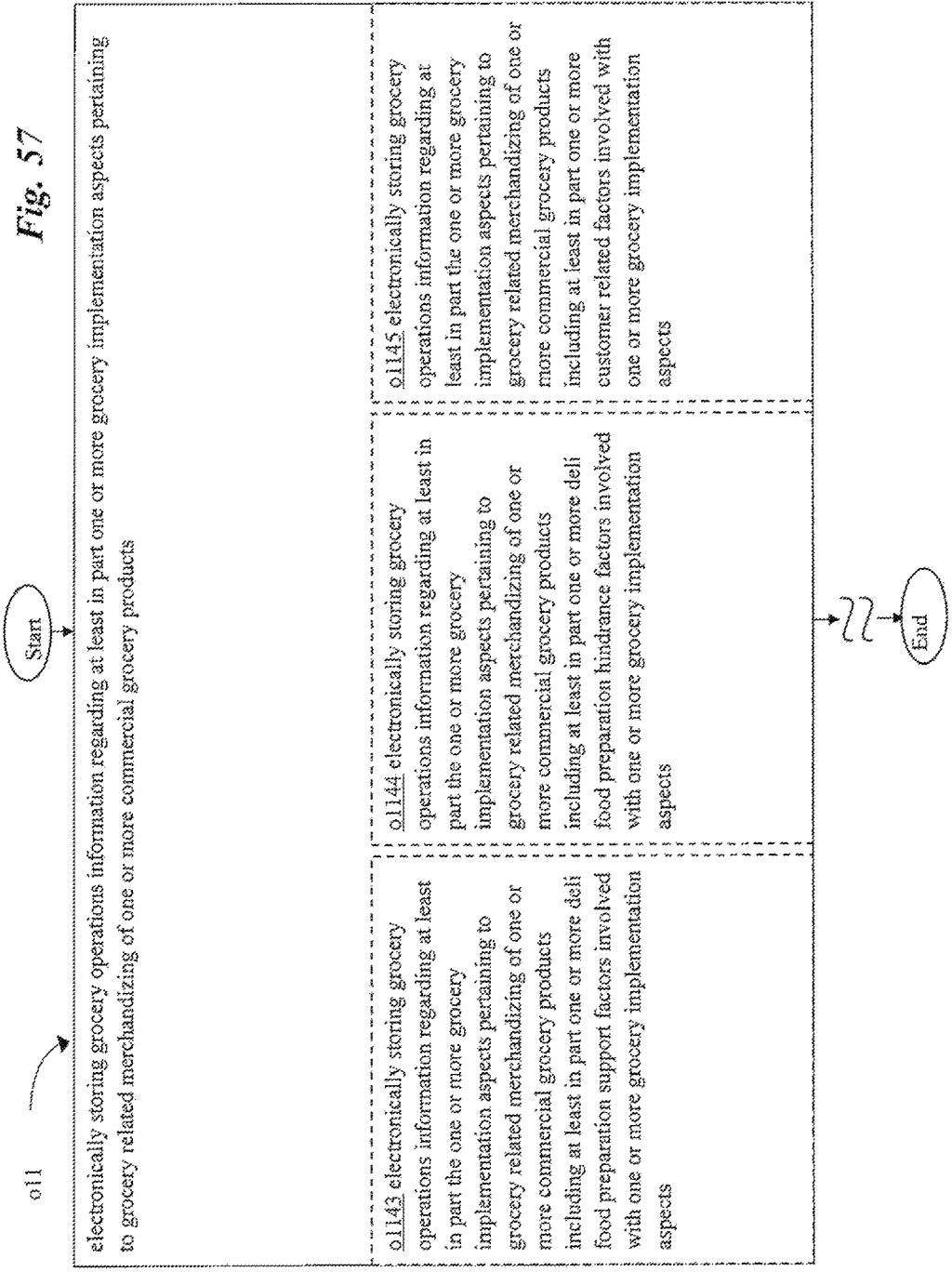
FIG. 57 is a high-level flowchart including exemplary implementations of operation o11 of FIG. 42.

In one or more implementations, as shown in FIG. 57, operation o11 includes an operation o1143 for electronically storing grocery operations information regarding at least in part the one or more grocery implementation aspects pertaining to grocery related merchandizing of one or more commercial grocery products including at least in part one or more deli food preparation support factors involved with one or more grocery implementation aspects. Origination of an illustratively derived storing deli support component group can be accomplished through skilled in the art design choice selection of one or more of the above depicted components from one or more of the above depicted subsystems shown in FIG. 12. Components from the storing deli support component group can be used in implementing execution of the one or more storing deli support instructions i1143 of FIG. 30, can be used in performance of the storing deli support electrical circuitry arrangement e1143 of FIG. 23, and/or can be used in otherwise fulfillment of the operation o1143. An exemplary non-transitory signal bearing medium version of the information storage subsystem s200 is depicted in FIG. 30 as bearing the one or more storing deli support instructions i1143 that when executed will direct performance of the operation o1143. Furthermore, the storing deli support electrical circuitry arrangement ("elec circ arrange") e1143, when activated, will perform the operation o1143. Also, the storing deli support module m1143, when executed and/or activated, will direct performance of and/or perform the operation o1143. For instance, in one or more exemplary implementations, the one or more storing deli support instructions i1143, when executed, direct performance of the operation o1143 in the illustrative depiction as follows, and/or the storing deli support electrical circuitry arrangement e1143, when activated, performs the operation o1143 in the illustrative depiction as follows, and/or the storing deli support module m1143, when executed and/or activated, directs performance of and/or performs the operation o1143 in the illustrative depiction as follows, and/or the operation o1143 is otherwise carried out in the illustrative depiction as follows: electronically storing (e.g. via IEEE 802.11, etc.) grocery operations information (e.g. poultry quality observed as received from various farms, etc.) regarding at least in part (e.g. engrossing, etc.) the one or more grocery implementation aspects (e.g. customer occupation statistics, etc.) pertaining to (e.g. engrossing, etc.) grocery related merchandizing of (e.g. hospital grocery item receiving, etc.) one or more commercial grocery products (e.g. fish side dish grocery item, etc.) including at least in part one or more deli food preparation support factors involved with one or more grocery implementation aspects (e.g. grocery worker leave of absence histories, etc.).

In one or more implementations, as shown in FIG. 57, operation o11 includes an operation o1144 for electronically storing grocery operations information regarding at least in part the one or more grocery implementation aspects pertaining to grocery related merchandizing of one or more commercial grocery products including at least in part one or more deli food preparation hindrance factors involved with one or more grocery implementation aspects. Origination of an illustratively derived storing deli hindrance component group can be accomplished through skilled in the art design choice selection of one or more of the above depicted components from one or more of the above depicted subsystems shown in FIG. 12. Components from the storing deli hindrance component group can be used in implementing execution of the one or more storing deli hindrance instructions i1144 of FIG. 30, can be used in performance of the storing deli hindrance electrical circuitry arrangement e1144 of FIG. 23, and/or can be used in otherwise fulfillment of the operation o1144. An exemplary non-transitory signal bearing medium version of the information storage subsystem s200 is depicted in FIG. 30 as bearing the one or more storing deli hindrance instructions i1144 that when executed will direct performance of the operation o1144. Furthermore, the storing deli hindrance electrical circuitry arrangement ("elec circ arrange") e1144, when activated, will perform the operation o1144. Also, the storing deli hindrance module m1144, when executed and/or activated, will direct performance of and/or perform the operation o1144. For instance, in one or more exemplary implementations, the one or more storing deli hindrance instructions i1144, when executed, direct performance of the operation o1144 in the illustrative depiction as follows, and/or the storing deli hindrance electrical circuitry arrangement e1144, when activated, performs the operation o1144 in the illustrative depiction as follows, and/or the storing deli hindrance module m1144, when executed and/or activated, directs performance of and/or performs the operation o1144 in the illustrative depiction as follows, and/or the operation o1144 is otherwise carried out in the illustrative depiction as follows: electronically storing (e.g. via CDMA, etc.) grocery operations information (e.g. shipping container information, etc.) regarding at least in part (e.g. implicate, etc.) the one or more grocery implementation aspects (e.g. garbage disposal practices, etc.) pertaining to (e.g. implicate, etc.) grocery related merchandizing of (e.g. deli department grocery item receiving, etc.) one or more commercial grocery products (e.g. tofu side dish grocery item, etc.) including at least in part one or more deli food preparation hindrance factors involved with one or more grocery implementation aspects (e.g. grocery garbage disposal practices, etc.).

In one or more implementations, as shown in FIG. 57, operation o11 includes an operation o1145 for electronically storing grocery operations information regarding at least in part the one or more grocery implementation aspects pertaining to grocery related merchandizing of one or more commercial grocery products including at least in part one or more customer related factors involved with one or more grocery implementation aspects. Origination of an illustratively derived storing customer factors component group can be accomplished through skilled in the art design choice selection of one or more of the above depicted components from one or more of the above depicted subsystems shown in FIG. 12. Components from the storing customer factors component group can be used in implementing execution of the one or more storing customer factors instructions i1145 of FIG. 30, can be used in performance of the storing customer factors electrical circuitry arrangement e1145 of FIG. 23, and/or can be used in otherwise fulfillment of the operation o1145. An exemplary non-transitory signal bearing medium version of the information storage subsystem s200 is depicted in FIG. 30 as bearing the one or more storing customer factors instructions i1145 that when executed will direct performance of the operation o1145. Furthermore, the storing customer factors electrical circuitry arrangement ("elec circ arrange") e1145, when activated, will perform the operation o1145. Also, the storing customer factors module m1145, when executed and/or activated, will direct performance of and/or perform the operation o1145. For instance, in one or more exemplary implementations, the one or more storing customer factors instructions i1145, when executed, direct performance of the operation o1145 in the illustrative depiction as follows, and/or the storing customer factors electrical circuitry arrangement e1145, when activated, performs the operation o1145 in the illustrative depiction as follows, and/or the storing customer factors module m1145, when executed and/or activated, directs performance of and/or performs the operation o1145 in the illustrative depiction as follows, and/or the operation o1145 is otherwise carried out in the illustrative depiction as follows: electronically storing (e.g. from GPRS, etc.) grocery operations information (e.g. dairy quality observed from various farms, etc.) regarding at least in part (e.g. necessitate, etc.) the one or more grocery implementation aspects (e.g. standards used to classify condition of grocery items received, etc.) pertaining to (e.g. necessitate, etc.) grocery related merchandizing of (e.g. fine dining grocery item storing, etc.) one or more commercial grocery products (e.g. chicken side dish grocery item, etc.) including at least in part one or more customer related factors involved with one or more grocery implementation aspects (e.g. occupancy statistics for grocery customers with respect to specials of the day, etc.).

Figure 58:
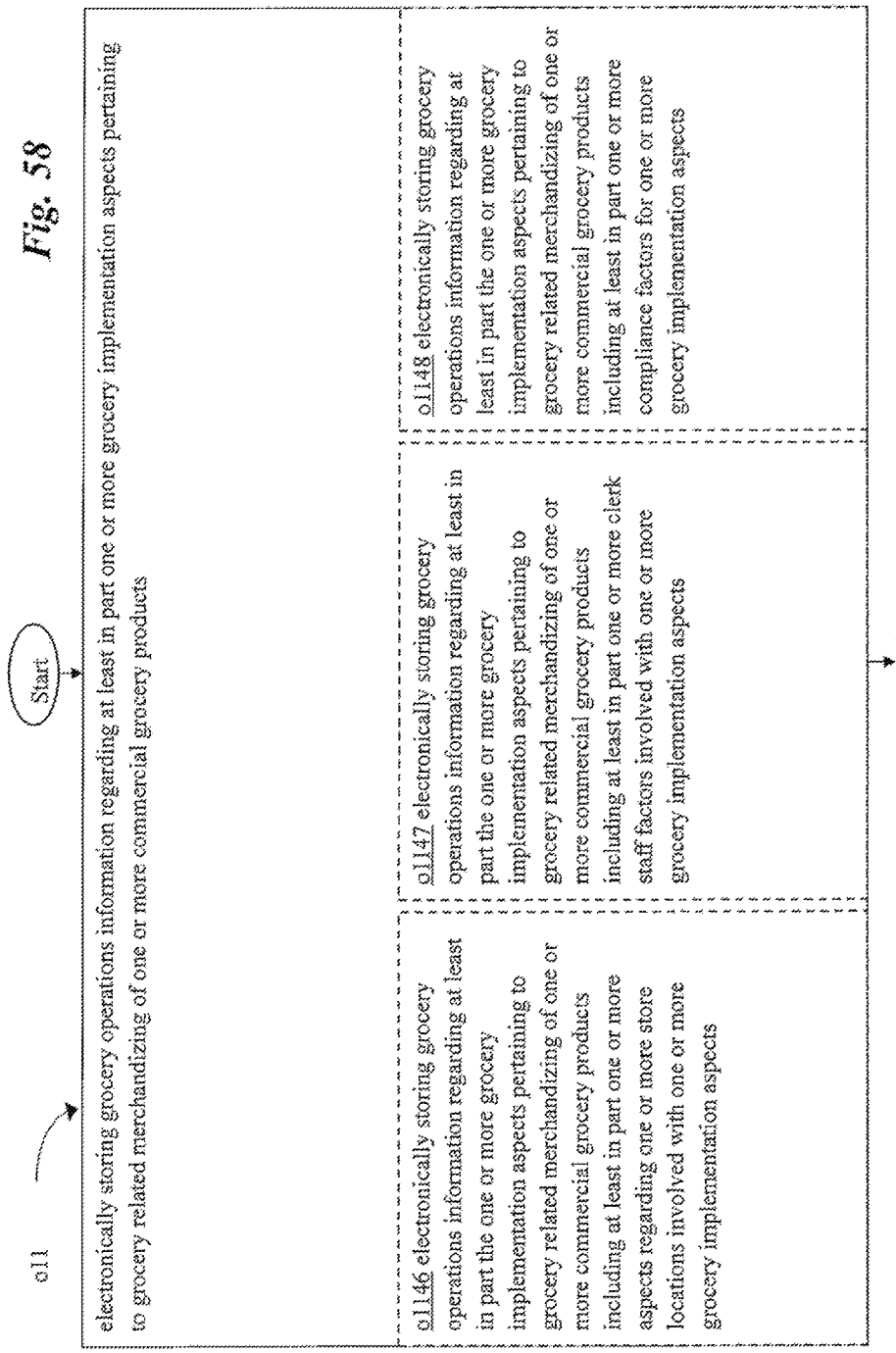
FIG. 58 is a high-level flowchart including exemplary implementations of operation o11 of FIG. 42.

In one or more implementations, as shown in FIG. 58, operation o11 includes an operation o1146 for electronically storing grocery operations information regarding at least in part the one or more grocery implementation aspects pertaining to grocery related merchandizing of one or more commercial grocery products including at least in part one or more aspects regarding one or more store locations involved with one or more grocery implementation aspects. Origination of an illustratively derived storing store locations component group can be accomplished through skilled in the art design choice selection of one or more of the above depicted components from one or more of the above depicted subsystems shown in FIG. 12. Components from the storing store locations component group can be used in implementing execution of the one or more storing store locations instructions i1146 of FIG. 30, can be used in performance of the storing store locations electrical circuitry arrangement e1146 of FIG. 23, and/or can be used in otherwise fulfillment of the operation o1146. An exemplary non-transitory signal bearing medium version of the information storage subsystem s200 is depicted in FIG. 30 as bearing the one or more storing store locations instructions i1146 that when executed will direct performance of the operation o1146. Furthermore, the storing store locations electrical circuitry arrangement ("elec circ arrange") e1146, when activated, will perform the operation o1146. Also, the storing store locations module m1146, when executed and/or activated, will direct performance of and/or perform the operation o1146. For instance, in one or more exemplary implementations, the one or more storing store locations instructions i1146, when executed, direct performance of the operation o1146 in the illustrative depiction as follows, and/or the storing store locations electrical circuitry arrangement e1146, when activated, performs the operation o1146 in the illustrative depiction as follows, and/or the storing store locations module m1146, when executed and/or activated, directs performance of and/or performs the operation o1146 in the illustrative depiction as follows, and/or the operation o1146 is otherwise carried out in the illustrative depiction as follows: electronically storing (e.g. via G3, etc.) grocery operations information (e.g. AVI file format, etc.) regarding at least in part (e.g. presuppose, etc.) the one or more grocery implementation aspects (e.g. standards used to classify condition of food stored, etc.) pertaining to (e.g. presuppose, etc.) grocery related merchandizing of (e.g. fast grocery item storing, etc.) one or more commercial grocery products (e.g. seafood side dish grocery item, etc.) including at least in part one or more aspects regarding one or more store locations involved with one or more grocery implementation aspects (e.g. condition of water supply and air quality of grocery warehouse and store facilities, etc.).

In one or more implementations, as shown in FIG. 58, operation o11 includes an operation o1147 for electronically storing grocery operations information regarding at least in part the one or more grocery implementation aspects pertaining to grocery related merchandizing of one or more commercial grocery products including at least in part one or more clerk staff factors involved with one or more grocery implementation aspects. Origination of an illustratively derived storing clerk staff component group can be accomplished through skilled in the art design choice selection of one or more of the above depicted components from one or more of the above depicted subsystems shown in FIG. 12. Components from the storing clerk staff component group can be used in implementing execution of the one or more storing clerk staff instructions i1147 of FIG. 30, can be used in performance of the storing clerk staff electrical circuitry arrangement e1147 of FIG. 23, and/or can be used in otherwise fulfillment of the operation o1147. An exemplary non-transitory signal bearing medium version of the information storage subsystem s200 is depicted in FIG. 30 as bearing the one or more storing clerk staff instructions i1147 that when executed will direct performance of the operation o1147. Furthermore, the storing clerk staff electrical circuitry arrangement ("elec circ arrange") e1147, when activated, will perform the operation o1147. Also, the storing clerk staff module m1147, when executed and/or activated, will direct performance of and/or perform the operation o1147. For instance, in one or more exemplary implementations, the one or more storing clerk staff instructions i1147, when executed, direct performance of the operation o1147 in the illustrative depiction as follows, and/or the storing clerk staff electrical circuitry arrangement e1147, when activated, performs the operation o1147 in the illustrative depiction as follows, and/or the storing clerk staff module m1147, when executed and/or activated, directs performance of and/or performs the operation o1147 in the illustrative depiction as follows, and/or the operation o1147 is otherwise carried out in the illustrative depiction as follows: electronically storing (e.g. via G4, etc.) grocery operations information (e.g. MP3 file format, etc.) regarding at least in part (e.g. related to, etc.) the one or more grocery implementation aspects (e.g. grocery worker exemplary behavior, etc.) pertaining to (e.g. related to, etc.) grocery related merchandizing of (e.g. family buffet grocery item storing, etc.) one or more commercial grocery products (e.g. poultry side dish grocery item, etc.) including at least in part one or more clerk staff factors involved with one or more grocery implementation aspects (e.g. grocery worker turnover statistics, etc.).

In one or more implementations, as shown in FIG. 58, operation o11 includes an operation o1148 for electronically storing grocery operations information regarding at least in part the one or more grocery implementation aspects pertaining to grocery related merchandizing of one or more commercial grocery products including at least in part one or more compliance factors for one or more grocery implementation aspects. Origination of an illustratively derived storing compliance factors component group can be accomplished through skilled in the art design choice selection of one or more of the above depicted components from one or more of the above depicted subsystems shown in FIG. 12. Components from the storing compliance factors component group can be used in implementing execution of the one or more storing compliance factors instructions i1148 of FIG. 30, can be used in performance of the storing compliance factors electrical circuitry arrangement e1148 of FIG. 23, and/or can be used in otherwise fulfillment of the operation o1148. An exemplary non-transitory signal bearing medium version of the information storage subsystem s200 is depicted in FIG. 30 as bearing the one or more storing compliance factors instructions i1148 that when executed will direct performance of the operation o1148. Furthermore, the storing compliance factors electrical circuitry arrangement ("elec circ arrange") e1148, when activated, will perform the operation o1148. Also, the storing compliance factors module m1148, when executed and/or activated, will direct performance of and/or perform the operation o1148. For instance, in one or more exemplary implementations, the one or more storing compliance factors instructions i1148, when executed, direct performance of the operation o1148 in the illustrative depiction as follows, and/or the storing compliance factors electrical circuitry arrangement e1148, when activated, performs the operation o1148 in the illustrative depiction as follows, and/or the storing compliance factors module m1148, when executed and/or activated, directs performance of and/or performs the operation o1148 in the illustrative depiction as follows, and/or the operation o1148 is otherwise carried out in the illustrative depiction as follows: electronically storing (e.g. onto CD-ROM, etc.) grocery operations information (e.g. audio descriptions, etc.) regarding at least in part (e.g. relationship, etc.) the one or more grocery implementation aspects (e.g. grocery worker poor behavior, etc.) pertaining to (e.g. relationship, etc.) grocery related merchandizing of (e.g. mobile catering grocery item storing, etc.) one or more commercial grocery products (e.g. diary side dish grocery item, etc.) including at least in part one or more compliance factors for one or more grocery implementation aspects (e.g. health inspection violations of grocery store or warehouse facilities, etc.).

Figure 59:
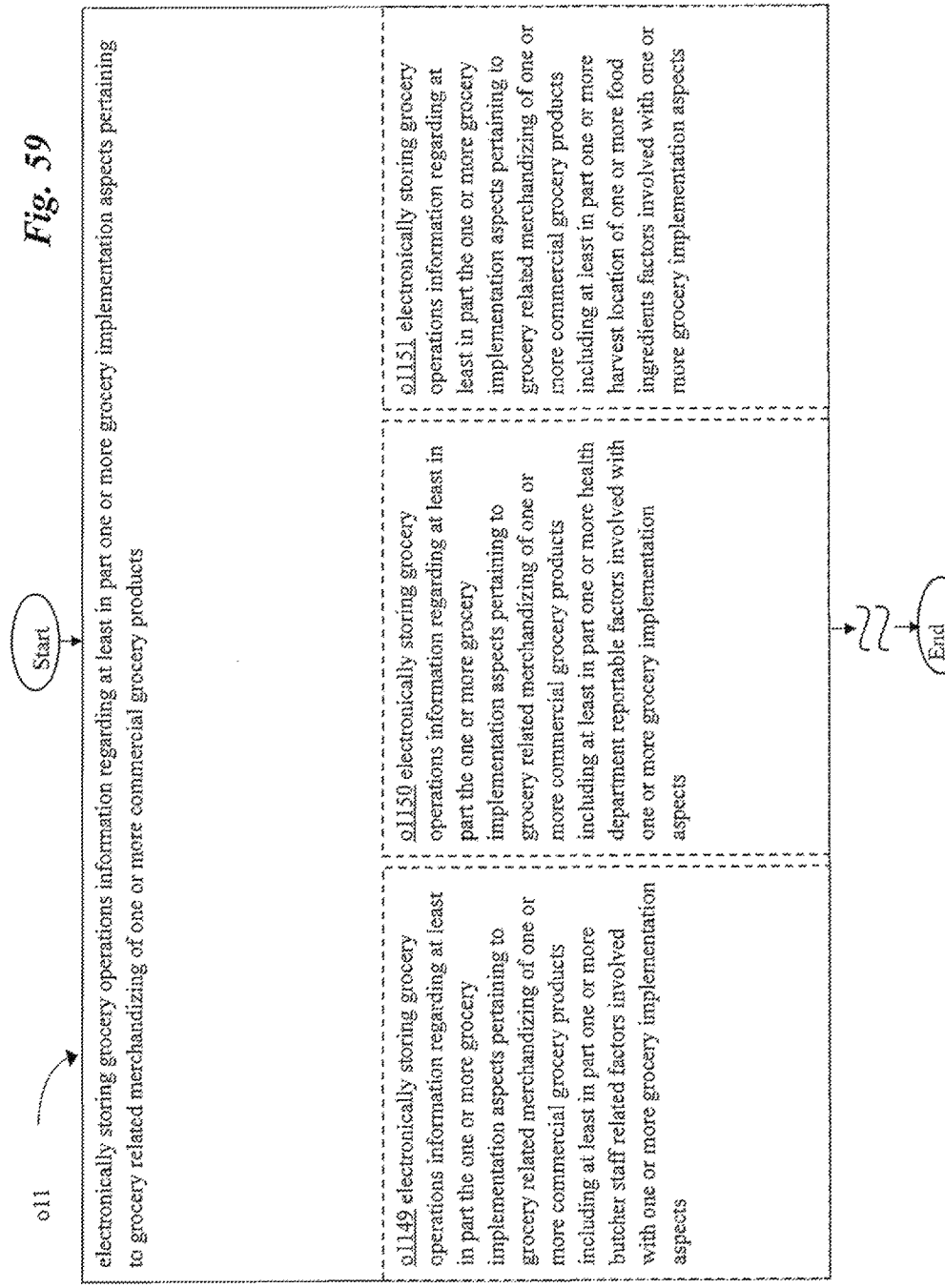
FIG. 59 is a high-level flowchart including exemplary implementations of operation o11 of FIG. 42.

In one or more implementations, as shown in FIG. 59, operation o11 includes an operation o1149 for electronically storing grocery operations information regarding at least in part the one or more grocery implementation aspects pertaining to grocery related merchandizing of one or more commercial grocery products including at least in part one or more butcher staff related factors involved with one or more grocery implementation aspects. Origination of an illustratively derived storing butcher staff component group can be accomplished through skilled in the art design choice selection of one or more of the above depicted components from one or more of the above depicted subsystems shown in FIG. 12. Components from the storing butcher staff component group can be used in implementing execution of the one or more storing butcher staff instructions i1149 of FIG. 30, can be used in performance of the storing butcher staff electrical circuitry arrangement e1149 of FIG. 23, and/or can be used in otherwise fulfillment of the operation o1149. An exemplary non-transitory signal bearing medium version of the information storage subsystem s200 is depicted in FIG. 30 as bearing the one or more storing butcher staff instructions i1149 that when executed will direct performance of the operation o1149. Furthermore, the storing butcher staff electrical circuitry arrangement ("elec circ arrange") e1149, when activated, will perform the operation o1149. Also, the storing butcher staff module m1149, when executed and/or activated, will direct performance of and/or perform the operation o1149. For instance, in one or more exemplary implementations, the one or more storing butcher staff instructions i1149, when executed, direct performance of the operation o1149 in the illustrative depiction as follows, and/or the storing butcher staff electrical circuitry arrangement e1149, when activated, performs the operation o1149 in the illustrative depiction as follows, and/or the storing butcher staff module m1149, when executed and/or activated, directs performance of and/or performs the operation o1149 in the illustrative depiction as follows, and/or the operation o1149 is otherwise carried out in the illustrative depiction as follows: electronically storing (e.g. onto DVD, etc.) grocery operations information (e.g. disobeying safety protocols, etc.) regarding at least in part (e.g. suggest, etc.) the one or more grocery implementation aspects (e.g. identified issues regarding food quality from one or more wholesalers, etc.) pertaining to (e.g. suggest, etc.) grocery related merchandizing of (e.g. institutional grocery item storing, etc.) one or more commercial grocery products (e.g. vegetarian side dish grocery item, etc.) including at least in part one or more butcher staff related factors involved with one or more grocery implementation aspects (e.g. illness histories of butcher staff, etc.).

In one or more implementations, as shown in FIG. 59, operation o11 includes an operation o1150 for electronically storing grocery operations information regarding at least in part the one or more grocery implementation aspects pertaining to grocery related merchandizing of one or more commercial grocery products including at least in part one or more health department reportable factors involved with one or more grocery implementation aspects. Origination of an illustratively derived storing health department component group can be accomplished through skilled in the art design choice selection of one or more of the above depicted components from one or more of the above depicted subsystems shown in FIG. 12. Components from the storing health department component group can be used in implementing execution of the one or more storing health department instructions i1150 of FIG. 30, can be used in performance of the storing health department electrical circuitry arrangement e1150 of FIG. 23, and/or can be used in otherwise fulfillment of the operation o1150. An exemplary non-transitory signal bearing medium version of the information storage subsystem s200 is depicted in FIG. 30 as bearing the one or more storing health department instructions i1150 that when executed will direct performance of the operation o1150. Furthermore, the storing health department electrical circuitry arrangement ("elec circ arrange") e1150, when activated, will perform the operation o1150. Also, the storing health department module m1150, when executed and/or activated, will direct performance of and/or perform the operation o1150. For instance, in one or more exemplary implementations, the one or more storing health department instructions i1150, when executed, direct performance of the operation o1150 in the illustrative depiction as follows, and/or the storing health department electrical circuitry arrangement e1150, when activated, performs the operation o1150 in the illustrative depiction as follows, and/or the storing health department module m1150, when executed and/or activated, directs performance of and/or performs the operation o1150 in the illustrative depiction as follows, and/or the operation o1150 is otherwise carried out in the illustrative depiction as follows: electronically storing (e.g. onto hard drive, etc.) grocery operations information (e.g. grocery commissary occupation rates, etc.) regarding at least in part (e.g. tangle, etc.) the one or more grocery implementation aspects (e.g. identified issues regarding food quality from one or more farms, etc.) pertaining to (e.g. tangle, etc.) grocery related merchandizing of (e.g. school cafeteria grocery item storing, etc.) one or more commercial grocery products (e.g. salad side dish grocery item, etc.) including at least in part one or more health department reportable factors involved with one or more grocery implementation aspects (e.g. sanitation procedures mandated by health department, etc.).

In one or more implementations, as shown in FIG. 59, operation o11 includes an operation o1151 for electronically storing grocery operations information regarding at least in part the one or more grocery implementation aspects pertaining to grocery related merchandizing of one or more commercial grocery products including at least in part one or more harvest location of one or more food ingredients factors involved with one or more grocery implementation aspects. Origination of an illustratively derived storing harvest location component group can be accomplished through skilled in the art design choice selection of one or more of the above depicted components from one or more of the above depicted subsystems shown in FIG. 12. Components from the storing harvest location component group can be used in implementing execution of the one or more storing harvest location instructions i1151 of FIG. 30, can be used in performance of the storing harvest location electrical circuitry arrangement e1151 of FIG. 23, and/or can be used in otherwise fulfillment of the operation o1151. An exemplary non-transitory signal bearing medium version of the information storage subsystem s200 is depicted in FIG. 30 as bearing the one or more storing harvest location instructions i1151 that when executed will direct performance of the operation o1151. Furthermore, the storing harvest location electrical circuitry arrangement ("elec circ arrange") e1151, when activated, will perform the operation o1151. Also, the storing harvest location module m1151, when executed and/or activated, will direct performance of and/or perform the operation o1151. For instance, in one or more exemplary implementations, the one or more storing harvest location instructions i1151, when executed, direct performance of the operation o1151 in the illustrative depiction as follows, and/or the storing harvest location electrical circuitry arrangement e1151, when activated, performs the operation o1151 in the illustrative depiction as follows, and/or the storing harvest location module m1151, when executed and/or activated, directs performance of and/or performs the operation o1151 in the illustrative depiction as follows, and/or the operation o1151 is otherwise carried out in the illustrative depiction as follows: electronically storing (e.g. from wifi, etc.) grocery operations information (e.g. turnover in machine vending of grocery items, etc.) regarding at least in part (e.g. exclude, etc.) the one or more grocery implementation aspects (e.g. identified issues regarding one or more grocery workers, etc.) pertaining to (e.g. exclude, etc.) grocery related merchandizing of (e.g. nursing home grocery item storing, etc.) one or more commercial grocery products (e.g. grain side dish grocery item, etc.) including at least in part one or more harvest location of one or more food ingredients factors involved with one or more grocery implementation aspects (e.g. country, state and county of origin for produce used in grocery items, etc.).

Figure 60:
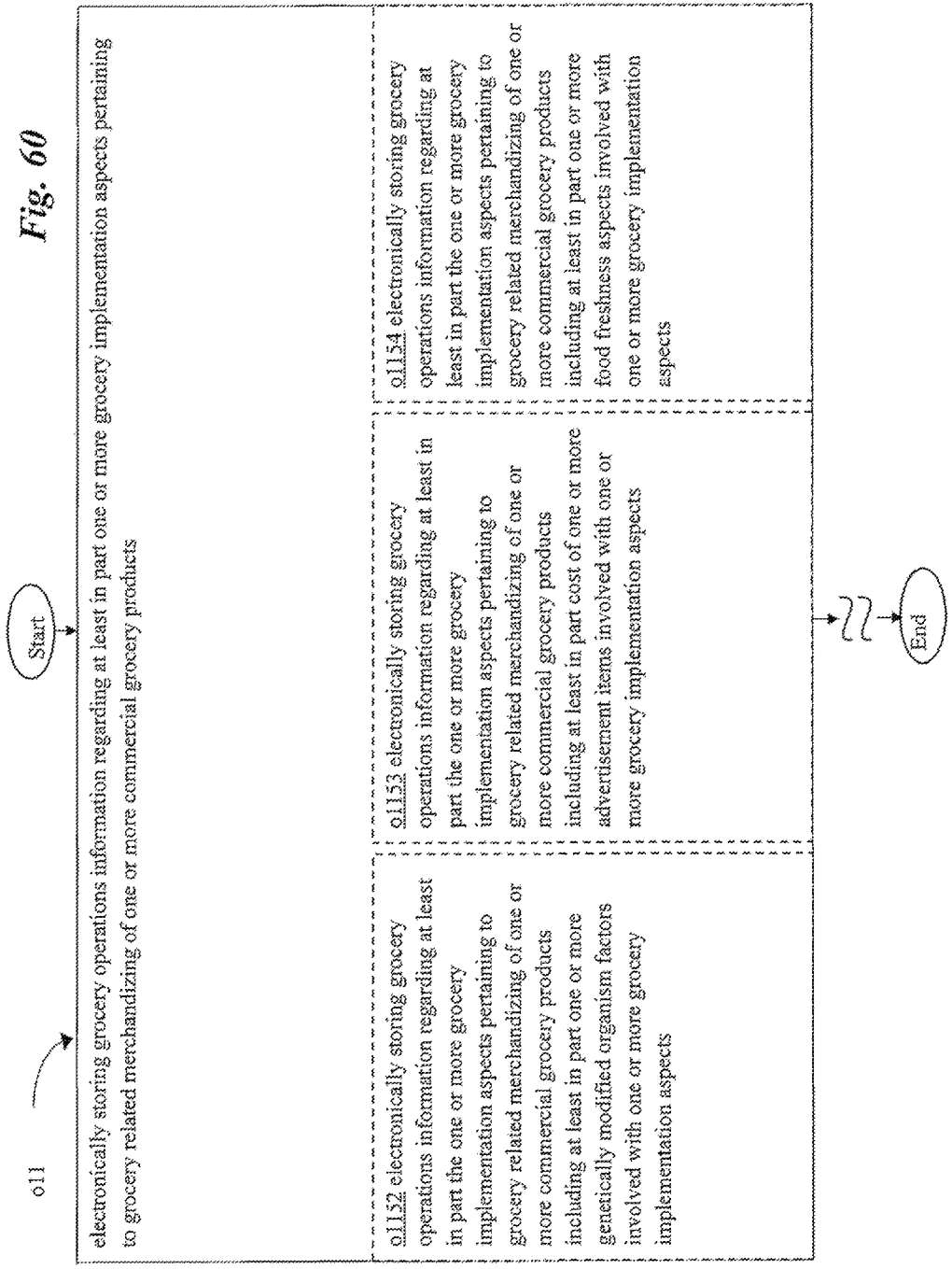
FIG. 60 is a high-level flowchart including exemplary implementations of operation o11 of FIG. 42.

In one or more implementations, as shown in FIG. 60, operation o11 includes an operation o1152 for electronically storing grocery operations information regarding at least in part the one or more grocery implementation aspects pertaining to grocery related merchandizing of one or more commercial grocery products including at least in part one or more genetically modified organism factors involved with one or more grocery implementation aspects. Origination of an illustratively derived storing genetically modified component group can be accomplished through skilled in the art design choice selection of one or more of the above depicted components from one or more of the above depicted subsystems shown in FIG. 12. Components from the storing genetically modified component group can be used in implementing execution of the one or more storing genetically modified instructions i1152 of FIG. 30, can be used in performance of the storing genetically modified electrical circuitry arrangement e1152 of FIG. 23, and/or can be used in otherwise fulfillment of the operation o1152. An exemplary non-transitory signal bearing medium version of the information storage subsystem s200 is depicted in FIG. 30 as bearing the one or more storing genetically modified instructions i1152 that when executed will direct performance of the operation o1152. Furthermore, the storing genetically modified electrical circuitry arrangement ("elec circ arrange") e1152, when activated, will perform the operation o1152. Also, the storing genetically modified module m1152, when executed and/or activated, will direct performance of and/or perform the operation o1152. For instance, in one or more exemplary implementations, the one or more storing genetically modified instructions i1152, when executed, direct performance of the operation o1152 in the illustrative depiction as follows, and/or the storing genetically modified electrical circuitry arrangement e1152, when activated, performs the operation o1152 in the illustrative depiction as follows, and/or the storing genetically modified module m1152, when executed and/or activated, directs performance of and/or performs the operation o1152 in the illustrative depiction as follows, and/or the operation o1152 is otherwise carried out in the illustrative depiction as follows: electronically storing (e.g. from laptop entry, etc.) grocery operations information (e.g. UV index of current climate, etc.) regarding at least in part (e.g. bound, etc.) the one or more grocery implementation aspects (e.g. identified issues regarding one or more grocery equipment, etc.) pertaining to (e.g. bound, etc.) grocery related merchandizing of (e.g. street vendor grocery item storing, etc.) one or more commercial grocery products (e.g. bean side dish grocery item, etc.) including at least in part one or more genetically modified organism factors involved with one or more grocery implementation aspects (e.g. existence of certification on non-GMO produce used in grocery items, etc.).

In one or more implementations, as shown in FIG. 60, operation o11 includes an operation o1153 for electronically storing grocery operations information regarding at least in part the one or more grocery implementation aspects pertaining to grocery related merchandizing of one or more commercial grocery products including at least in part cost of one or more advertisement items involved with one or more grocery implementation aspects. Origination of an illustratively derived storing advertisement items component group can be accomplished through skilled in the art design choice selection of one or more of the above depicted components from one or more of the above depicted subsystems shown in FIG. 12. Components from the storing advertisement items component group can be used in implementing execution of the one or more storing advertisement items instructions i1153 of FIG. 30, can be used in performance of the storing advertisement items electrical circuitry arrangement e1153 of FIG. 23, and/or can be used in otherwise fulfillment of the operation o1153. An exemplary non-transitory signal bearing medium version of the information storage subsystem s200 is depicted in FIG. 30 as bearing the one or more storing advertisement items instructions i1153 that when executed will direct performance of the operation o1153. Furthermore, the storing advertisement items electrical circuitry arrangement ("elec circ arrange") e1153, when activated, will perform the operation o1153. Also, the storing advertisement items module m1153, when executed and/or activated, will direct performance of and/or perform the operation o1153. For instance, in one or more exemplary implementations, the one or more storing advertisement items instructions i1153, when executed, direct performance of the operation o1153 in the illustrative depiction as follows, and/or the storing advertisement items electrical circuitry arrangement e1153, when activated, performs the operation o1153 in the illustrative depiction as follows, and/or the storing advertisement items module m1153, when executed and/or activated, directs performance of and/or performs the operation o1153 in the illustrative depiction as follows, and/or the operation o1153 is otherwise carried out in the illustrative depiction as follows: electronically storing (e.g. from RFID scan, etc.) grocery operations information (e.g. carbon dioxide levels in grocery facilities, etc.) regarding at least in part (e.g. requiring, etc.) the one or more grocery implementation aspects (e.g. identified issues regarding one or more types of food materials used to prepare one or more grocery items to be sold, etc.) pertaining to (e.g. requiring, etc.) grocery related merchandizing of (e.g. mobile kitchen grocery item storing, etc.) one or more commercial grocery products (e.g. cooked side dish grocery item, etc.) including at least in part cost of one or more advertisement items involved with one or more grocery implementation aspects (e.g. seasonal fluctuations of grocery item pricing, etc.).

In one or more implementations, as shown in FIG. 60, operation o11 includes an operation o1154 for electronically storing grocery operations information regarding at least in part the one or more grocery implementation aspects pertaining to grocery related merchandizing of one or more commercial grocery products including at least in part one or more food freshness aspects involved with one or more grocery implementation aspects. Origination of an illustratively derived storing food freshness component group can be accomplished through skilled in the art design choice selection of one or more of the above depicted components from one or more of the above depicted subsystems shown in FIG. 12. Components from the storing food freshness component group can be used in implementing execution of the one or more storing food freshness instructions i1154 of FIG. 30, can be used in performance of the storing food freshness electrical circuitry arrangement e1154 of FIG. 23, and/or can be used in otherwise fulfillment of the operation o1154. An exemplary non-transitory signal bearing medium version of the information storage subsystem s200 is depicted in FIG. 30 as bearing the one or more storing food freshness instructions i1154 that when executed will direct performance of the operation o1154. Furthermore, the storing food freshness electrical circuitry arrangement ("elec circ arrange") e1154, when activated, will perform the operation o1154. Also, the storing food freshness module m1154, when executed and/or activated, will direct performance of and/or perform the operation o1154. For instance, in one or more exemplary implementations, the one or more storing food freshness instructions i1154, when executed, direct performance of the operation o1154 in the illustrative depiction as follows, and/or the storing food freshness electrical circuitry arrangement e1154, when activated, performs the operation o1154 in the illustrative depiction as follows, and/or the storing food freshness module m1154, when executed and/or activated, directs performance of and/or performs the operation o1154 in the illustrative depiction as follows, and/or the operation o1154 is otherwise carried out in the illustrative depiction as follows: electronically storing (e.g. via ethernet, etc.) grocery operations information (e.g. water usage, etc.) regarding at least in part (e.g. enveloped, etc.) the one or more grocery implementation aspects (e.g. identified issues regarding one or more types of grocery items sold by grocery facility, etc.) pertaining to (e.g. enveloped, etc.) grocery related merchandizing of (e.g. hospital grocery item storing, etc.) one or more commercial grocery products (e.g. raw side dish grocery item, etc.) including at least in part one or more food freshness aspects involved with one or more grocery implementation aspects (e.g. transit time between farm, wholesaler and grocery store, etc.).

Figure 61:
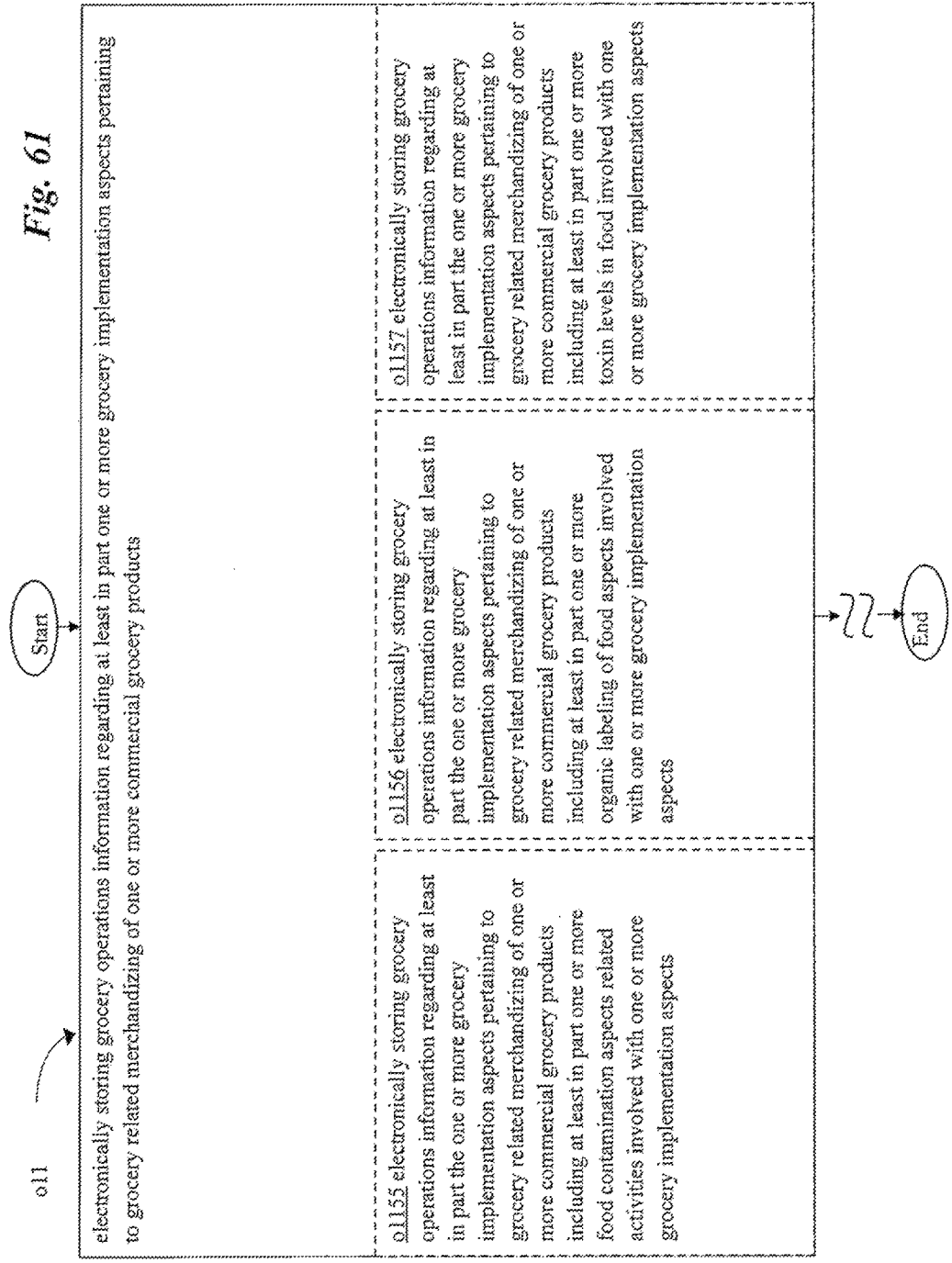
FIG. 61 is a high-level flowchart including exemplary implementations of operation o11 of FIG. 42.

In one or more implementations, as shown in FIG. 61, operation o11 includes an operation o1155 for electronically storing grocery operations information regarding at least in part the one or more grocery implementation aspects pertaining to grocery related merchandizing of one or more commercial grocery products including at least in part one or more food contamination aspects related activities involved with one or more grocery implementation aspects. Origination of an illustratively derived storing food contamination component group can be accomplished through skilled in the art design choice selection of one or more of the above depicted components from one or more of the above depicted subsystems shown in FIG. 12. Components from the storing food contamination component group can be used in implementing execution of the one or more storing food contamination instructions i1155 of FIG. 30, can be used in performance of the storing food contamination electrical circuitry arrangement e1155 of FIG. 23, and/or can be used in otherwise fulfillment of the operation o1155. An exemplary non-transitory signal bearing medium version of the information storage subsystem s200 is depicted in FIG. 30 as bearing the one or more storing food contamination instructions i1155 that when executed will direct performance of the operation o1155. Furthermore, the storing food contamination electrical circuitry arrangement ("elec circ arrange") e1155, when activated, will perform the operation o1155. Also, the storing food contamination module m1155, when executed and/or activated, will direct performance of and/or perform the operation o1155. For instance, in one or more exemplary implementations, the one or more storing food contamination instructions i1155, when executed, direct performance of the operation o1155 in the illustrative depiction as follows, and/or the storing food contamination electrical circuitry arrangement e1155, when activated, performs the operation o1155 in the illustrative depiction as follows, and/or the storing food contamination module m1155, when executed and/or activated, directs performance of and/or performs the operation o1155 in the illustrative depiction as follows, and/or the operation o1155 is otherwise carried out in the illustrative depiction as follows: electronically storing (e.g. via UPC scan, etc.) grocery operations information (e.g. natural gas usage, etc.) regarding at least in part (e.g. envelope, etc.) the one or more grocery implementation aspects (e.g. identified issues regarding one or more types of non-food items sold by grocery facility, etc.) pertaining to (e.g. envelope, etc.) grocery related merchandizing of (e.g. deli department grocery item storing, etc.) one or more commercial grocery products (e.g. buffet side dish grocery item, etc.) including at least in part one or more food contamination aspects related activities involved with one or more grocery implementation aspects (e.g. recall notices for food-based ingredients used in grocery items, etc.).

In one or more implementations, as shown in FIG. 61, operation o11 includes an operation o1156 for electronically storing grocery operations information regarding at least in part the one or more grocery implementation aspects pertaining to grocery related merchandizing of one or more commercial grocery products including at least in part one or more organic labeling of food aspects involved with one or more grocery implementation aspects. Origination of an illustratively derived storing organic labeling component group can be accomplished through skilled in the art design choice selection of one or more of the above depicted components from one or more of the above depicted subsystems shown in FIG. 12. Components from the storing organic labeling component group can be used in implementing execution of the one or more storing organic labeling instructions i1156 of FIG. 30, can be used in performance of the storing organic labeling electrical circuitry arrangement e1156 of FIG. 23, and/or can be used in otherwise fulfillment of the operation o1156. An exemplary non-transitory signal bearing medium version of the information storage subsystem s200 is depicted in FIG. 30 as bearing the one or more storing organic labeling instructions i1156 that when executed will direct performance of the operation o1156. Furthermore, the storing organic labeling electrical circuitry arrangement ("elec circ arrange") e1156, when activated, will perform the operation o1156. Also, the storing organic labeling module m1156, when executed and/or activated, will direct performance of and/or perform the operation o1156. For instance, in one or more exemplary implementations, the one or more storing organic labeling instructions i1156, when executed, direct performance of the operation o1156 in the illustrative depiction as follows, and/or the storing organic labeling electrical circuitry arrangement e1156, when activated, performs the operation o1156 in the illustrative depiction as follows, and/or the storing organic labeling module m1156, when executed and/or activated, directs performance of and/or performs the operation o1156 in the illustrative depiction as follows, and/or the operation o1156 is otherwise carried out in the illustrative depiction as follows: electronically storing (e.g. via HTML code, etc.) grocery operations information (e.g. methane gas usage, etc.) regarding at least in part (e.g. associate with, etc.) the one or more grocery implementation aspects (e.g. identified issues regarding one or more procedures used to prepare one or more food items sold by grocery facility, etc.) pertaining to (e.g. associate with, etc.) grocery related merchandizing of (e.g. fine dining grocery item packaging, etc.) one or more commercial grocery products (e.g. soup side dish grocery item, etc.) including at least in part one or more organic labeling of food aspects involved with one or more grocery implementation aspects (e.g. verification of organic labeling of ingredients used for the grocery items, etc.).

In one or more implementations, as shown in FIG. 61, operation o11 includes an operation o1157 for electronically storing grocery operations information regarding at least in part the one or more grocery implementation aspects pertaining to grocery related merchandizing of one or more commercial grocery products including at least in part one or more toxin levels in food involved with one or more grocery implementation aspects. Origination of an illustratively derived storing toxin levels component group can be accomplished through skilled in the art design choice selection of one or more of the above depicted components from one or more of the above depicted subsystems shown in FIG. 12. Components from the storing toxin levels component group can be used in implementing execution of the one or more storing toxin levels instructions i1157 of FIG. 30, can be used in performance of the storing toxin levels electrical circuitry arrangement e1157 of FIG. 23, and/or can be used in otherwise fulfillment of the operation o1157. An exemplary non-transitory signal bearing medium version of the information storage subsystem s200 is depicted in FIG. 30 as bearing the one or more storing toxin levels instructions i1157 that when executed will direct performance of the operation o1157. Furthermore, the storing toxin levels electrical circuitry arrangement ("elec circ arrange") e1157, when activated, will perform the operation o1157. Also, the storing toxin levels module m1157, when executed and/or activated, will direct performance of and/or perform the operation o1157. For instance, in one or more exemplary implementations, the one or more storing toxin levels instructions i1157, when executed, direct performance of the operation o1157 in the illustrative depiction as follows, and/or the storing toxin levels electrical circuitry arrangement e1157, when activated, performs the operation o1157 in the illustrative depiction as follows, and/or the storing toxin levels module m1157, when executed and/or activated, directs performance of and/or performs the operation o1157 in the illustrative depiction as follows, and/or the operation o1157 is otherwise carried out in the illustrative depiction as follows: electronically storing (e.g. via MMS, etc.) grocery operations information (e.g. MPEG file format, etc.) regarding at least in part (e.g. embroil, etc.) the one or more grocery implementation aspects (e.g. age profile of equipment used, etc.) pertaining to (e.g. embroil, etc.) grocery related merchandizing of (e.g. fast grocery item packaging, etc.) one or more commercial grocery products (e.g. stew side dish grocery item, etc.) including at least in part one or more toxin levels in food involved with one or more grocery implementation aspects (e involved with one or more grocery implementation aspects (e.g. temperature profiles of receiving docks, etc.).

Figure 62:
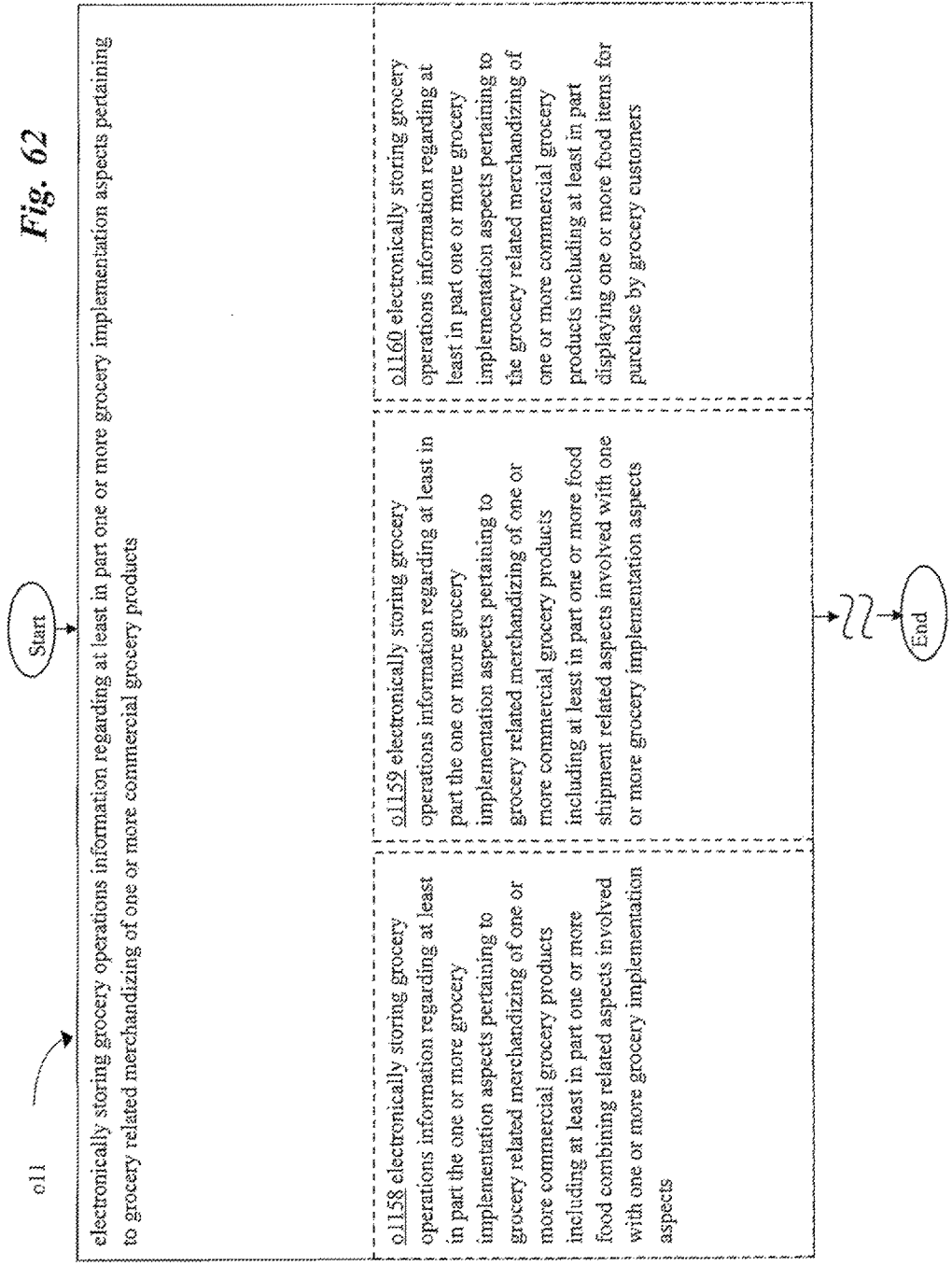
FIG. 62 is a high-level flowchart including exemplary implementations of operation o11 of FIG. 42.

In one or more implementations, as shown in FIG. 62, operation o11 includes an operation o1160 for electronically storing grocery operations information regarding at least in part one or more grocery implementation aspects pertaining to the grocery related merchandizing of one or more commercial grocery products including at least in part displaying one or more food items for purchase by grocery customers. Origination of an illustratively derived storing displaying items component group can be accomplished through skilled in the art design choice selection of one or more of the above depicted components from one or more of the above depicted subsystems shown in FIG. 12. Components from the storing displaying items component group can be used in implementing execution of the one or more storing displaying items instructions i1160 of FIG. 31, can be used in performance of the storing displaying items electrical circuitry arrangement e1160 of FIG. 24, and/or can be used in otherwise fulfillment of the operation o1160. An exemplary non-transitory signal bearing medium version of the information storage subsystem s200 is depicted in FIG. 31 as bearing the one or more storing displaying items instructions i1160 that when executed will direct performance of the operation o1160. Furthermore, the storing displaying items electrical circuitry arrangement ("elec circ arrange") e1160, when activated, will perform the operation o1160. Also, the storing displaying items module m1160, when executed and/or activated, will direct performance of and/or perform the operation o1160. For instance, in one or more exemplary implementations, the one or more storing displaying items instructions i1160, when executed, direct performance of the operation o1160 in the illustrative depiction as follows, and/or the storing displaying items electrical circuitry arrangement e1160, when activated, performs the operation o1160 in the illustrative depiction as follows, and/or the storing displaying items module m1160, when executed and/or activated, directs performance of and/or performs the operation o1160 in the illustrative depiction as follows, and/or the operation o1160 is otherwise carried out in the illustrative depiction as follows: electronically storing (e.g. as push-based, etc.) grocery operations information (e.g. adherence to safety protocols, etc.) regarding at least in part (e.g. comprehend, etc.) one or more grocery implementation aspects (e.g. location of grocery facility, etc.) pertaining to (e.g. comprehend, etc.) the grocery related merchandizing of (e.g. institutional grocery item packaging, etc.) one or more commercial grocery products (e.g. weight loss side dish grocery item, etc.) including at least in part displaying one or more food items for purchase by grocery customers (e.g. preparation of sample pasta dishes for special merchandizing event, etc.).

Figure 63:
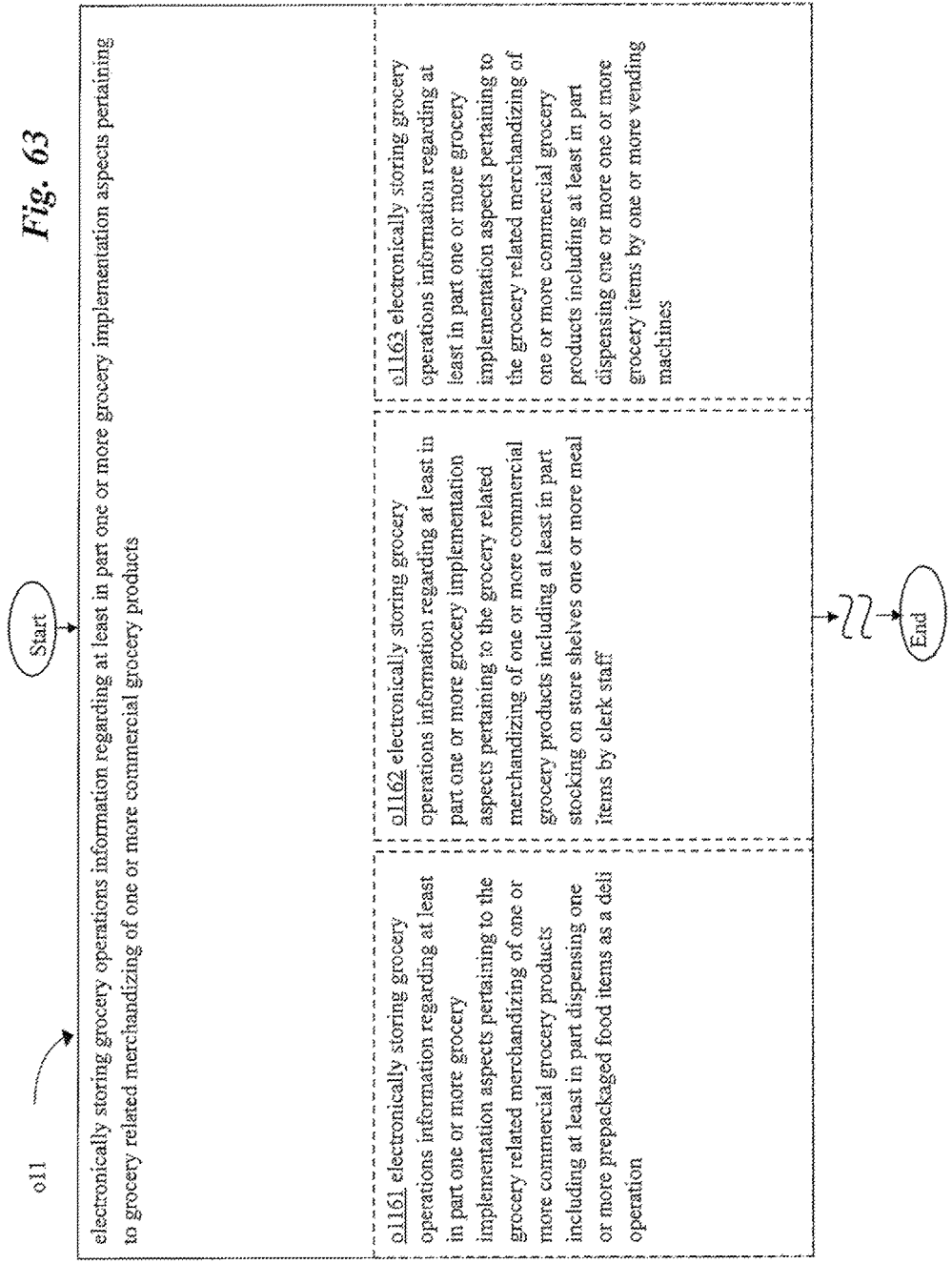
FIG. 63 is a high-level flowchart including exemplary implementations of operation o11 of FIG. 42.

In one or more implementations, as shown in FIG. 63, operation o11 includes an operation o1161 for electronically storing grocery operations information regarding at least in part one or more grocery implementation aspects pertaining to the grocery related merchandizing of one or more commercial grocery products including at least in part dispensing one or more prepackaged food items as a deli operation. Origination of an illustratively derived storing dispensing prepackaged component group can be accomplished through skilled in the art design choice selection of one or more of the above depicted components from one or more of the above depicted subsystems shown in FIG. 12. Components from the storing dispensing prepackaged component group can be used in implementing execution of the one or more storing dispensing prepackaged instructions i1161 of FIG. 31, can be used in performance of the storing dispensing prepackaged electrical circuitry arrangement e1161 of FIG. 24, and/or can be used in otherwise fulfillment of the operation o1161. An exemplary non-transitory signal bearing medium version of the information storage subsystem s200 is depicted in FIG. 31 as bearing the one or more storing dispensing prepackaged instructions i1161 that when executed will direct performance of the operation o1161. Furthermore, the storing dispensing prepackaged electrical circuitry arrangement ("elec circ arrange") e1161, when activated, will perform the operation o1161. Also, the storing dispensing prepackaged module m1161, when executed and/or activated, will direct performance of and/or perform the operation o1161. For instance, in one or more exemplary implementations, the one or more storing dispensing prepackaged instructions i1161, when executed, direct performance of the operation o1161 in the illustrative depiction as follows, and/or the storing dispensing prepackaged electrical circuitry arrangement e1161, when activated, performs the operation o1161 in the illustrative depiction as follows, and/or the storing dispensing prepackaged module m1161, when executed and/or activated, directs performance of and/or performs the operation o1161 in the illustrative depiction as follows, and/or the operation o1161 is otherwise carried out in the illustrative depiction as follows: electronically storing (e.g. onto SMTP server, etc.) grocery operations information (e.g. document forgery, etc.) regarding at least in part (e.g. calculate, etc.) one or more grocery implementation aspects (e.g. type of grocery facility, etc.) pertaining to (e.g. calculate, etc.) the grocery related merchandizing of (e.g. school cafeteria grocery item packaging, etc.) one or more commercial grocery products (e.g. sports nutrition side dish grocery item, etc.) including at least in part dispensing one or more prepackaged food items as a deli operation (e.g. quality of food item packaging by deli department, etc.).

In one or more implementations, as shown in FIG. 63, operation o11 includes an operation o1162 for electronically storing grocery operations information regarding at least in part one or more grocery implementation aspects pertaining to the grocery related merchandizing of one or more commercial grocery products including at least in part stocking on store shelves one or more meal items by clerk staff. Origination of an illustratively derived storing stocking shelves component group can be accomplished through skilled in the art design choice selection of one or more of the above depicted components from one or more of the above depicted subsystems shown in FIG. 12. Components from the storing stocking shelves component group can be used in implementing execution of the one or more storing stocking shelves instructions i1162 of FIG. 31, can be used in performance of the storing stocking shelves electrical circuitry arrangement e1162 of FIG. 24, and/or can be used in otherwise fulfillment of the operation o1162. An exemplary non-transitory signal bearing medium version of the information storage subsystem s200 is depicted in FIG. 31 as bearing the one or more storing stocking shelves instructions i1162 that when executed will direct performance of the operation o1162. Furthermore, the storing stocking shelves electrical circuitry arrangement ("elec circ arrange") e1162, when activated, will perform the operation o1162. Also, the storing stocking shelves module m1162, when executed and/or activated, will direct performance of and/or perform the operation o1162. For instance, in one or more exemplary implementations, the one or more storing stocking shelves instructions i1162, when executed, direct performance of the operation o1162 in the illustrative depiction as follows, and/or the storing stocking shelves electrical circuitry arrangement e1162, when activated, performs the operation o1162 in the illustrative depiction as follows, and/or the storing stocking shelves module m1162, when executed and/or activated, directs performance of and/or performs the operation o1162 in the illustrative depiction as follows, and/or the operation o1162 is otherwise carried out in the illustrative depiction as follows: electronically storing (e.g. from radio wave, etc.) grocery operations information (e.g. scheduled stock turnover, etc.) regarding at least in part (e.g. affected, etc.) one or more grocery implementation aspects (e.g. whether grocery facility is part of a franchise, etc.) pertaining to (e.g. affected, etc.) the grocery related merchandizing of (e.g. nursing home grocery item packaging, etc.) one or more commercial grocery products (e.g. baked side dish grocery item, etc.) including at least in part stocking on store shelves one or more meal items by clerk staff (e.g. handling of produce by produce manager when restocking produce department, etc.).

In one or more implementations, as shown in FIG. 63, operation o11 includes an operation o1163 for electronically storing grocery operations information regarding at least in part one or more grocery implementation aspects pertaining to the grocery related merchandizing of one or more commercial grocery products including at least in part dispensing one or more one or more grocery items by one or more vending machines. Origination of an illustratively derived storing dispensing machines component group can be accomplished through skilled in the art design choice selection of one or more of the above depicted components from one or more of the above depicted subsystems shown in FIG. 12. Components from the storing dispensing machines component group can be used in implementing execution of the one or more storing dispensing machines instructions i1163 of FIG. 31, can be used in performance of the storing dispensing machines electrical circuitry arrangement e1163 of FIG. 24, and/or can be used in otherwise fulfillment of the operation o1163. An exemplary non-transitory signal bearing medium version of the information storage subsystem s200 is depicted in FIG. 31 as bearing the one or more storing dispensing machines instructions i1163 that when executed will direct performance of the operation o1163. Furthermore, the storing dispensing machines electrical circuitry arrangement ("elec circ arrange") e1163, when activated, will perform the operation o1163. Also, the storing dispensing machines module m1163, when executed and/or activated, will direct performance of and/or perform the operation o1163. For instance, in one or more exemplary implementations, the one or more storing dispensing machines instructions i1163, when executed, direct performance of the operation o1163 in the illustrative depiction as follows, and/or the storing dispensing machines electrical circuitry arrangement e1163, when activated, performs the operation o1163 in the illustrative depiction as follows, and/or the storing dispensing machines module m1163, when executed and/or activated, directs performance of and/or performs the operation o1163 in the illustrative depiction as follows, and/or the operation o1163 is otherwise carried out in the illustrative depiction as follows: electronically storing (e.g. from infra-red, etc.) grocery operations information (e.g. storage room temperature. profiles, etc.) regarding at least in part (e.g. affecting, etc.) one or more grocery implementation aspects (e.g. relative amounts of saturated to unsaturated fat sold, etc.) pertaining to (e.g. affecting, etc.) the grocery related merchandizing of (e.g. street vendor grocery item packaging, etc.) one or more commercial grocery products (e.g. fried side dish grocery item, etc.) including at least in part dispensing one or more one or more grocery items by one or more vending machines (e.g. dispensing meal replacement shakes from vending machine, etc.).

Figure 64:
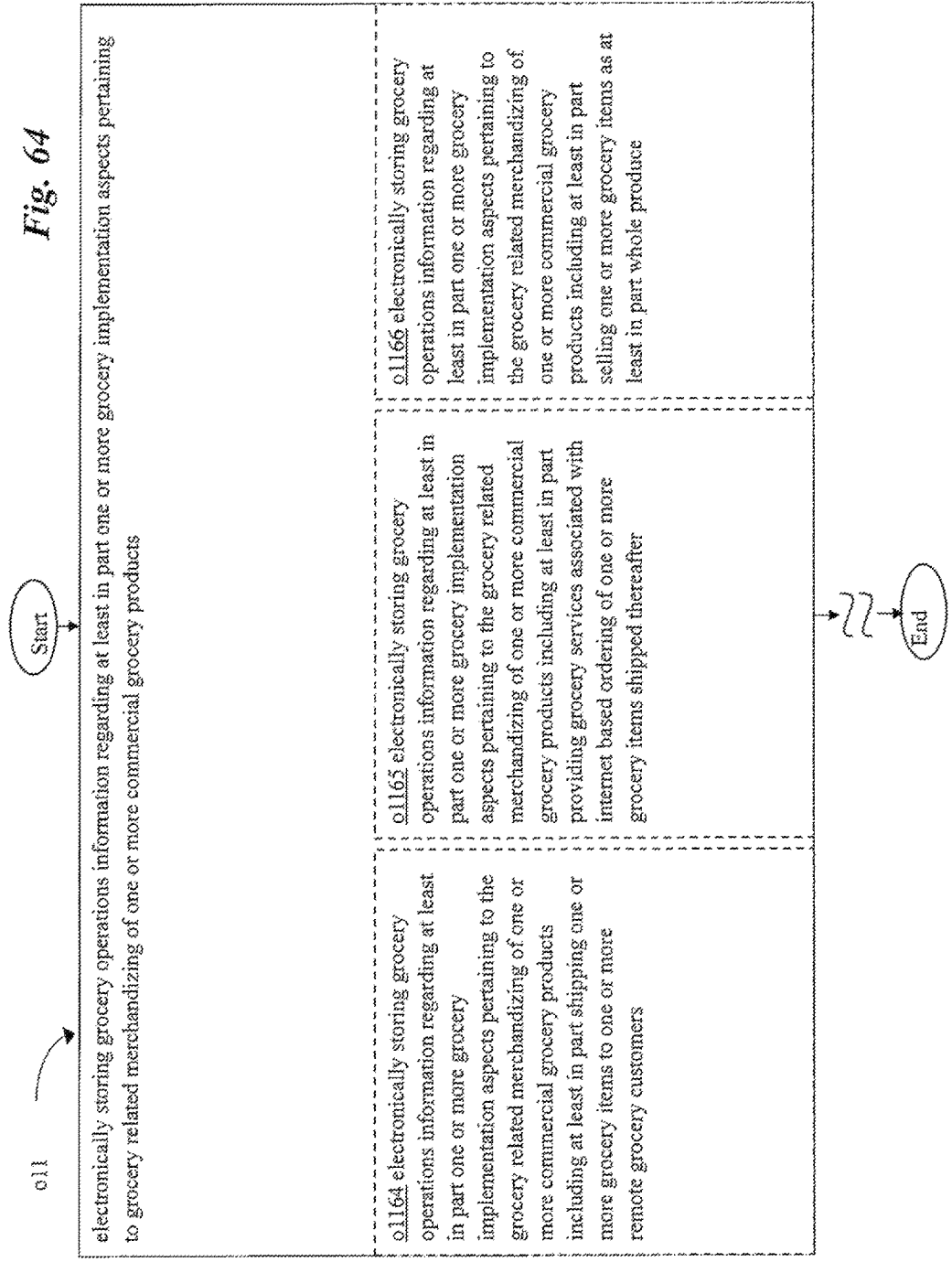
FIG. 64 is a high-level flowchart including exemplary implementations of operation o11 of FIG. 42.

In one or more implementations, as shown in FIG. 64, operation o11 includes an operation o1164 for electronically storing grocery operations information regarding at least in part one or more grocery implementation aspects pertaining to the grocery related merchandizing of one or more commercial grocery products including at least in part shipping one or more grocery items to one or more remote grocery customers. Origination of an illustratively derived storing remote customers component group can be accomplished through skilled in the art design choice selection of one or more of the above depicted components from one or more of the above depicted subsystems shown in FIG. 12. Components from the storing remote customers component group can be used in implementing execution of the one or more storing remote customers instructions i1164 of FIG. 31, can be used in performance of the storing remote customers electrical circuitry arrangement e1164 of FIG. 24, and/or can be used in otherwise fulfillment of the operation o1164. An exemplary non-transitory signal bearing medium version of the information storage subsystem s200 is depicted in FIG. 31 as bearing the one or more storing remote customers instructions i1164 that when executed will direct performance of the operation o1164. Furthermore, the storing remote customers electrical circuitry arrangement ("elec circ arrange") e1164, when activated, will perform the operation o1164. Also, the storing remote customers module m1164, when executed and/or activated, will direct performance of and/or perform the operation o1164. For instance, in one or more exemplary implementations, the one or more storing remote customers instructions i1164, when executed, direct performance of the operation o1164 in the illustrative depiction as follows, and/or the storing remote customers electrical circuitry arrangement e1164, when activated, performs the operation o1164 in the illustrative depiction as follows, and/or the storing remote customers module m1164, when executed and/or activated, directs performance of and/or performs the operation o1164 in the illustrative depiction as follows, and/or the operation o1164 is otherwise carried out in the illustrative depiction as follows: electronically storing (e.g. from bluetooth, etc.) grocery operations information (e.g. cold storage data for stored food materials, etc.) regarding at least in part (e.g. argue, etc.) one or more grocery implementation aspects (e.g. labor laws, etc.) pertaining to (e.g. argue, etc.) the grocery related merchandizing of (e.g. mobile kitchen grocery item packaging, etc.) one or more commercial grocery products (e.g. grilled side dish grocery item, etc.) including at least in part shipping one or more grocery items to one or more remote grocery customers (e.g. shipping grocery items through private carrier such as, etc.).

In one or more implementations, as shown in FIG. 64, operation o11 includes an operation o1165 for electronically storing grocery operations information regarding at least in part one or more grocery implementation aspects pertaining to the grocery related merchandizing of one or more commercial grocery products including at least in part providing grocery services associated with internet based ordering of one or more grocery items shipped thereafter. Origination of an illustratively derived storing internet ordering component group can be accomplished through skilled in the art design choice selection of one or more of the above depicted components from one or more of the above depicted subsystems shown in FIG. 12. Components from the storing internet ordering component group can be used in implementing execution of the one or more storing internet ordering instructions i1165 of FIG. 31, can be used in performance of the storing internet ordering electrical circuitry arrangement e1165 of FIG. 24, and/or can be used in otherwise fulfillment of the operation o1165. An exemplary non-transitory signal bearing medium version of the information storage subsystem s200 is depicted in FIG. 31 as bearing the one or more storing internet ordering instructions i1165 that when executed will direct performance of the operation o1165. Furthermore, the storing internet ordering electrical circuitry arrangement ("elec circ arrange") e1165, when activated, will perform the operation o1165. Also, the storing internet ordering module m1165, when executed and/or activated, will direct performance of and/or perform the operation o1165. For instance, in one or more exemplary implementations, the one or more storing internet ordering instructions i1165, when executed, direct performance of the operation o1165 in the illustrative depiction as follows, and/or the storing internet ordering electrical circuitry arrangement e1165, when activated, performs the operation o1165 in the illustrative depiction as follows, and/or the storing internet ordering module m1165, when executed and/or activated, directs performance of and/or performs the operation o1165 in the illustrative depiction as follows, and/or the operation o1165 is otherwise carried out in the illustrative depiction as follows: electronically storing (e.g. from webpage, etc.) grocery operations information (e.g. stove maintenance operation, etc.) regarding at least in part (e.g. connected, etc.) one or more grocery implementation aspects (e.g. safety regulations, etc.) pertaining to (e.g. connected, etc.) the grocery related merchandizing of (e.g. hospital grocery item packaging, etc.) one or more commercial grocery products (e.g. steamed side dish grocery item, etc.) including at least in part providing grocery services associated with internet based ordering of one or more grocery items shipped thereafter (e.g. transporting grocery items locally in response to internet ordering, etc.).

In one or more implementations, as shown in FIG. 64, operation o11 includes an operation o1166 for electronically storing grocery operations information regarding at least in part one or more grocery implementation aspects pertaining to the grocery related merchandizing of one or more commercial grocery products including at least in part selling one or more grocery items as at least in part whole produce. Origination of an illustratively derived storing whole produce component group can be accomplished through skilled in the art design choice selection of one or more of the above depicted components from one or more of the above depicted subsystems shown in FIG. 12. Components from the storing whole produce component group can be used in implementing execution of the one or more storing whole produce instructions i1166 of FIG. 31, can be used in performance of the storing whole produce electrical circuitry arrangement e1166 of FIG. 24, and/or can be used in otherwise fulfillment of the operation o1166. An exemplary non-transitory signal bearing medium version of the information storage subsystem s200 is depicted in FIG. 31 as bearing the one or more storing whole produce instructions i1166 that when executed will direct performance of the operation o1166. Furthermore, the storing whole produce electrical circuitry arrangement ("elec circ arrange") e1166, when activated, will perform the operation o1166. Also, the storing whole produce module m1166, when executed and/or activated, will direct performance of and/or perform the operation o1166. For instance, in one or more exemplary implementations, the one or more storing whole produce instructions i1166, when executed, direct performance of the operation o1166 in the illustrative depiction as follows, and/or the storing whole produce electrical circuitry arrangement e1166, when activated, performs the operation o1166 in the illustrative depiction as follows, and/or the storing whole produce module m1166, when executed and/or activated, directs performance of and/or performs the operation o1166 in the illustrative depiction as follows, and/or the operation o1166 is otherwise carried out in the illustrative depiction as follows: electronically storing (e.g. from website, etc.) grocery operations information (e.g. electricity usage, etc.) regarding at least in part (e.g. commit to, etc.) one or more grocery implementation aspects (e.g. relative amounts of sugars to slowly digesting starches sold, etc.) pertaining to (e.g. commit to, etc.) the grocery related merchandizing of (e.g. deli department grocery item packaging, etc.) one or more commercial grocery products (e.g. chilled side dish grocery item, etc.) including at least in part selling one or more grocery items as at least in part whole produce (e.g. selling whole apples, potatoes, and squashes, etc.).

Figure 65:
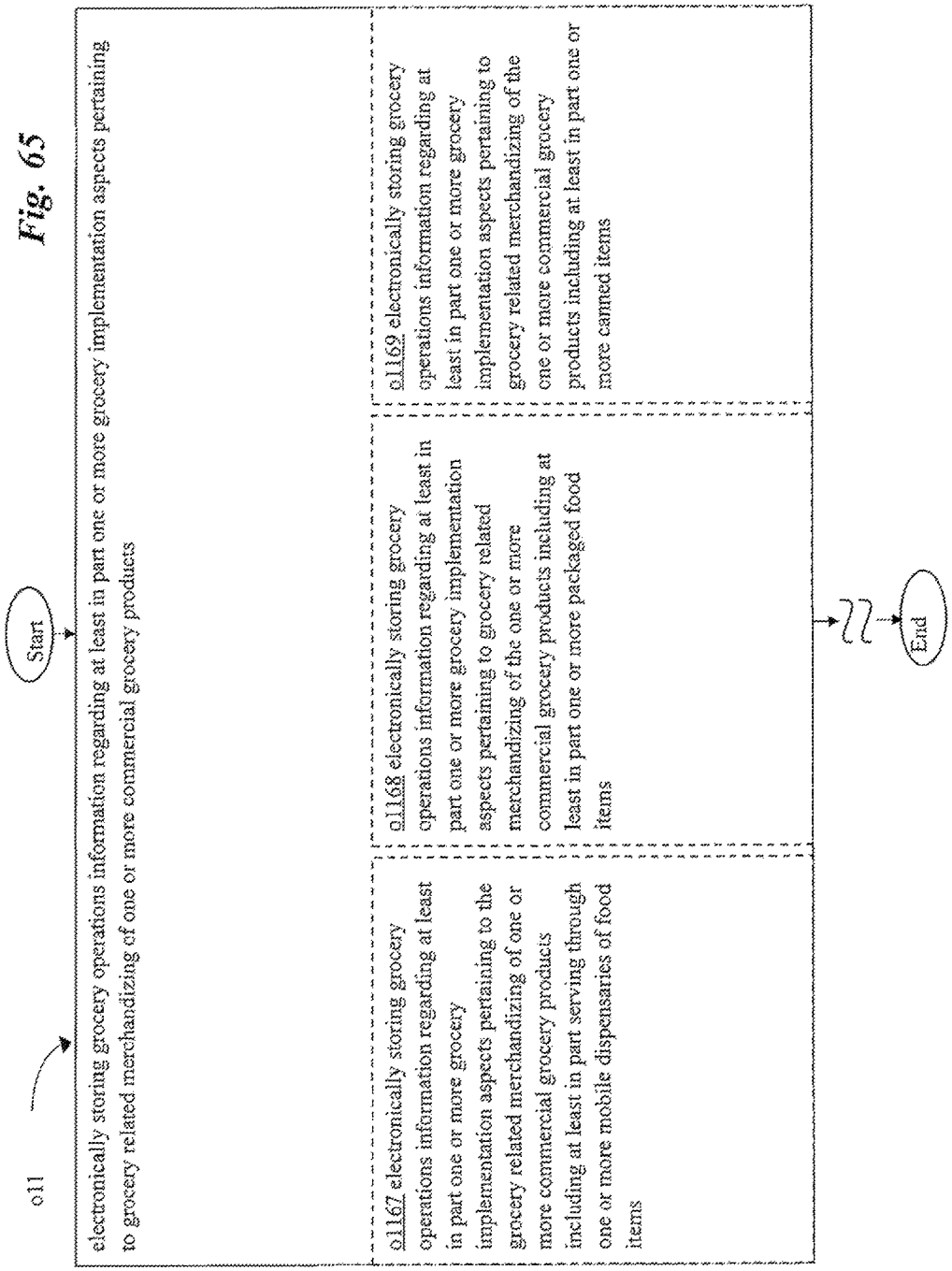
FIG. 65 is a high-level flowchart including exemplary implementations of operation o11 of FIG. 42.

In one or more implementations, as shown in FIG. 65, operation o11 includes an operation o1167 for electronically storing grocery operations information regarding at least in part one or more grocery implementation aspects pertaining to the grocery related merchandizing of one or more commercial grocery products including at least in part serving through one or more mobile dispensaries of food items. Origination of an illustratively derived storing mobile dispensaries component group can be accomplished through skilled in the art design choice selection of one or more of the above depicted components from one or more of the above depicted subsystems shown in FIG. 12. Components from the storing mobile dispensaries component group can be used in implementing execution of the one or more storing mobile dispensaries instructions i1167 of FIG. 31, can be used in performance of the storing mobile dispensaries electrical circuitry arrangement e1167 of FIG. 24, and/or can be used in otherwise fulfillment of the operation o1167. An exemplary non-transitory signal bearing medium version of the information storage subsystem s200 is depicted in FIG. 31 as bearing the one or more storing mobile dispensaries instructions i1167 that when executed will direct performance of the operation o1167. Furthermore, the storing mobile dispensaries electrical circuitry arrangement ("elec circ arrange") e1167, when activated, will perform the operation o1167. Also, the storing mobile dispensaries module m1167, when executed and/or activated, will direct performance of and/or perform the operation o1167. For instance, in one or more exemplary implementations, the one or more storing mobile dispensaries instructions i1167, when executed, direct performance of the operation o1167 in the illustrative depiction as follows, and/or the storing mobile dispensaries electrical circuitry arrangement e1167, when activated, performs the operation o1167 in the illustrative depiction as follows, and/or the storing mobile dispensaries module m1167, when executed and/or activated, directs performance of and/or performs the operation o1167 in the illustrative depiction as follows, and/or the operation o1167 is otherwise carried out in the illustrative depiction as follows: electronically storing (e.g. as cellphone entry, etc.) grocery operations information (e.g. customer water usage, etc.) regarding at least in part (e.g. absorbed by, etc.) one or more grocery implementation aspects (e.g. relative amounts of denatured to nondenatured protein sold, etc.) pertaining to (e.g. absorbed by, etc.) the grocery related merchandizing of (e.g. fine dining grocery item transporting, etc.) one or more commercial grocery products (e.g. microwaved side dish grocery item, etc.) including at least in part serving through one or more mobile dispensaries of food items (e.g. truck based framer market grocery sales that visit local community parks, etc.).

In one or more implementations, as shown in FIG. 65, operation o11 includes an operation o1168 for electronically storing grocery operations information regarding at least in part one or more grocery implementation aspects pertaining to grocery related merchandizing of the one or more commercial grocery products including at least in part one or more packaged food items. Origination of an illustratively derived storing packaged food component group can be accomplished through skilled in the art design choice selection of one or more of the above depicted components from one or more of the above depicted subsystems shown in FIG. 12. Components from the storing packaged food component group can be used in implementing execution of the one or more storing packaged food instructions i1168 of FIG. 31, can be used in performance of the storing packaged food electrical circuitry arrangement e1168 of FIG. 24, and/or can be used in otherwise fulfillment of the operation o1168. An exemplary non-transitory signal bearing medium version of the information storage subsystem s200 is depicted in FIG. 31 as bearing the one or more storing packaged food instructions i1168 that when executed will direct performance of the operation o1168. Furthermore, the storing packaged food electrical circuitry arrangement ("elec circ arrange") e1168, when activated, will perform the operation o1168. Also, the storing packaged food module m1168, when executed and/or activated, will direct performance of and/or perform the operation o1168. For instance, in one or more exemplary implementations, the one or more storing packaged food instructions i1168, when executed, direct performance of the operation o1168 in the illustrative depiction as follows, and/or the storing packaged food electrical circuitry arrangement e1168, when activated, performs the operation o1168 in the illustrative depiction as follows, and/or the storing packaged food module m1168, when executed and/or activated, directs performance of and/or performs the operation o1168 in the illustrative depiction as follows, and/or the operation o1168 is otherwise carried out in the illustrative depiction as follows: electronically storing (e.g. as satellite transmission, etc.) grocery operations information (e.g. distribution of grocery item costs, etc.) regarding at least in part (e.g. embraced, etc.) one or more grocery implementation aspects (e.g. relative amounts of animal protein to plant protein sold, etc.) pertaining to (e.g. embraced, etc.) grocery related merchandizing of (e.g. fast grocery item transporting, etc.) the one or more commercial grocery products (e.g. convection oven prepared side dish grocery item, etc.) including at least in part one or more packaged food items (e.g. pre-packaged roasted chicken, etc.).

In one or more implementations, as shown in FIG. 65, operation o11 includes an operation o1169 for electronically storing grocery operations information regarding at least in part one or more grocery implementation aspects pertaining to grocery related merchandizing of the one or more commercial grocery products including at least in part one or more canned items. Origination of an illustratively derived storing canned items component group can be accomplished through skilled in the art design choice selection of one or more of the above depicted components from one or more of the above depicted subsystems shown in FIG. 12. Components from the storing canned items component group can be used in implementing execution of the one or more storing canned items instructions i1169 of FIG. 31, can be used in performance of the storing canned items electrical circuitry arrangement e1169 of FIG. 24, and/or can be used in otherwise fulfillment of the operation o1169. An exemplary non-transitory signal bearing medium version of the information storage subsystem s200 is depicted in FIG. 31 as bearing the one or more storing canned items instructions i1169 that when executed will direct performance of the operation o1169. Furthermore, the storing canned items electrical circuitry arrangement ("elec circ arrange") e1169, when activated, will perform the operation o1169. Also, the storing canned items module m1169, when executed and/or activated, will direct performance of and/or perform the operation o1169. For instance, in one or more exemplary implementations, the one or more storing canned items instructions i1169, when executed, direct performance of the operation o1169 in the illustrative depiction as follows, and/or the storing canned items electrical circuitry arrangement e1169, when activated, performs the operation o1169 in the illustrative depiction as follows, and/or the storing canned items module m1169, when executed and/or activated, directs performance of and/or performs the operation o1169 in the illustrative depiction as follows, and/or the operation o1169 is otherwise carried out in the illustrative depiction as follows: electronically storing (e.g. as pull-based, etc.) grocery operations information (e.g. toxin levels in food sources, etc.) regarding at least in part (e.g. contain, etc.) one or more grocery implementation aspects (e.g. levels of one or more vitamins present in one or more grocery items sold, etc.) pertaining to (e.g. contain, etc.) grocery related merchandizing of (e.g. family buffet grocery item transporting, etc.) the one or more commercial grocery products (e.g. smoked side dish grocery item, etc.) including at least in part one or more canned items (e.g. canned tomato products, etc.).

Figure 66:
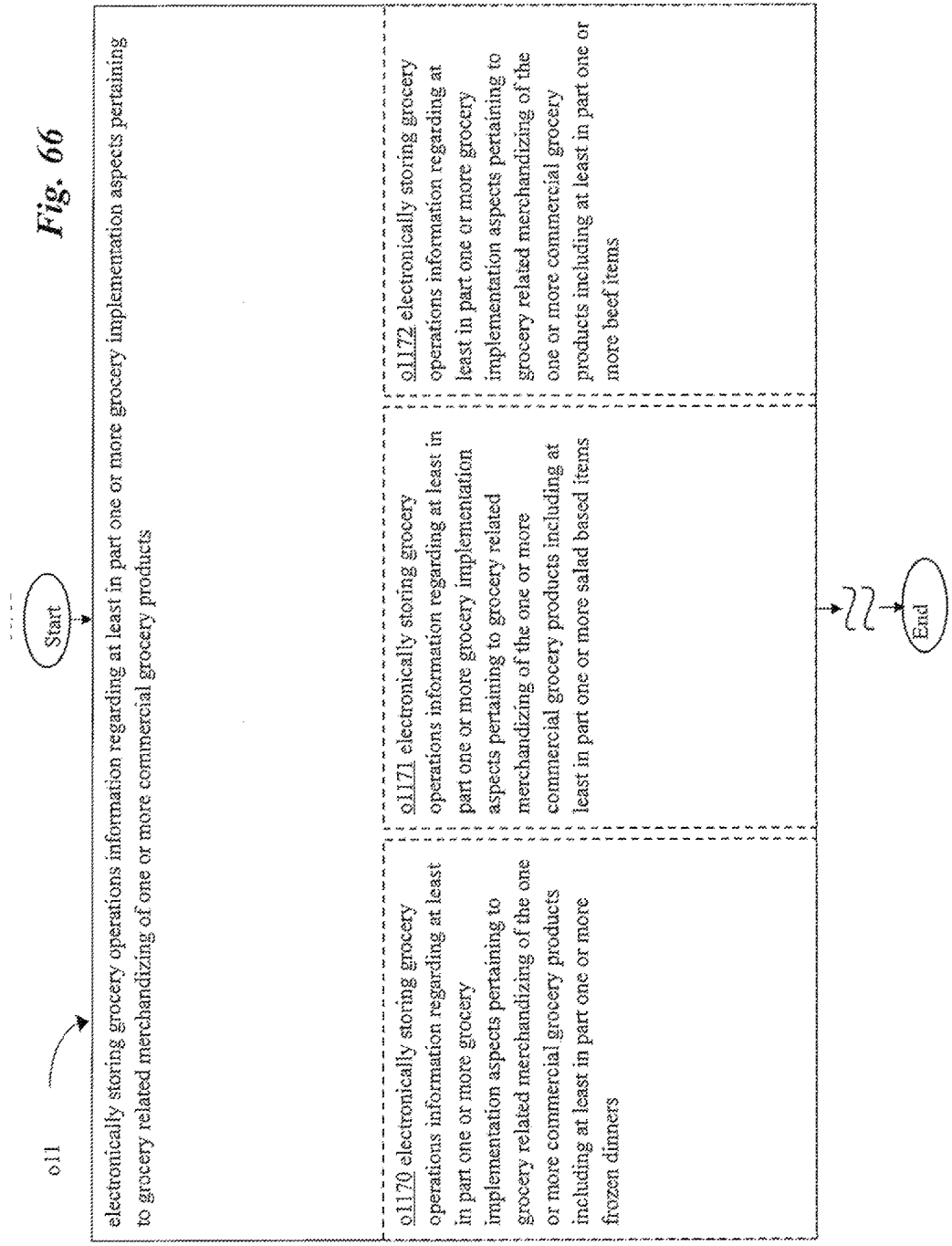
FIG. 66 is a high-level flowchart including exemplary implementations of operation o11 of FIG. 42.

In one or more implementations, as shown in FIG. 66, operation o11 includes an operation o1170 for electronically storing grocery operations information regarding at least in part one or more grocery implementation aspects pertaining to grocery related merchandizing of the one or more commercial grocery products including at least in part one or more frozen dinners. Origination of an illustratively derived storing frozen dinners component group can be accomplished through skilled in the art design choice selection of one or more of the above depicted components from one or more of the above depicted subsystems shown in FIG. 12. Components from the storing frozen dinners component group can be used in implementing execution of the one or more storing frozen dinners instructions i1170 of FIG. 31, can be used in performance of the storing frozen dinners electrical circuitry arrangement e1170 of FIG. 24, and/or can be used in otherwise fulfillment of the operation o1170. An exemplary non-transitory signal bearing medium version of the information storage subsystem s200 is depicted in FIG. 31 as bearing the one or more storing frozen dinners instructions i1170 that when executed will direct performance of the operation o1170. Furthermore, the storing frozen dinners electrical circuitry arrangement ("elec circ arrange") e1170, when activated, will perform the operation o1170. Also, the storing frozen dinners module m1170, when executed and/or activated, will direct performance of and/or perform the operation o1170. For instance, in one or more exemplary implementations, the one or more storing frozen dinners instructions i1170, when executed, direct performance of the operation o1170 in the illustrative depiction as follows, and/or the storing frozen dinners electrical circuitry arrangement e1170, when activated, performs the operation o1170 in the illustrative depiction as follows, and/or the storing frozen dinners module m1170, when executed and/or activated, directs performance of and/or performs the operation o1170 in the illustrative depiction as follows, and/or the operation o1170 is otherwise carried out in the illustrative depiction as follows: electronically storing (e.g. onto POP3 server, etc.) grocery operations information (e.g. beverage sales rates, etc.) regarding at least in part (e.g. engage, etc.) one or more grocery implementation aspects (e.g. levels of one or more minerals present in one or more grocery items sold, etc.) pertaining to (e.g. engage, etc.) grocery related merchandizing of (e.g. mobile catering grocery item transporting, etc.) the one or more commercial grocery products (e.g. boiled side dish grocery item, etc.) including at least in part one or more frozen dinners (e.g. frozen steak dinner, etc.).

In one or more implementations, as shown in FIG. 66, operation o11 includes an operation o1171 for electronically storing grocery operations information regarding at least in part one or more grocery implementation aspects pertaining to grocery related merchandizing of the one or more commercial grocery products including at least in part one or more salad based items. Origination of an illustratively derived storing salad based component group can be accomplished through skilled in the art design choice selection of one or more of the above depicted components from one or more of the above depicted subsystems shown in FIG. 12. Components from the storing salad based component group can be used in implementing execution of the one or more storing salad based instructions i1171 of FIG. 31, can be used in performance of the storing salad based electrical circuitry arrangement e1171 of FIG. 24, and/or can be used in otherwise fulfillment of the operation o1171. An exemplary non-transitory signal bearing medium version of the information storage subsystem s200 is depicted in FIG. 31 as bearing the one or more storing salad based instructions i1171 that when executed will direct performance of the operation o1171. Furthermore, the storing salad based electrical circuitry arrangement ("elec circ arrange") e1171, when activated, will perform the operation o1171. Also, the storing salad based module m1171, when executed and/or activated, will direct performance of and/or perform the operation o1171. For instance, in one or more exemplary implementations, the one or more storing salad based instructions i1171, when executed, direct performance of the operation o1171 in the illustrative depiction as follows, and/or the storing salad based electrical circuitry arrangement e1171, when activated, performs the operation o1171 in the illustrative depiction as follows, and/or the storing salad based module m1171, when executed and/or activated, directs performance of and/or performs the operation o1171 in the illustrative depiction as follows, and/or the operation o1171 is otherwise carried out in the illustrative depiction as follows: electronically storing (e.g. as hardware based encryption, etc.) grocery operations information (e.g. labor force scheduling, etc.) regarding at least in part (e.g. engaged by, etc.) one or more grocery implementation aspects (e.g. level of one or more antioxidants present in one or more grocery items sold, etc.) pertaining to (e.g. engaged by, etc.) grocery related merchandizing of (e.g. institutional grocery item transporting, etc.) the one or more commercial grocery products (e.g. sandwich side dish grocery item, etc.) including at least in part one or more salad based items (e.g. pre-packaged chef salad, etc.).

In one or more implementations, as shown in FIG. 66, operation o11 includes an operation o1172 for electronically storing grocery operations information regarding at least in part one or more grocery implementation aspects pertaining to grocery related merchandizing of the one or more commercial grocery products including at least in part one or more beef items. Origination of an illustratively derived storing beef items component group can be accomplished through skilled in the art design choice selection of one or more of the above depicted components from one or more of the above depicted subsystems shown in FIG. 12. Components from the storing beef items component group can be used in implementing execution of the one or more storing beef items instructions i1172 of FIG. 31, can be used in performance of the storing beef items electrical circuitry arrangement e1172 of FIG. 24, and/or can be used in otherwise fulfillment of the operation o1172. An exemplary non-transitory signal bearing medium version of the information storage subsystem s200 is depicted in FIG. 31 as bearing the one or more storing beef items instructions i1172 that when executed will direct performance of the operation o1172. Furthermore, the storing beef items electrical circuitry arrangement ("elec circ arrange") e1172, when activated, will perform the operation o1172. Also, the storing beef items module m1172, when executed and/or activated, will direct performance of and/or perform the operation o1172. For instance, in one or more exemplary implementations, the one or more storing beef items instructions i1172, when executed, direct performance of the operation o1172 in the illustrative depiction as follows, and/or the storing beef items electrical circuitry arrangement e1172, when activated, performs the operation o1172 in the illustrative depiction as follows, and/or the storing beef items module m1172, when executed and/or activated, directs performance of and/or performs the operation o1172 in the illustrative depiction as follows, and/or the operation o1172 is otherwise carried out in the illustrative depiction as follows: electronically storing (e.g. as software based encryption, etc.) grocery operations information (e.g. future market demands, etc.) regarding at least in part (e.g. incorporate, etc.) one or more grocery implementation aspects (e.g. characterization of the grocery in terms of type of grocery trade dress used, etc.) pertaining to (e.g. incorporate, etc.) grocery related merchandizing of (e.g. school cafeteria grocery item transporting, etc.) the one or more commercial grocery products (e.g. rotisserie side dish grocery item, etc.) including at least in part one or more beef items (e.g. pre-packaged bowl of beef stew, etc.).

Figure 67:
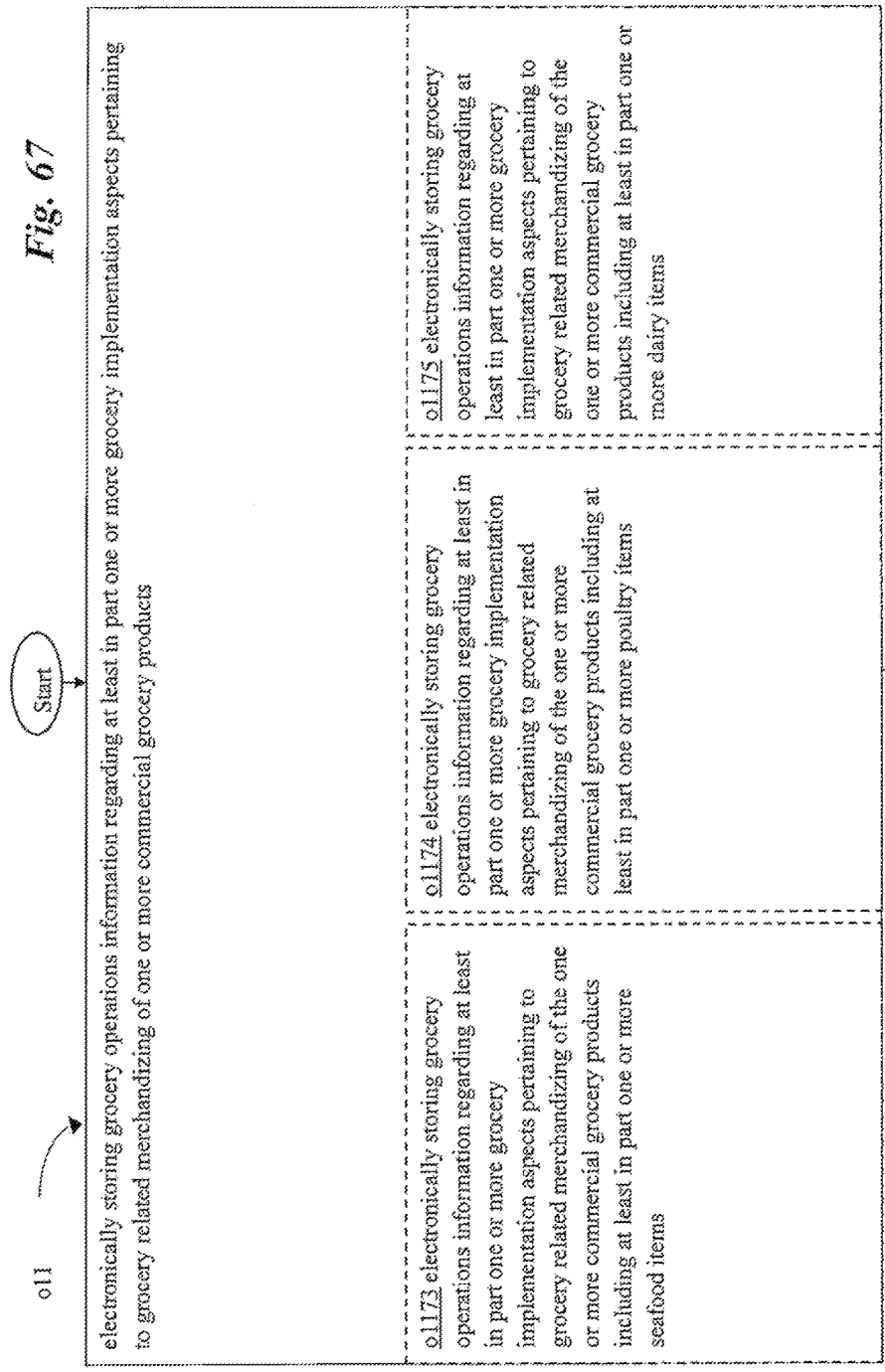
FIG. 67 is a high-level flowchart including exemplary implementations of operation o11 of FIG. 42.

In one or more implementations, as shown in FIG. 67, operation o11 includes an operation o1173 for electronically storing grocery operations information regarding at least in part one or more grocery implementation aspects pertaining to grocery related merchandizing of the one or more commercial grocery products including at least in part one or more seafood items. Origination of an illustratively derived storing seafood items component group can be accomplished through skilled in the art design choice selection of one or more of the above depicted components from one or more of the above depicted subsystems shown in FIG. 12. Components from the storing seafood items component group can be used in implementing execution of the one or more storing seafood items instructions i1173 of FIG. 31, can be used in performance of the storing seafood items electrical circuitry arrangement e1173 of FIG. 24, and/or can be used in otherwise fulfillment of the operation o1173. An exemplary non-transitory signal bearing medium version of the information storage subsystem s200 is depicted in FIG. 31 as bearing the one or more storing seafood items instructions i1173 that when executed will direct performance of the operation o1173. Furthermore, the storing seafood items electrical circuitry arrangement ("elec circ arrange") e1173, when activated, will perform the operation o1173. Also, the storing seafood items module m1173, when executed and/or activated, will direct performance of and/or perform the operation o1173. For instance, in one or more exemplary implementations, the one or more storing seafood items instructions i1173, when executed, direct performance of the operation o1173 in the illustrative depiction as follows, and/or the storing seafood items electrical circuitry arrangement e1173, when activated, performs the operation o1173 in the illustrative depiction as follows, and/or the storing seafood items module m1173, when executed and/or activated, directs performance of and/or performs the operation o1173 in the illustrative depiction as follows, and/or the operation o1173 is otherwise carried out in the illustrative depiction as follows: electronically storing (e.g. onto SD card, etc.) grocery operations information (e.g. improper data calculation, etc.) regarding at least in part (e.g. engross, etc.) one or more grocery implementation aspects (e.g. distance between one or more farms and one or more wholesalers supplying grocery items to grocery, etc.) pertaining to (e.g. engross, etc.) grocery related merchandizing of (e.g. nursing home grocery item transporting, etc.) the one or more commercial grocery products (e.g. braised side dish grocery item, etc.) including at least in part one or more seafood items (e.g. pre-packaged baked flounder, etc.).

In one or more implementations, as shown in FIG. 67, operation o11 includes an operation o1174 for electronically storing grocery operations information regarding at least in part one or more grocery implementation aspects pertaining to grocery related merchandizing of the one or more commercial grocery products including at least in part one or more poultry items. Origination of an illustratively derived storing poultry items component group can be accomplished through skilled in the art design choice selection of one or more of the above depicted components from one or more of the above depicted subsystems shown in FIG. 12. Components from the storing poultry items component group can be used in implementing execution of the one or more storing poultry items instructions i1174 of FIG. 31, can be used in performance of the storing poultry items electrical circuitry arrangement e1174 of FIG. 24, and/or can be used in otherwise fulfillment of the operation o1174. An exemplary non-transitory signal bearing medium version of the information storage subsystem s200 is depicted in FIG. 31 as bearing the one or more storing poultry items instructions i1174 that when executed will direct performance of the operation o1174. Furthermore, the storing poultry items electrical circuitry arrangement ("elec circ arrange") e1174, when activated, will perform the operation o1174. Also, the storing poultry items module m1174, when executed and/or activated, will direct performance of and/or perform the operation o1174. For instance, in one or more exemplary implementations, the one or more storing poultry items instructions i1174, when executed, direct performance of the operation o1174 in the illustrative depiction as follows, and/or the storing poultry items electrical circuitry arrangement e1174, when activated, performs the operation o1174 in the illustrative depiction as follows, and/or the storing poultry items module m1174, when executed and/or activated, directs performance of and/or performs the operation o1174 in the illustrative depiction as follows, and/or the operation o1174 is otherwise carried out in the illustrative depiction as follows: electronically storing (e.g. onto SIM card, etc.) grocery operations information (e.g. rodent infestation of facilities, etc.) regarding at least in part (e.g. implicated, etc.) one or more grocery implementation aspects (e.g. distance between grocery and one or more wholesalers providing material to grocery, etc.) pertaining to (e.g. implicated, etc.) grocery related merchandizing of (e.g. street vendor grocery item transporting, etc.) the one or more commercial grocery products (e.g. sous-vide side dish grocery item, etc.) including at least in part one or more poultry items (e.g. chicken pot pie, etc.).

In one or more implementations, as shown in FIG. 67, operation o11 includes an operation o1175 for electronically storing grocery operations information regarding at least in part one or more grocery implementation aspects pertaining to grocery related merchandizing of the one or more commercial grocery products including at least in part one or more dairy items. Origination of an illustratively derived storing dairy items component group can be accomplished through skilled in the art design choice selection of one or more of the above depicted components from one or more of the above depicted subsystems shown in FIG. 12. Components from the storing dairy items component group can be used in implementing execution of the one or more storing dairy items instructions i1175 of FIG. 31, can be used in performance of the storing dairy items electrical circuitry arrangement e1175 of FIG. 24, and/or can be used in otherwise fulfillment of the operation o1175. An exemplary non-transitory signal bearing medium version of the information storage subsystem s200 is depicted in FIG. 31 as bearing the one or more storing dairy items instructions i1175 that when executed will direct performance of the operation o1175. Furthermore, the storing dairy items electrical circuitry arrangement ("elec circ arrange") e1175, when activated, will perform the operation o1175. Also, the storing dairy items module m1175, when executed and/or activated, will direct performance of and/or perform the operation o1175. For instance, in one or more exemplary implementations, the one or more storing dairy items instructions i1175, when executed, direct performance of the operation o1175 in the illustrative depiction as follows, and/or the storing dairy items electrical circuitry arrangement e1175, when activated, performs the operation o1175 in the illustrative depiction as follows, and/or the storing dairy items module m1175, when executed and/or activated, directs performance of and/or performs the operation o1175 in the illustrative depiction as follows, and/or the operation o1175 is otherwise carried out in the illustrative depiction as follows: electronically storing (e.g. from email, etc.) grocery operations information (e.g. sanitizer usage, etc.) regarding at least in part (e.g. necessitate, etc.) one or more grocery implementation aspects (e.g. one or more activity aspects of grocery as an upscale grocer, etc.) pertaining to (e.g. necessitate, etc.) grocery related merchandizing of (e.g. mobile kitchen grocery item transporting, etc.) the one or more commercial grocery products (e.g. blended side dish grocery item, etc.) including at least in part one or more dairy items (e.g. packaged cheese cake, etc.).

Figure 68:
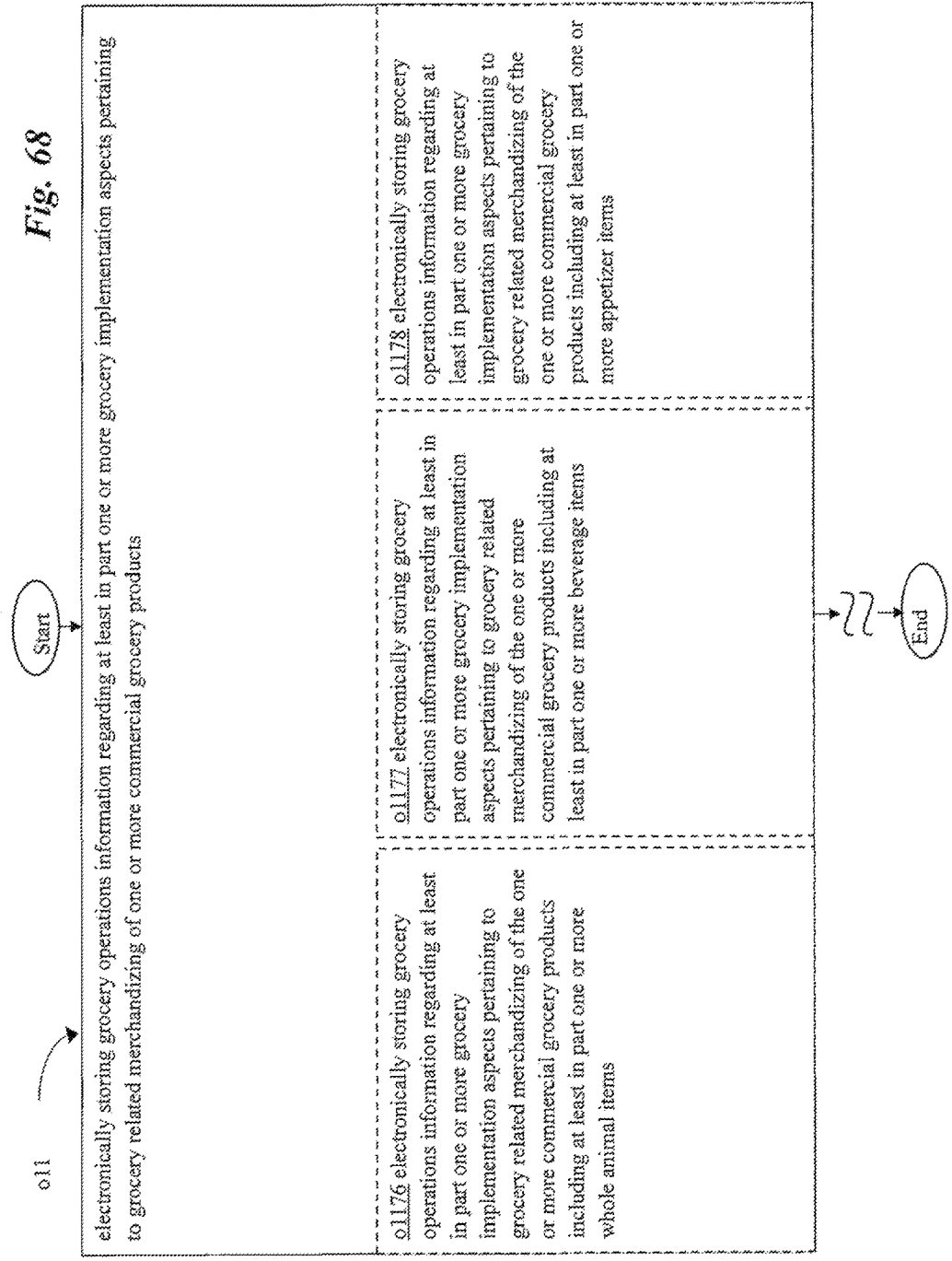
FIG. 68 is a high-level flowchart including exemplary implementations of operation o11 of FIG. 42.

In one or more implementations, as shown in FIG. 68, operation o11 includes an operation o1176 for electronically storing grocery operations information regarding at least in part one or more grocery implementation aspects pertaining to grocery related merchandizing of the one or more commercial grocery products including at least in part one or more whole animal items. Origination of an illustratively derived storing whole animal component group can be accomplished through skilled in the art design choice selection of one or more of the above depicted components from one or more of the above depicted subsystems shown in FIG. 12. Components from the storing whole animal component group can be used in implementing execution of the one or more storing whole animal instructions i1176 of FIG. 31, can be used in performance of the storing whole animal electrical circuitry arrangement e1176 of FIG. 24, and/or can be used in otherwise fulfillment of the operation o1176. An exemplary non-transitory signal bearing medium version of the information storage subsystem s200 is depicted in FIG. 31 as bearing the one or more storing whole animal instructions i1176 that when executed will direct performance of the operation o1176. Furthermore, the storing whole animal electrical circuitry arrangement ("elec circ arrange") e1176, when activated, will perform the operation o1176. Also, the storing whole animal module m1176, when executed and/or activated, will direct performance of and/or perform the operation o1176. For instance, in one or more exemplary implementations, the one or more storing whole animal instructions i1176, when executed, direct performance of the operation o1176 in the illustrative depiction as follows, and/or the storing whole animal electrical circuitry arrangement e1176, when activated, performs the operation o1176 in the illustrative depiction as follows, and/or the storing whole animal module m1176, when executed and/or activated, directs performance of and/or performs the operation o1176 in the illustrative depiction as follows, and/or the operation o1176 is otherwise carried out in the illustrative depiction as follows: electronically storing (e.g. as peer to peer, etc.) grocery operations information (e.g. distribution of tips by grocery customers, etc.) regarding at least in part (e.g. presuppose, etc.) one or more grocery implementation aspects (e.g. one or more activity aspects of grocery service as convenience grocer, etc.) pertaining to (e.g. presuppose, etc.) grocery related merchandizing of (e.g. hospital grocery item transporting, etc.) the one or more commercial grocery products (e.g. beverage side dish grocery item, etc.) including at least in part one or more whole animal items (e.g. whole eggs, etc.).

In one or more implementations, as shown in FIG. 68, operation o11 includes an operation o1177 for electronically storing grocery operations information regarding at least in part one or more grocery implementation aspects pertaining to grocery related merchandizing of the one or more commercial grocery products including at least in part one or more beverage items. Origination of an illustratively derived storing beverage items component group can be accomplished through skilled in the art design choice selection of one or more of the above depicted components from one or more of the above depicted subsystems shown in FIG. 12. Components from the storing beverage items component group can be used in implementing execution of the one or more storing beverage items instructions i1177 of FIG. 31, can be used in performance of the storing beverage items electrical circuitry arrangement e1177 of FIG. 24, and/or can be used in otherwise fulfillment of the operation o1177. An exemplary non-transitory signal bearing medium version of the information storage subsystem s200 is depicted in FIG. 31 as bearing the one or more storing beverage items instructions i1177 that when executed will direct performance of the operation o1177. Furthermore, the storing beverage items electrical circuitry arrangement ("elec circ arrange") e1177, when activated, will perform the operation o1177. Also, the storing beverage items module m1177, when executed and/or activated, will direct performance of and/or perform the operation o1177. For instance, in one or more exemplary implementations, the one or more storing beverage items instructions i1177, when executed, direct performance of the operation o1177 in the illustrative depiction as follows, and/or the storing beverage items electrical circuitry arrangement e1177, when activated, performs the operation o1177 in the illustrative depiction as follows, and/or the storing beverage items module m1177, when executed and/or activated, directs performance of and/or performs the operation o1177 in the illustrative depiction as follows, and/or the operation o1177 is otherwise carried out in the illustrative depiction as follows: electronically storing (e.g. from 10-key, etc.) grocery operations information (e.g. humidity profiles of storage rooms, etc.) regarding at least in part (e.g. related to, etc.) one or more grocery implementation aspects (e.g. one or more activity aspects of grocer as an institutional grocer, etc.) pertaining to (e.g. related to, etc.) grocery related merchandizing of (e.g. deli department grocery item transporting, etc.) the one or more commercial grocery products (e.g. protein dominant side dish grocery item, etc.) including at least in part one or more beverage items (e.g. weight-loss shake, etc.).

In one or more implementations, as shown in FIG. 68, operation o11 includes an operation o1178 for electronically storing grocery operations information regarding at least in part one or more grocery implementation aspects pertaining to grocery related merchandizing of the one or more commercial grocery products including at least in part one or more appetizer items. Origination of an illustratively derived storing appetizer items component group can be accomplished through skilled in the art design choice selection of one or more of the above depicted components from one or more of the above depicted subsystems shown in FIG. 12. Components from the storing appetizer items component group can be used in implementing execution of the one or more storing appetizer items instructions i1178 of FIG. 31, can be used in performance of the storing appetizer items electrical circuitry arrangement e1178 of FIG. 24, and/or can be used in otherwise fulfillment of the operation o1178. An exemplary non-transitory signal bearing medium version of the information storage subsystem s200 is depicted in FIG. 31 as bearing the one or more storing appetizer items instructions i1178 that when executed will direct performance of the operation o1178. Furthermore, the storing appetizer items electrical circuitry arrangement ("elec circ arrange") e1178, when activated, will perform the operation o1178. Also, the storing appetizer items module m1178, when executed and/or activated, will direct performance of and/or perform the operation o1178. For instance, in one or more exemplary implementations, the one or more storing appetizer items instructions i1178, when executed, direct performance of the operation o1178 in the illustrative depiction as follows, and/or the storing appetizer items electrical circuitry arrangement e1178, when activated, performs the operation o1178 in the illustrative depiction as follows, and/or the storing appetizer items module m1178, when executed and/or activated, directs performance of and/or performs the operation o1178 in the illustrative depiction as follows, and/or the operation o1178 is otherwise carried out in the illustrative depiction as follows: electronically storing (e.g. via USB port, etc.) grocery operations information (e.g. profile of oxygen levels in produce facilities, etc.) regarding at least in part (e.g. relationship, etc.) one or more grocery implementation aspects (e.g. one or more activity aspects of grocery as factory food item seller, etc.) pertaining to (e.g. relationship, etc.) grocery related merchandizing of (e.g. fine dining grocery item planning, etc.) the one or more commercial grocery products (e.g. carbohydrate dominant side dish grocery item, etc.) including at least in part one or more appetizer items (e.g. packaged crackers and cheese snacks, etc.).

Figure 69:
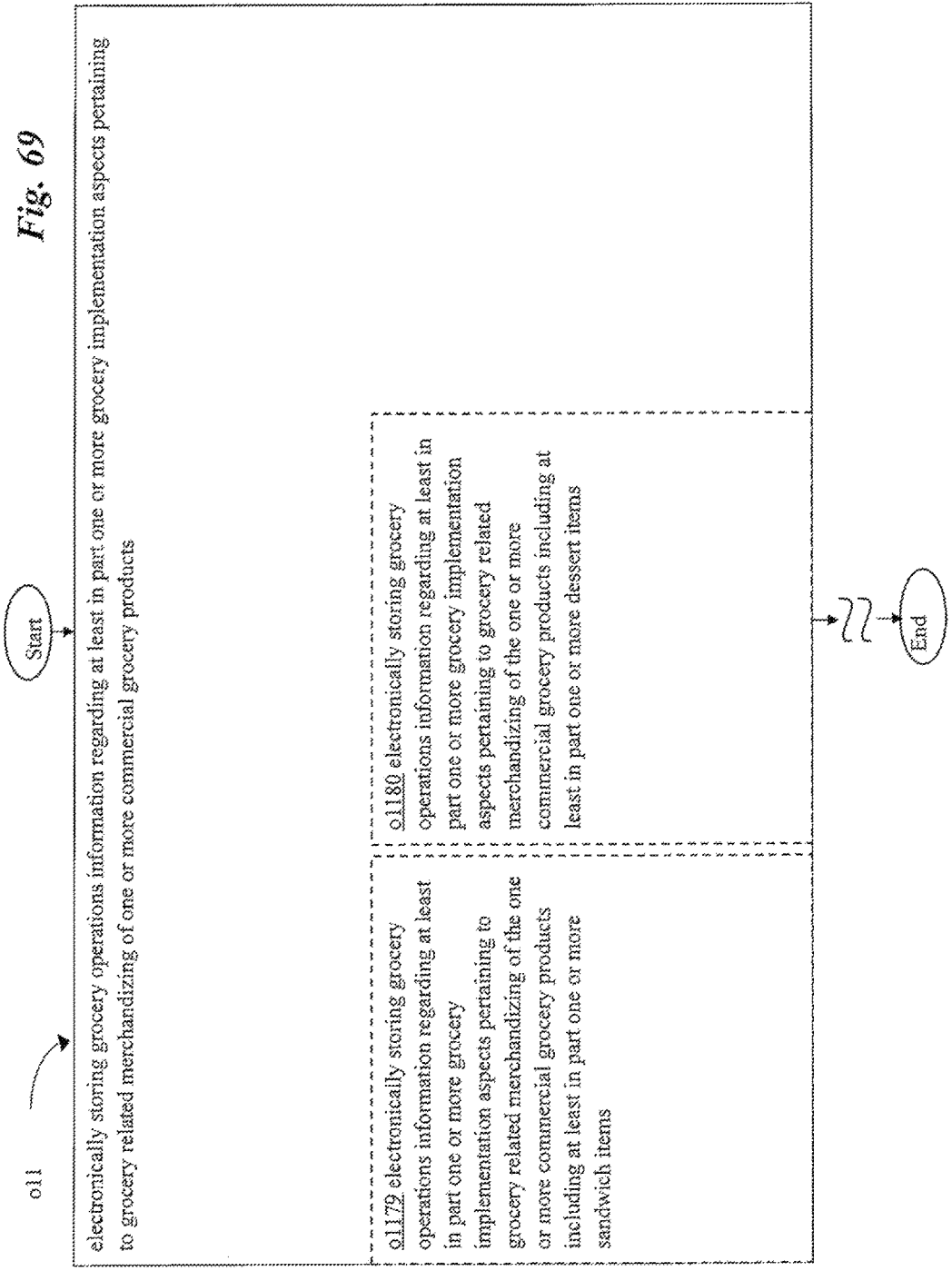
FIG. 69 is a high-level flowchart including exemplary implementations of operation o11 of FIG. 42.

In one or more implementations, as shown in FIG. 69, operation o11 includes an operation o1179 for electronically storing grocery operations information regarding at least in part one or more grocery implementation aspects pertaining to grocery related merchandizing of the one or more commercial grocery products including at least in part one or more sandwich items. Origination of an illustratively derived storing sandwich items component group can be accomplished through skilled in the art design choice selection of one or more of the above depicted components from one or more of the above depicted subsystems shown in FIG. 12. Components from the storing sandwich items component group can be used in implementing execution of the one or more storing sandwich items instructions i1179 of FIG. 31, can be used in performance of the storing sandwich items electrical circuitry arrangement e1179 of FIG. 24, and/or can be used in otherwise fulfillment of the operation o1179. An exemplary non-transitory signal bearing medium version of the information storage subsystem s200 is depicted in FIG. 31 as bearing the one or more storing sandwich items instructions i1179 that when executed will direct performance of the operation o1179. Furthermore, the storing sandwich items electrical circuitry arrangement ("elec circ arrange") e1179, when activated, will perform the operation o1179. Also, the storing sandwich items module m1179, when executed and/or activated, will direct performance of and/or perform the operation o1179. For instance, in one or more exemplary implementations, the one or more storing sandwich items instructions i1179, when executed, direct performance of the operation o1179 in the illustrative depiction as follows, and/or the storing sandwich items electrical circuitry arrangement e1179, when activated, performs the operation o1179 in the illustrative depiction as follows, and/or the storing sandwich items module m1179, when executed and/or activated, directs performance of and/or performs the operation o1179 in the illustrative depiction as follows, and/or the operation o1179 is otherwise carried out in the illustrative depiction as follows: electronically storing (e.g. as FTP, etc.) grocery operations information (e.g. profile of carbon dioxide levels in grocery facilities, etc.) regarding at least in part (e.g. suggest, etc.) one or more grocery implementation aspects (e.g. one or more activity aspects of grocery as mobile based grocer, etc.) pertaining to (e.g. suggest, etc.) grocery related merchandizing of (e.g. fast grocery item planning, etc.) the one or more commercial grocery products (e.g. fat dominant side dish grocery item, etc.) including at least in part one or more sandwich items (e.g. packaged ham and cheese sandwich, etc.).

In one or more implementations, as shown in FIG. 69, operation o11 includes an operation o1180 for electronically storing grocery operations information regarding at least in part one or more grocery implementation aspects pertaining to grocery related merchandizing of the one or more commercial grocery products including at least in part one or more dessert items. Origination of an illustratively derived storing dessert items component group can be accomplished through skilled in the art design choice selection of one or more of the above depicted components from one or more of the above depicted subsystems shown in FIG. 12. Components from the storing dessert items component group can be used in implementing execution of the one or more storing dessert items instructions i1180 of FIG. 32, can be used in performance of the storing dessert items electrical circuitry arrangement e1180 of FIG. 25, and/or can be used in otherwise fulfillment of the operation o1180. An exemplary non-transitory signal bearing medium version of the information storage subsystem s200 is depicted in FIG. 32 as bearing the one or more storing dessert items instructions i1180 that when executed will direct performance of the operation o1180. Furthermore, the storing dessert items electrical circuitry arrangement ("elec circ arrange") e1180, when activated, will perform the operation o1180. Also, the storing dessert items module m1180, when executed and/or activated, will direct performance of and/or perform the operation o1180. For instance, in one or more exemplary implementations, the one or more storing dessert items instructions i1180, when executed, direct performance of the operation o1180 in the illustrative depiction as follows, and/or the storing dessert items electrical circuitry arrangement e1180, when activated, performs the operation o1180 in the illustrative depiction as follows, and/or the storing dessert items module m1180, when executed and/or activated, directs performance of and/or performs the operation o1180 in the illustrative depiction as follows, and/or the operation o1180 is otherwise carried out in the illustrative depiction as follows: electronically storing (e.g. as HTTP, etc.) grocery operations information (e.g. grocery customer loyalty profiles, etc.) regarding at least in part (e.g. entangle, etc.) one or more grocery implementation aspects (e.g. one or more activity aspects of grocery as internet based grocer, etc.) pertaining to (e.g. entangle, etc.) grocery related merchandizing of (e.g. family buffet grocery item planning, etc.) the one or more commercial grocery products (e.g. pasta side dish grocery item, etc.) including at least in part one or more dessert items (e.g. chocolate cake, etc.).

As shown in FIG. 42, the operational flow o10 proceeds to operation o12 for electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances. An exemplary version of a non-transitory signal bearing medium of information storage subsystem s200 is depicted as bearing one or more electronically associating instructions i12 that when executed will direct performance of the operation o12. In an implementation, the one or more electronically associating instructions i12 when executed direct electronically associating (e.g. through database index, through database pointers, common attributes found in data set, etc.) at least a portion of grocery operations information (e.g. grocer cleaning protocols implemented, humidity of storage units, oxygen sensor of grocery item preparation equipment, etc.) concerning at least in part (e.g. associated, affected, affecting, etc.) one or more grocery implementation aspects (e.g. lease costs for facilities and equipment, equipment maintenance schedule, tool requirements for repair of grocery facility equipment, etc.) pertaining to (e.g. associated, affected, affecting, etc.) grocery related merchandizing of (e.g. nursing home grocery item receiving, school cafeteria grocery item receiving, institutional grocery item receiving, etc.) one or more commercial grocery products (e.g. weight loss grocery item side dish, cold grocery item side dish, hot grocery item side dish, etc.) with identification information (e.g. document discriminator, hologram, color code, etc.) obtainable through (e.g. through electromagnetic reception, through search terms, through storage retrieval, etc.) one or more tags (e.g. high frequency RFID, UHF emitter, ISM band emitter, etc.) said one or more tags logged (e.g. via server information, via index information, via body information, etc.) as being at least temporarily (e.g. time since introduction of oxygen absorber, shipping time on truck from distribution center to grocery, portion of shipping time returning from laboratory, etc.) within at least a vicinity of (e.g. adhered to container, tied to material, stapled to container, etc.) one or more food based substances (e.g. filleted salmon, carrot, wheat product, etc.). Furthermore, the electronically associating electrical circuitry arrangement e12 when activated will perform the operation o12. Also, the electronically associating module m12, when executed and/or activated, will direct performance of and/or perform the operation o12. In an implementation, the electronically associating electrical circuitry arrangement e12, when activated performs the operation o12 in the illustrative depiction as follows, and/or the electronically associating module m12, when executed and/or activated, directs performance of and/or performs electronically associating (e.g. through database index, through database pointers, common attributes found in data set, etc.) at least a portion of grocery operations information (e.g. grocer cleaning protocols implemented, humidity of storage units, oxygen sensor of grocery item preparation equipment, etc.) concerning at least in part (e.g. associated, affected, affecting, etc.) one or more grocery implementation aspects (e.g. lease costs for facilities and equipment, equipment maintenance schedule, tool requirements for repair of grocery facility equipment, etc.) pertaining to (e.g. associated, affected, affecting, etc.) grocery related merchandizing of (e.g. nursing home grocery item receiving, school cafeteria grocery item receiving, institutional grocery item receiving, etc.) one or more commercial grocery products (e.g. weight loss grocery item side dish, cold grocery item side dish, hot grocery item side dish, etc.) with identification information (e.g. document discriminator, hologram, color code, etc.) obtainable through (e.g. through electromagnetic reception, through search terms, through storage retrieval, etc.) one or more tags (e.g. high frequency RFID, UHF emitter, ISM band emitter, etc.) said one or more tags logged (e.g. via server information, via index information, via body information, etc.) as being at least temporarily (e.g. time since introduction of oxygen absorber, shipping time on truck from distribution center to grocery, portion of shipping time returning from laboratory, etc.) within at least a vicinity of (e.g. adhered to container, tied to material, stapled to container, etc.) one or more food based substances (e.g. filleted salmon, carrot, wheat product, etc.). In an implementation, the electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances is carried out by electronically associating (e.g. through database index, through database pointers, common attributes found in data set, etc.) at least a portion of grocery operations information (e.g. grocer cleaning protocols implemented, humidity of storage units, oxygen sensor of grocery item preparation equipment, etc.) concerning at least in part (e.g. associated, affected, affecting, etc.) one or more grocery implementation aspects (e.g. lease costs for facilities and equipment, equipment maintenance schedule, tool requirements for repair of grocery facility equipment, etc.) pertaining to (e.g. associated, affected, affecting, etc.) grocery related merchandizing of (e.g. nursing home grocery item receiving, school cafeteria grocery item receiving, institutional grocery item receiving, etc.) one or more commercial grocery products (e.g. weight loss grocery item side dish, cold grocery item side dish, hot grocery item side dish, etc.) with identification information (e.g. document discriminator, hologram, color code, etc.) obtainable through (e.g. through electromagnetic reception, through search terms, through storage retrieval, etc.) one or more tags (e.g. high frequency RFID, UHF emitter, ISM band emitter, etc.) said one or more tags logged (e.g. via server information, via index information, via body information, etc.) as being at least temporarily (e.g. time since introduction of oxygen absorber, shipping time on truck from distribution center to grocery, portion of shipping time returning from laboratory, etc.) within at least a vicinity of (e.g. adhered to container, tied to material, stapled to container, etc.) one or more food based substances (e.g. filleted salmon, carrot, wheat product, etc.).

Figure 70:
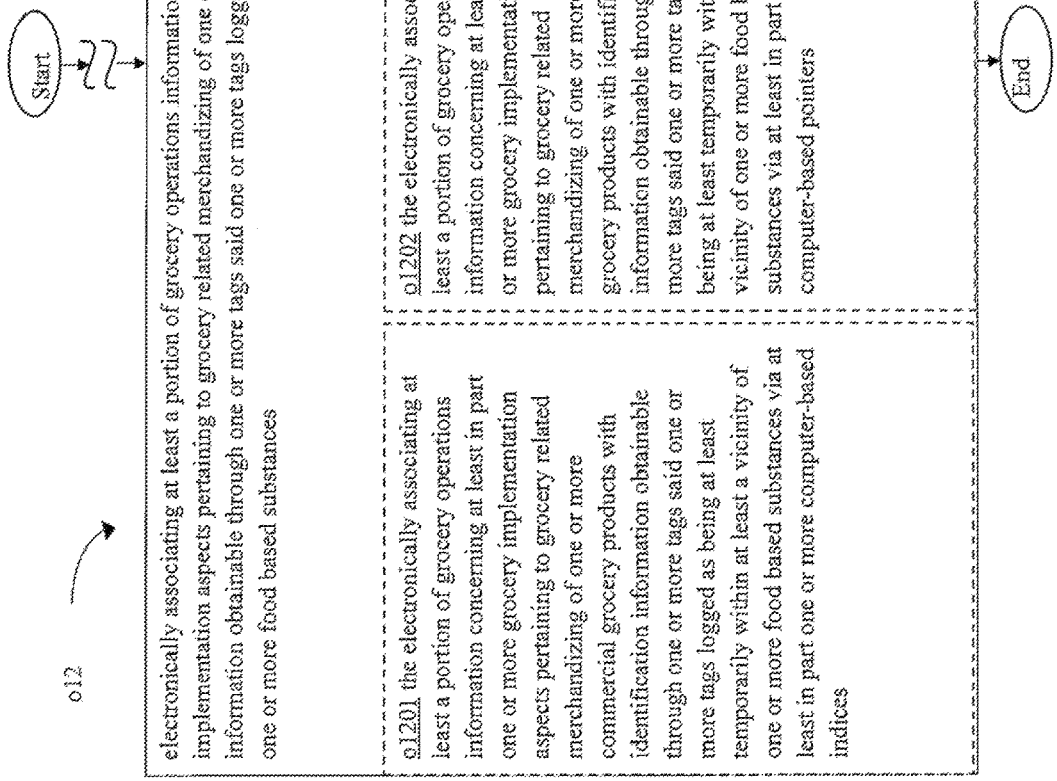
FIG. 70 is a high-level flowchart including exemplary implementations of operation o12 of FIG. 42.

In one or more implementations, as shown in FIG. 70, operation o12 includes an operation o1201 for the electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances via at least in part one or more computer-based indices. Origination of an illustratively derived associating computer-based indices component group can be accomplished through skilled in the art design choice selection of one or more of the above depicted components from one or more of the above depicted subsystems shown in FIG. 12. Components from the associating computer-based indices component group can be used in implementing execution of the one or more associating computer-based indices instructions i1201 of FIG. 33, can be used in performance of the associating computer-based indices electrical circuitry arrangement e1201 of FIG. 26, and/or can be used in otherwise fulfillment of the operation o1201. An exemplary non-transitory signal bearing medium version of the information storage subsystem s200 is depicted in FIG. 33 as bearing the one or more associating computer-based indices instructions i1201 that when executed will direct performance of the operation o1201. Furthermore, the associating computer-based indices electrical circuitry arrangement ("elec circ arrange") e1201, when activated, will perform the operation o1201. Also, the associating computer-based indices module m1201, when executed and/or activated, will direct performance of and/or perform the operation o1201. For instance, in one or more exemplary implementations, the one or more associating computer-based indices instructions i1201, when executed, direct performance of the operation o1201 in the illustrative depiction as follows, and/or the associating computer-based indices electrical circuitry arrangement e1201, when activated, performs the operation o1201 in the illustrative depiction as follows, and/or the associating computer-based indices module m1201, when executed and/or activated, directs performance of and/or performs the operation o1201 in the illustrative depiction as follows, and/or the operation o1201 is otherwise carried out in the illustrative depiction as follows: the electronically associating (e.g. through database index, etc.) at least a portion of grocery operations information (e.g. grocer cleaning protocols implemented, etc.) concerning at least in part (e.g. associated, etc.) one or more grocery implementation aspects (e.g. lease costs for facilities and equipment, etc.) pertaining to (e.g. associated, etc.) grocery related merchandizing of (e.g. nursing home grocery item receiving, etc.) one or more commercial grocery products (e.g. weight loss grocery item side dish, etc.) with identification information (e.g. document discriminator, etc.) obtainable through (e.g. through electromagnetic reception, etc.) one or more tags (e.g. high frequency RFID, etc.) said one or more tags logged (e.g. via server information, etc.) as being at least temporarily (e.g. time since introduction of oxygen absorber, etc.) within at least a vicinity of (e.g. adhered to container, etc.) one or more food based substances (e.g. filleted salmon, etc.) via at least in part one or more computer-based indices (e.g. through database index, etc.).

In one or more implementations, as shown in FIG. 70, operation o12 includes an operation o1202 for the electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances via at least in part one or more computer-based pointers. Origination of an illustratively derived associating computer-based pointers component group can be accomplished through skilled in the art design choice selection of one or more of the above depicted components from one or more of the above depicted subsystems shown in FIG. 12. Components from the associating computer-based pointers component group can be used in implementing execution of the one or more associating computer-based pointers instructions i1202 of FIG. 33, can be used in performance of the associating computer-based pointers electrical circuitry arrangement e1202 of FIG. 26, and/or can be used in otherwise fulfillment of the operation o1202. An exemplary non-transitory signal bearing medium version of the information storage subsystem s200 is depicted in FIG. 33 as bearing the one or more associating computer-based pointers instructions i1202 that when executed will direct performance of the operation o1202. Furthermore, the associating computer-based pointers electrical circuitry arrangement ("elec circ arrange") e1202, when activated, will perform the operation o1202. Also, the associating computer-based pointers module m1202, when executed and/or activated, will direct performance of and/or perform the operation o1202. For instance, in one or more exemplary implementations, the one or more associating computer-based pointers instructions i1202, when executed, direct performance of the operation o1202 in the illustrative depiction as follows, and/or the associating computer-based pointers electrical circuitry arrangement e1202, when activated, performs the operation o1202 in the illustrative depiction as follows, and/or the associating computer-based pointers module m1202, when executed and/or activated, directs performance of and/or performs the operation o1202 in the illustrative depiction as follows, and/or the operation o1202 is otherwise carried out in the illustrative depiction as follows: the electronically associating (e.g. through database pointers, etc.) at least a portion of grocery operations information (e.g. humidity of storage units, etc.) concerning at least in part (e.g. affected, etc.) one or more grocery implementation aspects (e.g. equipment maintenance schedule, etc.) pertaining to (e.g. affected, etc.) grocery related merchandizing of (e.g. school cafeteria grocery item receiving, etc.) one or more commercial grocery products (e.g. cold grocery item side dish, etc.) with identification information (e.g. hologram, etc.) obtainable through (e.g. through search terms, etc.) one or more tags (e.g. UHF emitter, etc.) said one or more tags logged (e.g. via index information, etc.) as being at least temporarily (e.g. shipping time on truck from distribution center to grocery, etc.) within at least a vicinity of (e.g. tied to material, etc.) one or more food based substances (e.g. carrot, etc.) via at least in part one or more computer-based pointers (e.g. through database pointers, etc.).

In one or more implementations, as shown in FIG. 70, operation o12 includes an operation o1203 for the electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances through at least in part one or more computer-based relational databases. Origination of an illustratively derived associating relational databases component group can be accomplished through skilled in the art design choice selection of one or more of the above depicted components from one or more of the above depicted subsystems shown in FIG. 12. Components from the associating relational databases component group can be used in implementing execution of the one or more associating relational databases instructions i1203 of FIG. 33, can be used in performance of the associating relational databases electrical circuitry arrangement e1203 of FIG. 26, and/or can be used in otherwise fulfillment of the operation o1203. An exemplary non-transitory signal bearing medium version of the information storage subsystem s200 is depicted in FIG. 33 as bearing the one or more associating relational databases instructions i1203 that when executed will direct performance of the operation o1203. Furthermore, the associating relational databases electrical circuitry arrangement ("elec circ arrange") e1203, when activated, will perform the operation o1203. Also, the associating relational databases module m1203, when executed and/or activated, will direct performance of and/or perform the operation o1203. For instance, in one or more exemplary implementations, the one or more associating relational databases instructions i1203, when executed, direct performance of the operation o1203 in the illustrative depiction as follows, and/or the associating relational databases electrical circuitry arrangement e1203, when activated, performs the operation o1203 in the illustrative depiction as follows, and/or the associating relational databases module m1203, when executed and/or activated, directs performance of and/or performs the operation o1203 in the illustrative depiction as follows, and/or the operation o1203 is otherwise carried out in the illustrative depiction as follows: the electronically associating (e.g. common attributes found in data set, etc.) at least a portion of grocery operations information (e.g. oxygen sensor of grocery item preparation equipment, etc.) concerning at least in part (e.g. affecting, etc.) one or more grocery implementation aspects (e.g. tool requirements for repair of grocery facility equipment, etc.) pertaining to (e.g. affecting, etc.) grocery related merchandizing of (e.g. institutional grocery item receiving, etc.) one or more commercial grocery products (e.g. hot grocery item side dish, etc.) with identification information (e.g. color code, etc.) obtainable through (e.g. through storage retrieval, etc.) one or more tags (e.g. ISM band emitter, etc.) said one or more tags logged (e.g. via body information, etc.) as being at least temporarily (e.g. portion of shipping time returning from laboratory, etc.) within at least a vicinity of (e.g. stapled to container, etc.) one or more food based substances (e.g. wheat product, etc.) through at least in part one or more computer-based relational databases (e.g. common attributes found in data set, etc.).

Figure 71:
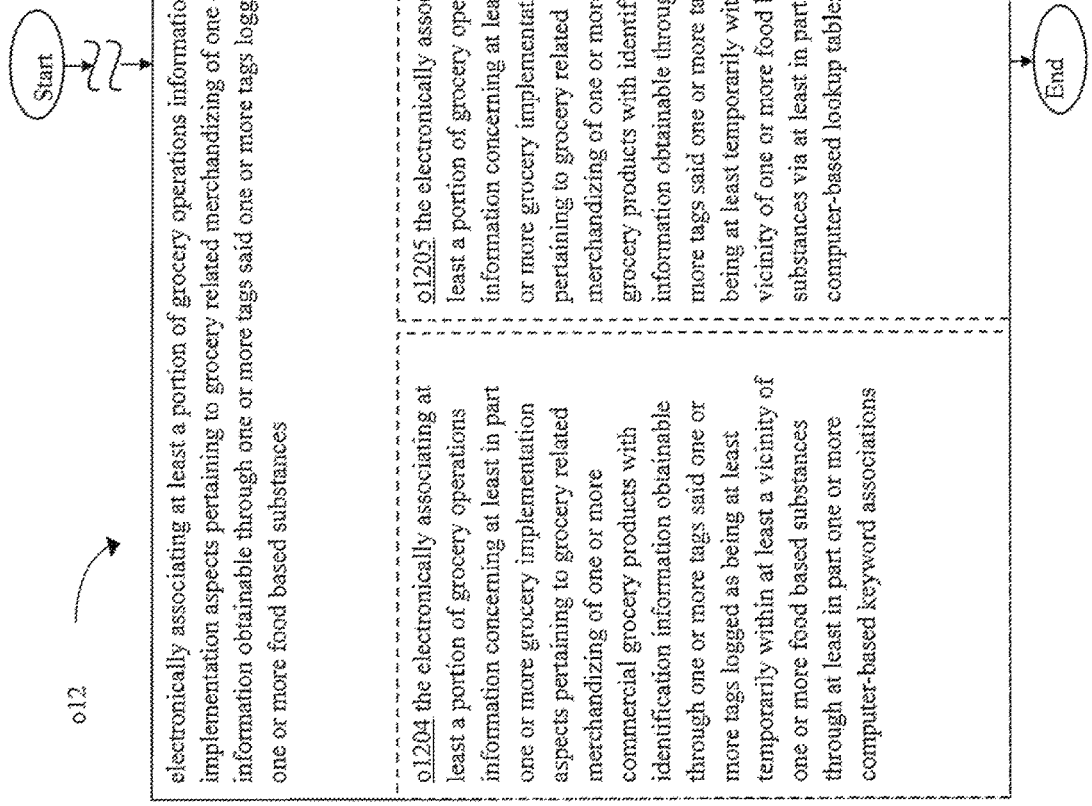
FIG. 71 is a high-level flowchart including exemplary implementations of operation o12 of FIG. 42.

In one or more implementations, as shown in FIG. 71, operation o12 includes an operation o1204 for the electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances through at least in part one or more computer-based keyword associations. Origination of an illustratively derived associating keyword associations component group can be accomplished through skilled in the art design choice selection of one or more of the above depicted components from one or more of the above depicted subsystems shown in FIG. 12. Components from the associating keyword associations component group can be used in implementing execution of the one or more associating keyword associations instructions i1204 of FIG. 33, can be used in performance of the associating keyword associations electrical circuitry arrangement e1204 of FIG. 26, and/or can be used in otherwise fulfillment of the operation o1204. An exemplary non-transitory signal bearing medium version of the information storage subsystem s200 is depicted in FIG. 33 as bearing the one or more associating keyword associations instructions i1204 that when executed will direct performance of the operation o1204. Furthermore, the associating keyword associations electrical circuitry arrangement ("elec circ arrange") e1204, when activated, will perform the operation o1204. Also, the associating keyword associations module m1204, when executed and/or activated, will direct performance of and/or perform the operation o1204. For instance, in one or more exemplary implementations, the one or more associating keyword associations instructions i1204, when executed, direct performance of the operation o1204 in the illustrative depiction as follows, and/or the associating keyword associations electrical circuitry arrangement e1204, when activated, performs the operation o1204 in the illustrative depiction as follows, and/or the associating keyword associations module m1204, when executed and/or activated, directs performance of and/or performs the operation o1204 in the illustrative depiction as follows, and/or the operation o1204 is otherwise carried out in the illustrative depiction as follows: the electronically associating (e.g. through search terms, etc.) at least a portion of grocery operations information (e.g. bacteria count in grocery produce, etc.) concerning at least in part (e.g. argue, etc.) one or more grocery implementation aspects (e.g. local regulations, etc.) pertaining to (e.g. argue, etc.) grocery related merchandizing of (e.g. mobile catering grocery item receiving, etc.) one or more commercial grocery products (e.g. stew grocery item side dish, etc.) with identification information (e.g. visual pattern, etc.) obtainable through (e.g. through barcode scanning, etc.) one or more tags (e.g. microwave emitter, etc.) said one or more tags logged (e.g. via food composition database, etc.) as being at least temporarily (e.g. time spent on conveyor belt, etc.) within at least a vicinity of (e.g. laser etched onto container, etc.) one or more food based substances (e.g. ground chicken ingredient, etc.) through at least in part one or more computer-based keyword associations (e.g. through search terms, etc.).

In one or more implementations, as shown in FIG. 71, operation o12 includes an operation o1205 for the electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily within at least a vicinity of one or more food based substances via at least in part one or more computer-based lookup tables. Origination of an illustratively derived associating lookup tables component group can be accomplished through skilled in the art design choice selection of one or more of the above depicted components from one or more of the above depicted subsystems shown in FIG. 12. Components from the associating lookup tables component group can be used in implementing execution of the one or more associating lookup tables instructions i1205 of FIG. 33, can be used in performance of the associating lookup tables electrical circuitry arrangement e1205 of FIG. 26, and/or can be used in otherwise fulfillment of the operation o1205. An exemplary non-transitory signal bearing medium version of the information storage subsystem s200 is depicted in FIG. 33 as bearing the one or more associating lookup tables instructions i1205 that when executed will direct performance of the operation o1205. Furthermore, the associating lookup tables electrical circuitry arrangement ("elec circ arrange") e1205, when activated, will perform the operation o1205. Also, the associating lookup tables module m1205, when executed and/or activated, will direct performance of and/or perform the operation o1205. For instance, in one or more exemplary implementations, the one or more associating lookup tables instructions i1205, when executed, direct performance of the operation o1205 in the illustrative depiction as follows, and/or the associating lookup tables electrical circuitry arrangement e1205, when activated, performs the operation o1205 in the illustrative depiction as follows, and/or the associating lookup tables module m1205, when executed and/or activated, directs performance of and/or performs the operation o1205 in the illustrative depiction as follows, and/or the operation o1205 is otherwise carried out in the illustrative depiction as follows: the electronically associating (e.g. through a query table, etc.) at least a portion of grocery operations information (e.g. bacteria count on shelf surfaces, etc.) concerning at least in part (e.g. connected, etc.) one or more grocery implementation aspects (e.g. type of cuisine grocery items sold by the grocery facility, etc.) pertaining to (e.g. connected, etc.) grocery related merchandizing of (e.g. family buffet grocery item receiving, etc.) one or more commercial grocery products (e.g. soup grocery item side dish, etc.) with identification information (e.g. Morse code, etc.) obtainable through (e.g. through radiation detection, etc.) one or more tags (e.g. laser ranging tracker, etc.) said one or more tags logged (e.g. via DVD-ROM storage, etc.) as being at least temporarily (e.g. portion of time since sealed in carton, etc.) within at least a vicinity of (e.g. subdermally injected into material, etc.) one or more food based substances (e.g. substance for produce department product, etc.) via at least in part one or more computer-based lookup tables (e.g. the database table, etc.).

In one or more implementations, as shown in FIG. 71, operation o12 includes an operation o1206 for electronically associating at least a portion of grocery operations information concerning at least in part one or more grocery implementation aspects pertaining to grocery related merchandizing of one or more commercial grocery products the with identification information obtainable through one or more tags said one or more tags logged as being at least temporarily within at least a vicinity of one or more food based substances including at least in part one or more computer-based identification codes. Origination of an illustratively derived associating identification codes component group can be accomplished through skilled in the art design choice selection of one or more of the above depicted components from one or more of the above depicted subsystems shown in FIG. 12. Components from the associating identification codes component group can be used in implementing execution of the one or more associating identification codes instructions i1206 of FIG. 33, can be used in performance of the associating identification codes electrical circuitry arrangement e1206 of FIG. 26, and/or can be used in otherwise fulfillment of the operation o1206. An exemplary non-transitory signal bearing medium version of the information storage subsystem s200 is depicted in FIG. 33 as bearing the one or more associating identification codes instructions i1206 that when executed will direct performance of the operation o1206. Furthermore, the associating identification codes electrical circuitry arrangement ("elec circ arrange") e1206, when activated, will perform the operation o1206. Also, the associating identification codes module m1206, when executed and/or activated, will direct performance of and/or perform the operation o1206. For instance, in one or more exemplary implementations, the one or more associating identification codes instructions i1206, when executed, direct performance of the operation o1206 in the illustrative depiction as follows, and/or the associating identification codes electrical circuitry arrangement e1206, when activated, performs the operation o1206 in the illustrative depiction as follows, and/or the associating identification codes module m1206, when executed and/or activated, directs performance of and/or performs the operation o1206 in the illustrative depiction as follows, and/or the operation o1206 is otherwise carried out in the illustrative depiction as follows: electronically associating (e.g. through data structure, etc.) at least a portion of grocery operations information (e.g. equipment maintenance, etc.) concerning at least in part (e.g. commit to, etc.) one or more grocery implementation aspects (e.g. demographic location of the grocery facility, etc.) pertaining to (e.g. commit to, etc.) grocery related merchandizing of (e.g. fast grocery item receiving, etc.) one or more commercial grocery products (e.g. buffet grocery item side dish, etc.) the with identification information (e.g. tertiary code, etc.) obtainable through (e.g. through isotope identification, etc.) one or more tags (e.g. ultrasonic emitter, etc.) said one or more tags logged (e.g. via relational database, etc.) as being at least temporarily (e.g. portion of time spent packaged with similar material, etc.) within at least a vicinity of (e.g. adhered to material, etc.) one or more food based substances (e.g. substance for dairy department product, etc.) including at least in part one or more computer-based identification codes (e.g. HTML code, etc.).

In one or more implementations, as shown in FIG. 72, operation o12 includes an operation o1207 for electronically associating at least a portion of grocery operations information concerning at least in part one or more grocery implementation aspects pertaining to grocery related merchandizing of one or more commercial grocery products the with identification information obtainable through one or more tags said one or more tags logged as being at least temporarily within at least a vicinity of one or more food based substances including at least in part one or more computer-based encrypted identifications. Origination of an illustratively derived associating encrypted identifications component group can be accomplished through skilled in the art design choice selection of one or more of the above depicted components from one or more of the above depicted subsystems shown in FIG. 12. Components from the associating encrypted identifications component group can be used in implementing execution of the one or more associating encrypted identifications instructions i1207 of FIG. 33, can be used in performance of the associating encrypted identifications electrical circuitry arrangement e1207 of FIG. 26, and/or can be used in otherwise fulfillment of the operation o1207. An exemplary non-transitory signal bearing medium version of the information storage subsystem s200 is depicted in FIG. 33 as bearing the one or more associating encrypted identifications instructions i1207 that when executed will direct performance of the operation o1207. Furthermore, the associating encrypted identifications electrical circuitry arrangement ("elec circ arrange") e1207, when activated, will perform the operation o1207. Also, the associating encrypted identifications module m1207, when executed and/or activated, will direct performance of and/or perform the operation o1207. For instance, in one or more exemplary implementations, the one or more associating encrypted identifications instructions i1207, when executed, direct performance of the operation o1207 in the illustrative depiction as follows, and/or the associating encrypted identifications electrical circuitry arrangement e1207, when activated, performs the operation o1207 in the illustrative depiction as follows, and/or the associating encrypted identifications module m1207, when executed and/or activated, directs performance of and/or performs the operation o1207 in the illustrative depiction as follows, and/or the operation o1207 is otherwise carried out in the illustrative depiction as follows: electronically associating (e.g. through database table, etc.) at least a portion of grocery operations information (e.g. nitrogen gas levels of storage units, etc.) concerning at least in part (e.g. absorbed by, etc.) one or more grocery implementation aspects (e.g. age of equipment used in the grocery facility, etc.) pertaining to (e.g. absorbed by, etc.) grocery related merchandizing of (e.g. fine dining grocery item receiving, etc.) one or more commercial grocery products (e.g. raw grocery item side dish, etc.) the with identification information (e.g. model number, etc.) obtainable through (e.g. through beacon signal reception, etc.) one or more tags (e.g. gyroscope, etc.) said one or more tags logged (e.g. via database management layer, etc.) as being at least temporarily (e.g. portion of time spent on shipping vessel, etc.) within at least a vicinity of (e.g. ink stamped directly onto material, etc.) one or more food based substances (e.g. canned soup, etc.) including at least in part one or more computer-based encrypted identifications (e.g. through 256 bit encryption, etc.).

In one or more implementations, as shown in FIG. 72, operation o12 includes an operation o1208 for electronically associating at least a portion of grocery operations information concerning at least in part one or more grocery implementation aspects pertaining to grocery related merchandizing of one or more commercial grocery products the with identification information obtainable through one or more tags said one or more tags logged as being at least temporarily within at least a vicinity of one or more food based substances including at least in part one or more computer-based naming information. Origination of an illustratively derived associating naming information component group can be accomplished through skilled in the art design choice selection of one or more of the above depicted components from one or more of the above depicted subsystems shown in FIG. 12. Components from the associating naming information component group can be used in implementing execution of the one or more associating naming information instructions i1208 of FIG. 33, can be used in performance of the associating naming information electrical circuitry arrangement e1208 of FIG. 26, and/or can be used in otherwise fulfillment of the operation o1208. An exemplary non-transitory signal bearing medium version of the information storage subsystem s200 is depicted in FIG. 33 as bearing the one or more associating naming information instructions i1208 that when executed will direct performance of the operation o1208. Furthermore, the associating naming information electrical circuitry arrangement ("elec circ arrange") e1208, when activated, will perform the operation o1208. Also, the associating naming information module m1208, when executed and/or activated, will direct performance of and/or perform the operation o1208. For instance, in one or more exemplary implementations, the one or more associating naming information instructions i1208, when executed, direct performance of the operation o1208 in the illustrative depiction as follows, and/or the associating naming information electrical circuitry arrangement e1208, when activated, performs the operation o1208 in the illustrative depiction as follows, and/or the associating naming information module m1208, when executed and/or activated, directs performance of and/or performs the operation o1208 in the illustrative depiction as follows, and/or the operation o1208 is otherwise carried out in the illustrative depiction as follows: electronically associating (e.g. through access of ordered records, etc.) at least a portion of grocery operations information (e.g. amount of waste to disposed of, etc.) concerning at least in part (e.g. embraced by, etc.) one or more grocery implementation aspects (e.g. distribution of various types of grocery items sold, etc.) pertaining to (e.g. embraced by, etc.) grocery related merchandizing of (e.g. deli department grocery item serving, etc.) one or more commercial grocery products (e.g. cooked grocery item side dish, etc.) the with identification information (e.g. phonetic alphabet, etc.) obtainable through (e.g. through image scanning, etc.) one or more tags (e.g. inertial sensor, etc.) said one or more tags logged (e.g. via footer information, etc.) as being at least temporarily (e.g. time spent in cold storage, etc.) within at least a vicinity of (e.g. placed inside material, etc.) one or more food based substances (e.g. substance for meat department product, etc.) including at least in part one or more computer-based naming information (e.g. through hierarchical nomenclature, etc.).

In one or more implementations, as shown in FIG. 72, operation o12 includes an operation o1209 for electronically associating at least a portion of grocery operations information concerning at least in part one or more grocery implementation aspects pertaining to grocery related merchandizing of one or more commercial grocery products the with identification information obtainable through one or more tags said one or more tags logged as being at least temporarily within at least a vicinity of one or more food based substances including at least in part one or more computer-based stored alpha-numeric text. Origination of an illustratively derived associating alpha-numeric text component group can be accomplished through skilled in the art design choice selection of one or more of the above depicted components from one or more of the above depicted subsystems shown in FIG. 12. Components from the associating alpha-numeric text component group can be used in implementing execution of the one or more associating alpha-numeric text instructions i1209 of FIG. 33, can be used in performance of the associating alpha-numeric text electrical circuitry arrangement e1209 of FIG. 26, and/or can be used in otherwise fulfillment of the operation o1209. An exemplary non-transitory signal bearing medium version of the information storage subsystem s200 is depicted in FIG. 33 as bearing the one or more associating alpha-numeric text instructions i1209 that when executed will direct performance of the operation o1209. Furthermore, the associating alpha-numeric text electrical circuitry arrangement ("elec circ arrange") e1209, when activated, will perform the operation o1209. Also, the associating alpha-numeric text module m1209, when executed and/or activated, will direct performance of and/or perform the operation o1209. For instance, in one or more exemplary implementations, the one or more associating alpha-numeric text instructions i1209, when executed, direct performance of the operation o1209 in the illustrative depiction as follows, and/or the associating alpha-numeric text electrical circuitry arrangement e1209, when activated, performs the operation o1209 in the illustrative depiction as follows, and/or the associating alpha-numeric text module m1209, when executed and/or activated, directs performance of and/or performs the operation o1209 in the illustrative depiction as follows, and/or the operation o1209 is otherwise carried out in the illustrative depiction as follows: electronically associating (e.g. via functions, etc.) at least a portion of grocery operations information (e.g. carrier information for grocery item shipments, etc.) concerning at least in part (e.g. containing, etc.) one or more grocery implementation aspects (e.g. labor laws, etc.) pertaining to (e.g. containing, etc.) grocery related merchandizing of (e.g. hospital grocery item serving, etc.) one or more commercial grocery products (e.g. bean grocery item side dish, etc.) the with identification information (e.g. Arabic alphabet, etc.) obtainable through (e.g. through audio reception, etc.) one or more tags (e.g. accelerometer, etc.) said one or more tags logged (e.g. via header information, etc.) as being at least temporarily (e.g. portion of time spent on shipping vessel, etc.) within at least a vicinity of (e.g. placed inside container, etc.) one or more food based substances (e.g. substance for fish department product, etc.) including at least in part one or more computer-based stored alpha-numeric text (e.g. via textual descriptors, etc.).

Figure 73:
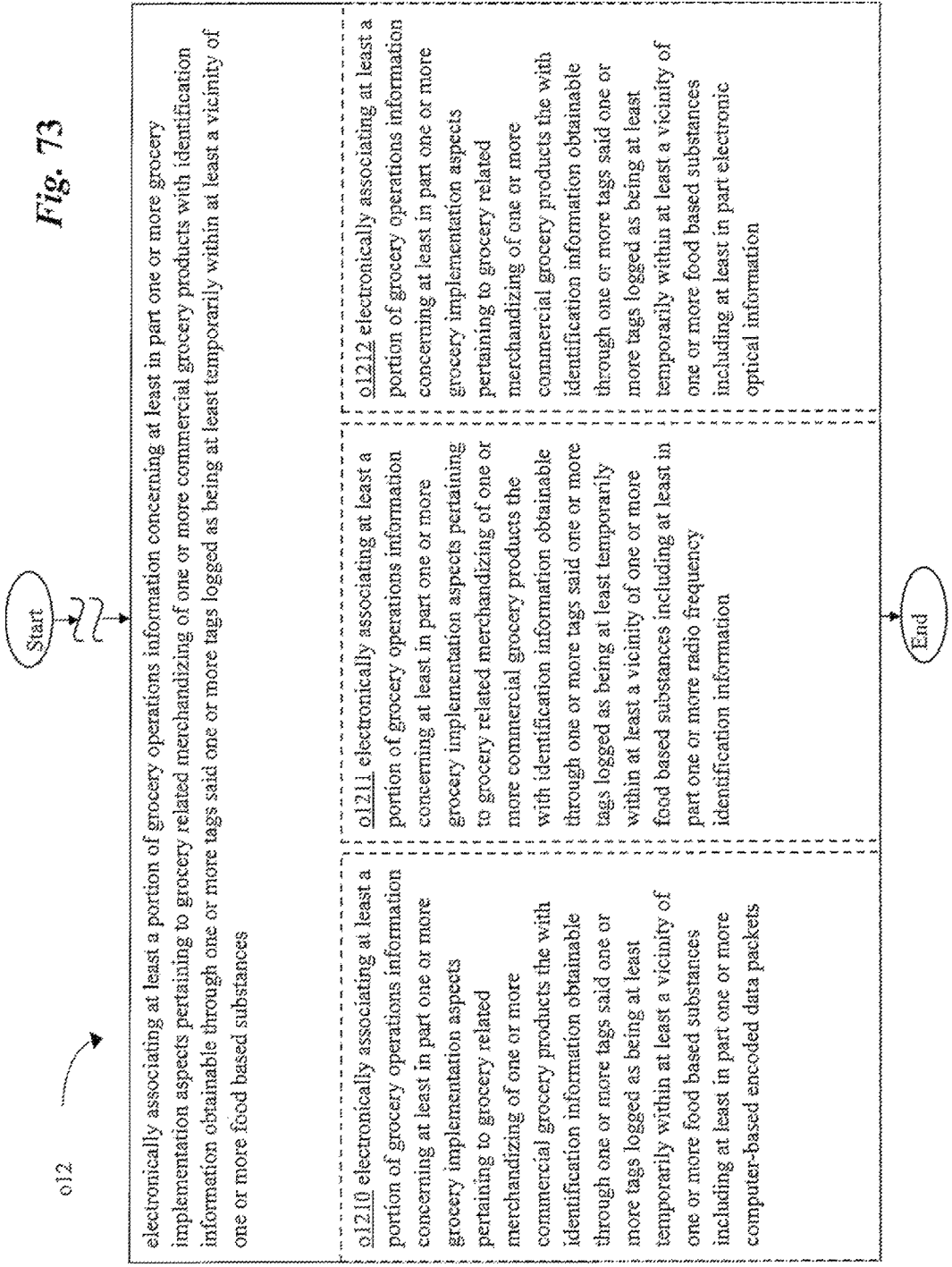
FIG. 73 is a high-level flowchart including exemplary implementations of operation o12 of FIG. 42.

In one or more implementations, as shown in FIG. 73, operation o12 includes an operation o1210 for electronically associating at least a portion of grocery operations information concerning at least in part one or more grocery implementation aspects pertaining to grocery related merchandizing of one or more commercial grocery products the with identification information obtainable through one or more tags said one or more tags logged as being at least temporarily within at least a vicinity of one or more food based substances including at least in part one or more computer-based encoded data packets. Origination of an illustratively derived associating encoded data component group can be accomplished through skilled in the art design choice selection of one or more of the above depicted components from one or more of the above depicted subsystems shown in FIG. 12. Components from the associating encoded data component group can be used in implementing execution of the one or more associating encoded data instructions i1210 of FIG. 33, can be used in performance of the associating encoded data electrical circuitry arrangement e1210 of FIG. 26, and/or can be used in otherwise fulfillment of the operation o1210. An exemplary non-transitory signal bearing medium version of the information storage subsystem s200 is depicted in FIG. 33 as bearing the one or more associating encoded data instructions i1210 that when executed will direct performance of the operation o1210. Furthermore, the associating encoded data electrical circuitry arrangement ("elec circ arrange") e1210, when activated, will perform the operation o1210. Also, the associating encoded data module m1210, when executed and/or activated, will direct performance of and/or perform the operation o1210. For instance, in one or more exemplary implementations, the one or more associating encoded data instructions i1210, when executed, direct performance of the operation o1210 in the illustrative depiction as follows, and/or the associating encoded data electrical circuitry arrangement e1210, when activated, performs the operation o1210 in the illustrative depiction as follows, and/or the associating encoded data module m1210, when executed and/or activated, directs performance of and/or performs the operation o1210 in the illustrative depiction as follows, and/or the operation o1210 is otherwise carried out in the illustrative depiction as follows: electronically associating (e.g. via expressions, etc.) at least a portion of grocery operations information (e.g. water usage, etc.) concerning at least in part (e.g. engaging, etc.) one or more grocery implementation aspects (e.g. safety regulations, etc.) pertaining to (e.g. engaging, etc.) grocery related merchandizing of (e.g. mobile kitchen grocery item serving, etc.) one or more commercial grocery products (e.g. grain grocery item side dish, etc.) the with identification information (e.g. security data, etc.) obtainable through (e.g. through visual identification, etc.) one or more tags (e.g. phase difference sensor, etc.) said one or more tags logged (e.g. via portion of packet information, etc.) as being at least temporarily (e.g. time spent exposed to air before packaging, etc.) within at least a vicinity of (e.g. riveted to container, etc.) one or more food based substances (e.g. ground beef, etc.) including at least in part one or more computer-based encoded data packets (e.g. tcp-ip packet, etc.).

In one or more implementations, as shown in FIG. 73, operation o12 includes an operation o1211 for electronically associating at least a portion of grocery operations information concerning at least in part one or more grocery implementation aspects pertaining to grocery related merchandizing of one or more commercial grocery products the with identification information obtainable through one or more tags said one or more tags logged as being at least temporarily within at least a vicinity of one or more food based substances including at least in part one or more radio frequency identification information. Origination of an illustratively derived associating frequency identification component group can be accomplished through skilled in the art design choice selection of one or more of the above depicted components from one or more of the above depicted subsystems shown in FIG. 12. Components from the associating frequency identification component group can be used in implementing execution of the one or more associating frequency identification instructions i1211 of FIG. 33, can be used in performance of the associating frequency identification electrical circuitry arrangement e1211 of FIG. 26, and/or can be used in otherwise fulfillment of the operation o1211. An exemplary non-transitory signal bearing medium version of the information storage subsystem s200 is depicted in FIG. 33 as bearing the one or more associating frequency identification instructions i1211 that when executed will direct performance of the operation o1211. Furthermore, the associating frequency identification electrical circuitry arrangement ("elec circ arrange") e1211, when activated, will perform the operation o1211. Also, the associating frequency identification module m1211, when executed and/or activated, will direct performance of and/or perform the operation o1211. For instance, in one or more exemplary implementations, the one or more associating frequency identification instructions i1211, when executed, direct performance of the operation o1211 in the illustrative depiction as follows, and/or the associating frequency identification electrical circuitry arrangement e1211, when activated, performs the operation o1211 in the illustrative depiction as follows, and/or the associating frequency identification module m1211, when executed and/or activated, directs performance of and/or performs the operation o1211 in the illustrative depiction as follows, and/or the operation o1211 is otherwise carried out in the illustrative depiction as follows: electronically associating (e.g. via sub-linear time lookup, etc.) at least a portion of grocery operations information (e.g. produce quality observed as received from various warehouses or farms, etc.) concerning at least in part (e.g. engaged by, etc.) one or more grocery implementation aspects (e.g. neighboring grocery facilities, etc.) pertaining to (e.g. engaged by, etc.) grocery related merchandizing of (e.g. street vendor grocery item serving, etc.) one or more commercial grocery products (e.g. salad grocery item side dish, etc.) the with identification information (e.g. binary sequence, etc.) obtainable through (e.g. through light reception, etc.) one or more tags (e.g. magnetic field sensor, etc.) said one or more tags logged (e.g. via solid state memory, etc.) as being at least temporarily (e.g. portion of time spent in ice bath, etc.) within at least a vicinity of (e.g. enveloping container, etc.) one or more food based substances (e.g. cod fish, etc.) including at least in part one or more radio frequency identification information (e.g. RFID tag, etc.).

In one or more implementations, as shown in FIG. 73, operation o12 includes an operation o1212 for electronically associating at least a portion of grocery operations information concerning at least in part one or more grocery implementation aspects pertaining to grocery related merchandizing of one or more commercial grocery products the with identification information obtainable through one or more tags said one or more tags logged as being at least temporarily within at least a vicinity of one or more food based substances including at least in part electronic optical information. Origination of an illustratively derived associating electronic optical component group can be accomplished through skilled in the art design choice selection of one or more of the above depicted components from one or more of the above depicted subsystems shown in FIG. 12. Components from the associating electronic optical component group can be used in implementing execution of the one or more associating electronic optical instructions i1212 of FIG. 33, can be used in performance of the associating electronic optical electrical circuitry arrangement e1212 of FIG. 26, and/or can be used in otherwise fulfillment of the operation o1212. An exemplary non-transitory signal bearing medium version of the information storage subsystem s200 is depicted in FIG. 33 as bearing the one or more associating electronic optical instructions i1212 that when executed will direct performance of the operation o1212. Furthermore, the associating electronic optical electrical circuitry arrangement ("elec circ arrange") e1212, when activated, will perform the operation o1212. Also, the associating electronic optical module m1212, when executed and/or activated, will direct performance of and/or perform the operation o1212. For instance, in one or more exemplary implementations, the one or more associating electronic optical instructions i1212, when executed, direct performance of the operation o1212 in the illustrative depiction as follows, and/or the associating electronic optical electrical circuitry arrangement e1212, when activated, performs the operation o1212 in the illustrative depiction as follows, and/or the associating electronic optical module m1212, when executed and/or activated, directs performance of and/or performs the operation o1212 in the illustrative depiction as follows, and/or the operation o1212 is otherwise carried out in the illustrative depiction as follows: electronically associating (e.g. through linear search, etc.) at least a portion of grocery operations information (e.g. meat quality observed as received from various warehouses or farms, etc.) concerning at least in part (e.g. incorporating, etc.) one or more grocery implementation aspects (e.g. any quarantines imposed in surrounding area, etc.) pertaining to (e.g. incorporating, etc.) grocery related merchandizing of (e.g. nursing home grocery item serving, etc.) one or more commercial grocery products (e.g. vegetarian grocery item side dish, etc.) the with identification information (e.g. ASCII string, etc.) obtainable through (e.g. through color spectrum identification, etc.) one or more tags (e.g. compass, etc.) said one or more tags logged (e.g. via food composition database, etc.) as being at least temporarily (e.g. shipping time from warehouse grocery, etc.) within at least a vicinity of (e.g. debossed on material, etc.) one or more food based substances (e.g. substance for bakery department product, etc.) including at least in part electronic optical information (e.g. holographic coded tags, etc.).

In one or more implementations, as shown in FIG. 74, operation o12 includes an operation o1213 for electronically associating at least a portion of grocery operations information concerning at least in part one or more grocery implementation aspects pertaining to grocery related merchandizing of one or more commercial grocery products the with identification information obtainable through one or more tags said one or more tags logged as being at least temporarily within at least a vicinity of one or more food based substances including at least in part one or more electronic quick response codes. Origination of an illustratively derived associating quick response component group can be accomplished through skilled in the art design choice selection of one or more of the above depicted components from one or more of the above depicted subsystems shown in FIG. 12. Components from the associating quick response component group can be used in implementing execution of the one or more associating quick response instructions i1213 of FIG. 33, can be used in performance of the associating quick response electrical circuitry arrangement e1213 of FIG. 26, and/or can be used in otherwise fulfillment of the operation o1213. An exemplary non-transitory signal bearing medium version of the information storage subsystem s200 is depicted in FIG. 33 as bearing the one or more associating quick response instructions i1213 that when executed will direct performance of the operation o1213. Furthermore, the associating quick response electrical circuitry arrangement ("elec circ arrange") e1213, when activated, will perform the operation o1213. Also, the associating quick response module m1213, when executed and/or activated, will direct performance of and/or perform the operation o1213. For instance, in one or more exemplary implementations, the one or more associating quick response instructions i1213, when executed, direct performance of the operation o1213 in the illustrative depiction as follows, and/or the associating quick response electrical circuitry arrangement e1213, when activated, performs the operation o1213 in the illustrative depiction as follows, and/or the associating quick response module m1213, when executed and/or activated, directs performance of and/or performs the operation o1213 in the illustrative depiction as follows, and/or the operation o1213 is otherwise carried out in the illustrative depiction as follows: electronically associating (e.g. through database constraints, etc.) at least a portion of grocery operations information (e.g. poultry quality observed as received from various warehouses or farms, etc.) concerning at least in part (e.g. engrossing, etc.) one or more grocery implementation aspects (e.g. pesticide levels of food materials used to prepare grocery items sold, etc.) pertaining to (e.g. engrossing, etc.) grocery related merchandizing of (e.g. school cafeteria grocery item serving, etc.) one or more commercial grocery products (e.g. diary grocery item side dish, etc.) the with identification information (e.g. alpha-numeric, etc.) obtainable through (e.g. through RF reception, etc.) one or more tags (e.g. inclinometer, etc.) said one or more tags logged (e.g. via database table information, etc.) as being at least temporarily (e.g. time spent in laboratory for testing, etc.) within at least a vicinity of (e.g. embossed on material, etc.) one or more food based substances (e.g. substance for cereal department product, etc.) including at least in part one or more electronic quick response codes (e.g. quick response code packaging labels, etc.).

In one or more implementations, as shown in FIG. 74, operation o12 includes an operation o1214 for electronically associating at least a portion of grocery operations information concerning at least in part one or more grocery implementation aspects pertaining to grocery related merchandizing of one or more commercial grocery products with identification information the obtainable through one or more tags said one or more tags logged as being at least temporarily within at least a vicinity of one or more food based substances at least in part obtaining identification information from one or more electronic computer servers. Origination of an illustratively derived associating computer servers component group can be accomplished through skilled in the art design choice selection of one or more of the above depicted components from one or more of the above depicted subsystems shown in FIG. 12. Components from the associating computer servers component group can be used in implementing execution of the one or more associating computer servers instructions i1214 of FIG. 33, can be used in performance of the associating computer servers electrical circuitry arrangement e1214 of FIG. 26, and/or can be used in otherwise fulfillment of the operation o1214. An exemplary non-transitory signal bearing medium version of the information storage subsystem s200 is depicted in FIG. 33 as bearing the one or more associating computer servers instructions i1214 that when executed will direct performance of the operation o1214. Furthermore, the associating computer servers electrical circuitry arrangement ("elec circ arrange") e1214, when activated, will perform the operation o1214. Also, the associating computer servers module m1214, when executed and/or activated, will direct performance of and/or perform the operation o1214. For instance, in one or more exemplary implementations, the one or more associating computer servers instructions i1214, when executed, direct performance of the operation o1214 in the illustrative depiction as follows, and/or the associating computer servers electrical circuitry arrangement e1214, when activated, performs the operation o1214 in the illustrative depiction as follows, and/or the associating computer servers module m1214, when executed and/or activated, directs performance of and/or performs the operation o1214 in the illustrative depiction as follows, and/or the operation o1214 is otherwise carried out in the illustrative depiction as follows: electronically associating (e.g. through unique exclusions of data, etc.) at least a portion of grocery operations information (e.g. shipping container information, etc.) concerning at least in part (e.g. implicate, etc.) one or more grocery implementation aspects (e.g. type of sanitizers used, etc.) pertaining to (e.g. implicate, etc.) grocery related merchandizing of (e.g. institutional grocery item serving, etc.) one or more commercial grocery products (e.g. poultry grocery item side dish, etc.) with identification information (e.g. ISO basic Latin alphabet, etc.) the obtainable through (e.g. through scanning, etc.) one or more tags (e.g. hybrid positioning system, etc.) said one or more tags logged (e.g. via database object information, etc.) as being at least temporarily (e.g. partial time spent on retail display, etc.) within at least a vicinity of (e.g. welded onto container, etc.) one or more food based substances (e.g. corn on cob, etc.) at least in part obtaining identification information from one or more electronic computer servers (e.g. challenge-response server system, etc.).

In one or more implementations, as shown in FIG. 74, operation o12 includes an operation o1215 for electronically associating at least a portion of grocery operations information concerning at least in part one or more grocery implementation aspects pertaining to grocery related merchandizing of one or more commercial grocery products with identification information the obtainable through one or more tags said one or more tags logged as being at least temporarily within at least a vicinity of one or more food based substances at least in part using information obtained from one or more tags to electronically access identification information via a computer-based network. Origination of an illustratively derived associating computer-based network component group can be accomplished through skilled in the art design choice selection of one or more of the above depicted components from one or more of the above depicted subsystems shown in FIG. 12. Components from the associating computer-based network component group can be used in implementing execution of the one or more associating computer-based network instructions i1215 of FIG. 33, can be used in performance of the associating computer-based network electrical circuitry arrangement e1215 of FIG. 26, and/or can be used in otherwise fulfillment of the operation o1215. An exemplary non-transitory signal bearing medium version of the information storage subsystem s200 is depicted in FIG. 33 as bearing the one or more associating computer-based network instructions i1215 that when executed will direct performance of the operation o1215. Furthermore, the associating computer-based network electrical circuitry arrangement ("elec circ arrange") e1215, when activated, will perform the operation o1215. Also, the associating computer-based network module m1215, when executed and/or activated, will direct performance of and/or perform the operation o1215. For instance, in one or more exemplary implementations, the one or more associating computer-based network instructions i1215, when executed, direct performance of the operation o1215 in the illustrative depiction as follows, and/or the associating computer-based network electrical circuitry arrangement e1215, when activated, performs the operation o1215 in the illustrative depiction as follows, and/or the associating computer-based network module m1215, when executed and/or activated, directs performance of and/or performs the operation o1215 in the illustrative depiction as follows, and/or the operation o1215 is otherwise carried out in the illustrative depiction as follows: electronically associating (e.g. through primary key, etc.) at least a portion of grocery operations information (e.g. dairy quality observed from various warehouses or farms, etc.) concerning at least in part (e.g. necessitate, etc.) one or more grocery implementation aspects (e.g. whether any GMO foods are sold, etc.) pertaining to (e.g. necessitate, etc.) grocery related merchandizing of (e.g. mobile catering grocery item serving, etc.) one or more commercial grocery products (e.g. seafood grocery item side dish, etc.) with identification information (e.g. symmetrically encrypted data packet, etc.) the obtainable through (e.g. through database query, etc.) one or more tags (e.g. high frequency RFID, etc.) said one or more tags logged (e.g. via flat database, etc.) as being at least temporarily (e.g. time on train between two terminals, etc.) within at least a vicinity of (e.g. bolted to container, etc.) one or more food based substances (e.g. wheat substance, etc.) at least in part using information obtained from one or more tags to electronically access identification information via a computer-based network (e.g. identifier located on a server accessed through the internet, etc.).

In one or more implementations, as shown in FIG. 75, operation o12 includes an operation o1216 for electronically associating at least a portion of grocery operations information concerning at least in part one or more grocery implementation aspects pertaining to grocery related merchandizing of one or more commercial grocery products with identification information obtainable through the one or more tags said one or more tags logged as being at least temporarily within at least a vicinity of one or more food based substances include at least in part one or more radio frequency identification tags. Origination of an illustratively derived associating radio frequency component group can be accomplished through skilled in the art design choice selection of one or more of the above depicted components from one or more of the above depicted subsystems shown in FIG. 12. Components from the associating radio frequency component group can be used in implementing execution of the one or more associating radio frequency instructions i1216 of FIG. 33, can be used in performance of the associating radio frequency electrical circuitry arrangement e1216 of FIG. 26, and/or can be used in otherwise fulfillment of the operation o1216. An exemplary non-transitory signal bearing medium version of the information storage subsystem s200 is depicted in FIG. 33 as bearing the one or more associating radio frequency instructions i1216 that when executed will direct performance of the operation o1216. Furthermore, the associating radio frequency electrical circuitry arrangement ("elec circ arrange") e1216, when activated, will perform the operation o1216. Also, the associating radio frequency module m1216, when executed and/or activated, will direct performance of and/or perform the operation o1216. For instance, in one or more exemplary implementations, the one or more associating radio frequency instructions i1216, when executed, direct performance of the operation o1216 in the illustrative depiction as follows, and/or the associating radio frequency electrical circuitry arrangement e1216, when activated, performs the operation o1216 in the illustrative depiction as follows, and/or the associating radio frequency module m1216, when executed and/or activated, directs performance of and/or performs the operation o1216 in the illustrative depiction as follows, and/or the operation o1216 is otherwise carried out in the illustrative depiction as follows: electronically associating (e.g. through foreign key search, etc.) at least a portion of grocery operations information (e.g. AVI file format, etc.) concerning at least in part (e.g. presuppose, etc.) one or more grocery implementation aspects (e.g. instances of health violations in grocery facilities, etc.) pertaining to (e.g. presuppose, etc.) grocery related merchandizing of (e.g. family buffet grocery item serving, etc.) one or more commercial grocery products (e.g. chicken grocery item side dish, etc.) with identification information (e.g. serial number, etc.) obtainable through (e.g. through electromagnetic reception, etc.) the one or more tags (e.g. low frequency RFID, etc.) said one or more tags logged (e.g. via relational database, etc.) as being at least temporarily (e.g. time held in port for inspection period, etc.) within at least a vicinity of (e.g. embossed on container, etc.) one or more food based substances (e.g. pork meat, etc.) include at least in part one or more radio frequency identification tags (e.g. separate RFID chips for each shipment carton of stock materials, etc.).

In one or more implementations, as shown in FIG. 75, operation o12 includes an operation o1217 for electronically associating at least a portion of grocery operations information concerning at least in part one or more grocery implementation aspects pertaining to grocery related merchandizing of one or more commercial grocery products with identification information obtainable through the one or more tags said one or more tags logged as being at least temporarily within at least a vicinity of one or more food based substances include at least in part one or more emitter beacons. Origination of an illustratively derived associating emitter beacons component group can be accomplished through skilled in the art design choice selection of one or more of the above depicted components from one or more of the above depicted subsystems shown in FIG. 12. Components from the associating emitter beacons component group can be used in implementing execution of the one or more associating emitter beacons instructions i1217 of FIG. 33, can be used in performance of the associating emitter beacons electrical circuitry arrangement e1217 of FIG. 26, and/or can be used in otherwise fulfillment of the operation o1217. An exemplary non-transitory signal bearing medium version of the information storage subsystem s200 is depicted in FIG. 33 as bearing the one or more associating emitter beacons instructions i1217 that when executed will direct performance of the operation o1217. Furthermore, the associating emitter beacons electrical circuitry arrangement ("elec circ arrange") e1217, when activated, will perform the operation o1217. Also, the associating emitter beacons module m1217, when executed and/or activated, will direct performance of and/or perform the operation o1217. For instance, in one or more exemplary implementations, the one or more associating emitter beacons instructions i1217, when executed, direct performance of the operation o1217 in the illustrative depiction as follows, and/or the associating emitter beacons electrical circuitry arrangement e1217, when activated, performs the operation o1217 in the illustrative depiction as follows, and/or the associating emitter beacons module m1217, when executed and/or activated, directs performance of and/or performs the operation o1217 in the illustrative depiction as follows, and/or the operation o1217 is otherwise carried out in the illustrative depiction as follows: electronically associating (e.g. through a hash table search, etc.) at least a portion of grocery operations information (e.g. MP3 file format, etc.) concerning at least in part (e.g. related to, etc.) one or more grocery implementation aspects (e.g. purchasing patterns from wholesalers, etc.) pertaining to (e.g. related to, etc.) grocery related merchandizing of (e.g. fast grocery item serving, etc.) one or more commercial grocery products (e.g. tofu grocery item side dish, etc.) with identification information (e.g. barcode, etc.) obtainable through (e.g. through search terms, etc.) the one or more tags (e.g. ultrasonic tracker, etc.) said one or more tags logged (e.g. via ROM storage, etc.) as being at least temporarily (e.g. time in holding bay, etc.) within at least a vicinity of (e.g. snapped onto container, etc.) one or more food based substances (e.g. water, etc.) include at least in part one or more emitter beacons (e.g. radio frequency beacon for each shipment from farm to wholesaler to grocery store, etc.).

In one or more implementations, as shown in FIG. 75, operation o12 includes an operation o1218 for electronically associating at least a portion of grocery operations information concerning at least in part one or more grocery implementation aspects pertaining to grocery related merchandizing of one or more commercial grocery products with identification information obtainable through the one or more tags said one or more tags logged as being at least temporarily within at least a vicinity of one or more food based substances include at least in part one or more barcode tags. Origination of an illustratively derived associating barcode tags component group can be accomplished through skilled in the art design choice selection of one or more of the above depicted components from one or more of the above depicted subsystems shown in FIG. 12. Components from the associating barcode tags component group can be used in implementing execution of the one or more associating barcode tags instructions i1218 of FIG. 33, can be used in performance of the associating barcode tags electrical circuitry arrangement e1218 of FIG. 26, and/or can be used in otherwise fulfillment of the operation o1218. An exemplary non-transitory signal bearing medium version of the information storage subsystem s200 is depicted in FIG. 33 as bearing the one or more associating barcode tags instructions i1218 that when executed will direct performance of the operation o1218. Furthermore, the associating barcode tags electrical circuitry arrangement ("elec circ arrange") e1218, when activated, will perform the operation o1218. Also, the associating barcode tags module m1218, when executed and/or activated, will direct performance of and/or perform the operation o1218. For instance, in one or more exemplary implementations, the one or more associating barcode tags instructions i1218, when executed, direct performance of the operation o1218 in the illustrative depiction as follows, and/or the associating barcode tags electrical circuitry arrangement e1218, when activated, performs the operation o1218 in the illustrative depiction as follows, and/or the associating barcode tags module m1218, when executed and/or activated, directs performance of and/or performs the operation o1218 in the illustrative depiction as follows, and/or the operation o1218 is otherwise carried out in the illustrative depiction as follows: electronically associating (e.g. via a SQL search, etc.) at least a portion of grocery operations information (e.g. audio listening, etc.) concerning at least in part (e.g. relationship, etc.) one or more grocery implementation aspects (e.g. rodent infestation history, etc.) pertaining to (e.g. relationship, etc.) grocery related merchandizing of (e.g. fine dining grocery item serving, etc.) one or more commercial grocery products (e.g. fish grocery item side dish, etc.) with identification information (e.g. kanji character set, etc.) obtainable through (e.g. through storage retrieval, etc.) the one or more tags (e.g. high capacity color barcode, etc.) said one or more tags logged (e.g. via database table information, etc.) as being at least temporarily (e.g. shipping time across Pacific Ocean, etc.) within at least a vicinity of (e.g. magnetically attached to container, etc.) one or more food based substances (e.g. substance for beverage department product, etc.) include at least in part one or more barcode tags (e.g. dedicated barcode tag for each shipment container received by grocery store, etc.).

Figure 76:
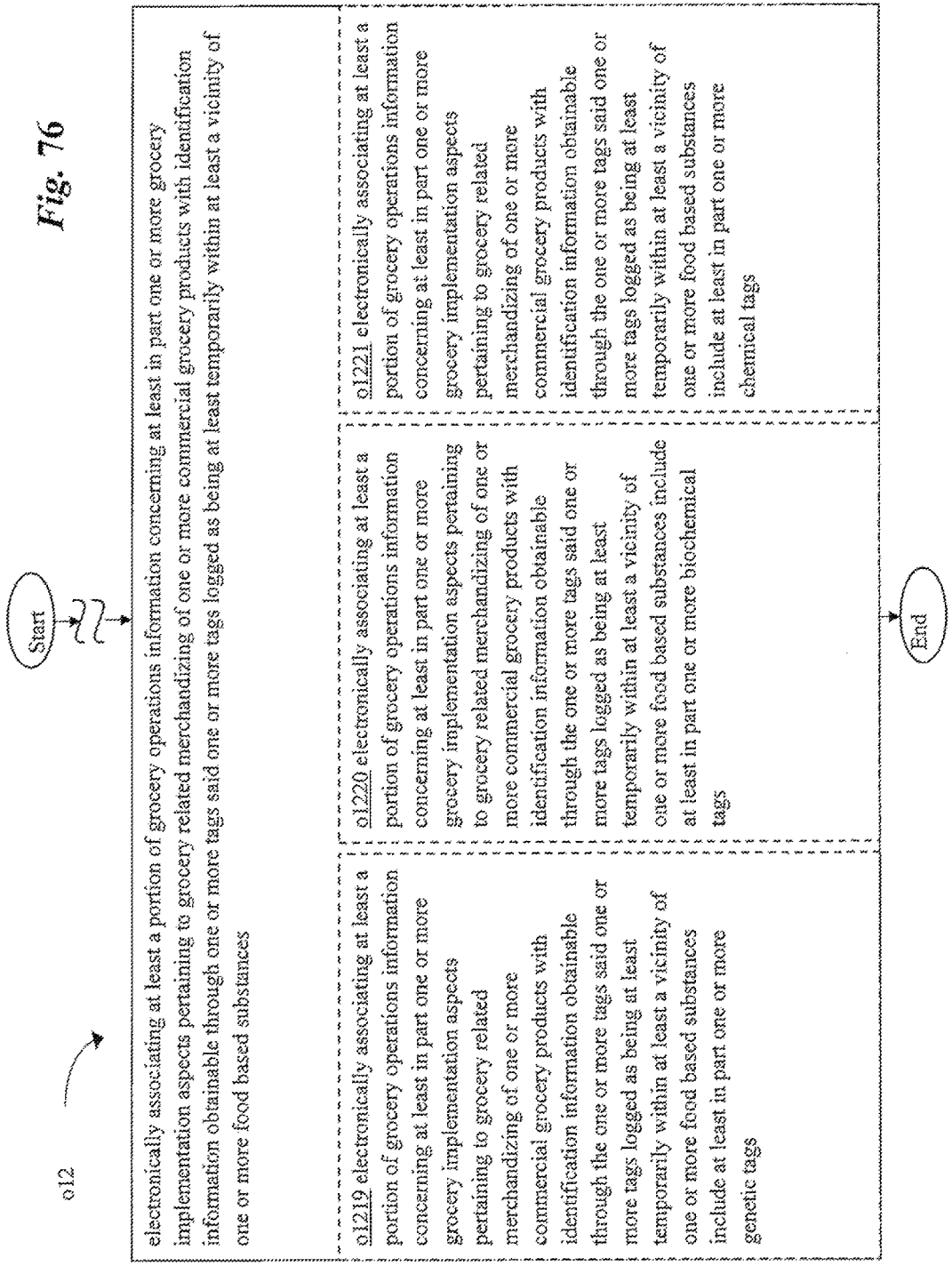
FIG. 76 is a high-level flowchart including exemplary implementations of operation o12 of FIG. 42.

In one or more implementations, as shown in FIG. 76, operation o12 includes an operation o1219 for electronically associating at least a portion of grocery operations information concerning at least in part one or more grocery implementation aspects pertaining to grocery related merchandizing of one or more commercial grocery products with identification information obtainable through the one or more tags said one or more tags logged as being at least temporarily within at least a vicinity of one or more food based substances include at least in part one or more genetic tags. Origination of an illustratively derived associating genetic tags component group can be accomplished through skilled in the art design choice selection of one or more of the above depicted components from one or more of the above depicted subsystems shown in FIG. 12. Components from the associating genetic tags component group can be used in implementing execution of the one or more associating genetic tags instructions i1219 of FIG. 33, can be used in performance of the associating genetic tags electrical circuitry arrangement e1219 of FIG. 26, and/or can be used in otherwise fulfillment of the operation o1219. An exemplary non-transitory signal bearing medium version of the information storage subsystem s200 is depicted in FIG. 33 as bearing the one or more associating genetic tags instructions i1219 that when executed will direct performance of the operation o1219. Furthermore, the associating genetic tags electrical circuitry arrangement ("elec circ arrange") e1219, when activated, will perform the operation o1219. Also, the associating genetic tags module m1219, when executed and/or activated, will direct performance of and/or perform the operation o1219. For instance, in one or more exemplary implementations, the one or more associating genetic tags instructions i1219, when executed, direct performance of the operation o1219 in the illustrative depiction as follows, and/or the associating genetic tags electrical circuitry arrangement e1219, when activated, performs the operation o1219 in the illustrative depiction as follows, and/or the associating genetic tags module m1219, when executed and/or activated, directs performance of and/or performs the operation o1219 in the illustrative depiction as follows, and/or the operation o1219 is otherwise carried out in the illustrative depiction as follows: electronically associating (e.g. through a bitmap index, etc.) at least a portion of grocery operations information (e.g. disobeying safety protocols, etc.) concerning at least in part (e.g. suggest, etc.) one or more grocery implementation aspects (e.g. recycling practices implemented, etc.) pertaining to (e.g. suggest, etc.) grocery related merchandizing of (e.g. fast grocery item preparation, etc.) one or more commercial grocery products (e.g. pork grocery item side dish, etc.) with identification information (e.g. matrix code, etc.) obtainable through (e.g. through barcode scanning, etc.) the one or more tags (e.g. expressed sequence tag, etc.) said one or more tags logged (e.g. via database object information, etc.) as being at least temporarily (e.g. time in storage and display after unpacking, etc.) within at least a vicinity of (e.g. stamped onto container, etc.) one or more food based substances (e.g. substance for pet food department, etc.) include at least in part one or more genetic tags (e.g. genetic tags imbedded in each stock item, etc.).

In one or more implementations, as shown in FIG. 76, operation o12 includes an operation o1220 for electronically associating at least a portion of grocery operations information concerning at least in part one or more grocery implementation aspects pertaining to grocery related merchandizing of one or more commercial grocery products with identification information obtainable through the one or more tags said one or more tags logged as being at least temporarily within at least a vicinity of one or more food based substances include at least in part one or more biochemical tags. Origination of an illustratively derived associating biochemical tags component group can be accomplished through skilled in the art design choice selection of one or more of the above depicted components from one or more of the above depicted subsystems shown in FIG. 12. Components from the associating biochemical tags component group can be used in implementing execution of the one or more associating biochemical tags instructions i1220 of FIG. 34, can be used in performance of the associating biochemical tags electrical circuitry arrangement e1220 of FIG. 27, and/or can be used in otherwise fulfillment of the operation o1220. An exemplary non-transitory signal bearing medium version of the information storage subsystem s200 is depicted in FIG. 34 as bearing the one or more associating biochemical tags instructions i1220 that when executed will direct performance of the operation o1220. Furthermore, the associating biochemical tags electrical circuitry arrangement ("elec circ arrange") e1220, when activated, will perform the operation o1220. Also, the associating biochemical tags module m1220, when executed and/or activated, will direct performance of and/or perform the operation o1220. For instance, in one or more exemplary implementations, the one or more associating biochemical tags instructions i1220, when executed, direct performance of the operation o1220 in the illustrative depiction as follows, and/or the associating biochemical tags electrical circuitry arrangement e1220, when activated, performs the operation o1220 in the illustrative depiction as follows, and/or the associating biochemical tags module m1220, when executed and/or activated, directs performance of and/or performs the operation o1220 in the illustrative depiction as follows, and/or the operation o1220 is otherwise carried out in the illustrative depiction as follows: electronically associating (e.g. through a dense index, etc.) at least a portion of grocery operations information (e.g. grocery commissary occupation rates, etc.) concerning at least in part (e.g. tangle, etc.) one or more grocery implementation aspects (e.g. demographics of grocery customers, etc.) pertaining to (e.g. tangle, etc.) grocery related merchandizing of (e.g. fine dining grocery item preparation, etc.) one or more commercial grocery products (e.g. beef grocery item side dish, etc.) with identification information (e.g. SPARQCode, etc.) obtainable through (e.g. through radiation detection, etc.) the one or more tags (e.g. retrograde neuronal tracer, etc.) said one or more tags logged (e.g. via digital linear tape storage, etc.) as being at least temporarily (e.g. shipping time from farm to grocery, etc.) within at least a vicinity of (e.g. tied to container, etc.) one or more food based substances (e.g. cat fish, etc.) include at least in part one or more biochemical tags (e.g. biochemical painted on to stock material supplied to the grocery store, etc.).

In one or more implementations, as shown in FIG. 76, operation o12 includes an operation o1221 for electronically associating at least a portion of grocery operations information concerning at least in part one or more grocery implementation aspects pertaining to grocery related merchandizing of one or more commercial grocery products with identification information obtainable through the one or more tags said one or more tags logged as being at least temporarily within at least a vicinity of one or more food based substances include at least in part one or more chemical tags. Origination of an illustratively derived associating chemical tags component group can be accomplished through skilled in the art design choice selection of one or more of the above depicted components from one or more of the above depicted subsystems shown in FIG. 12. Components from the associating chemical tags component group can be used in implementing execution of the one or more associating chemical tags instructions i1221 of FIG. 34, can be used in performance of the associating chemical tags electrical circuitry arrangement e1221 of FIG. 27, and/or can be used in otherwise fulfillment of the operation o1221. An exemplary non-transitory signal bearing medium version of the information storage subsystem s200 is depicted in FIG. 34 as bearing the one or more associating chemical tags instructions i1221 that when executed will direct performance of the operation o1221. Furthermore, the associating chemical tags electrical circuitry arrangement ("elec circ arrange") e1221, when activated, will perform the operation o1221. Also, the associating chemical tags module m1221, when executed and/or activated, will direct performance of and/or perform the operation o1221. For instance, in one or more exemplary implementations, the one or more associating chemical tags instructions i1221, when executed, direct performance of the operation o1221 in the illustrative depiction as follows, and/or the associating chemical tags electrical circuitry arrangement e1221, when activated, performs the operation o1221 in the illustrative depiction as follows, and/or the associating chemical tags module m1221, when executed and/or activated, directs performance of and/or performs the operation o1221 in the illustrative depiction as follows, and/or the operation o1221 is otherwise carried out in the illustrative depiction as follows: electronically associating (e.g. through a sparse index, etc.) at least a portion of grocery operations information (e.g. turnover in sales of pre-packaged meals, etc.) concerning at least in part (e.g. exclude, etc.) one or more grocery implementation aspects (e.g. sales rates for various grocery items, etc.) pertaining to (e.g. exclude, etc.) grocery related merchandizing of (e.g. deli department grocery item sales, etc.) one or more commercial grocery products (e.g. pasta grocery item main course, etc.) with identification information (e.g. database records, etc.) obtainable through (e.g. through isotope identification, etc.) the one or more tags (e.g. macromolecule marker, etc.) said one or more tags logged (e.g. via server information, etc.) as being at least temporarily (e.g. time since introduction of oxygen absorber, etc.) within at least a vicinity of (e.g. stapled to container, etc.) one or more food based substances (e.g. green algae, etc.) include at least in part one or more chemical tags (e.g. chemical tag sprayed on to ingestible material before shipping from farm which is subsequently received by grocery facility, etc.).

Figure 77:
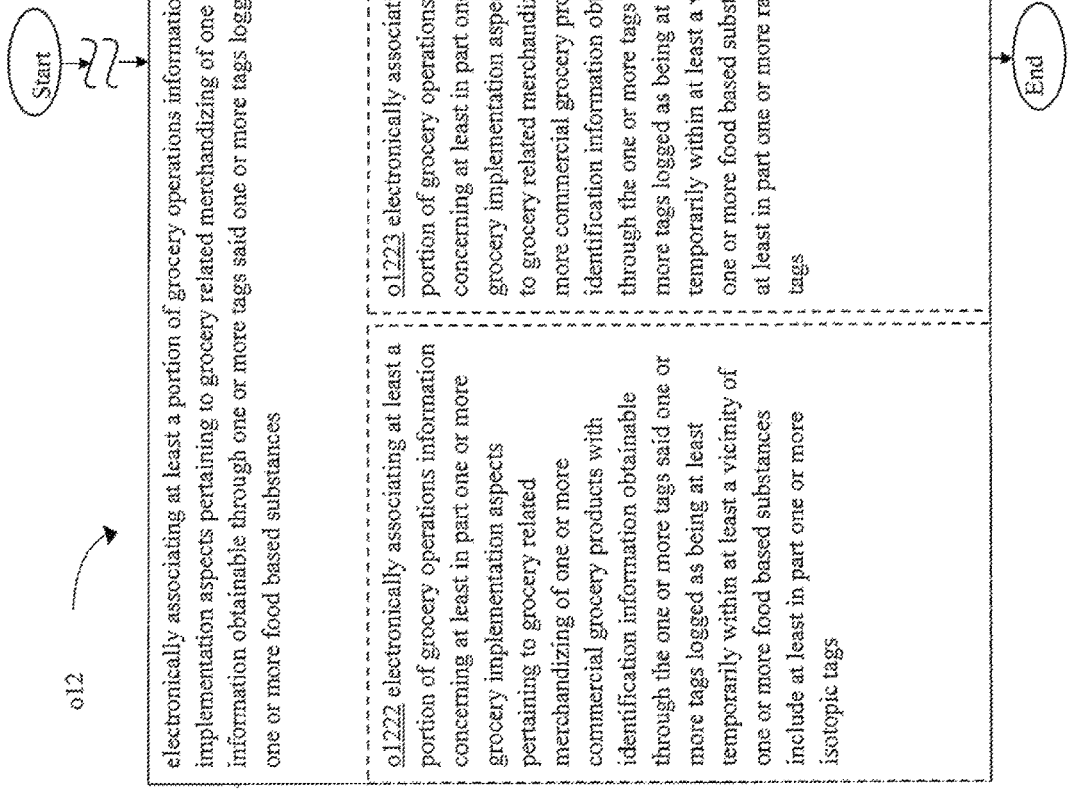
FIG. 77 is a high-level flowchart including exemplary implementations of operation o12 of FIG. 42.

In one or more implementations, as shown in FIG. 77, operation o12 includes an operation o1222 for electronically associating at least a portion of grocery operations information concerning at least in part one or more grocery implementation aspects pertaining to grocery related merchandizing of one or more commercial grocery products with identification information obtainable through the one or more tags said one or more tags logged as being at least temporarily within at least a vicinity of one or more food based substances include at least in part one or more isotopic tags. Origination of an illustratively derived associating isotopic tags component group can be accomplished through skilled in the art design choice selection of one or more of the above depicted components from one or more of the above depicted subsystems shown in FIG. 12. Components from the associating isotopic tags component group can be used in implementing execution of the one or more associating isotopic tags instructions i1222 of FIG. 34, can be used in performance of the associating isotopic tags electrical circuitry arrangement e1222 of FIG. 27, and/or can be used in otherwise fulfillment of the operation o1222. An exemplary non-transitory signal bearing medium version of the information storage subsystem s200 is depicted in FIG. 34 as bearing the one or more associating isotopic tags instructions i1222 that when executed will direct performance of the operation o1222. Furthermore, the associating isotopic tags electrical circuitry arrangement ("elec circ arrange") e1222, when activated, will perform the operation o1222. Also, the associating isotopic tags module m1222, when executed and/or activated, will direct performance of and/or perform the operation o1222. For instance, in one or more exemplary implementations, the one or more associating isotopic tags instructions i1222, when executed, direct performance of the operation o1222 in the illustrative depiction as follows, and/or the associating isotopic tags electrical circuitry arrangement e1222, when activated, performs the operation o1222 in the illustrative depiction as follows, and/or the associating isotopic tags module m1222, when executed and/or activated, directs performance of and/or performs the operation o1222 in the illustrative depiction as follows, and/or the operation o1222 is otherwise carried out in the illustrative depiction as follows: electronically associating (e.g. through a reverse index, etc.) at least a portion of grocery operations information (e.g. daylight hours of current climate, etc.) concerning at least in part (e.g. bound, etc.) one or more grocery implementation aspects (e.g. profit margin on various grocery items, etc.) pertaining to (e.g. bound, etc.) grocery related merchandizing of (e.g. hospital grocery item sales, etc.) one or more commercial grocery products (e.g. fat dominant grocery item main course, etc.) with identification information (e.g. computer clock, etc.) obtainable through (e.g. through beacon signal reception, etc.) the one or more tags (e.g. carbon-12 marker, etc.) said one or more tags logged (e.g. via index information, etc.) as being at least temporarily (e.g. shipping time on truck from distribution center to grocery, etc.) within at least a vicinity of (e.g. snapped onto container, etc.) one or more food based substances (e.g. cow heart, etc.) include at least in part one or more isotopic tags (e.g. individual isotopic tags assigned to separate shipping containers to be received at grocery store, etc.).

In one or more implementations, as shown in FIG. 77, operation o12 includes an operation o1223 for electronically associating at least a portion of grocery operations information concerning at least in part one or more grocery implementation aspects pertaining to grocery related merchandizing of one or more commercial grocery products with identification information obtainable through the one or more tags said one or more tags logged as being at least temporarily within at least a vicinity of one or more food based substances include at least in part one or more radioactive tags. Origination of an illustratively derived associating radioactive tags component group can be accomplished through skilled in the art design choice selection of one or more of the above depicted components from one or more of the above depicted subsystems shown in FIG. 12. Components from the associating radioactive tags component group can be used in implementing execution of the one or more associating radioactive tags instructions i1223 of FIG. 34, can be used in performance of the associating radioactive tags electrical circuitry arrangement e1223 of FIG. 27, and/or can be used in otherwise fulfillment of the operation o1223. An exemplary non-transitory signal bearing medium version of the information storage subsystem s200 is depicted in FIG. 34 as bearing the one or more associating radioactive tags instructions i1223 that when executed will direct performance of the operation o1223. Furthermore, the associating radioactive tags electrical circuitry arrangement ("elec circ arrange") e1223, when activated, will perform the operation o1223. Also, the associating radioactive tags module m1223, when executed and/or activated, will direct performance of and/or perform the operation o1223. For instance, in one or more exemplary implementations, the one or more associating radioactive tags instructions i1223, when executed, direct performance of the operation o1223 in the illustrative depiction as follows, and/or the associating radioactive tags electrical circuitry arrangement e1223, when activated, performs the operation o1223 in the illustrative depiction as follows, and/or the associating radioactive tags module m1223, when executed and/or activated, directs performance of and/or performs the operation o1223 in the illustrative depiction as follows, and/or the operation o1223 is otherwise carried out in the illustrative depiction as follows: electronically associating (e.g. via index concurrency control, etc.) at least a portion of grocery operations information (e.g. carbon dioxide levels in facility rooms, etc.) concerning at least in part (e.g. requiring, etc.) one or more grocery implementation aspects (e.g. grocery customer facility occupation statistics, etc.) pertaining to (e.g. requiring, etc.) grocery related merchandizing of (e.g. mobile kitchen grocery item sales, etc.) one or more commercial grocery products (e.g. carbohydrate dominant grocery item main course, etc.) with identification information (e.g. network protocol time indicator, etc.) obtainable through (e.g. through image scanning, etc.) the one or more tags (e.g. scintillation counter, etc.) said one or more tags logged (e.g. via body information, etc.) as being at least temporarily (e.g. time spent unpackaged in grocery environment, etc.) within at least a vicinity of (e.g. burned into material, etc.) one or more food based substances (e.g. whole lobster, etc.) include at least in part one or more radioactive tags (e.g. radioactive tag to be assigned to general shipment vehicle to track through transportation check points from farm to wholesaler to grocery store, etc.).

In one or more implementations, as shown in FIG. 77, operation o12 includes an operation o1224 for electronically associating at least a portion of grocery operations information concerning at least in part one or more grocery implementation aspects pertaining to grocery related merchandizing of one or more commercial grocery products with identification information obtainable through the one or more tags said one or more tags logged as being at least temporarily within at least a vicinity of one or more food based substances include at least in part one or more signal emitting tags. Origination of an illustratively derived associating signal emitting tags component group can be accomplished through skilled in the art design choice selection of one or more of the above depicted components from one or more of the above depicted subsystems shown in FIG. 12. Components from the associating signal emitting tags component group can be used in implementing execution of the one or more associating signal emitting tags instructions i1224 of FIG. 34, can be used in performance of the associating signal emitting tags electrical circuitry arrangement e1224 of FIG. 27, and/or can be used in otherwise fulfillment of the operation o1224. An exemplary non-transitory signal bearing medium version of the information storage subsystem s200 is depicted in FIG. 34 as bearing the one or more associating signal emitting tags instructions i1224 that when executed will direct performance of the operation o1224. Furthermore, the associating signal emitting tags electrical circuitry arrangement ("elec circ arrange") e1224, when activated, will perform the operation o1224. Also, the associating signal emitting tags module m1224, when executed and/or activated, will direct performance of and/or perform the operation o1224. For instance, in one or more exemplary implementations, the one or more associating signal emitting tags instructions i1224, when executed, direct performance of the operation o1224 in the illustrative depiction as follows, and/or the associating signal emitting tags electrical circuitry arrangement e1224, when activated, performs the operation o1224 in the illustrative depiction as follows, and/or the associating signal emitting tags module m1224, when executed and/or activated, directs performance of and/or performs the operation o1224 in the illustrative depiction as follows, and/or the operation o1224 is otherwise carried out in the illustrative depiction as follows: electronically associating (e.g. through index locking, etc.) at least a portion of grocery operations information (e.g. water usage, etc.) concerning at least in part (e.g. enveloped, etc.) one or more grocery implementation aspects (e.g. garbage disposal practices, etc.) pertaining to (e.g. enveloped, etc.) grocery related merchandizing of (e.g. street vendor grocery item sales, etc.) one or more commercial grocery products (e.g. protein dominant grocery item main course, etc.) with identification information (e.g. server clock, etc.) obtainable through (e.g. through audio reception, etc.) the one or more tags (e.g. light emitting diode, etc.) said one or more tags logged (e.g. via food composition database, etc.) as being at least temporarily (e.g. time spent on conveyor belt in factory, etc.) within at least a vicinity of (e.g. burned into container, etc.) one or more food based substances (e.g. potato, etc.) include at least in part one or more signal emitting tags (e.g. radio frequency tag attached to each shipment container from farm to grocery store, etc.).

Figure 78:
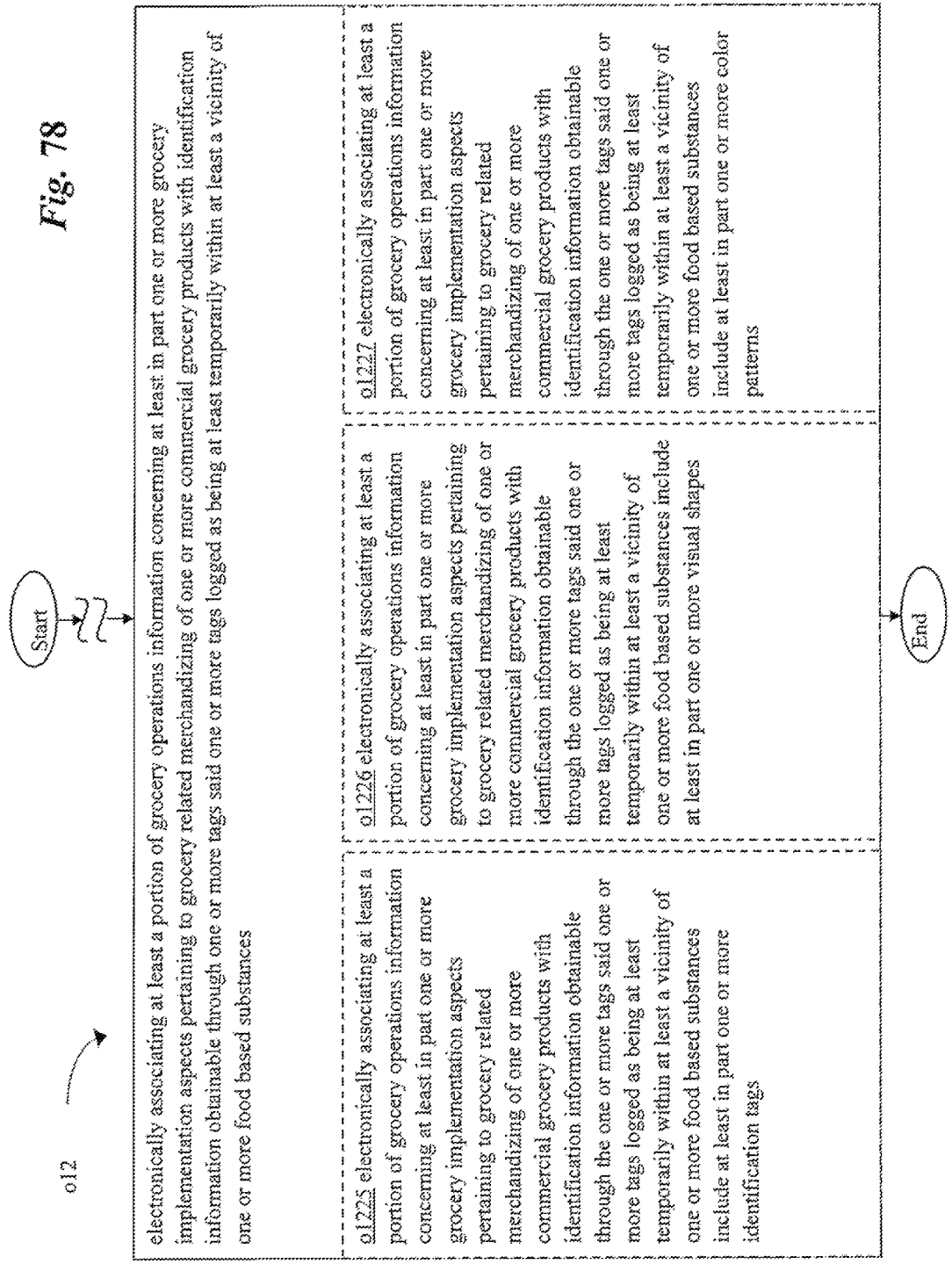
FIG. 78 is a high-level flowchart including exemplary implementations of operation o12 of FIG. 42.

In one or more implementations, as shown in FIG. 78, operation o12 includes an operation o1225 for electronically associating at least a portion of grocery operations information concerning at least in part one or more grocery implementation aspects pertaining to grocery related merchandizing of one or more commercial grocery products with identification information obtainable through the one or more tags said one or more tags logged as being at least temporarily within at least a vicinity of one or more food based substances include at least in part one or more identification tags. Origination of an illustratively derived associating identification tags component group can be accomplished through skilled in the art design choice selection of one or more of the above depicted components from one or more of the above depicted subsystems shown in FIG. 12. Components from the associating identification tags component group can be used in implementing execution of the one or more associating identification tags instructions i1225 of FIG. 34, can be used in performance of the associating identification tags electrical circuitry arrangement e1225 of FIG. 27, and/or can be used in otherwise fulfillment of the operation o1225. An exemplary non-transitory signal bearing medium version of the information storage subsystem s200 is depicted in FIG. 34 as bearing the one or more associating identification tags instructions i1225 that when executed will direct performance of the operation o1225. Furthermore, the associating identification tags electrical circuitry arrangement ("elec circ arrange") e1225, when activated, will perform the operation o1225. Also, the associating identification tags module m1225, when executed and/or activated, will direct performance of and/or perform the operation o1225. For instance, in one or more exemplary implementations, the one or more associating identification tags instructions i1225, when executed, direct performance of the operation o1225 in the illustrative depiction as follows, and/or the associating identification tags electrical circuitry arrangement e1225, when activated, performs the operation o1225 in the illustrative depiction as follows, and/or the associating identification tags module m1225, when executed and/or activated, directs performance of and/or performs the operation o1225 in the illustrative depiction as follows, and/or the operation o1225 is otherwise carried out in the illustrative depiction as follows:

electronically associating (e.g. through standardization of index, etc.) at least a portion of grocery operations information (e.g. natural gas usage, etc.) concerning at least in part (e.g. envelope, etc.) one or more grocery implementation aspects (e.g. standards used to classify condition of grocery stock received at the grocery store, etc.) pertaining to (e.g. envelope, etc.) grocery related merchandizing of (e.g. nursing home grocery item sales, etc.) one or more commercial grocery products (e.g. beverage grocery item main course, etc.) with identification information (e.g. operating system time, etc.) obtainable through (e.g. through visual identification, etc.) the one or more tags (e.g. asset tag, etc.) said one or more tags logged (e.g. via DVD-ROM storage, etc.) as being at least temporarily (e.g. shipping time from vessel to factory, etc.) within at least a vicinity of (e.g. riveted to container, etc.) one or more food based substances (e.g. goat cheese, etc.) include at least in part one or more identification tags (e.g. tag containing textual description assigned to each food item received at grocery store at point of receipt, etc.).

In one or more implementations, as shown in FIG. 78, operation o12 includes an operation o1226 for electronically associating at least a portion of grocery operations information concerning at least in part one or more grocery implementation aspects pertaining to grocery related merchandizing of one or more commercial grocery products with identification information obtainable through the one or more tags said one or more tags logged as being at least temporarily within at least a vicinity of one or more food based substances include at least in part one or more visual shapes. Origination of an illustratively derived associating visual shapes component group can be accomplished through skilled in the art design choice selection of one or more of the above depicted components from one or more of the above depicted subsystems shown in FIG. 12. Components from the associating visual shapes component group can be used in implementing execution of the one or more associating visual shapes instructions i1226 of FIG. 34, can be used in performance of the associating visual shapes electrical circuitry arrangement e1226 of FIG. 27, and/or can be used in otherwise fulfillment of the operation o1226. An exemplary non-transitory signal bearing medium version of the information storage subsystem s200 is depicted in FIG. 34 as bearing the one or more associating visual shapes instructions i1226 that when executed will direct performance of the operation o1226. Furthermore, the associating visual shapes electrical circuitry arrangement ("elec circ arrange") e1226, when activated, will perform the operation o1226. Also, the associating visual shapes module m1226, when executed and/or activated, will direct performance of and/or perform the operation o1226. For instance, in one or more exemplary implementations, the one or more associating visual shapes instructions i1226, when executed, direct performance of the operation o1226 in the illustrative depiction as follows, and/or the associating visual shapes electrical circuitry arrangement e1226, when activated, performs the operation o1226 in the illustrative depiction as follows, and/or the associating visual shapes module m1226, when executed and/or activated, directs performance of and/or performs the operation o1226 in the illustrative depiction as follows, and/or the operation o1226 is otherwise carried out in the illustrative depiction as follows: electronically associating (e.g. through data structure, etc.) at least a portion of grocery operations information (e.g. methane gas usage, etc.) concerning at least in part (e.g. associate with, etc.) one or more grocery implementation aspects (e.g. standards used to classify condition of grocery items stored, etc.) pertaining to (e.g. associate with, etc.) grocery related merchandizing of (e.g. school cafeteria grocery item sales, etc.) one or more commercial grocery products (e.g. blended grocery item main course, etc.) with identification information (e.g. indicating electronically receiving sent as response to electronically transmitting, etc.) obtainable through (e.g. through light reception, etc.) the one or more tags (e.g. cylindrical, etc.) said one or more tags logged (e.g. via floppy disk storage, etc.) as being at least temporarily (e.g. portion of time spent packaged with similar material, etc.) within at least a vicinity of (e.g. enveloping container, etc.) one or more food based substances (e.g. beet pulp, etc.) include at least in part one or more visual shapes (e.g. database of stock material shapes for electronic shape recognition program, etc.).

In one or more implementations, as shown in FIG. 78, operation o12 includes an operation o1227 for electronically associating at least a portion of grocery operations information concerning at least in part one or more grocery implementation aspects pertaining to grocery related merchandizing of one or more commercial grocery products with identification information obtainable through the one or more tags said one or more tags logged as being at least temporarily within at least a vicinity of one or more food based substances include at least in part one or more color patterns. Origination of an illustratively derived associating color patterns component group can be accomplished through skilled in the art design choice selection of one or more of the above depicted components from one or more of the above depicted subsystems shown in FIG. 12. Components from the associating color patterns component group can be used in implementing execution of the one or more associating color patterns instructions i1227 of FIG. 34, can be used in performance of the associating color patterns electrical circuitry arrangement e1227 of FIG. 27, and/or can be used in otherwise fulfillment of the operation o1227. An exemplary non-transitory signal bearing medium version of the information storage subsystem s200 is depicted in FIG. 34 as bearing the one or more associating color patterns instructions i1227 that when executed will direct performance of the operation o1227. Furthermore, the associating color patterns electrical circuitry arrangement ("elec circ arrange") e1227, when activated, will perform the operation o1227. Also, the associating color patterns module m1227, when executed and/or activated, will direct performance of and/or perform the operation o1227. For instance, in one or more exemplary implementations, the one or more associating color patterns instructions i1227, when executed, direct performance of the operation o1227 in the illustrative depiction as follows, and/or the associating color patterns electrical circuitry arrangement e1227, when activated, performs the operation o1227 in the illustrative depiction as follows, and/or the associating color patterns module m1227, when executed and/or activated, directs performance of and/or performs the operation o1227 in the illustrative depiction as follows, and/or the operation o1227 is otherwise carried out in the illustrative depiction as follows: electronically associating (e.g. through common search terms, etc.) at least a portion of grocery operations information (e.g. MPEG file format, etc.) concerning at least in part (e.g. embroil, etc.) one or more grocery implementation aspects (e.g. grocery worker exemplary behavior, etc.) pertaining to (e.g. embroil, etc.) grocery related merchandizing of (e.g. institutional grocery item sales, etc.) one or more commercial grocery products (e.g. sous-vide grocery item main course, etc.) with identification information (e.g. textual input, etc.) obtainable through (e.g. through color spectrum identification, etc.) the one or more tags (e.g. checkered, etc.) said one or more tags logged (e.g. via ROM storage, etc.) as being at least temporarily (e.g. portion of time spent on shipping vessel, etc.) within at least a vicinity of (e.g. enveloping material, etc.) one or more food based substances (e.g. substance for produce department product, etc.) include at least in part one or more color patterns (e.g. database of stock material colors for electronic color recognition program, etc.).

Figure 79:
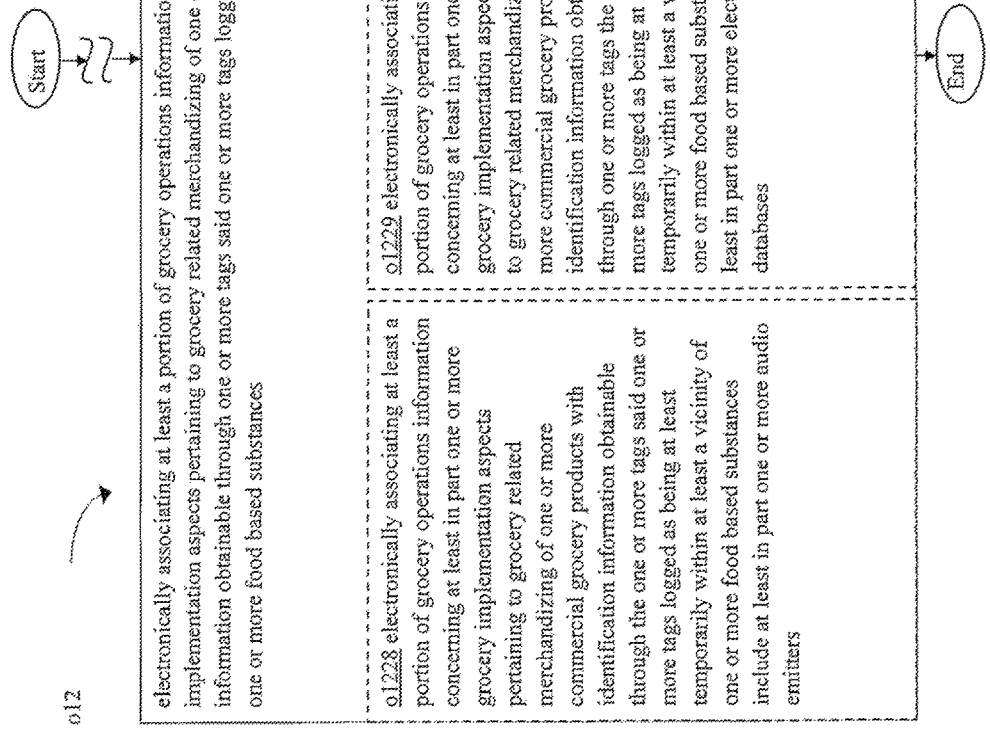
FIG. 79 is a high-level flowchart including exemplary implementations of operation o12 of FIG. 42.

In one or more implementations, as shown in FIG. 79, operation o12 includes an operation o1228 for electronically associating at least a portion of grocery operations information concerning at least in part one or more grocery implementation aspects pertaining to grocery related merchandizing of one or more commercial grocery products with identification information obtainable through the one or more tags said one or more tags logged as being at least temporarily within at least a vicinity of one or more food based substances include at least in part one or more audio emitters. Origination of an illustratively derived associating audio emitters component group can be accomplished through skilled in the art design choice selection of one or more of the above depicted components from one or more of the above depicted subsystems shown in FIG. 12. Components from the associating audio emitters component group can be used in implementing execution of the one or more associating audio emitters instructions i1228 of FIG. 34, can be used in performance of the associating audio emitters electrical circuitry arrangement e1228 of FIG. 27, and/or can be used in otherwise fulfillment of the operation o1228. An exemplary non-transitory signal bearing medium version of the information storage subsystem s200 is depicted in FIG. 34 as bearing the one or more associating audio emitters instructions i1228 that when executed will direct performance of the operation o1228. Furthermore, the associating audio emitters electrical circuitry arrangement ("elec circ arrange") e1228, when activated, will perform the operation o1228. Also, the associating audio emitters module m1228, when executed and/or activated, will direct performance of and/or perform the operation o1228. For instance, in one or more exemplary implementations, the one or more associating audio emitters instructions i1228, when executed, direct performance of the operation o1228 in the illustrative depiction as follows, and/or the associating audio emitters electrical circuitry arrangement e1228, when activated, performs the operation o1228 in the illustrative depiction as follows, and/or the associating audio emitters module m1228, when executed and/or activated, directs performance of and/or performs the operation o1228 in the illustrative depiction as follows, and/or the operation o1228 is otherwise carried out in the illustrative depiction as follows: electronically associating (e.g. through access of ordered records, etc.) at least a portion of grocery operations information (e.g. WAV file format, etc.) concerning at least in part (e.g. take in, etc.) one or more grocery implementation aspects (e.g. grocery worker poor behavior, etc.) pertaining to (e.g. take in, etc.) grocery related merchandizing of (e.g. mobile catering grocery item sales, etc.) one or more commercial grocery products (e.g. braised grocery item main course, etc.) with identification information (e.g. audio input, etc.) obtainable through (e.g. through RF reception, etc.) the one or more tags (e.g. speaker, etc.) said one or more tags logged (e.g. via database table information, etc.) as being at least temporarily (e.g. time spent in flight, etc.) within at least a vicinity of (e.g. placed inside material, etc.) one or more food based substances (e.g. venison, etc.) include at least in part one or more audio emitters (e.g. audio emitter dedicated to each container received at grocery facility, etc.).

In one or more implementations, as shown in FIG. 79, operation o12 includes an operation o1229 for electronically associating at least a portion of grocery operations information concerning at least in part one or more grocery implementation aspects pertaining to grocery related merchandizing of one or more commercial grocery products with identification information obtainable through one or more tags the said one or more tags logged as being at least temporarily within at least a vicinity of one or more food based substances via at least in part one or more electronic databases. Origination of an illustratively derived associating electronic databases component group can be accomplished through skilled in the art design choice selection of one or more of the above depicted components from one or more of the above depicted subsystems shown in FIG. 12. Components from the associating electronic databases component group can be used in implementing execution of the one or more associating electronic databases instructions i1229 of FIG. 34, can be used in performance of the associating electronic databases electrical circuitry arrangement e1229 of FIG. 27, and/or can be used in otherwise fulfillment of the operation o1229. An exemplary non-transitory signal bearing medium version of the information storage subsystem s200 is depicted in FIG. 34 as bearing the one or more associating electronic databases instructions i1229 that when executed will direct performance of the operation o1229. Furthermore, the associating electronic databases electrical circuitry arrangement ("elec circ arrange") e1229, when activated, will perform the operation o1229. Also, the associating electronic databases module m1229, when executed and/or activated, will direct performance of and/or perform the operation o1229. For instance, in one or more exemplary implementations, the one or more associating electronic databases instructions i1229, when executed, direct performance of the operation o1229 in the illustrative depiction as follows, and/or the associating electronic databases electrical circuitry arrangement e1229, when activated, performs the operation o1229 in the illustrative depiction as follows, and/or the associating electronic databases module m1229, when executed and/or activated, directs performance of and/or performs the operation o1229 in the illustrative depiction as follows, and/or the operation o1229 is otherwise carried out in the illustrative depiction as follows: electronically associating (e.g. via functions, etc.) at least a portion of grocery operations information (e.g. visual observation, etc.) concerning at least in part (e.g. comprised of, etc.) one or more grocery implementation aspects (e.g. identified issues regarding food quality from one or more wholesalers, etc.) pertaining to (e.g. comprised of, etc.) grocery related merchandizing of (e.g. family buffet grocery item sales, etc.) one or more commercial grocery products (e.g. rotisserie grocery item main course, etc.) with identification information (e.g. e-mail record, etc.) obtainable through (e.g. through scanning, etc.) one or more tags (e.g. UHF emitter, etc.) the said one or more tags logged (e.g. via database object information, etc.) as being at least temporarily (e.g. time spent in cold storage, etc.) within at least a vicinity of (e.g. placed inside container, etc.) one or more food based substances (e.g. edible frog, etc.) via at least in part one or more electronic databases (e.g. electronic database at grocery facility to report details regarding shipments received, etc.).

In one or more implementations, as shown in FIG. 79, operation o12 includes an operation o1234 for electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily the within at least a vicinity of one or more food based substances including at least in part logged as affixed to one or more grocery items. Origination of an illustratively derived associating affixed to items component group can be accomplished through skilled in the art design choice selection of one or more of the above depicted components from one or more of the above depicted subsystems shown in FIG. 12. Components from the associating affixed to items component group can be used in implementing execution of the one or more associating affixed to items instructions i1234 of FIG. 34, can be used in performance of the associating affixed to items electrical circuitry arrangement e1234 of FIG. 27, and/or can be used in otherwise fulfillment of the operation o1234. An exemplary non-transitory signal bearing medium version of the information storage subsystem s200 is depicted in FIG. 34 as bearing the one or more associating affixed to items instructions i1234 that when executed will direct performance of the operation o1234. Furthermore, the associating affixed to items electrical circuitry arrangement ("elec circ arrange") e1234, when activated, will perform the operation o1234. Also, the associating affixed to items module m1234, when executed and/or activated, will direct performance of and/or perform the operation o1234. For instance, in one or more exemplary implementations, the one or more associating affixed to items instructions i1234, when executed, direct performance of the operation o1234 in the illustrative depiction as follows, and/or the associating affixed to items electrical circuitry arrangement e1234, when activated, performs the operation o1234 in the illustrative depiction as follows, and/or the associating affixed to items module m1234, when executed and/or activated, directs performance of and/or performs the operation o1234 in the illustrative depiction as follows, and/or the operation o1234 is otherwise carried out in the illustrative depiction as follows: electronically associating (e.g. through unique exclusions of data, etc.) at least a portion of grocery operations information (e.g. cold storage data for stored food materials, etc.) concerning at least in part (e.g. argue, etc.) one or more grocery implementation aspects (e.g. identified issues regarding one or more types of dishes sold by the grocery facility, etc.) pertaining to (e.g. argue, etc.) grocery related merchandizing of (e.g. mobile kitchen grocery item preparation, etc.) one or more commercial grocery products (e.g. microwaved main course, etc.) with identification information (e.g. as being recorded thereafter due in part to application response delay, etc.) obtainable through (e.g. through barcode scanning, etc.) one or more tags (e.g. gyroscope, etc.) said one or more tags logged (e.g. via CD-ROM storage, etc.) as being at least temporarily (e.g. partial time spent on retail display, etc.) the within at least a vicinity of (e.g. welded onto container, etc.) one or more food based substances (e.g. feed grain, etc.) including at least in part logged as affixed to one or more grocery items (e.g. label adhesively attached to whole vegetable, etc.).

Figure 80:
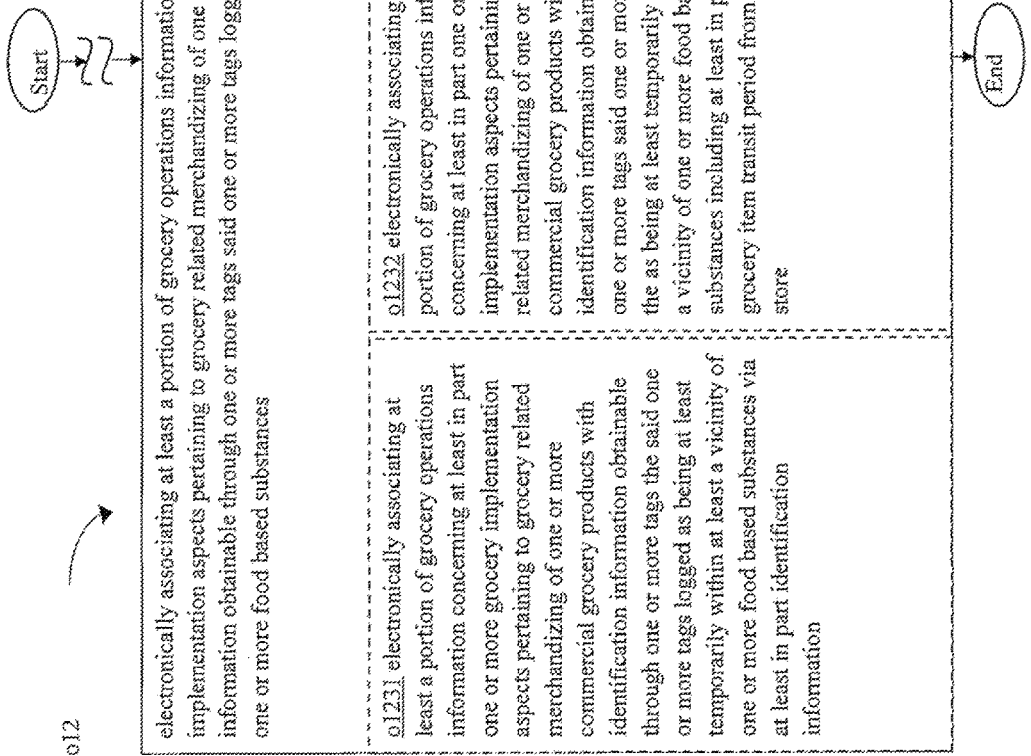
FIG. 80 is a high-level flowchart including exemplary implementations of operation o12 of FIG. 42.

In one or more implementations, as shown in FIG. 80, operation o12 includes an operation o1231 for electronically associating at least a portion of grocery operations information concerning at least in part one or more grocery implementation aspects pertaining to grocery related merchandizing of one or more commercial grocery products with identification information obtainable through one or more tags the said one or more tags logged as being at least temporarily within at least a vicinity of one or more food based substances via at least in part identification information. Origination of an illustratively derived associating identification information component group can be accomplished through skilled in the art design choice selection of one or more of the above depicted components from one or more of the above depicted subsystems shown in FIG. 12. Components from the associating identification information component group can be used in implementing execution of the one or more associating identification information instructions i1231 of FIG. 34, can be used in performance of the associating identification information electrical circuitry arrangement e1231 of FIG. 27, and/or can be used in otherwise fulfillment of the operation o1231. An exemplary non-transitory signal bearing medium version of the information storage subsystem s200 is depicted in FIG. 34 as bearing the one or more associating identification information instructions i1231 that when executed will direct performance of the operation o1231. Furthermore, the associating identification information electrical circuitry arrangement ("elec circ arrange") e1231, when activated, will perform the operation o1231. Also, the associating identification information module m1231, when executed and/or activated, will direct performance of and/or perform the operation o1231. For instance, in one or more exemplary implementations, the one or more associating identification information instructions i1231, when executed, direct performance of the operation o1231 in the illustrative depiction as follows, and/or the associating identification information electrical circuitry arrangement e1231, when activated, performs the operation o1231 in the illustrative depiction as follows, and/or the associating identification information module m1231, when executed and/or activated, directs performance of and/or performs the operation o1231 in the illustrative depiction as follows, and/or the operation o1231 is otherwise carried out in the illustrative depiction as follows: electronically associating (e.g. via sub-linear time lookup, etc.) at least a portion of grocery operations information (e.g. document forgery, etc.) concerning at least in part (e.g. associated, etc.) one or more grocery implementation aspects (e.g. identified issues regarding one or more grocery workers, etc.) pertaining to (e.g. associated, etc.) grocery related merchandizing of (e.g. fine dining grocery item sales, etc.) one or more commercial grocery products (e.g. boiled grocery item main course, etc.) with identification information (e.g. identifying as being recorded immediately thereafter one or more events, etc.) obtainable through (e.g. through electromagnetic reception, etc.) one or more tags (e.g. microwave emitter, etc.) the said one or more tags logged (e.g. via relational database, etc.) as being at least temporarily (e.g. portion of time spent in ice bath, etc.) within at least a vicinity of (e.g. embossed on container, etc.) one or more food based substances (e.g. cow liver, etc.) via at least in part identification information (e.g. one or more identifiers containing textual descriptions of stock material contained therein, etc.).

In one or more implementations, as shown in FIG. 80, operation o12 includes an operation o1232 for electronically associating at least a portion of grocery operations information concerning at least in part one or more grocery implementation aspects pertaining to grocery related merchandizing of one or more commercial grocery products with identification information obtainable through one or more tags said one or more tags logged the as being at least temporarily within at least a vicinity of one or more food based substances including at least in part the grocery item transit period from factory to store. Origination of an illustratively derived associating factory to store component group can be accomplished through skilled in the art design choice selection of one or more of the above depicted components from one or more of the above depicted subsystems shown in FIG. 12. Components from the associating factory to store component group can be used in implementing execution of the one or more associating factory to store instructions i1232 of FIG. 34, can be used in performance of the associating factory to store electrical circuitry arrangement e1232 of FIG. 27, and/or can be used in otherwise fulfillment of the operation o1232. An exemplary non-transitory signal bearing medium version of the information storage subsystem s200 is depicted in FIG. 34 as bearing the one or more associating factory to store instructions i1232 that when executed will direct performance of the operation o1232. Furthermore, the associating factory to store electrical circuitry arrangement ("elec circ arrange") e1232, when activated, will perform the operation o1232. Also, the associating factory to store module m1232, when executed and/or activated, will direct performance of and/or perform the operation o1232. For instance, in one or more exemplary implementations, the one or more associating factory to store instructions i1232, when executed, direct performance of the operation o1232 in the illustrative depiction as follows, and/or the associating factory to store electrical circuitry arrangement e1232, when activated, performs the operation o1232 in the illustrative depiction as follows, and/or the associating factory to store module m1232, when executed and/or activated, directs performance of and/or performs the operation o1232 in the illustrative depiction as follows, and/or the operation o1232 is otherwise carried out in the illustrative depiction as follows: electronically associating (e.g. through linear search, etc.) at least a portion of grocery operations information (e.g. missed scheduled deliveries of grocery items, etc.) concerning at least in part (e.g. affected, etc.) one or more grocery implementation aspects (e.g. identified issues regarding grocery equipment, etc.) pertaining to (e.g. affected, etc.) grocery related merchandizing of (e.g. deli department grocery item preparation, etc.) one or more commercial grocery products (e.g. smoked grocery item main course, etc.) with identification information (e.g. as being recording thereafter one or more events due to server delay, etc.) obtainable through (e.g. through search terms, etc.) one or more tags (e.g. laser ranging tracker, etc.) said one or more tags logged (e.g. via database management layer, etc.) the as being at least temporarily (e.g. shipping time from farm to grocery store, etc.) within at least a vicinity of (e.g. debossed on material, etc.) one or more food based substances (e.g. goat milk, etc.) including at least in part the grocery item transit period from factory to store (e.g. transit period between farm and wholesaler and grocery store facility, etc.).

In one or more implementations, as shown in FIG. 80, operation o12 includes an operation o1233 for electronically associating at least a portion of grocery operations information concerning at least in part one or more grocery implementation aspects pertaining to grocery related merchandizing of one or more commercial grocery products with identification information obtainable through one or more tags said one or more tags logged the as being at least temporarily within at least a vicinity of one or more food based substances including at least in part grocery item shelf life. Origination of an illustratively derived associating shelf life component group can be accomplished through skilled in the art design choice selection of one or more of the above depicted components from one or more of the above depicted subsystems shown in FIG. 12. Components from the associating shelf life component group can be used in implementing execution of the one or more associating shelf life instructions i1233 of FIG. 34, can be used in performance of the associating shelf life electrical circuitry arrangement e1233 of FIG. 27, and/or can be used in otherwise fulfillment of the operation o1233. An exemplary non-transitory signal bearing medium version of the information storage subsystem s200 is depicted in FIG. 34 as bearing the one or more associating shelf life instructions i1233 that when executed will direct performance of the operation o1233. Furthermore, the associating shelf life electrical circuitry arrangement ("elec circ arrange") e1233, when activated, will perform the operation o1233. Also, the associating shelf life module m1233, when executed and/or activated, will direct performance of and/or perform the operation o1233. For instance, in one or more exemplary implementations, the one or more associating shelf life instructions i1233, when executed, direct performance of the operation o1233 in the illustrative depiction as follows, and/or the associating shelf life electrical circuitry arrangement e1233, when activated, performs the operation o1233 in the illustrative depiction as follows, and/or the associating shelf life module m1233, when executed and/or activated, directs performance of and/or performs the operation o1233 in the illustrative depiction as follows, and/or the operation o1233 is otherwise carried out in the illustrative depiction as follows: electronically associating (e.g. through database constraints, etc.) at least a portion of grocery operations information (e.g. storage room temperature. profiles, etc.) concerning at least in part (e.g. affecting, etc.) one or more grocery implementation aspects (e.g. identified issues regarding one or more types of food materials used to prepare one or more grocery items to be sold, etc.) pertaining to (e.g. affecting, etc.) grocery related merchandizing of (e.g. hospital grocery item preparation, etc.) one or more commercial grocery products (e.g. convection oven prepared grocery item main course, etc.) with identification information (e.g. as being thereafter due in part to database retrieval times, etc.) obtainable through (e.g. through storage retrieval, etc.) one or more tags (e.g. ultrasonic emitter, etc.) said one or more tags logged (e.g. via flat database, etc.) the as being at least temporarily (e.g. time spent in laboratory for testing, etc.) within at least a vicinity of (e.g. embossed on material, etc.) one or more food based substances (e.g. whole king crab, etc.) including at least in part grocery item shelf life (e.g. including shelf life of steak packed with dry ice, etc.).

In one or more implementations, as shown in FIG. 81, operation o12 includes an operation o1234 for electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily the within at least a vicinity of one or more food based substances including at least in part logged as affixed to one or more grocery items. Origination of an illustratively derived associating affixed to items component group can be accomplished through skilled in the art design choice selection of one or more of the above depicted components from one or more of the above depicted subsystems shown in FIG. 12. Components from the associating affixed to items component group can be used in implementing execution of the one or more associating affixed to items instructions i1234 of FIG. 34, can be used in performance of the associating affixed to items electrical circuitry arrangement e1234 of FIG. 27, and/or can be used in otherwise fulfillment of the operation o1234. An exemplary non-transitory signal bearing medium version of the information storage subsystem s200 is depicted in FIG. 34 as bearing the one or more associating affixed to items instructions i1234 that when executed will direct performance of the operation o1234. Furthermore, the associating affixed to items electrical circuitry arrangement ("elec circ arrange") e1234, when activated, will perform the operation o1234. Also, the associating affixed to items module m1234, when executed and/or activated, will direct performance of and/or perform the operation o1234. For instance, in one or more exemplary implementations, the one or more associating affixed to items instructions i1234, when executed, direct performance of the operation o1234 in the illustrative depiction as follows, and/or the associating affixed to items electrical circuitry arrangement e1234, when activated, performs the operation o1234 in the illustrative depiction as follows, and/or the associating affixed to items module m1234, when executed and/or activated, directs performance of and/or performs the operation o1234 in the illustrative depiction as follows, and/or the operation o1234 is otherwise carried out in the illustrative depiction as follows: electronically associating (e.g. through unique exclusions of data, etc.) at least a portion of grocery operations information (e.g. cold storage data for stored food materials, etc.) concerning at least in part (e.g. argue, etc.) one or more grocery implementation aspects (e.g. identified issues regarding one or more types of dishes sold by the grocery facility, etc.) pertaining to (e.g. argue, etc.) grocery related merchandizing of (e.g. mobile kitchen grocery item preparation, etc.) one or more commercial grocery products (e.g. microwaved main course, etc.) with identification information (e.g. as being recorded thereafter due in part to application response delay, etc.) obtainable through (e.g. through barcode scanning, etc.) one or more tags (e.g. gyroscope, etc.) said one or more tags logged (e.g. via CD-ROM storage, etc.) as being at least temporarily (e.g. partial time spent on retail display, etc.) the within at least a vicinity of (e.g. welded onto container, etc.) one or more food based substances (e.g. feed grain, etc.) including at least in part logged as affixed to one or more grocery items (e.g. label adhesively attached to whole vegetable, etc.).

In one or more implementations, as shown in FIG. 81, operation o12 includes an operation o1235 for electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily the within at least a vicinity of one or more food based substances including at least in part logged as affixed to pre-processed forms of grocery items. Origination of an illustratively derived associating pre-processed forms component group can be accomplished through skilled in the art design choice selection of one or more of the above depicted components from one or more of the above depicted subsystems shown in FIG. 12. Components from the associating pre-processed forms component group can be used in implementing execution of the one or more associating pre-processed forms instructions i1235 of FIG. 34, can be used in performance of the associating pre-processed forms electrical circuitry arrangement e1235 of FIG. 27, and/or can be used in otherwise fulfillment of the operation o1235. An exemplary non-transitory signal bearing medium version of the information storage subsystem s200 is depicted in FIG. 34 as bearing the one or more associating pre-processed forms instructions i1235 that when executed will direct performance of the operation o1235. Furthermore, the associating pre-processed forms electrical circuitry arrangement ("elec circ arrange") e1235, when activated, will perform the operation o1235. Also, the associating pre-processed forms module m1235, when executed and/or activated, will direct performance of and/or perform the operation o1235. For instance, in one or more exemplary implementations, the one or more associating pre-processed forms instructions i1235, when executed, direct performance of the operation o1235 in the illustrative depiction as follows, and/or the associating pre-processed forms electrical circuitry arrangement e1235, when activated, performs the operation o1235 in the illustrative depiction as follows, and/or the associating pre-processed forms module m1235, when executed and/or activated, directs performance of and/or performs the operation o1235 in the illustrative depiction as follows, and/or the operation o1235 is otherwise carried out in the illustrative depiction as follows: electronically associating (e.g. through primary key, etc.) at least a portion of grocery operations information (e.g. stove maintenance operation, etc.) concerning at least in part (e.g. connected, etc.) one or more grocery implementation aspects (e.g. identified issues regarding one or more types of food items sold by the grocery facility, etc.) pertaining to (e.g. connected, etc.) grocery related merchandizing of (e.g. street vendor grocery item preparation, etc.) one or more commercial grocery products (e.g. chilled main course, etc.) with identification information (e.g. as being recorded thereafter due in part to network transmission delays, etc.) obtainable through (e.g. through radiation detection, etc.) one or more tags (e.g. inertial sensor, etc.) said one or more tags logged (e.g. via digital linear tape storage, etc.) as being at least temporarily (e.g. time on train between two terminals, etc.) the within at least a vicinity of (e.g. bolted to container, etc.) one or more food based substances (e.g. sturgeon eggs, etc.) including at least in part logged as affixed to pre-processed forms of grocery items (e.g. RFID tag clipped to raw steak, etc.).

In one or more implementations, as shown in FIG. 81, operation o12 includes an operation o1236 for electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily the within at least a vicinity of one or more food based substances including at least in part affixed to another portion of a biological structure that is logged as being physically connected with one or more grocery items. Origination of an illustratively derived associating physically connected component group can be accomplished through skilled in the art design choice selection of one or more of the above depicted components from one or more of the above depicted subsystems shown in FIG. 12. Components from the associating physically connected component group can be used in implementing execution of the one or more associating physically connected instructions i1236 of FIG. 34, can be used in performance of the associating physically connected electrical circuitry arrangement e1236 of FIG. 27, and/or can be used in otherwise fulfillment of the operation o1236. An exemplary non-transitory signal bearing medium version of the information storage subsystem s200 is depicted in FIG. 34 as bearing the one or more associating physically connected instructions i1236 that when executed will direct performance of the operation o1236. Furthermore, the associating physically connected electrical circuitry arrangement ("elec circ arrange") e1236, when activated, will perform the operation o1236. Also, the associating physically connected module m1236, when executed and/or activated, will direct performance of and/or perform the operation o1236. For instance, in one or more exemplary implementations, the one or more associating physically connected instructions i1236, when executed, direct performance of the operation o1236 in the illustrative depiction as follows, and/or the associating physically connected electrical circuitry arrangement e1236, when activated, performs the operation o1236 in the illustrative depiction as follows, and/or the associating physically connected module m1236, when executed and/or activated, directs performance of and/or performs the operation o1236 in the illustrative depiction as follows, and/or the operation o1236 is otherwise carried out in the illustrative depiction as follows: electronically associating (e.g. through foreign key search, etc.) at least a portion of grocery operations information (e.g. electricity usage, etc.) concerning at least in part (e.g. commit to, etc.) one or more grocery implementation aspects (e.g. identified issues regarding one or more procedures used to prepare one or more grocery items by the grocery facility, etc.) pertaining to (e.g. commit to, etc.) grocery related merchandizing of (e.g. nursing home grocery item preparation, etc.) one or more commercial grocery products (e.g. steamed grocery item main course, etc.) with identification information (e.g. via application records, etc.) obtainable through (e.g. through genetic testing, etc.) one or more tags (e.g. accelerometer, etc.) said one or more tags logged (e.g. via hard disk drive storage, etc.) as being at least temporarily (e.g. time held in port for inspection period, etc.) the within at least a vicinity of (e.g. stapled to container, etc.) one or more food based substances (e.g. shrimp, etc.) including at least in part affixed to another portion of a biological structure that is logged as being physically connected with one or more grocery items (e.g. tag attached to apple stem, etc.).

In one or more implementations, as shown in FIG. 82, operation o12 includes an operation o1237 for electronically associating at least a portion of grocery operations information concerning at least in part one or more grocery implementation aspects pertaining to grocery related merchandizing of one or more commercial grocery products with identification information obtainable through one or more tags said one or more tags logged as being at least temporarily the within at least a vicinity of one or more food based substances including at least in part logged as affixed to one or more containers at least temporarily containing one or more grocery items. Origination of an illustratively derived associating temporarily containing component group can be accomplished through skilled in the art design choice selection of one or more of the above depicted components from one or more of the above depicted subsystems shown in FIG. 12. Components from the associating temporarily containing component group can be used in implementing execution of the one or more associating temporarily containing instructions i1237 of FIG. 34, can be used in performance of the associating temporarily containing electrical circuitry arrangement e1237 of FIG. 27, and/or can be used in otherwise fulfillment of the operation o1237. An exemplary non-transitory signal bearing medium version of the information storage subsystem s200 is depicted in FIG. 34 as bearing the one or more associating temporarily containing instructions i1237 that when executed will direct performance of the operation o1237. Furthermore, the associating temporarily containing electrical circuitry arrangement ("elec circ arrange") e1237, when activated, will perform the operation o1237. Also, the associating temporarily containing module m1237, when executed and/or activated, will direct performance of and/or perform the operation o1237. For instance, in one or more exemplary implementations, the one or more associating temporarily containing instructions i1237, when executed, direct performance of the operation o1237 in the illustrative depiction as follows, and/or the associating temporarily containing electrical circuitry arrangement e1237, when activated, performs the operation o1237 in the illustrative depiction as follows, and/or the associating temporarily containing module m1237, when executed and/or activated, directs performance of and/or performs the operation o1237 in the illustrative depiction as follows, and/or the operation o1237 is otherwise carried out in the illustrative depiction as follows: electronically associating (e.g. through a hash table search, etc.) at least a portion of grocery operations information (e.g. customer accident reports, etc.) concerning at least in part (e.g. absorbed by, etc.) one or more grocery implementation aspects (e.g. age profile of equipment used, etc.) pertaining to (e.g. absorbed by, etc.) grocery related merchandizing of (e.g. school cafeteria grocery item preparation, etc.) one or more commercial grocery products (e.g. grilled grocery item main, etc.) with identification information (e.g. via operating system records, etc.) obtainable through (e.g. through beacon signal reception, etc.) one or more tags (e.g. compass, etc.) said one or more tags logged (e.g. via index information, etc.) as being at least temporarily (e.g. time in holding bay, etc.) the within at least a vicinity of (e.g. snapped onto container, etc.) one or more food based substances (e.g. domestic goose, etc.) including at least in part logged as affixed to one or more containers at least temporarily containing one or more grocery items (e.g. tag embedded into shipping container, etc.).

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

The one or more instructions discussed herein may be, for example, computer executable and/or logic-implemented instructions. In some implementations, signal-bearing medium as articles of manufacture may store the one or more instructions. In some implementations, the signal bearing medium may include a computer-readable medium. In some implementations, the signal-bearing medium may include a recordable medium. In some implementations, the signal-bearing medium may include a communication medium.

Those having skill in the art will recognize that the state of the art has progressed to the point where there is little distinction left between hardware and software implementations of aspects of systems; the use of hardware or software is generally (but not always, in that in certain contexts the choice between hardware an d software can become significant) a design choice representing cost vs. efficiency tradeoffs. Those having skill in the art will appreciate that there are various vehicles by which processes and/or systems and/or other technologies described herein can be effected (e.g., hardware, software, and/or firmware in one or more machines or articles of manufacture), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation that is implemented in one or more machines or articles of manufacture; or, yet again alternatively, the implementer may opt for some combination of hardware, software, and/or firmware in one or more machines or articles of manufacture (limited to patentable subject matter under 35 USC 101). Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware in one or more machines or articles of manufacture.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof (limited to patentable subject matter under 35 U.S.C. 101). In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure (limited to patentable subject matter under 35 USC 101). In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, (e.g., transmitter, receiver, transmission logic, reception logic, etc.), etc.).

Electro-Mechanical System Support

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

Electrical Circuitry Support

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Image Processing System Support

Those skilled in the art will recognize that at least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Data Processing System Support

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Software as Patentable Subject Matter Support

The claims, description, and drawings of this application may describe one or more of the instant technologies in operational/functional language, for example as a set of operations to be performed by a computer. Such operational/functional description in most instances would be understood by one skilled the art as specifically-configured hardware (e.g., because a general purpose computer in effect becomes a special purpose computer once it is programmed to perform particular functions pursuant to instructions from program software).

Importantly, although the operational/functional descriptions described herein are understandable by the human mind, they are not abstract ideas of the operations/functions divorced from computational implementation of those operations/functions. Rather, the operations/functions represent a specification for the massively complex computational machines or other means. As discussed in detail below, the operational/functional language must be read in its proper technological context, i.e., as concrete specifications for physical implementations.

The logical operations/functions described herein are a distillation of machine specifications or other physical mechanisms specified by the operations/functions such that the otherwise inscrutable machine specifications may be comprehensible to the human mind. The distillation also allows one of skill in the art to adapt the operational/functional description of the technology across many different specific vendors' hardware configurations or platforms, without being limited to specific vendors' hardware configurations or platforms.

Some of the present technical description (e.g., detailed description, drawings, claims, etc.) may be set forth in terms of logical operations/functions. As described in more detail in the following paragraphs, these logical operations/functions are not representations of abstract ideas, but rather representative of static or sequenced specifications of various hardware elements. Differently stated, unless context dictates otherwise, the logical operations/functions will be understood by those of skill in the art to be representative of static or sequenced specifications of various hardware elements. This is true because tools available to one of skill in the art to implement technical disclosures set forth in operational/functional formats—tools in the form of a high-level programming language (e.g., C, java, visual basic), etc.), or tools in the form of Very high speed Hardware Description Language ("VHDL," which is a language that uses text to describe logic circuits)—are generators of static or sequenced specifications of various hardware configurations. This fact is sometimes obscured by the broad term "software," but, as shown by the following explanation, those skilled in the art understand that what is termed "software" is a shorthand for a massively complex inter-chaining/specification of ordered-matter elements. The term "ordered-matter elements" may refer to physical components of computation, such as assemblies of electronic logic gates, molecular computing logic constituents, quantum computing mechanisms, etc.

For example, a high-level programming language is a programming language with strong abstraction, e.g., multiple levels of abstraction, from the details of the sequential organizations, states, inputs, outputs, etc., of the machines that a high-level programming language actually specifies. See, e.g., Wikipedia, High-level programming language, http://en.wikipedia.org/wiki/High-level_programming_language (as of Jun. 5, 2012, 21:00 GMT). In order to facilitate human comprehension, in many instances, high-level programming languages resemble or even share symbols with natural languages. See, e.g., Wikipedia, Natural language, http://en.wikipedia.org/wiki/Natural_language (as of Jun. 5, 2012, 21:00 GMT).

It has been argued that because high-level programming languages use strong abstraction (e.g., that they may resemble or share symbols with natural languages), they are therefore a "purely mental construct." (e.g., that "software"—a computer program or computer programming—is somehow an ineffable mental construct, because at a high level of abstraction, it can be conceived and understood in the human mind). This argument has been used to characterize technical description in the form of functions/operations as somehow "abstract ideas." In fact, in technological arts (e.g., the information and communication technologies) this is not true.

The fact that high-level programming languages use strong abstraction to facilitate human understanding should not be taken as an indication that what is expressed is an abstract idea. In fact, those skilled in the art understand that just the opposite is true. If a high-level programming language is the tool used to implement a technical disclosure in the form of functions/operations, those skilled in the art will recognize that, far from being abstract, imprecise, "fuzzy," or "mental" in any significant semantic sense, such a tool is instead a near incomprehensibly precise sequential specification of specific computational machines—the parts of which are built up by activating/selecting such parts from typically more general computational machines over time (e.g., clocked time). This fact is sometimes obscured by the superficial similarities between high-level programming languages and natural languages. These superficial similarities also may cause a glossing over of the fact that high-level programming language implementations ultimately perform valuable work by creating/controlling many different computational machines.

The many different computational machines that a high-level programming language specifies are almost unimaginably complex. At base, the hardware used in the computational machines typically consists of some type of ordered matter (e.g., traditional electronic devices (e.g., transistors), deoxyribonucleic acid (DNA), quantum devices, mechanical switches, optics, fluidics, pneumatics, optical devices (e.g., optical interference devices), molecules, etc.) that are arranged to form logic gates. Logic gates are typically physical devices that may be electrically, mechanically, chemically, or otherwise driven to change physical state in order to create a physical reality of Boolean logic.

Logic gates may be arranged to form logic circuits, which are typically physical devices that may be electrically, mechanically, chemically, or otherwise driven to create a physical reality of certain logical functions. Types of logic circuits include such devices as multiplexers, registers, arithmetic logic units (ALUs), computer memory, etc., each type of which may be combined to form yet other types of physical devices, such as a central processing unit (CPU)—the best known of which is the microprocessor. A modern microprocessor will often contain more than one hundred million logic gates in its many logic circuits (and often more than a billion transistors). See, e.g., Wikipedia, Logic gates, http://en.wikipedia.org/wiki/Logic_gates (as of Jun. 5, 2012, 21:03 GMT).

The logic circuits forming the microprocessor are arranged to provide a microarchitecture that will carry out the instructions defined by that microprocessor's defined Instruction Set Architecture. The Instruction Set Architecture is the part of the microprocessor architecture related to programming, including the native data types, instructions, registers, addressing modes, memory architecture, interrupt and exception handling, and external Input/Output. See, e.g., Wikipedia, Computer architecture, http://en.wikipedia.org/wiki/Computer_architecture (as of Jun. 5, 2012, 21:03 GMT).

The Instruction Set Architecture includes a specification of the machine language that can be used by programmers to use/control the microprocessor. Since the machine language instructions are such that they may be executed directly by the microprocessor, typically they consist of strings of binary digits, or bits. For example, a typical machine language instruction might be many bits long (e.g., 32, 64, or 128 bit strings are currently common). A typical machine language instruction might take the form "11110000101011110000111100111111" (a 32 bit instruction).

It is significant here that, although the machine language instructions are written as sequences of binary digits, in actuality those binary digits specify physical reality. For example, if certain semiconductors are used to make the operations of Boolean logic a physical reality, the apparently mathematical bits "1" and "0" in a machine language instruction actually constitute a shorthand that specifies the application of specific voltages to specific wires. For example, in some semiconductor technologies, the binary number "1" (e.g., logical "1") in a machine language instruction specifies around +5 volts applied to a specific "wire" (e.g., metallic traces on a printed circuit board) and the binary number "0" (e.g., logical "0") in a machine language instruction specifies around −5 volts applied to a specific "wire." In addition to specifying voltages of the machines' configuration, such machine language instructions also select out and activate specific groupings of logic gates from the millions of logic gates of the more general machine. Thus, far from abstract mathematical expressions, machine language instruction programs, even though written as a string of zeros and ones, specify many, many constructed physical machines or physical machine states.

Machine language is typically incomprehensible by most humans (e.g., the above example was just ONE instruction, and some personal computers execute more than two billion instructions every second). See, e.g., Wikipedia, Instructions per second, http://en.wikipedia.org/wiki/Instructions_per_second (as of Jun. 5, 2012, 21:04 GMT). Thus, programs written in machine language—which may be tens of millions of machine language instructions long—are incomprehensible. In view of this, early assembly languages were developed that used mnemonic codes to refer to machine language instructions, rather than using the machine language instructions' numeric values directly (e.g., for performing a multiplication operation, programmers coded the abbreviation "mult," which represents the binary number "011000" in MIPS machine code). While assembly languages were initially a great aid to humans controlling the microprocessors to perform work, in time the complexity of the work that needed to be done by the humans outstripped the ability of humans to control the microprocessors using merely assembly languages.

At this point, it was noted that the same tasks needed to be done over and over, and the machine language necessary to do those repetitive tasks was the same. In view of this, compilers were created. A compiler is a device that takes a statement that is more comprehensible to a human than either machine or assembly language, such as "add 2+2 and output the result," and translates that human understandable statement into a complicated, tedious, and immense machine language code (e.g., millions of 32, 64, or 128 bit length strings). Compilers thus translate high-level programming language into machine language.

This compiled machine language, as described above, is then used as the technical specification which sequentially constructs and causes the interoperation of many different computational machines such that humanly useful, tangible, and concrete work is done. For example, as indicated above, such machine language—the compiled version of the higher-level language—functions as a technical specification which selects out hardware logic gates, specifies voltage levels, voltage transition timings, etc., such that the humanly useful work is accomplished by the hardware.

Thus, a functional/operational technical description, when viewed by one of skill in the art, is far from an abstract idea. Rather, such a functional/operational technical description, when understood through the tools available in the art such as those just described, is instead understood to be a humanly understandable representation of a hardware specification, the complexity and specificity of which far exceeds the comprehension of most any one human. With this in mind, those skilled in the art will understand that any such operational/functional technical descriptions—in view of the disclosures herein and the knowledge of those skilled in the art—may be understood as operations made into physical reality by (a) one or more interchained physical machines, (b) interchained logic gates configured to create one or more physical machine(s) representative of sequential/combinatorial logic(s), (c) interchained ordered matter making up logic gates (e.g., interchained electronic devices (e.g., transistors), DNA, quantum devices, mechanical switches, optics, fluidics, pneumatics, molecules, etc.) that create physical reality representative of logic(s), or (d) virtually any combination of the foregoing. Indeed, any physical object which has a stable, measurable, and changeable state may be used to construct a machine based on the above technical description. Charles Babbage, for example, constructed the first computer out of wood and powered by cranking a handle.

Thus, far from being understood as an abstract idea, those skilled in the art will recognize a functional/operational technical description as a humanly-understandable representation of one or more almost unimaginably complex and time sequenced hardware instantiations. The fact that functional/operational technical descriptions might lend themselves readily to high-level computing languages (or high-level block diagrams for that matter) that share some words, structures, phrases, etc. with natural language simply cannot be taken as an indication that such functional/operational technical descriptions are abstract ideas, or mere expressions of abstract ideas. In fact, as outlined herein, in the technological arts this is simply not true. When viewed through the tools available to those of skill in the art, such functional/operational technical descriptions are seen as specifying hardware configurations of almost unimaginable complexity.

As outlined above, the reason for the use of functional/operational technical descriptions is at least twofold. First, the use of functional/operational technical descriptions allows near-infinitely complex machines and machine operations arising from interchained hardware elements to be described in a manner that the human mind can process (e.g., by mimicking natural language and logical narrative flow). Second, the use of functional/operational technical descriptions assists the person of skill in the art in understanding the described subject matter by providing a description that is more or less independent of any specific vendor's piece(s) of hardware.

The use of functional/operational technical descriptions assists the person of skill in the art in understanding the described subject matter since, as is evident from the above discussion, one could easily, although not quickly, transcribe the technical descriptions set forth in this document as trillions of ones and zeroes, billions of single lines of assembly-level machine code, millions of logic gates, thousands of gate arrays, or any number of intermediate levels of abstractions. However, if any such low-level technical descriptions were to replace the present technical description, a person of skill in the art could encounter undue difficulty in implementing the disclosure, because such a low-level technical description would likely add complexity without a corresponding benefit (e.g., by describing the subject matter utilizing the conventions of one or more vendor-specific pieces of hardware). Thus, the use of functional/operational technical descriptions assists those of skill in the art by separating the technical descriptions from the conventions of any vendor-specific piece of hardware.

In view of the foregoing, the logical operations/functions set forth in the present technical description are representative of static or sequenced specifications of various ordered-matter elements, in order that such specifications may be comprehensible to the human mind and adaptable to create many various hardware configurations. The logical operations/functions disclosed herein should be treated as such, and should not be disparagingly characterized as abstract ideas merely because the specifications they represent are presented in a manner that one of skill in the art can readily understand and apply in a manner independent of a specific vendor's hardware implementation.

Mote System Support

Those skilled in the art will recognize that at least a portion of the devices and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

Licensing System Support Language

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

Extraterritorial Use Language

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

Residual Incorporation Language

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

Not Limited to Implementations Described Language

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Not Limited to Human User Language

Although user XXX is shown/described herein as a single illustrated figure, those skilled in the art will appreciate that user XXX may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

Plural Terms Language

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

Operably-Coupled Language

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Active/Inactive Component Language

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context requires otherwise.

Cloud Computing Standard Language

For the purposes of this application, "cloud" computing may be understood as described in the cloud computing literature. For example, cloud computing may be methods and/or systems for the delivery of computational capacity and/or storage capacity as a service. The "cloud" may refer to one or more hardware and/or software components that deliver or assist in the delivery of computational and/or storage capacity, including, but not limited to, one or more of a client, an application, a platform, an infrastructure, and/or a server The cloud may refer to any of the hardware and/or software associated with a client, an application, a platform, an infrastructure, and/or a server. For example, cloud and cloud computing may refer to one or more of a computer, a processor, a storage medium, a router, a switch, a modem, a virtual machine (e.g., a virtual server), a data center, an operating system, a middleware, a firmware, a hardware back-end, a software back-end, and/or a software application. A cloud may refer to a private cloud, a public cloud, a hybrid cloud, and/or a community cloud. A cloud may be a shared pool of configurable computing resources, which may be public, private, semi-private, distributable, scaleable, flexible, temporary, virtual, and/or physical. A cloud or cloud service may be delivered over one or more types of network, e.g., a mobile communication network, and the Internet.

As used in this application, a cloud or a cloud service may include one or more of infrastructure-as-a-service ("IaaS"), platform-as-a-service ("PaaS"), software-as-a-service ("SaaS"), and/or desktop-as-a-service ("DaaS"). As a non-exclusive example, IaaS may include, e.g., one or more virtual server instantiations that may start, stop, access, and/or configure virtual servers and/or storage centers (e.g., providing one or more processors, storage space, and/or network resources on-demand, e.g., EMC and Rackspace). PaaS may include, e.g., one or more software and/or development tools hosted on an infrastructure (e.g., a computing platform and/or a solution stack from which the client can create software interfaces and applications, e.g., Microsoft Azure). SaaS may include, e.g., software hosted by a service provider and accessible over a network (e.g., the software for the application and/or the data associated with that software application may be kept on the network, e.g., Google Apps, SalesForce). DaaS may include, e.g., providing desktop, applications, data, and/or services for the user over a network (e.g., providing a multi-application framework, the applications in the framework, the data associated with the applications, and/or services related to the applications and/or the data over the network, e.g., Citrix). The foregoing is intended to be exemplary of the types of systems and/or methods referred to in this application as "cloud" or "cloud computing" and should not be considered complete or exhaustive.

Use of Trademarks in Specification Language

This application may make reference to one or more trademarks, e.g., a word, letter, symbol, or device adopted by one manufacturer or merchant and used to identify and/or distinguish his or her product from those of others. Trademark names used herein are set forth in such language that makes clear their identity, that distinguishes them from common descriptive nouns, that have fixed and definite meanings, or, in many if not all cases, are accompanied by other specific identification using terms not covered by trademark. In addition, trademark names used herein have meanings that are well-known and defined in the literature, or do not refer to products or compounds for which knowledge of one or more trade secrets is required in order to divine their meaning. All trademarks referenced in this application are the property of their respective owners, and the appearance of one or more trademarks in this application does not diminish or otherwise adversely affect the validity of the one or more trademarks. All trademarks, registered or unregistered, that appear in this application are assumed to include a proper trademark symbol, e.g., the circle R or bracketed capitalization (e.g., [trademark name]), even when such trademark symbol does not explicitly appear next to the trademark. To the extent a trademark is used in a descriptive manner to refer to a product or process, that trademark should be interpreted to represent the corresponding product or process as of the date of the filing of this patent application.

Caselaw-Driven Clarification Language

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. A system for prevention of unsafe foods from advancing through a supply chain, comprising:
   circuitry configured for receiving one or more indications of one or more remote sensor measurements corresponding to one or more shipments of one or more foods to one or more destinations;
   circuitry configured for maintaining a food safety database including at least (a) one or more food safety criteria relating to one or more foods, (b) one or more tracers corresponding to the one or more shipments of one or more foods to one or more destinations, and (c) at least one received indication of the one or more remote sensor measurements in association with at least one of the one or more shipments of one or more foods to one or more destinations;
   circuitry configured for comparing at least one food safety criteria associated with at least one food and at least one remote sensor measurement corresponding to at least one shipment including the at least one food;

circuitry configured for generating at least one alert responsive to at least one indication of at least one unsafe food shipment at least partially based on comparing the at least one food safety criteria associated with the at least one food and the at least one remote sensor measurement corresponding to the at least one shipment including the at least one food, the at least one alert including at least one tracer of the one or more tracers that corresponds to the at least one unsafe food shipment; and circuitry configured for controlling at least one remote emitter to mark at least one container of the at least one food with at least one indication that the at least one container of the at least one food is not in compliance with the at least one food safety criteria associated with the at least one food.

2. The system for prevention of unsafe foods from advancing through a supply chain of claim 1, wherein circuitry configured for receiving one or more indications of one or more remote sensor measurements corresponding to one or more shipments of one or more foods to one or more destinations comprises:

circuitry configured for receiving at least one indication of at least one temperature sensor associated with at least one trucking container containing at least one food associated with at least one food safety criteria.

3. The system for prevention of unsafe foods from advancing through a supply chain of claim 2, wherein circuitry configured for receiving at least one indication of at least one temperature sensor associated with at least one trucking container containing at least one food associated with at least one food safety criteria comprises:

circuitry configured for receiving at least one indication of at least one amount of time that the at least one food associated with the at least one food safety criteria was exposed to at least one temperature sensed by the at least one temperature sensor.

4. The system for prevention of unsafe foods from advancing through a supply chain of claim 1, wherein circuitry configured for receiving one or more indications of one or more remote sensor measurements corresponding to one or more shipments of one or more foods to one or more destinations comprises:

circuitry configured for receiving at least one indication of at least one time at which at least one RFID reader associated with at least one receiving dock detected at least one container passing through the at least one receiving dock.

5. The system for prevention of unsafe foods from advancing through a supply chain of claim 1, wherein circuitry configured for receiving one or more indications of one or more remote sensor measurements corresponding to one or more shipments of one or more foods to one or more destinations comprises:

circuitry configured for receiving at least one indication of one or more of the at least one remote emitter or at least one other remote emitter having marked at least one container of at least one food with at least one other tracer while passing through at least one receiving dock.

6. The system for prevention of unsafe foods from advancing through a supply chain of claim 1, wherein circuitry configured for maintaining a food safety database including at least (a) one or more food safety criteria relating to one or more foods, (b) one or more tracers corresponding to the one or more shipments of one or more foods to one or more destinations, and (c) at least one received indication of the one or more remote sensor measurements in association with at least one of the one or more shipments of one or more foods to one or more destinations comprises:

circuitry configured for maintaining a food safety database including at least one or more food safety criteria including at least one or more maximum temperature values associated with the one or more foods.

7. The system for prevention of unsafe foods from advancing through a supply chain of claim 6, wherein circuitry configured for maintaining a food safety database including at least one or more food safety criteria including at least one or more maximum temperature values associated with the one or more foods comprises:

circuitry configured for maintaining at least one cold storage food safety criteria including at least one food safety protocol associated with at least one food, the at least one food safety protocol including at least a first maximum temperature value and a first duration of storage associated with the at least one food and a second maximum temperature value and a second duration of storage associated with the at least one food, the at least one food safety protocol associated with the at least one food including at least an inversely proportional relation between maximum temperature and duration of storage of the at least one food.

8. The system for prevention of unsafe foods from advancing through a supply chain of claim 1, wherein circuitry configured for maintaining a food safety database including at least (a) one or more food safety criteria relating to one or more foods, (b) one or more tracers corresponding to the one or more shipments of one or more foods to one or more destinations, and (c) at least one received indication of the one or more remote sensor measurements in association with at least one of the one or more shipments of one or more foods to one or more destinations comprises:

circuitry configured for maintaining a food safety database including at least one or more identifiers associated with one or more RFID tags adhered to one or more containers associated with at least one shipment of the one or more foods to the one or more destinations as the one or more tracers corresponding to the at least one shipment and at least one shipment time associated with the at least one shipment of the one or more foods to the one or more destinations.

9. The system for prevention of unsafe foods from advancing through a supply chain of claim 1, wherein circuitry configured for comparing at least one food safety criteria associated with at least one food and at least one remote sensor measurement corresponding to at least one shipment including the at least one food comprises:

circuitry configured for comparing at least one maximum temperature value for storage of the at least one food with at least one temperature received from at least one remote temperature sensor attached to at least one container of the at least one food to determine whether the at least one maximum temperature was exceeded during the at least one shipment including the at least one food.

10. The system for prevention of unsafe foods from advancing through a supply chain of claim 1, wherein circuitry configured for comparing at least one food safety criteria associated with at least one food and at least one remote sensor measurement corresponding to at least one shipment including the at least one food comprises:

circuitry configured for determining, at least partially based on at least one detection of at least one nitrogen sensor, at least one loss of packed gas within at least one container of the at least one food indicative of the at least one container being opened during the at least one shipment.

11. The system for prevention of unsafe foods from advancing through a supply chain of claim 1, wherein circuitry configured for comparing at least one food safety criteria associated with at least one food and at least one remote sensor measurement corresponding to at least one shipment including the at least one food comprises:
  circuitry configured for determining, at least partially based on image recognition of at least one image captured by at least one image sensor attached to at least one container of the at least one food during the at least one shipment, at least one spoliation condition of the at least one food at least partially based on at least one light condition detected via the image recognition, the at least one food associated with at least one food safety criteria including storage of the at least one food in dark conditions.

12. The system for prevention of unsafe foods from advancing through a supply chain of claim 1, wherein circuitry configured for comparing at least one food safety criteria associated with at least one food and at least one remote sensor measurement corresponding to at least one shipment including the at least one food comprises:
  circuitry configured for determining, at least partially based on image recognition of at least one image captured by at least one image sensor attached to at least one container of the at least one food during the at least one shipment, at least one condition related to handling of the at least one container of the at least one food, including at least determining whether at least one worker handling the at least one food has taken adequate food safety measures in accordance with the at least one food safety criteria.

13. The system for prevention of unsafe foods from advancing through a supply chain of claim 1, wherein circuitry configured for comparing at least one food safety criteria associated with at least one food and at least one remote sensor measurement corresponding to at least one shipment including the at least one food comprises:
  circuitry configured for comparing at least one maximum pesticide level associated with the at least one food with at least one value received from at least one remote oxygen sensor located within at least one receiving dock through which at least one container of the at least one food is passing to determine whether the at least one pesticide level was exceeded during production of the at least one food.

14. The system for prevention of unsafe foods from advancing through a supply chain of claim 1, wherein circuitry configured for generating at least one alert responsive to at least one indication of at least one unsafe food shipment at least partially based on comparing the at least one food safety criteria associated with the at least one food and the at least one remote sensor measurement corresponding to the at least one shipment including the at least one food, the at least one alert including at least one tracer of the one or more tracers that corresponds to the at least one unsafe food shipment comprises:
  circuitry configured for transmitting at least one request for at least one change in temperature of at least one conveyance transporting the at least one shipment including the at least one food at least partially based on the comparing the at least one food safety criteria associated with the at least one food and the at least one remote sensor measurement indicating that a maximum temperature value associated with storage of the at least one food is about to be exceeded during the at least one shipment.

15. The system for prevention of unsafe foods from advancing through a supply chain of claim 1, wherein circuitry configured for generating at least one alert responsive to at least one indication of at least one unsafe food shipment at least partially based on comparing the at least one food safety criteria associated with the at least one food and the at least one remote sensor measurement corresponding to the at least one shipment including the at least one food, the at least one alert including at least one tracer of the one or more tracers that corresponds to the at least one unsafe food shipment comprises:
  circuitry configured for transmitting at least one alert to initiate at least one test event of the at least one food at the at least one destination subsequent to the at least one shipment arriving at the at least one destination at least partially based on the comparing the at least one food safety criteria associated with the at least one food and the at least one remote sensor measurement indicating that a maximum temperature value associated with storage of the at least one food was exceeded during the at least one shipment.

16. The system for prevention of unsafe foods from advancing through a supply chain of claim 1, wherein circuitry configured for generating at least one alert responsive to at least one indication of at least one unsafe food shipment at least partially based on comparing the at least one food safety criteria associated with the at least one food and the at least one remote sensor measurement corresponding to the at least one shipment including the at least one food, the at least one alert including at least one tracer of the one or more tracers that corresponds to the at least one unsafe food shipment comprises:
  circuitry configured for transmitting at least one alert regarding payment for the at least one food at least partially based on the comparing the at least one food safety criteria associated with the at least one food and the at least one remote sensor measurement indicating at least one requirement against sale of fraudulent product was violated at least partially based on obtaining at least one image of at least one fraudulent label affixed to one or more of the at least one container or at least one other container of the at least one food from at least one remote image sensor.

17. The system for prevention of unsafe foods from advancing through a supply chain of claim 1, wherein circuitry configured for controlling at least one remote emitter to mark at least one container of the at least one food with at least one indication that the at least one container of the at least one food is not in compliance with the at least one food safety criteria associated with the at least one food comprises:
  circuitry configured for controlling the at least one remote emitter to mark the at least one container of the at least one food with one or more of at least one electronic, at least one magnetic, at least one invisible, at least one chemical, at least one dna, or at least one encrypted indication that the at least one container of the at least one food is not in compliance with the at least one food safety criteria associated with the at least one food.

18. The system for prevention of unsafe foods from advancing through a supply chain of claim 1, further comprising:

circuitry configured for determining at least one payment associated with the at least one shipment including the at least one food according to at least one percentage of the at least one food meeting at least one food safety criteria associated with the at least one food at least partially based on one or more comparisons of the at least one food safety criteria associated with the at least one food and one or more received remote sensor measurements during the at least one shipment.

19. A method for prevention of unsafe foods from advancing through a supply chain, comprising:

receiving one or more indications of one or more remote sensor measurements corresponding to one or more shipments of one or more foods to one or more destinations;

maintaining a food safety database including at least (a) one or more food safety criteria relating to one or more foods, (b) one or more tracers corresponding to the one or more shipments of one or more foods to one or more destinations, and (c) at least one received indication of the one or more remote sensor measurements in association with at least one of the one or more shipments of one or more foods to one or more destinations;

comparing at least one food safety criteria associated with at least one food and at least one remote sensor measurement corresponding to at least one shipment including the at least one food;

generating at least one alert responsive to at least one indication of at least one unsafe food shipment at least partially based on comparing the at least one food safety criteria associated with the at least one food and the at least one remote sensor measurement corresponding to the at least one shipment including the at least one food, the at least one alert including at least one tracer of the one or more tracers that corresponds to the at least one unsafe food shipment; and controlling at least one remote emitter to mark at least one container of the at least one food with at least one indication that the at least one container of the at least one food is not in compliance with the at least one food safety criteria associated with the at least one food, wherein at least one of the receiving, maintaining, comparing, generating, or controlling is at least partially implemented using at least one processing device.

20. A system for prevention of unsafe foods from advancing through a supply chain, comprising:

at least one computing device; and one or more instructions which, when executed by the at least one computing device, cause the at least one computing device to perform one or more operations including at least:

receiving one or more indications of one or more remote temperature sensors attached to one or more containers of one or more foods associated with one or more shipments to one or more destinations;

maintaining a food safety database including at least (a) one or more food safety criteria relating to maximum temperature for storage of one or more foods, (b) one or more tracers corresponding to the one or more shipments of one or more foods to one or more destinations, and (c) at least one received temperature of the one or more remote temperature sensors in association with at least one of the one or more shipments of one or more foods to one or more destinations;

comparing at least one food safety criteria relating to maximum temperature for storage of at least one food and at least one temperature obtained by at least one remote temperature sensor during at least one shipment including the at least one food;

generating at least one alert responsive to at least one determination of the at least one shipment of the at least one food including at least one unsafe portion at least partially based on the comparing the at least one food safety criteria relating to maximum temperature for storage of at least one food indicating that the maximum temperature for storage of the at least one food was exceeded during the at least one shipment;

controlling at least one remote emitter to mark at least one container of the at least one food with at least one indication that the at least one container of the at least one food is not in compliance with the at least one food safety criteria relating to maximum temperature associated with the at least one food; and transmitting at least one alert to initiate at least one test event of the at least one food contained by the marked at least one container at the at least one destination subsequent to the at least one shipment arriving at the at least one destination at least partially based on the at least one indication that the at least one container of the at least one food is not in compliance with the at least one food safety criteria relating to maximum temperature associated with the at least one food.

\* \* \* \* \*